(12) United States Patent
Wencewicz et al.

(10) Patent No.: US 10,655,153 B2
(45) Date of Patent: May 19, 2020

(54) CHEMOENZYMATIC SYNTHESIS OF PEPTIDE BETA-LACTONES AND BETA-HYDROXY ACIDS

(71) Applicants: Timothy A. Wencewicz, St. Louis, MO (US); Jason E. Schaffer, St. Louis, MO (US); Margaret R. Reck, St. Louis, MO (US)

(72) Inventors: Timothy A. Wencewicz, St. Louis, MO (US); Jason E. Schaffer, St. Louis, MO (US); Margaret R. Reck, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/921,442

(22) Filed: Mar. 14, 2018

(65) Prior Publication Data
US 2018/0265905 A1    Sep. 20, 2018

Related U.S. Application Data

(60) Provisional application No. 62/471,183, filed on Mar. 14, 2017.

(51) Int. Cl.
| | | |
|---|---|---|
| C12P 17/02 | (2006.01) | |
| C12P 17/08 | (2006.01) | |
| C12N 9/10 | (2006.01) | |
| C12M 1/40 | (2006.01) | |
| C12M 1/00 | (2006.01) | |

(52) U.S. Cl.
CPC .............. *C12P 17/02* (2013.01); *C12M 21/18* (2013.01); *C12M 23/20* (2013.01); *C12M 29/10* (2013.01); *C12Y 201/02001* (2013.01); *C12Y 207/08007* (2013.01); *C12Y 401/01001* (2013.01); *C12Y 401/02005* (2013.01)

(58) Field of Classification Search
CPC ................... C12P 17/181; C12P 17/02; C12Y 102/04001; C12Y 301/02; C12Y 201/02001; C12Y 401/01001
USPC ........ 435/252.34, 123, 197, 254.5, 69.7, 76, 435/117, 189, 113, 119
See application file for complete search history.

(56) References Cited

U.S. PATENT DOCUMENTS 4,600,786 A    7/1986   Sykes et al.

OTHER PUBLICATIONS

Whisstock et al., Quarterly Reviews of Biophysics 2003, vol. 36 (3): 307-340.*
Devos et al., Proteins: Structure, Function and Genetics, 2000, vol. 41: 98-107.*
Witkowski et al., Biochemistry 38:11643-11650, 1999.*
Kisselev L., Structure, 2002, vol. 10: 8-9.*
Bachmann et al., "Beta-Lactam synthetase: A new biosynthetic enzyme", Proceedings of the National Academy of Sciences, 1998, vol. 95, pp. 9082-9086.
Bachovchin et al., "Superfamily-wide portrait of serine hydrolase inhibition achieved by library-versus-library screening", Proceedings of the National Academy of Sciences, 2010, vol. 107, No. 49, pp. 20941-20946.
Bai et al., "Operon for Biosynthesis of Lipstatin, the Beta-Lactone Inhibitor of Human Pancreatic Lipase", Applied and Environmental Microbiology, Dec. 2014, vol. 80, No. 24, pp. 7473-7483.
Barnard-Britson et al., "Amalgamation of Nucleosides and Amino Acids in Antibiotic Biosynthesis: Discovery of an L-Threonine:Uridine-5'-Aldehyde Transaldolase", Journal of the American Chemical Society, 2012, vol. 134, pp. 18514-18517.
Bentley et al., "The Shikimate Pathway—A Metabolic Tree with Many Branche", Critical Reviews in Biochemistry and Molecular Biology, 2008, pp. 307-384.
Blanc et al., Identification and analysis of genes from *Streptomyces pristinaespiralis* encoding enzymes involved in the biosynthesis of the 4-dimethylamino-L-phenylalanine precursor of pristinamycin I, Molecular Microbiology, 1997, vol. 23, No. 2, pp. 191-202.
Chanco et al., "Characterization of the N-oxygenase AurF from *Streptomyces thioletus*", Bioorganic & Medicinal Chemistry, 2014, vol. 22, pp. 5569-5577.
Choi et al., "In vitro reconstitution and crystal structure of p-aminobenzoate N-oxygenase (AurF) involved in aureothin biosynthesis", Proceedings of the National Academy of Sciences, 2008, vol. 105, pp. 6858-6863.
Contestabile et al., "L-Threonine aldolase, serine hydroxymethyltransferase and fungal alanine racemase: A subgroup of strictly related enzymes specialized for different functions", European Journal of Biochemistry, FEBS 2001, vol. 268, pp. 6508-6525.
De Pascale et al., "Beta-Lactone natural products and derivatives inactivate homoserine transacetylase, a target for antimicrobial agents", The Journal of Antibiotics, 2011, vol. 64, pp. 483-487.
DeJong et al., "Polyketide and nonribosomal peptide retro-biosynthesis and global gene cluster matching", Nature Chemical Biology, 2016, vol. 12, pp. 1007-1014.

(Continued)

*Primary Examiner* — Robert B Mondesi
*Assistant Examiner* — Mohammad Y Meah
(74) *Attorney, Agent, or Firm* — Armstrong Teasdale LLP

(57) ABSTRACT

Methods of producing peptide beta-lactones and beta-hydroxy acids are disclosed that include contacting a beta-hydroxy-alpha-amino acid, an aryl carrier protein (ObiD), and ATP with a non-ribosomal protein synthetase. A continuous flow reactor is disclosed that includes an elongate conduit with at least one region that includes a first region with a non-ribosomal protein synthetase immobilized to a substrate. The non-ribosomal protein synthetase of the continuous flow reactor is configured to contact a flow of a reaction mixture that includes a beta-hydroxy-alpha-amino acid and an aryl carrier protein. The non-ribosomal protein synthetase is further configured to release a peptide beta-lactone into the flow of the reaction mixture.

14 Claims, 110 Drawing Sheets
(82 of 110 Drawing Sheet(s) Filed in Color)
Specification includes a Sequence Listing.

(56) References Cited

OTHER PUBLICATIONS

Dick et al., "Mechanistic Studies on the Inactivation of the Proteasome by Lactacystin: A Central Role for clasto-Lactacystin Beta-Lactone", The Journal of Biological Chemistry, 1996, vol. 271, pp. 7273-7276.

Drake et al., "Structures of two distinct conformations of holo-non-ribosomal peptide synthetases", Nature, 2016, vol. 529, pp. 235-238.

Ehmann et al., "The EntF and EntE adenylation domains of *Escherichia coli* enterobactin synthetase: Sequestration and selectivity in acyl-AMP transfers to thiolation domain cosubstrates", Proceedings of the National Academy of Sciences, 2000, vol. 97, pp. 2509-2514.

Eustaquio et al., "Biosynthesis of the salinosporamide A polyketide synthase substrate chloroethylmalonyl-coenzyme A from S-adenosyl-L-methionine", Proceedings of the National Academy of Sciences, 2009, vol. 106, pp. 12295-12300.

Fernandez-Martinez et al., "New Insights into Chloramphenicol Biosynthesis in *Streptomyces venezuelae* ATCC 10712", Antimicrobial Agents and Chemotherapy, 2014, vol. 58, No. 12, pp. 7441-7450.

Gaudelli et al., "Epimerization and substrate gating by a TE domain in Beta-lactam antibiotic biosynthesis", Nature Chemical Biology, 2014, vol. 10, pp. 251-258.

Gaudelli et al., "Beta-Lactam formation by a non-ribosomal peptide synthetase during antibiotic biosynthesis", Nature, 2015, vol. 520, pp. 383-387.

Gulder et al., "Salinosporamide Natural Products: Potent 20 S Proteasome Inhibitors as Promising Cancer Chemotherapeutics", Angewandte Chemie International Edition, 2010, vol. 49, pp. 9346-9367.

Hamed et al., "Crotonase Catalysis Enables Flexible Production of Functionalized Prolines and Carbapenams", Journal of the American Chemical Society, 2012, vol. 134, pp. 471-479.

Hamed et al., "The enzymes of beta-lactam biosynthesis", Natural Product Reports, 2013, vol. 30, pp. 21-107.

Haslinger et al., "The Structure of a Transient Complex of a Nonribosomal Peptide Synthetase and a Cytochrome P450 Monooxygenase", Angewandte Chemie International Edition, 2014, vol. 53, pp. 8518-8522.

Herbert et al., "Biosynthesis of the Antibiotic Obafluorin from D-[U-$^{13}$C]Glucose and p-Aminophenylalanine in Pseudomonas fluorescens", Journal of the Chemical Society, PerkinTrans. 1, 1992, pp. 103-107.

Herbert et al., "Biosynthesis of the Antibiotic Obafluorin from p-Aminophenylalanine and Glycine (Glyoxylate)", Journal of the Chemical Society, 1992, Perkin Trans. 1, pp. 109-113.

Hollenhorst et al., "The ATP-Dependent Amide Ligases DdaG and DdaF Assemble the Fumaramoyl-Dipeptide Scaffold of the Dapdiamide Antibiotics", Biochemistry, 2009, vol. 48, pp. 10467-10472.

Horsman et al., "Polyketide synthase and non-ribosomal peptide synthetase thioesterase selectivity: logic gate or a victim of fate?" Natural Product Reports, 2016, vol. 33, pp. 183-202.

Jensen et al., "Polyketide Proofreading by an Acyltransferase-like Enzyme", Chemistry & Biology, 2012, vol. 19, pp. 329-339.

Jiang et al., "EcdGHK are Three Tailoring Iron Oxygenases for Amino Acid Building Blocks of the Enchinocandin Scaffold", Journal of the American Chemical Society, 2013, vol. 135, pp. 4457-4466.

Jiang et al, "Different Active-Site Loop Orientation in Serine Hydrolases versus Acyltransferases", Chembiochem, 2011, vol. 12, pp. 768-776.

Kohli et al., "The thioesterase domain from a nonribosomal peptide synthetase as a cyclization catalyst for integrin binding peptides", Proceedings of the National Academy of Sciences, 2002, vol. 99, No. 3, pp. 1247-1252.

Kopp et al., "Macrocyclization strategies in polyketide and nonribosomal peptide biosynthesis", Natural Product Reports, 2007, vol. 24, pp. 735-749.

Lall et al., "Serine and Threonine Beta-Lactones: A New Class of Hepatitis A Virus 3C Cysteine Proteinase Inhibitors", The Journal of Organic Chemistry, 2002, vol. 67, pp. 1536-1547.

Li et al., "Conversion of Serine-114 to Cysteine-114 and the Role of the Active Site Nucleophile in Acyl Transfer by Myristoyl-ACP Thioesterase from Vibrio harveyi", Biochemistry, 1996, vol. 35, pp. 9967-9973.

Lowe et al., "Natural Occurring Beta-Lactones: Occurrence, Synthesis and Properties. A Review", Taylor & Francis, 1995, vol. 27, pp. 305-347.

Makris et al., "An Unusual Peroxo Intermediate of the Arylamine Oxygenase of the Chloramphenicol Biosyntheic Pathway", Journal of the American Chemical Society, 2015, vol. 137, pp. 1608-1617.

Makris et al., "A family of diiron monooxygenases catalyzing amino acid beta-hydroxylation in antibiotic biosynthesis", Proceedings of the National Academy of Sciences, 2010, vol. 107, No. 35, pp. 15391-15396.

McGrath et al., "Chemoselectivity in Chemical Biology: Acyl Transfer Reactions with Sulfur and Selenium", Accounts of Chemical Research, 2011, vol. 44, pp. 752-761.

Miller et al., "Structures of a Nonribosomal Peptide Synthetase Module Bound to MbtH-like Proteins Support a Highly Dynamic Domain Architecture", Journal of Biological Chemistry, 2016, vol. 291, No. 43, pp. 22559-22571.

Muliandi et al., "Biosynthesis of the 4-Methyloxazoline-Containing Nonribosomal Peptides, JBIR-34 and -35, in *Streptomyces* sp. Sp080513GE-23", Chemistry & Biology, 2014, vol. 21, pp. 923-934.

Pemble et al., "Crystal structure of the thioesterase domain of human fatty acid synthase inhibited by Orlistat", Nature Structural & Molecular Biology, 2007, vol. 14, No. 8, pp. 704-709.

Pu et al., "Synthesis, Stability, and Antimicrobial Activity of (+)-Obafluorin and Related beta-Lactone Antibiotics", The Journal of Organic Chemistry, 1994, vol. 59, pp. 3642-3655.

Quadri et al., "Characterization of Sfp, a Bacillus subtilis Phosphopantetheinyl Transferase for Peptidyl Carrier Protein Domains in Peptide Synthetases", Biochemistry, 1998, vol. 37, No. 6, pp. 1585-1595.

Reimer et al., "Synthetic cycle of the initiation module of a formylating nonribosomal peptide synthetase", Nature, 2016, vol. 529, No. 14, pp. 239-242.

Reimmann et al., "Dihydroaeruginoic acid synthetase and pyochelin synthetase, products of the pchEF genes, are induced by extracellular pyochelin in *Pseudomonas aeruginosa* ", Microbiology, 1998, vol. 144, pp. 3135-3148.

Roach et al., "Structure of isopenicillin N synthase complexed with substrate and the mechanism of penicillin formation", Nature, 1997, vol. 387, pp. 827-830.

Smith et al., "The type I fatty acid and polyketide synthases a tale of two megasynthases", Natural Product Reports, 2007, vol. 24, pp. 1041-1072.

Stachelhaus et al., "The specificity-conferring code of adenylation domains in nonribosomal peptide synthetases", Chemistry & Biology, 1999, vol. 6, No. 8, pp. 493-505.

Tymiak et al., "Structure of Obafluorin: An Antibacterial Beta-Lactone From Pseudomonas fluorescens", The Journal of Organic Chemistry, 1985, vol. 50, pp. 5491-5495.

Walsh et al., "Molecular Studies on Enzymes in Chorismate Metabolism and the Enterobactin Biosynthetic Pathway", Chemical Reviews, 1990, vol. 90, pp. 1105-1129.

Wells et al., "Obafluorin, A Novel Beta-Lactone Produced by Pseudomonas Fluorescens. Taxonomy, Fermentation and Biological Properties", The Journal of Antibiotics, 1984, vol. 37, No. 7, pp. 802-803.

Wyatt et al., "Biosynthesis of ebelactone A: isotopic tracer, advanced precursor and genetic studies reveal a thioesterase-independent cyclization to give a polyketide beta-lactone", The Journal of Antibiotics, 2013, vol. 66, pp. 421-430.

Zhang et al., "Characterization of the Amicetin Biosynthesis Gene Cluster from Streptomyces vinaceusdrappus NRRL 2363 Implicates Two Alternative Strategies for Amide Bond Formation", Applied and Environmental Microbiology, 2012, vol. 78, pp. 2393-2401.

(56) References Cited

OTHER PUBLICATIONS

Zhao et al., "Oxazolomycin Biosynthesis in Streptomyces albus J A3453 Featuring an Acyltransferase-less Type I Polyketide Synthase That Incorporates Two Distinct Extender Units", The Journal of Biological Chemistry, 2010, vol. 285, No. 26, pp. 20097-20108.

* cited by examiner

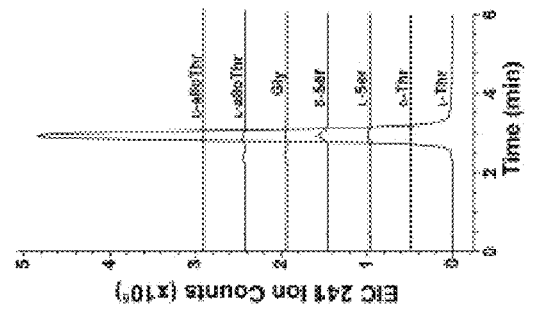
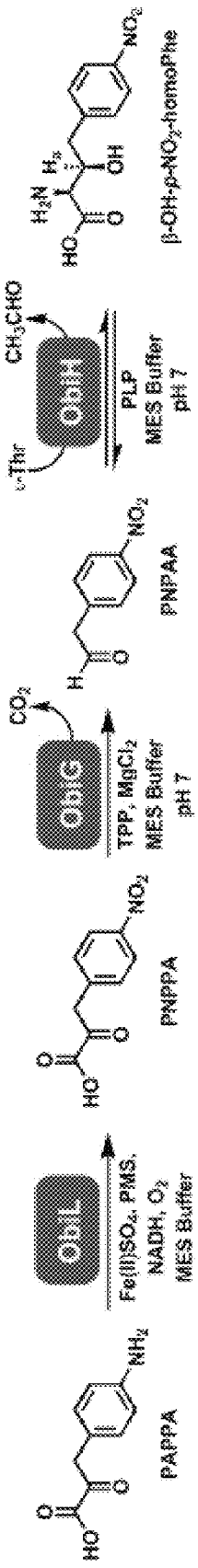
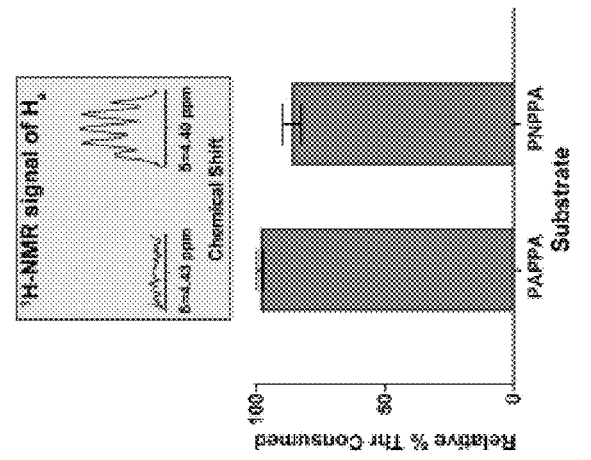
FIG. 2F
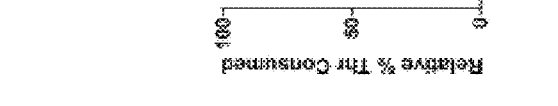
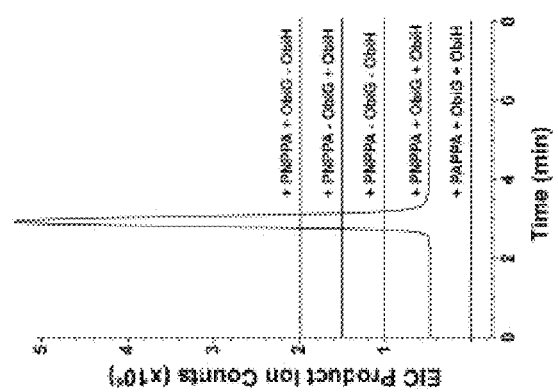
FIG. 2G
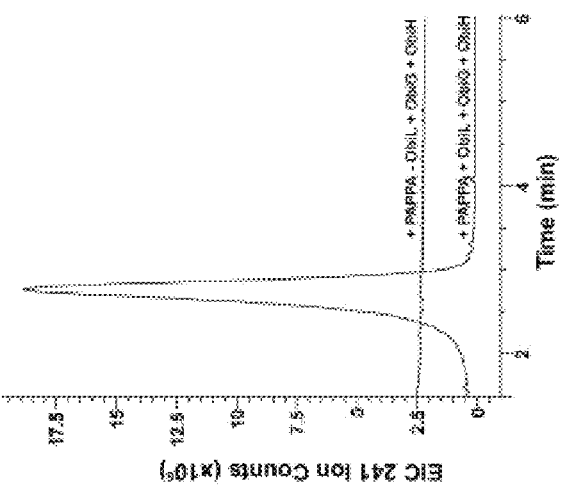
FIG. 2H
FIG. 2I
FIG. 2J

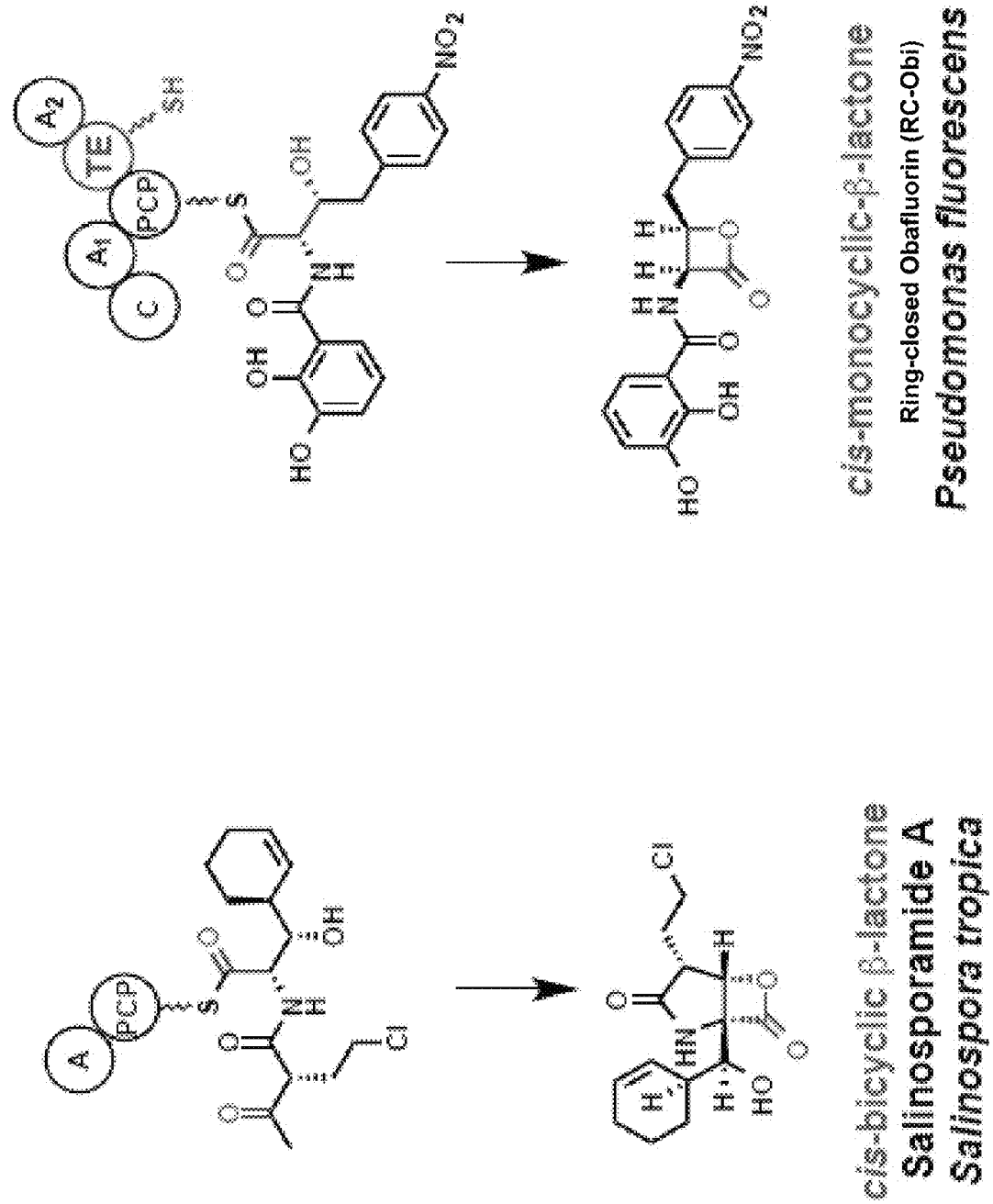

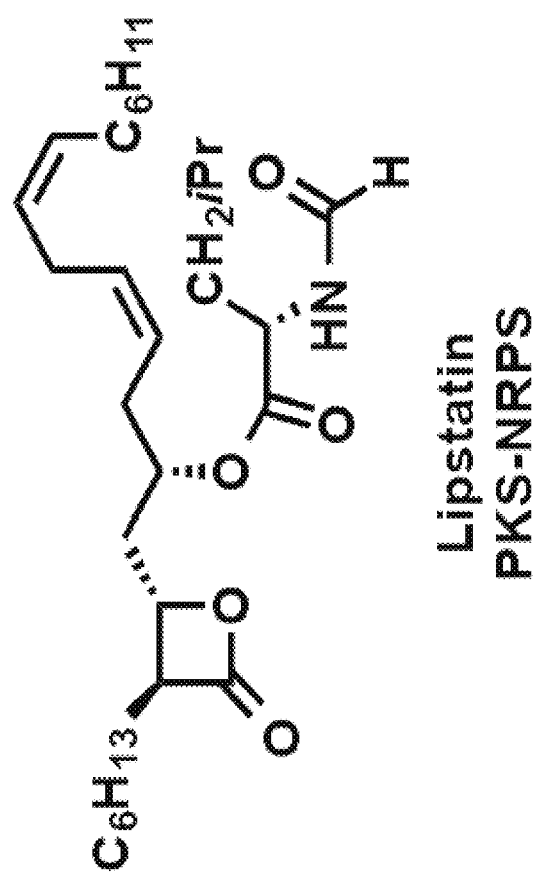
FIG. 5E Lipstatin PKS-NRPS

FIG. 7B

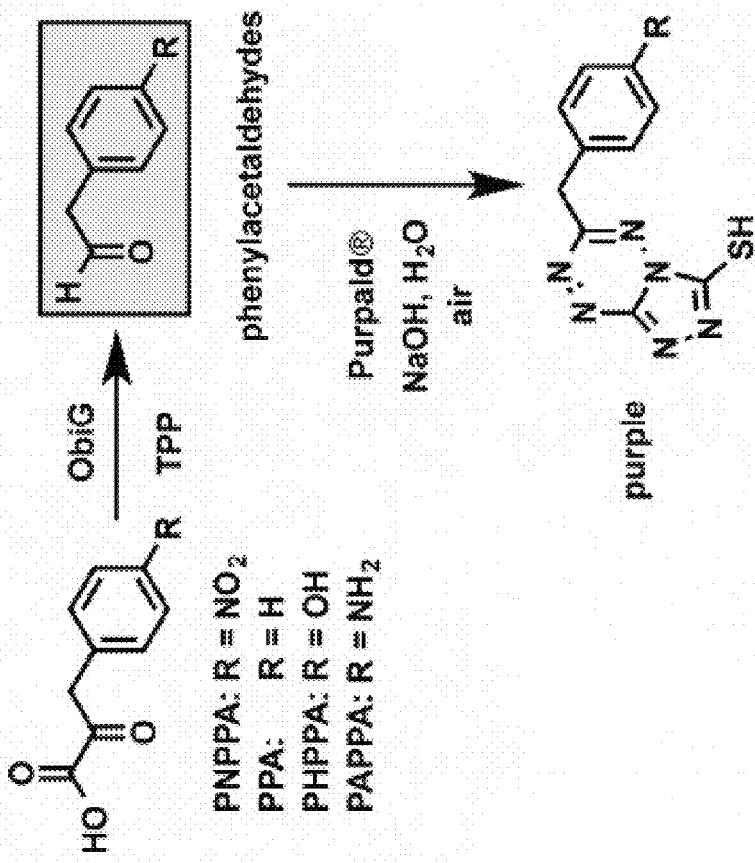
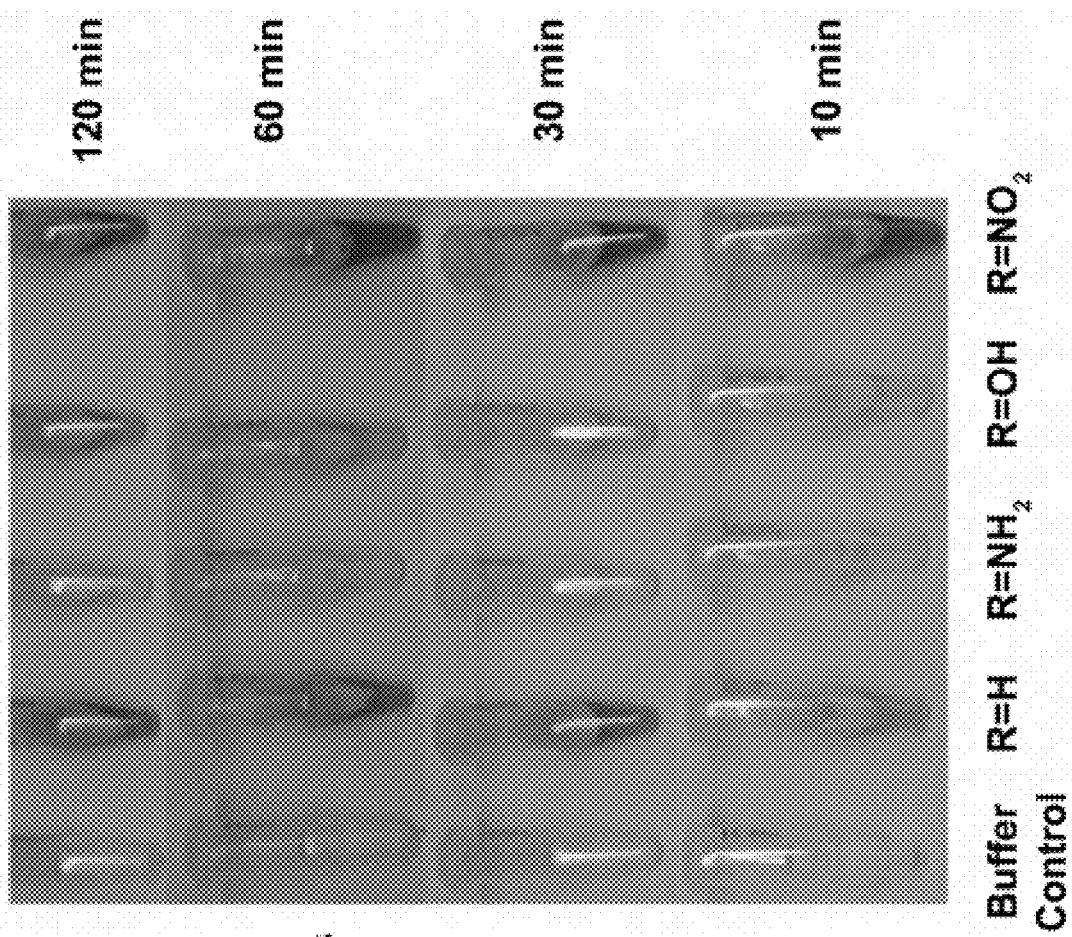
FIG. 10A
FIG. 10B

FIG. 14A

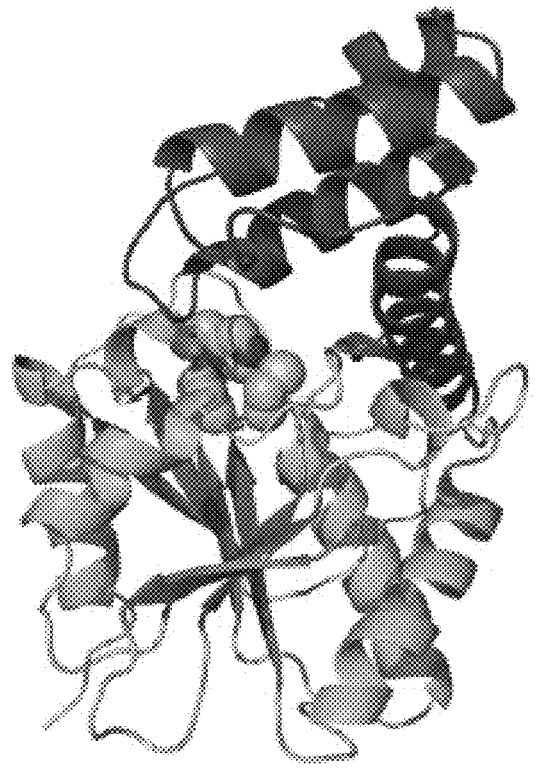
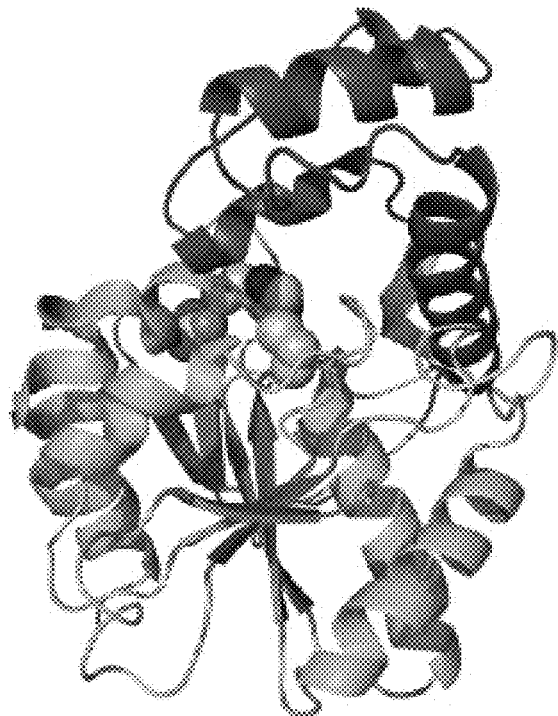
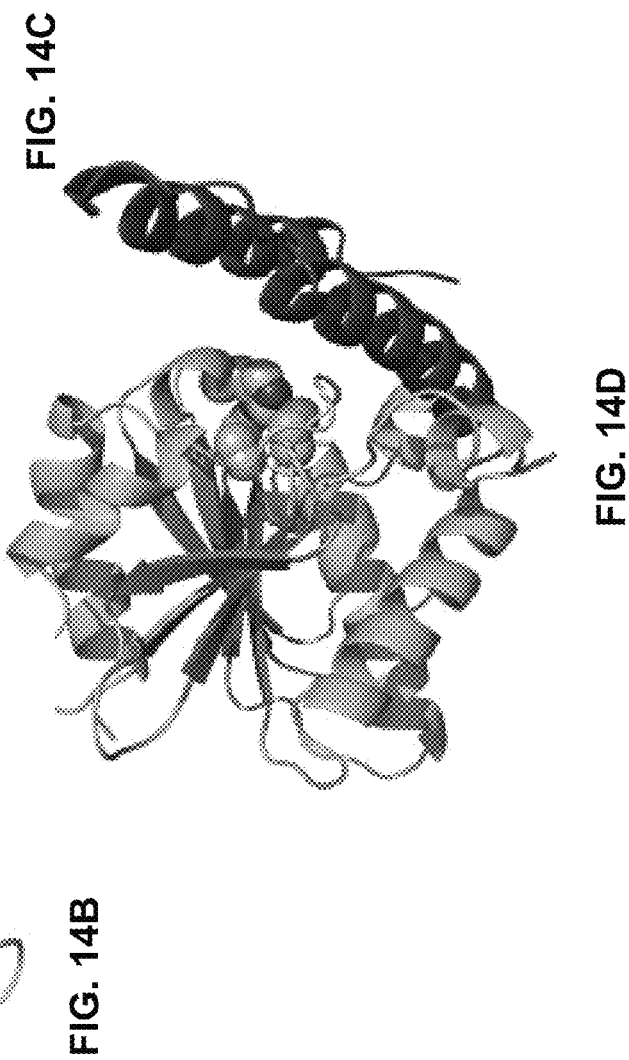
FIG. 14B
FIG. 14C
FIG. 14D

C = Condensation Domain
A = Adenylation Domain
$T_{Ar}$ = Peptidyl Carrier Domain
TE = Thioesterase Domain

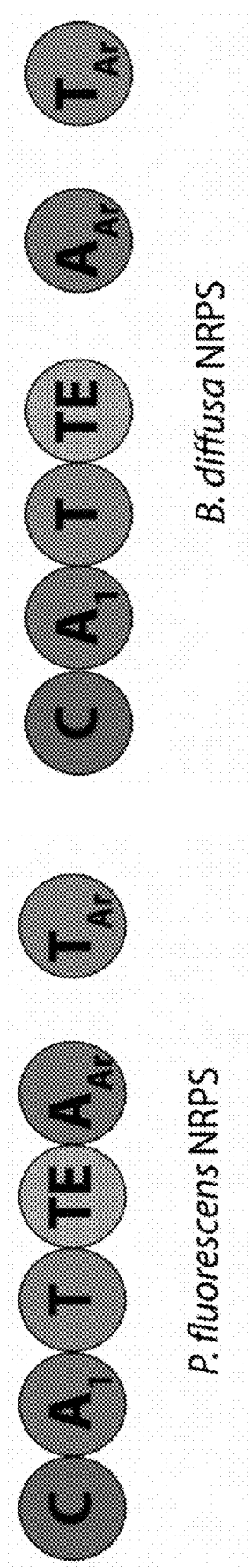
FIG. 76 P. fluorescens NRPS
FIG. 77 B. diffusa NRPS
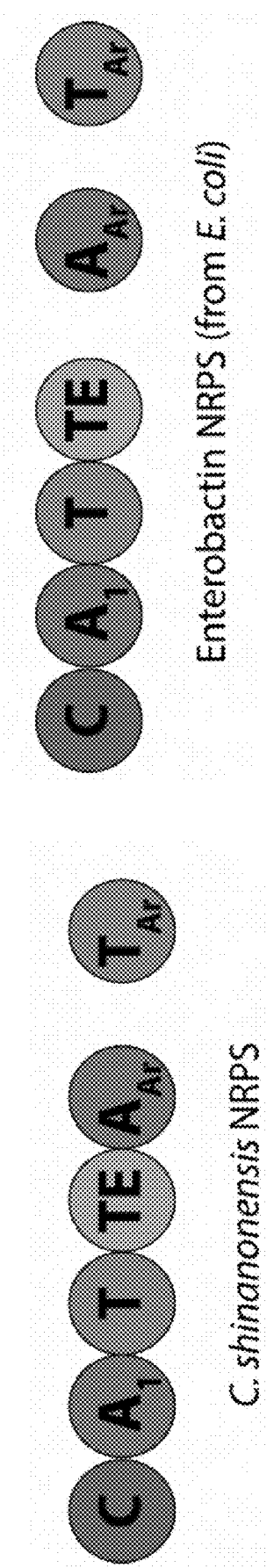
FIG. 78 C. shinanonensis NRPS
FIG. 79 Enterobactin NRPS (from E. coli)

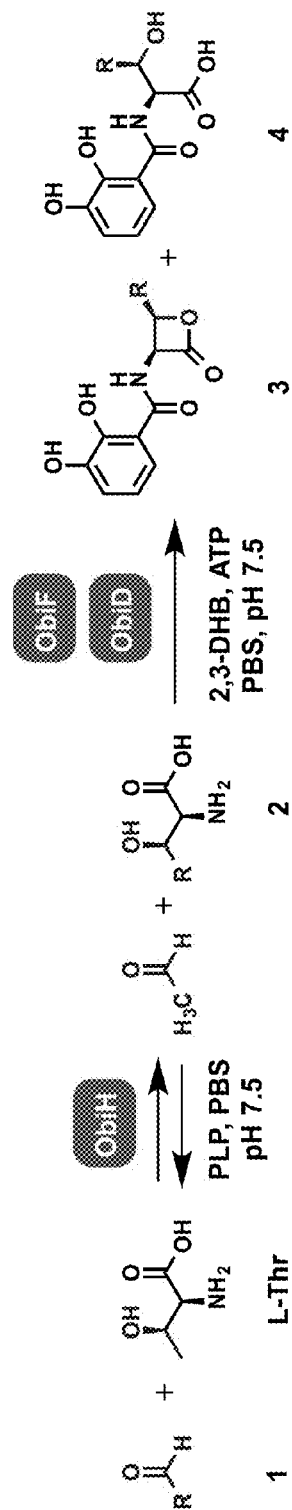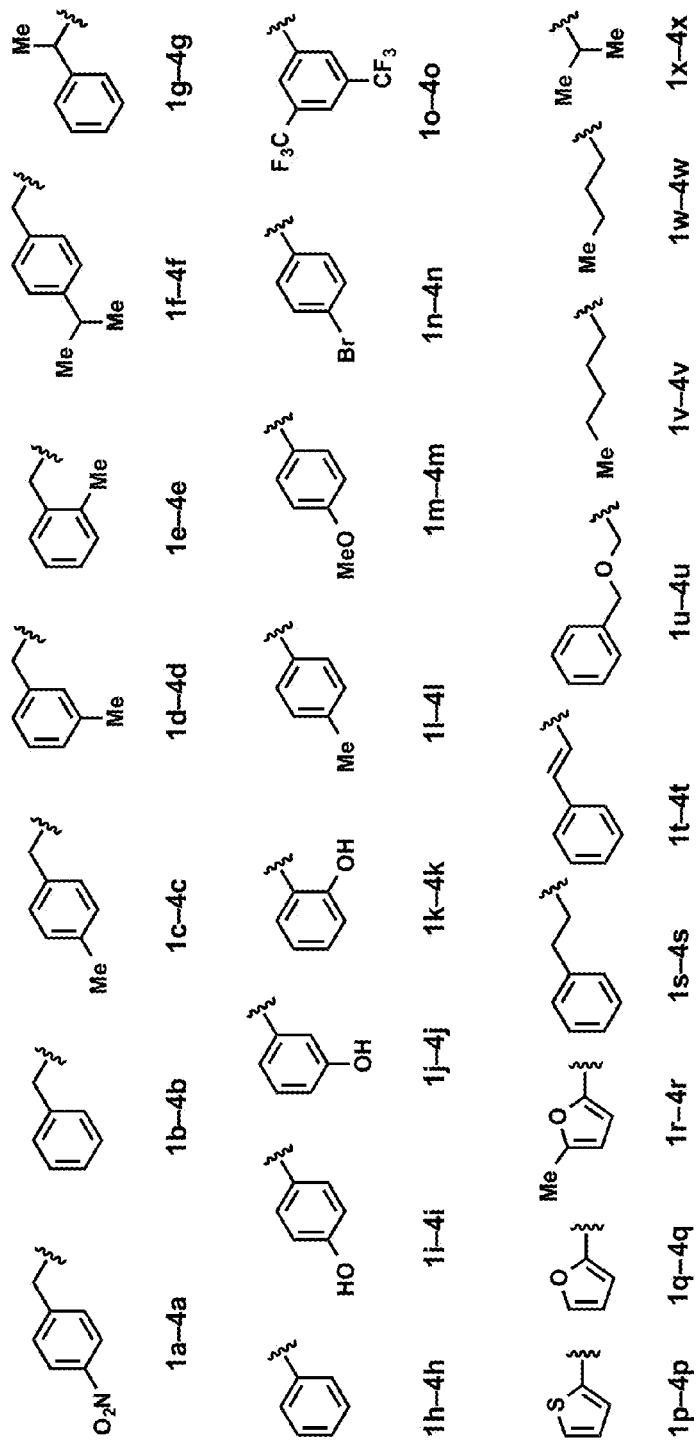
FIG. 80A
FIG. 80B

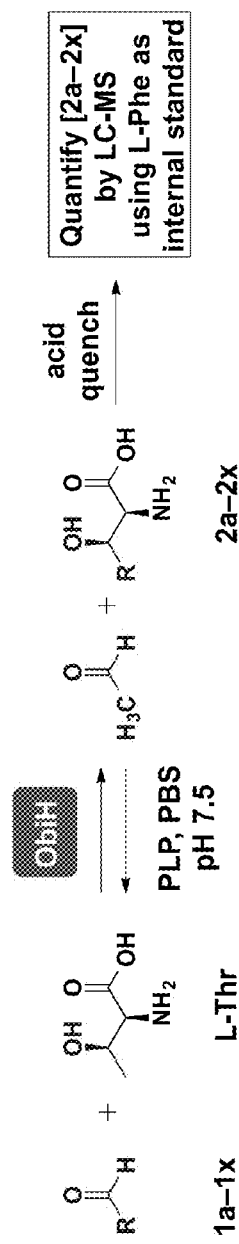
FIG. 81A
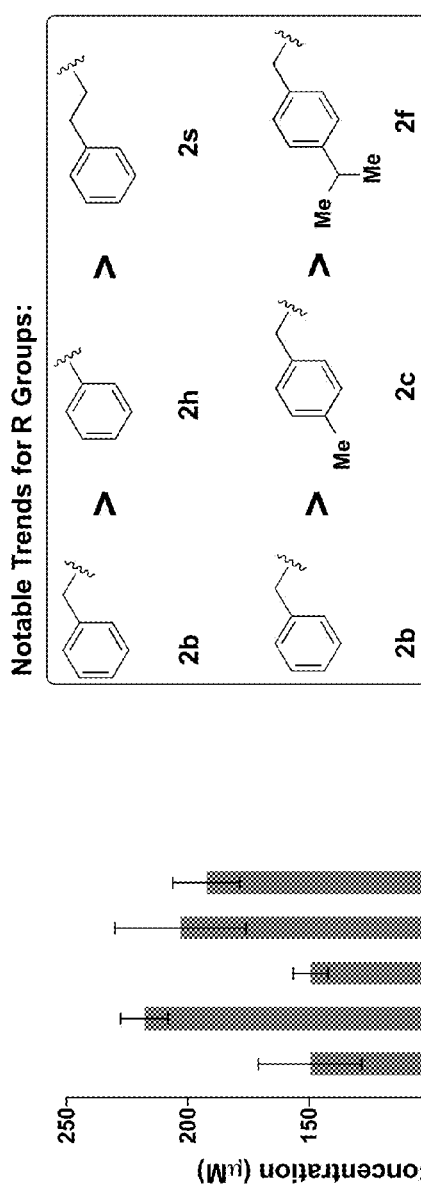
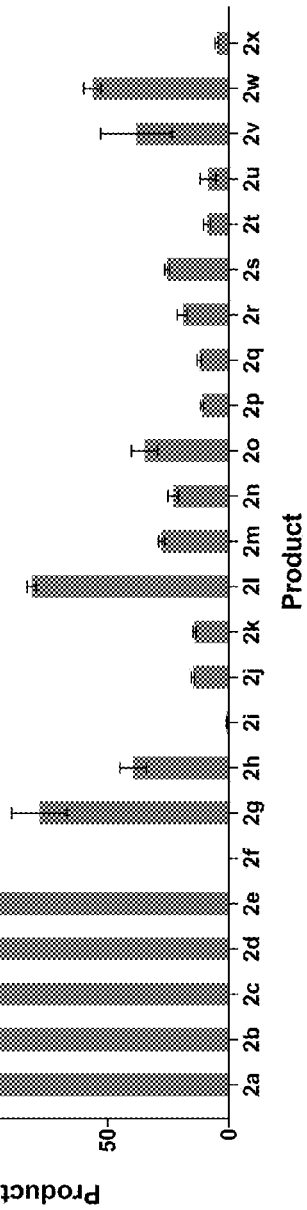
FIG. 81B

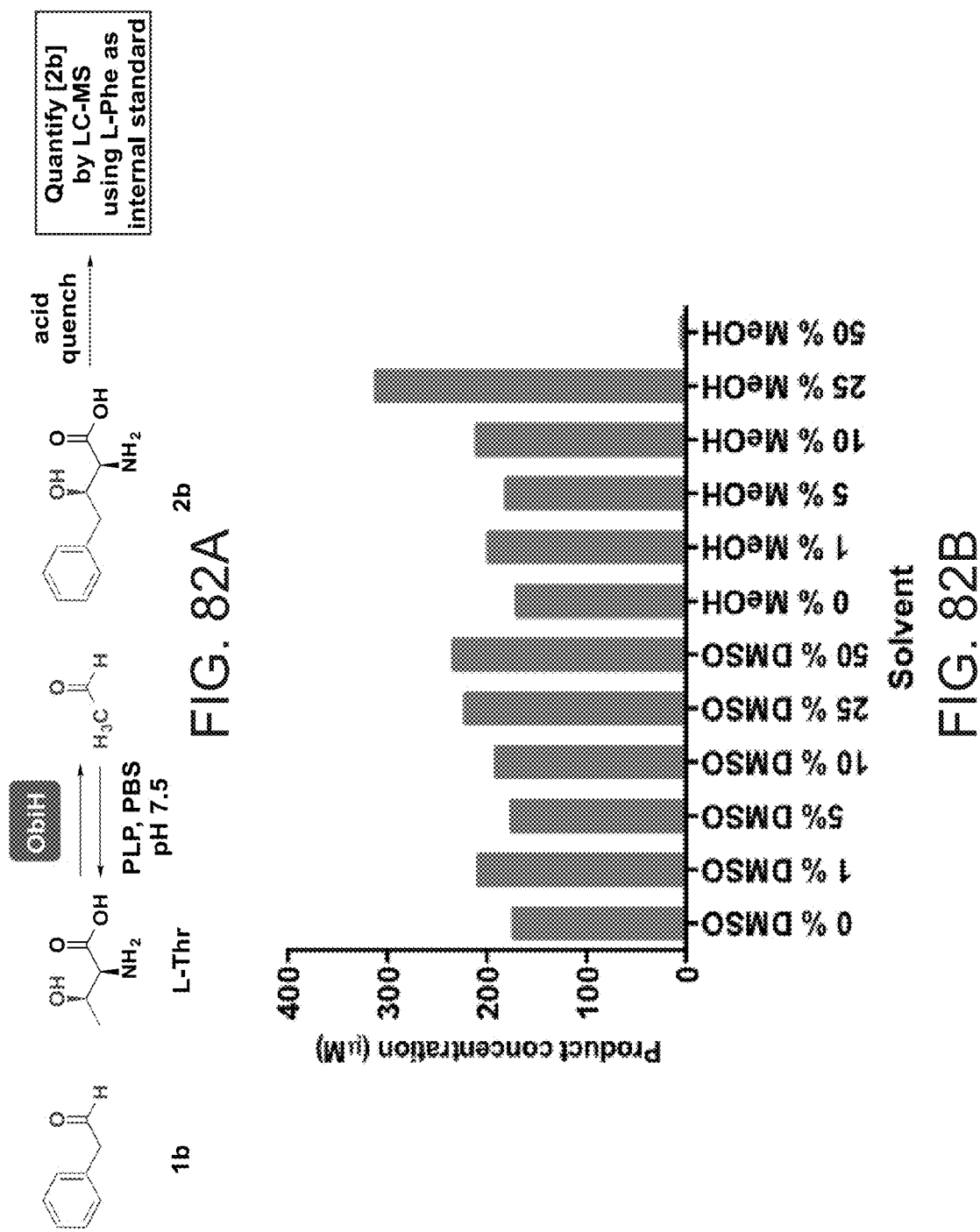

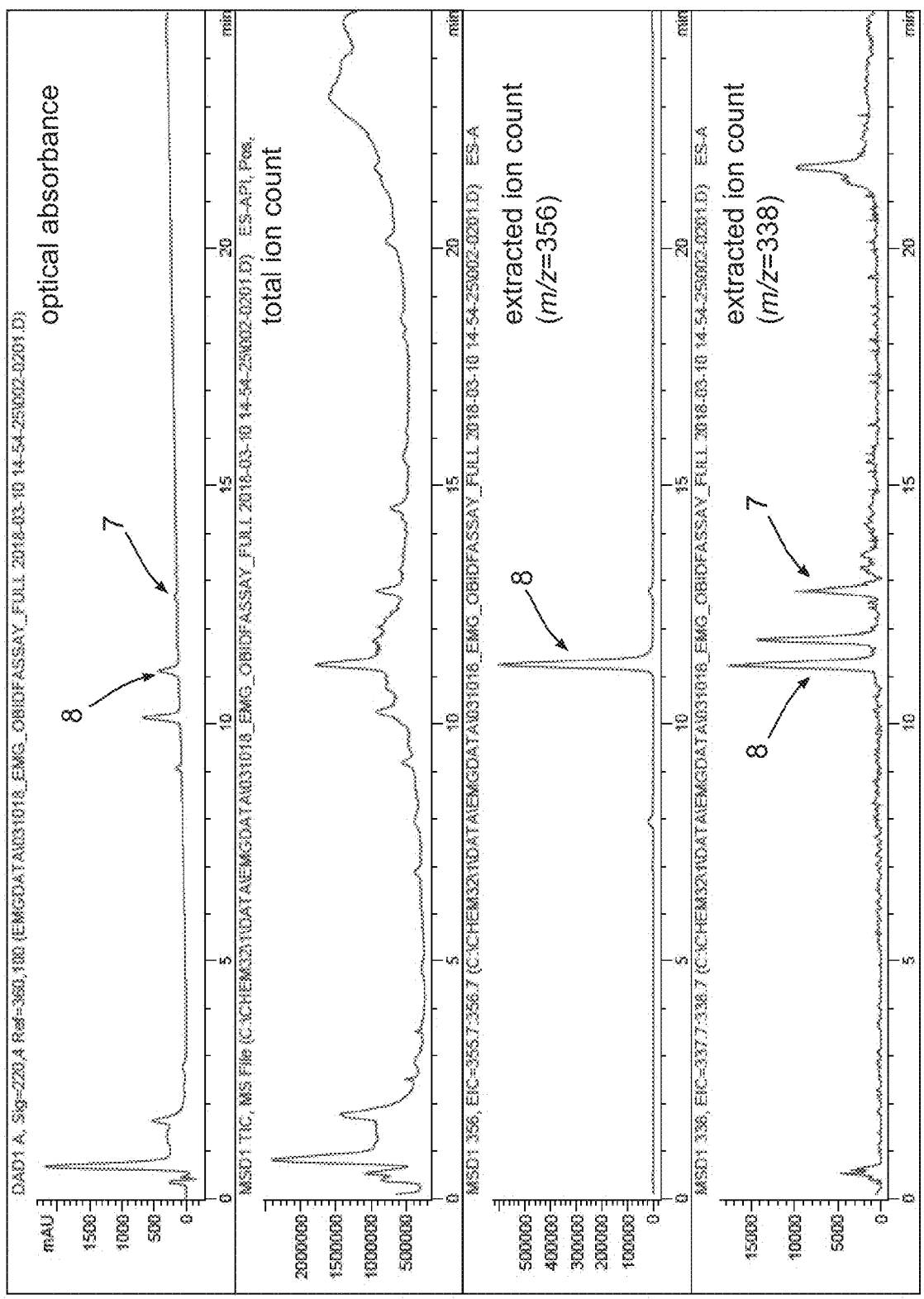

CHEMOENZYMATIC SYNTHESIS OF PEPTIDE BETA-LACTONES AND BETA-HYDROXY ACIDS

CROSS-REFERENCE TO RELATED APPLICATION

This application claims the benefit of U.S. Provisional Application No. 62/471,183 filed on Mar. 14, 2017, the contents of which are incorporated herein by reference in their entirety.

STATEMENT OF SEQUENCE LISTING

A paper copy of the Sequence Listing and a computer readable form of the Sequence Listing containing the file named "15060-950_sequence listing_ST25.txt", which is 74,04, bytes in size (as measured in MICROSOFT WINDOWS(EXPLORER), are herein incorporated by reference. This Sequence Listing consists of SEQ ID NOs: 1-28.

BACKGROUND OF THE DISCLOSURE

Non-ribosomal peptide synthetases (NRPSs) are multi-domain modular biosynthetic assembly lines that polymerize amino acids into a myriad of biologically active and often structurally complex molecules, including the life-saving non-ribosomal peptide (NRP) antibiotics vancomycin, daptomycin, and penicillin. To increase structural diversity, NRPSs draw from a pool of 23 proteinogenic and about 500 non-proteinogenic amino acids. Terminal thioesterase (TE) domains of modular NRPSs employ diverse release strategies for off-loading thioester-tethered polymeric peptides from termination modules via hydrolysis, aminolysis, reduction, or cyclization to provide mature antibiotics as carboxylic acids, esters, amides, aldehydes, macrolactams, and macrolactones, respectively.

Among the different types of macrolactones, strained β-lactone rings are found in diverse classes of natural products including polyketides (PKs), nonribosomal peptides (NRPs), amino acids, terpenoids, and hybrid molecules. Little is known about the biosynthetic origins of β-lactones despite wide therapeutic value of naturally occurring peptide β-lactones as inhibitors of enzymes in the serine hydrolase superfamily. One naturally occurring peptide β-lactone is tetrahydrolipstatin, a hybrid PK-NRP lipase inhibitor used as a treatment of obesity. Another naturally occurring peptide β-lactone, salinosporamide A (also known as marizomib and NPI-0052) is a hybrid PK-NRP proteasome inhibitor under clinical investigation as a treatment of multiple myeloma and other advanced malignancies. Other naturally-occurring β-lactones are reported to show promise as antimicrobial, anticancer, antiviral, and anti-obesity agents. The genetic and biochemical basis for β-lactone ring formation is an ongoing challenge in natural product biosynthesis, and to date no enzymes are known to catalyze the formation of a strained β-lactone ring.

There is precedent for enzymatic formation of strained 4-membered rings in the closely related β-lactam family of antibiotics. Three chemically distinct biosynthetic pathways leading to β-lactams have been reported. For example, penicillin and cephalosporin bicyclic β-lactam scaffolds may be formed via oxidative cyclization of a NRP tripeptide precursor by isopenicillin N synthase. In another example, the β-lactam rings in clavulanic acid and carbapenems may arise via ATP-dependent cyclization of n-amino acid precursors catalyzed by the β-lactam synthetase enzyme family.

In an additional example, the nocardicin family of monocyclic β-lactam antibiotics is derived from NRPS assembly lines with five catalytic modules that each covalently tethers the evolving substrate as a thioester on a peptidyl carrier protein, also known as thiolation (T) domain. In another additional example, a condensation domain of module 5 was identified with a rare HHHXXDG motif that is important for dehydration of a $T_4$-thioester tethered serine to the corresponding dehydroalanine. The newly formed $T_4$-dehydroalanine thioester serves as electrophile for a Michael addition/nucleophilic acyl substitution reaction cascade with the nucleophilic α-amino group of a downstream $T_5$-tyrosine thioester to produce the nocardicin β-lactam warhead. Potentially, modifications of these biosynthetic strategies may be employed to assemble β-lactone rings.

The biosynthetic gene clusters for the β-lactones lipstatin (FIG. 5E), ebelactone (FIG. 5A), salinosporamide (FIG. 5C), and oxazolomycin (FIG. 5B) are known, and corresponding biosynthetic pathways have been previously proposed. The mechanisms for β-lactone ring formation in these systems remain unclear and no enzyme domains have been experimentally linked to β-lactone cyclization. Interestingly, the terminating PKS or NRPS module for each β-lactone antibiotic lacks an embedded thioesterase (TE) domain. TE domains participate in acyl transfers, epimerization of stereogenic centers, proofreading, and release of tethered substrates from the enzymatic assembly line via hydrolysis or macrocyclization.

Lactacystin is a secondary metabolite produced by *Streptomyces* sp. OM-6519 and is structurally related to salinosporamides. Lactacystin is thought to be cleaved from the biosynthetic assembly line via transthioesterification with N-acetylcystein. The resulting β-hydroxy-N-acetylcysteinylthioester has been shown to be in equilibrium with the cis-fused bicyclic β-lactone believed to be an active proteasome inhibitor. It was previously demonstrated that the trans-monocyclic β-lactone ring found in ebelactone and lactacystin may form non-enzymatically from cyclization of the β-hydroxy-N-acetylcysteamine thioester in aqueous buffer at pH 7. The facile non-enzymatic formation of ebelactone and lactacystin β-lactones from precursor β-hydroxythioesters under these conditions may reduce the likelihood of identifying a biosynthetic enzyme catalysis of β-lactone ring formation. However, under certain conditions, enzyme catalysis of β-lactone ring formation may still prove advantageous, despite the relative stability of the β-lactones in aqueous solutions.

Obafluorin in its closed-ring form (RC-Obi) is a cis-monocyclic β-lactone antibiotic (see FIG. 1E) produced by plant-associated strains of *P. fluorescens*. RC-Obi was discovered during a highly selective antibiotic screening for β-lactam antibiotics that were deactivated in an assay organism expressing β-lactamase resistance enzymes, along with the N-acetyl threonine β-lactone compound SQ26,517. 25 Pseudomonads isolated from diverse soil habitats are known to produce RC-Obi, suggesting a conserved evolutionary role of this molecule in diverse soil ecosystems.

RC-Obi was reported to have broad-spectrum antibacterial activity and demonstrated efficacy in a *Streptococcus pneumonia* murine septicemia model. Although the biological target of RC-Obi is unknown, bacterial transpeptidases are thought to be potential targets due to the structural similarity of RC-Obi to monocyclic β-lactam antibiotics and the documented susceptibility of RC-Obi to hydrolysis by β-lactamases.

FIG. 1D is a chemical structure diagram illustrating the arrangement of atoms within a 3D model of the RC-Obi structure with color-coded surfaces corresponding to CDSs involved in fragment biosynthesis. The illustrated structure was generated using PyMOL v1.7 software and 3D coordinates obtained from PubChem CID 146354. As illustrated in FIG. 1D, the unique structure of RC-Obi contains a 2,3-dihydroxybenzoic acid (2,3-DHB) unit (pink-shaded region) coupled through an amide linkage (blue-shaded region) to an α-amino-β-lactone ring of the unusual nonproteinogenic amino acid β-hydroxy-p nitro-homoPhenylalanine (β-OH-p-$NO_2$-homoPhe).

FIG. 1E is a schematic diagram illustrating the non-enzymatic hydrolysis of obafluorin β-lactone (RC-Obi) to form a β-hydroxy carboxylic acid, the open-ring form of obafluorin (RO-Obi). Previous studies of the total synthesis of RC-Obi and related analogs confirmed the structure and biological activity of RC-Obi as well as demonstrating that RC-Obi hydrolyzes rapidly in aqueous solutions, as illustrated in FIG. 1E. A previous study using stable isotope feeding to investigate the biosynthesis of RC-Obi indicated that 2,3-DHB and β-OH-p-$NO_2$-homoPhe may be advanced intermediates in the biosynthesis of RC-Obi.

BRIEF DESCRIPTION OF THE DISCLOSURE

In one aspect, a method of producing a peptide beta-lactone is disclosed. The method includes contacting a beta-hydroxy-alpha-amino acid, an aryl carrier protein (ObiD), and ATP with a non-ribosomal protein synthetase. The beta-hydroxy-alpha-amino acid is selected from the group consisting of beta-OH-p-NO2-homoPhe and beta-OH-homoPhe. The aryl carrier protein is selected from the group consisting of ObiD, a homolog of ObiD, recombinant ObiD, and any variation thereof comprising the amino acid sequence of SEQ ID NO:1 or fragment thereof. The non-ribosomal protein synthetase is selected from the group consisting of ObiF, a homolog of ObiF, recombinant ObiF, and any variation thereof comprising the amino acid sequence of SEQ ID NO:2 or fragment thereof. The benzoic acid derivative is 2,3-dihydroxoybenzoic acid.

In another aspect, a method of producing a peptide beta-lactone is disclosed. The method includes forming a reaction mixture that includes a beta-hydroxy-alpha-amino acid, a benzoic acid derivative, ATP, an aryl carrier protein, and a non-ribosomal protein synthetase. The beta-hydroxy-alpha-amino acid is selected from the group consisting of beta-OH-p-$NO_2$-homoPhe and beta-OH-homoPhe. The benzoic acid derivative consists of 2,3-dihydroxoybenzoic acid. The aryl carrier protein is selected from the group consisting of ObiD, a homolog of ObiD, recombinant ObiD, and any variation thereof comprising the amino acid sequence of SEQ ID NO:1 or fragment thereof. The non-ribosomal protein synthetase is selected from the group consisting of ObiF, a homolog of ObiF, recombinant ObiF, and any variation thereof comprising the amino acid sequence of SEQ ID NO:2 or fragment thereof. The non-ribosomal protein synthetase further include a condensation domain (C), a first adenylation domain (A1), a peptidyl carrier domain (PCP), a thioesterase domain (TE), and a second adenylation domain (A2). The method may further include contacting the beta-hydroxy-alpha-amino acid with the non-ribosomal protein synthetase at the peptidyl carrier domain (PCP) with ATP activation by the first adenylation domain (A1) to form a PCP-beta-hydroxy-alpha-amino acid thioester that includes an alpha-amino moiety. The method may further include ATP activating the benzoic acid derivative at the second adenylation domain (A2) and contacting the ATP-activated benzoic acid derivative with the aryl carrier protein to form a benzoic acid derivative-aryl carrier protein thioester that includes a carbonyl moiety. The method also includes contacting the benzoic acid derivative-aryl carrier protein thioester with the condensation domain (C) to catalyze an amide bond between the alpha-amino moiety and the carbonyl moiety to form a PCP-peptide beta-lactone precursor thioester. The method additionally includes contacting the PCP-peptide beta-lactone precursor thioester with the thioesterase domain (TE) to form a transthioesterified peptide beta-lactone precursor. The method also additionally includes releasing the transthioesterified peptide beta-lactone precursor as a peptide beta-lactone from the non-ribosomal protein synthetase.

In an additional aspect, a continuous flow reactor is disclosed that includes an elongate conduit with at least one region. The at least one region includes a first region that includes a non-ribosomal protein synthetase immobilized to a substrate. The non-ribosomal protein synthetase is configured to contact a flow of a reaction mixture that includes a beta-hydroxy-alpha-amino acid and an aryl carrier protein. The non-ribosomal protein synthetase is further configured to release a peptide beta-lactone into the flow of the reaction mixture. The non-ribosomal protein synthetase is selected from the group consisting of ObiF, a homolog of ObiF, recombinant ObiF, and any variation thereof comprising the amino acid sequence of SEQ ID NO:2 or fragment thereof. The beta-hydroxy-alpha-amino acid is selected from the group consisting of beta-OH-p-$NO_2$-homoPhe and beta-OH-homoPhe. The aryl carrier protein is selected from the group consisting of ObiD, a homolog of ObiD, recombinant ObiD, and any variation thereof comprising the amino acid sequence of SEQ ID NO: 1 or fragment thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The figures described herein below illustrate various aspects of the disclosure.

FIG. 2F is a diagram illustrating the process of enzymatic conversion of PAPPA to β-OH-p-NO$_2$-homoPhe using recombinant oxidase ObiL, decarboxylase ObiG, and aldolase ObiH.

FIG. 2G is an extracted ion chromatogram (EIC) showing the formation of the β-OH-p-NO$_2$-homoPhe [M+H]$^+$ ion m/z=241 from starting PAPPA when all three enzymes, ObiL/ObiG/ObiH, and necessary cofactors and cosubstrates are present.

FIG. 2H is an extracted ion chromatogram (EIC) showing EIC product concentrations resulting from the double enzyme reaction with ObiG and ObiH.

FIG. 2I is a bar graph showing the relative amount of L-Thr consumed during the ObiG/ObiH double enzyme reactions with L-Thr and either PAPPA or PNPPA.

FIG. 2J is an extracted ion chromatogram (EIC) showing the β-OH-p-NO$_2$-homoPhe product concentrations resulting from the double enzyme reaction with ObiG and ObiH using PNPPA and a panel of amino acid substrates.

FIG. 5C is a schematic illustration showing the biosynthesis of a cis-bicyclic β-lactone (Salinosporamide A) by a *Salinospora tropica* β-lactone biosynthetic cluster that lacks a terminal TE-domain.

FIG. 5D is a schematic illustration showing the biosynthesis of a cis-monocyclic β-lactone (Obafluorin) by a *Pseudomonas fluorescens* β-lactone biosynthetic cluster that includes a terminal TE-domain. The TE-domain includes a rare catalytic Cys residue that participates in the β-lactone ring formation.

FIG. 5E is a chemical structure diagram showing lipstatin, a trans-monocyclic β-lactone.

FIG. 7B is an illustration showing the primary amino acid sequence alignments of the NRPS TE domains from the three Obi clusters illustrated in FIG. 7A.

FIG. 10A is a schematic illustration showing the enzymatic biosynthesis of various phenylacetaldehydes via an enzyme (ObiG) reaction and the subsequent treatment of the phenylacetaldehydes with Purpald®.

FIG. 10B is a photograph of reaction tubes containing reaction products resulting from the ObiG reaction illustrated in FIG. 10A that have been treated with Purpald®.

FIG. 14A shows a primary sequence alignment of the ObiF (GenBank KX134687, SEQ ID NO:2), AB3403 (GenBank WP_001060991.1, SEQ ID NO:27), and EntF (GenBank AAB40785.1, SEQ ID NO:28) TE-domains generated using ClustalW in MegAlign software.

FIG. 14B is a homology model of the ObiF TE domain generated with SWISS-MODEL using AB3403 TE-domain X-ray structure as template.

FIG. 14C is an X-ray crystal structure of the AB3403 TE domain (PDB 4ZXI).

FIG. 14D is an X-ray crystal structure of the EntF TE domain (PDB 3TEJ).

FIG. 59 is a structure homology model of ObiD modeled to the aryl carrier protein domain of EntB (PDB 2fq1).

FIG. 60 is a structure homology model of ObiH modeled as a homodimer to serine hydroxymethyltransferase from *Burkholderia cenocepacia* (PDB 4ot8). PLP and Ser ligands are shown as red sticks.

FIG. 61 is a structure homology model of ObiF C-A-T-TE domains modeled to the AB3403 NRPS from *Acinetobacter baumnannii* (PDB 4zxi) and MbtH-AAr domains modeled to a structure of the EntF/YbdZ complex (PDB 5ja1).

FIG. 62 is a chemical reaction diagram showing a proposed mechanism of ObiG modeled after phenylpyruvate decarboxylase.

FIG. 63 is a chemical structural diagram of thiamine pyrophosphate.

FIG. 64 is a chemical structural diagram showing the production of RC-Obi and RO-Obi using recombinant ObiF and ObiD from *C. shinanonensis* genome.

FIG. 65 is a graph showing LC-MS traces from samples of a reaction mixture obtained at various times of the reaction illustrated in FIG. 64, characterizing a time-dependent buildup of the RC-Obi peak (rt=0.5 min; m/z for [M+H]+=359).

FIG. 66 is a graph showing LC-MS traces from samples of a reaction mixture obtained at various times of the reaction illustrated in FIG. 64, characterizing a time-dependent buildup of the RO-Obi peak (rt=9.0 min; m/z for [M+H]$^+$=377).

FIG. 67 is a schematic diagram showing a proposed model for β-OH-p-NO$_2$-homoPhe selection by ObiF A domain specificity-conferring code.

FIG. 68 is a graph showing a LC-MS chromatogram of an ethyl acetate extraction of the culture supernatant from Obi-producing *P. fluorescens* ATCC 39502.

FIG. 69 is a graph showing a LC-MS chromatogram (extracted ion counts (y-axis) versus retention time (x-axis)) of an ethyl acetate extraction of the culture supernatant from Obi-producing *P. fluorescens* ATCC 39502.

FIG. 70 is a graph showing a LC-MS chromatogram (absorbance at 263 nm (y-axis) versus retention time (x-axis)) of RC-Obi purified via RP-C18 prep-HPLC from *P. fluorescens* culture supernatant.

Figure 71:
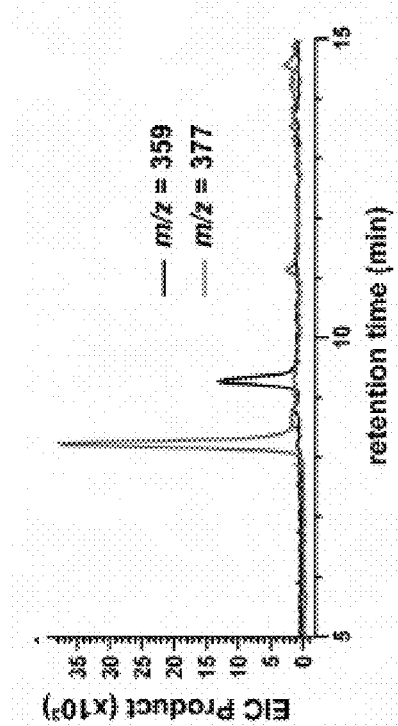

FIG. 71 is a graph showing a LC-MS chromatogram (extracted ion counts (y-axis) versus retention time (x-axis)) of RC-Obi purified via RP-C18 prep-HPLC from *P. fluorescens* culture supernatant.

Figure 72:
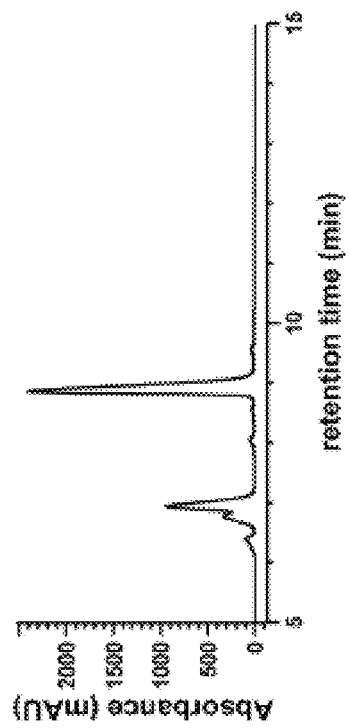

FIG. 72 is a graph showing a LC-MS chromatogram (absorbance at 263 nm (y-axis) versus retention time (x-axis)) of RO-Obi purified via RP-C18 prep-HPLC from *P. fluorescens* culture supernatant.

Figure 73:
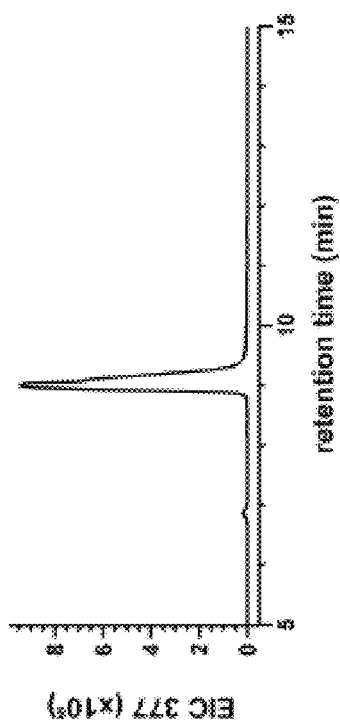

FIG. 73 is a graph showing a LC-MS chromatogram (extracted ion counts (y-axis) versus retention time (x-axis)) of RO-Obi purified via RP-C18 prep-HPLC from *P. fluorescens* culture supernatant.

Figure 74:
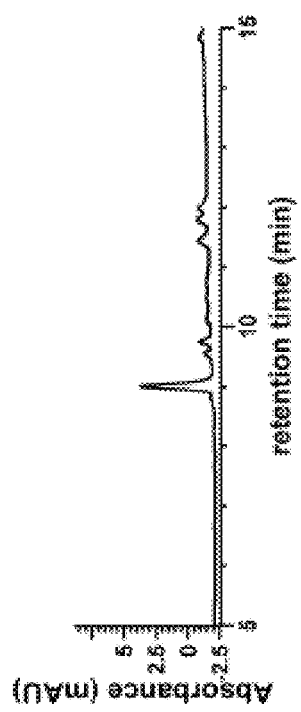

FIG. 74 is a graph showing a LC-MS chromatogram (absorbance at 263 nm (y-axis) versus retention time (x-axis)) of Obi-SNAC purified via RP-C18 prep-HPLC from *P. fluorescens* culture supernatant.

Figure 75:
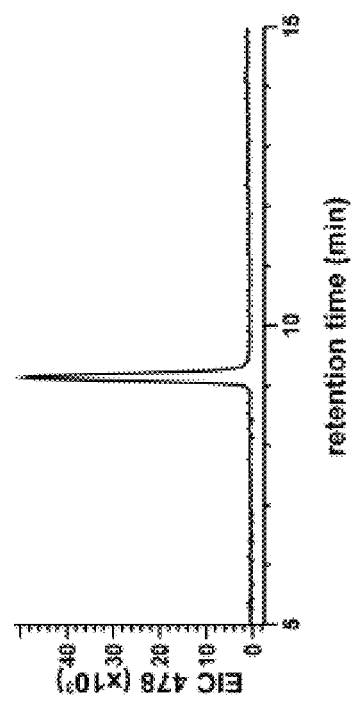

FIG. 75 is a graph showing a LC-MS chromatogram (extracted ion counts (y-axis) versus retention time (x-axis)) of Obi-SNAC purified via RP-C18 prep-HPLC from *P. fluorescens* culture supernatant.

FIG. 76 is a schematic diagram showing the domain orientation in NRPS modules for ObiF (C-A-T-TE-AAr) and ObiD (TAr) from *P. fluorescens* ATCC 39502 (GenBank KX134687 [SEQ ID NO:2] and KX134685 [SEQ ID NO: 1]).

FIG. 77 is a schematic diagram showing the domain orientation in NRPS modules for ObiF (C-A-T-TEf and separate $A_{Ar}$) and ObiD ($T_A$) from *B. diffusa* RF8-non_BP2 (GenBank WP_059467198.1, WP_059467197.1, and WP_059467195.1).

FIG. 78 is a schematic diagram showing the domain orientation in NRPS modules for ObiF (CA-T-TE-$A_A$) and ObiD ($T_{Ar}$) from *C. shinanonensis* SAY3 (GenBank WP_020608490.1 and WP_018749564.1).

FIG. 79 is a schematic diagram showing the domain orientation in NRPS modules for EntF (C-A-T-TE), EntE ($A_{Ar}$), and EntB ($T_{Ar}$) (PDB 5ja1 and 2fq1).

FIG. 80A is a reaction diagram illustrating enzymatic synthesis of a β-lactone ring used to screen various substrates.

FIG. 80B is a list of the substrates screened using the reaction illustrated in FIG. 80A.

FIG. 81A is a reaction diagram illustrating the reaction for producing a beta-hydroxy-alpha-amino acid from L-Thr used to screen various substrates.

FIG. 81B is a bar graph the product concentrations produced by the reaction described in FIG. 81A for various substrates illustrated in FIG. 80B.

FIG. 82A is a diagram illustrating a reaction for producing a beta-hydroxy-alpha-amino acid from L-Thr to be optimized.

FIG. 82B is a graph illustrating the use of variable levels of DMSO or MeOH to optimize the reaction described in FIG. 82A.

Figure 82C:
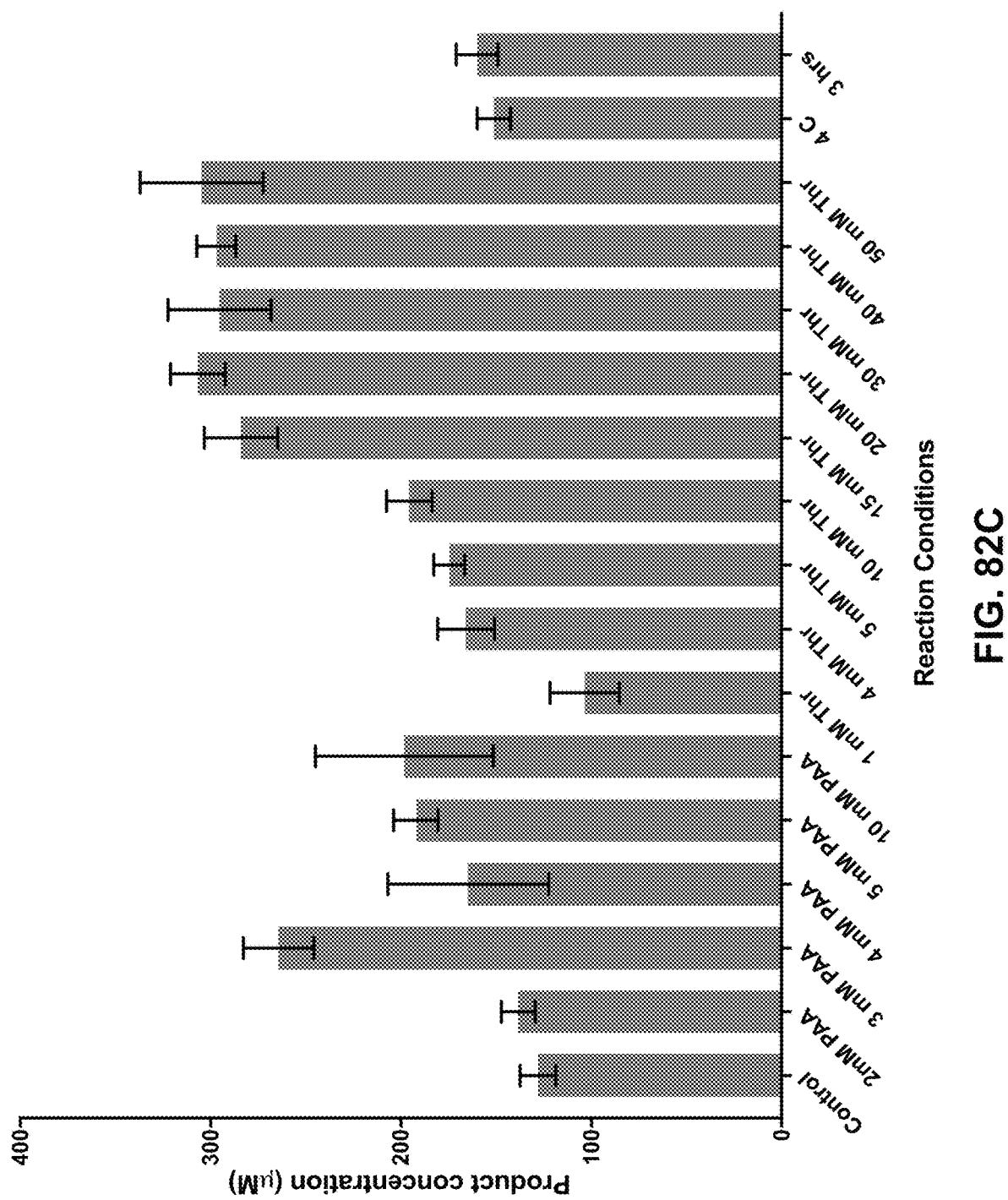

FIG. 82C is a graph illustrating the product concentrations resulting from use of variable levels of L-Thr and PAA in the reaction described in FIG. 82A.

Figure 83A:
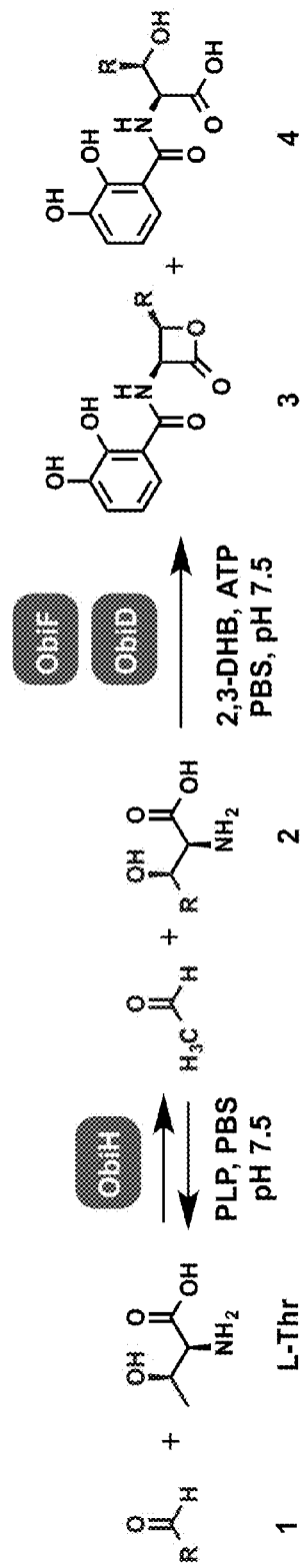

FIG. 83A is a diagram illustrating a reaction for the enzymatic synthesis of a β-lactone ring using various substrates.

Figure 83B:
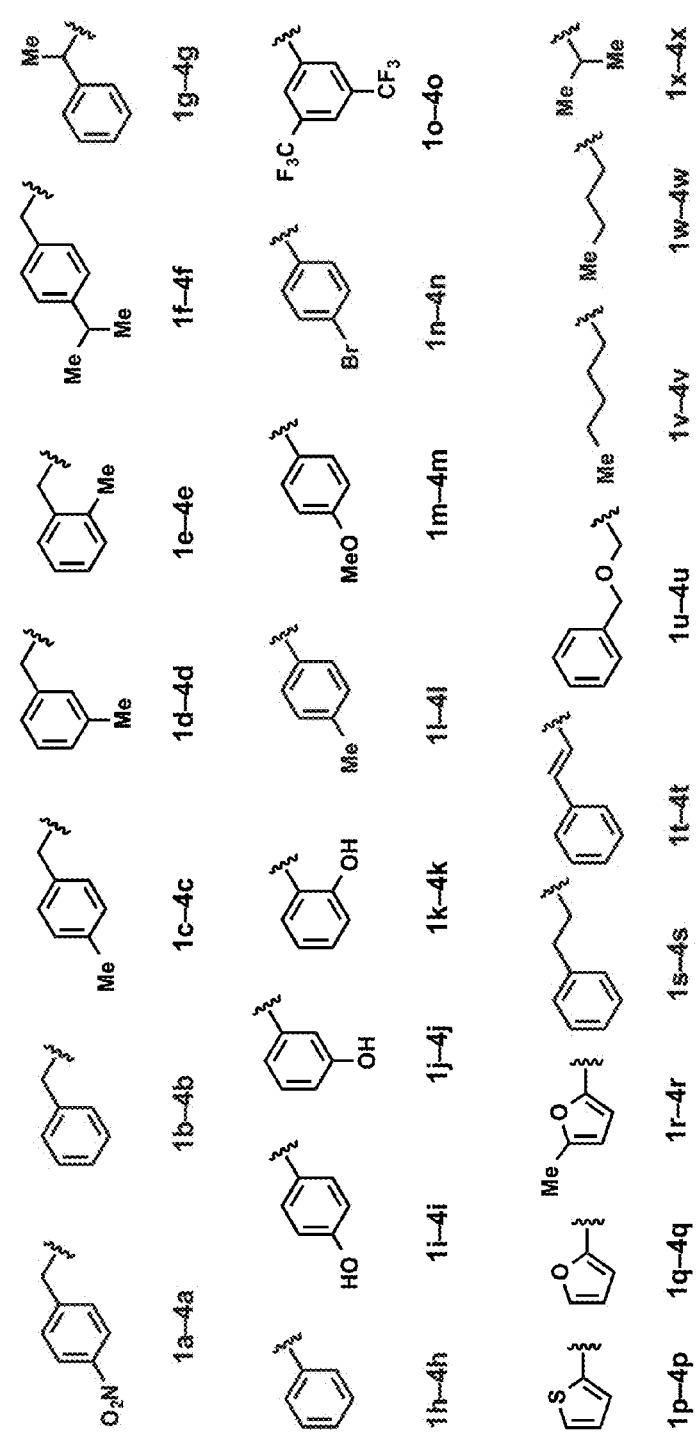

FIG. 83B is a list of substrates which were evaluated using the reaction illustrated in FIG. 83A; substrates shown in blue were demonstrated to provide useful concentrations of all corresponding products throughout the reaction illustrated in FIG. 83A.

Figure 84:
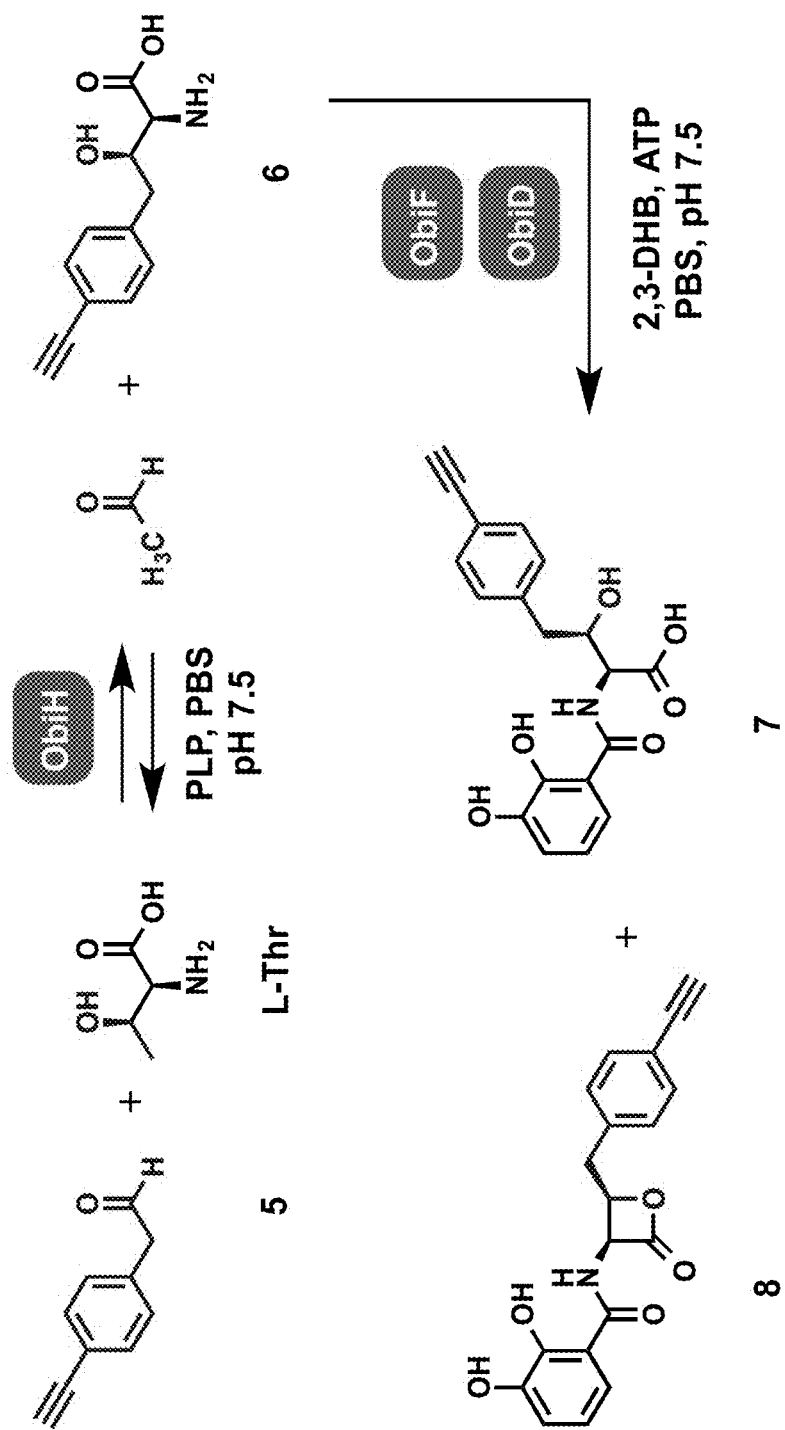

FIG. 84 is a diagram illustrating a reaction for the enzymatic synthesis of an alkyne-tagged ObiH product and alkyne-tagged ObiH products.

Figure 85:
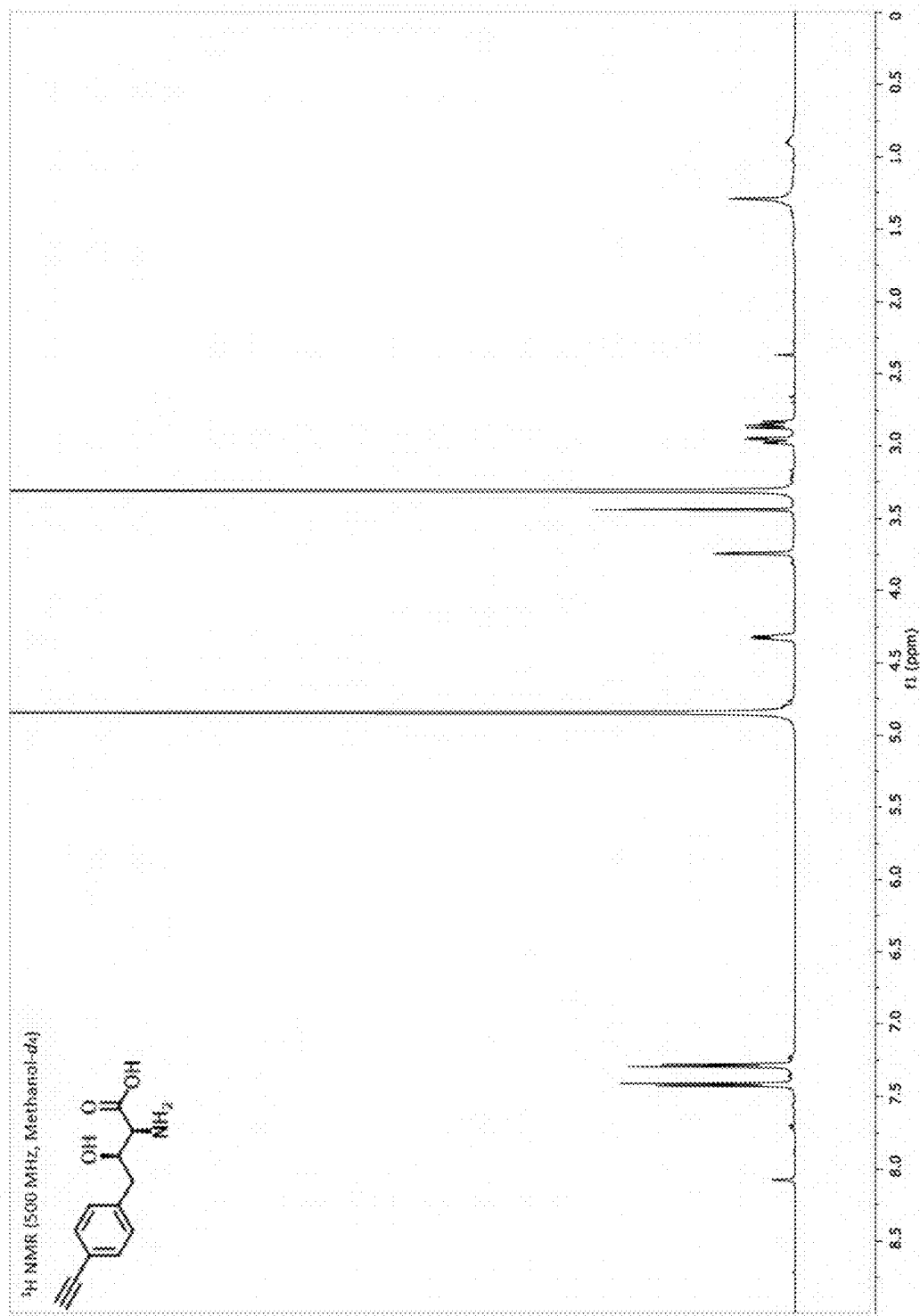

FIG. 85 is an $^1H$ NMR spectrum obtained from a sample containing an alkyne-tagged ObiH product.

Figure 86:
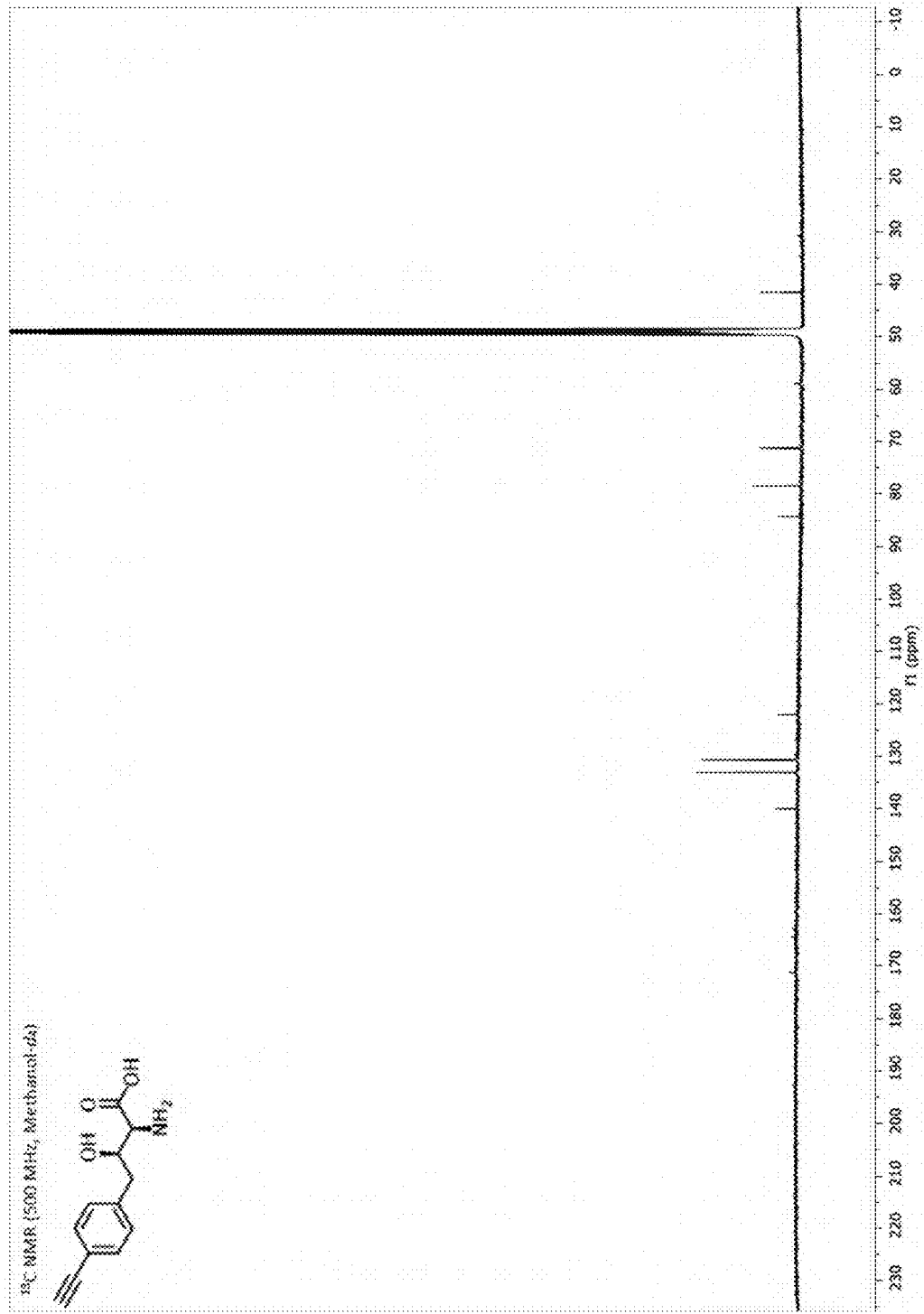

FIG. 86 is a $^{13}C$ NMR spectrum obtained from a sample containing an alkyne-tagged ObiH product.

Figure 87:
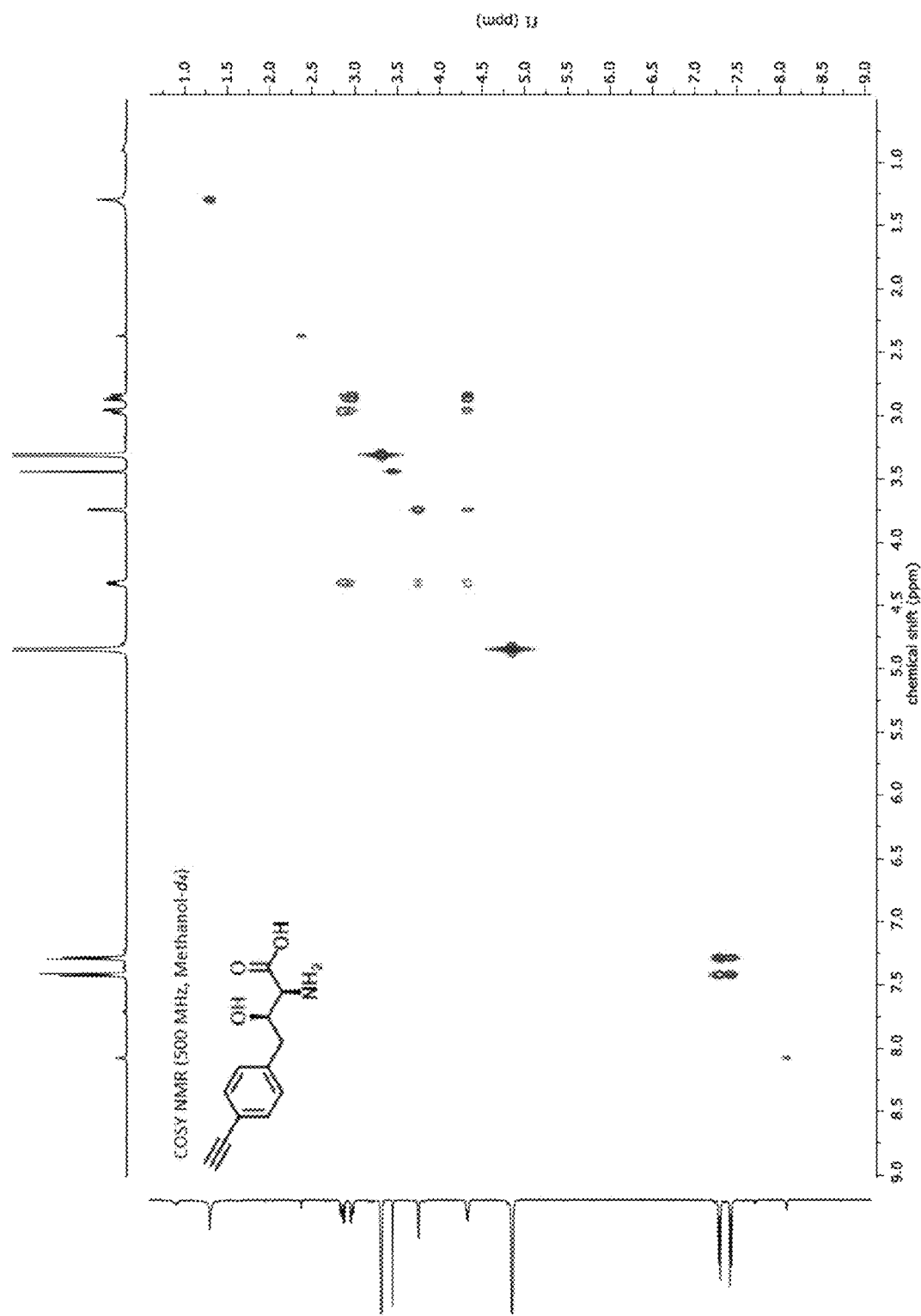

FIG. 87 is an $^1H$-$^{13}C$ COSY spectrum obtained from a sample containing an alkyne-tagged ObiH product.

Figure 88:
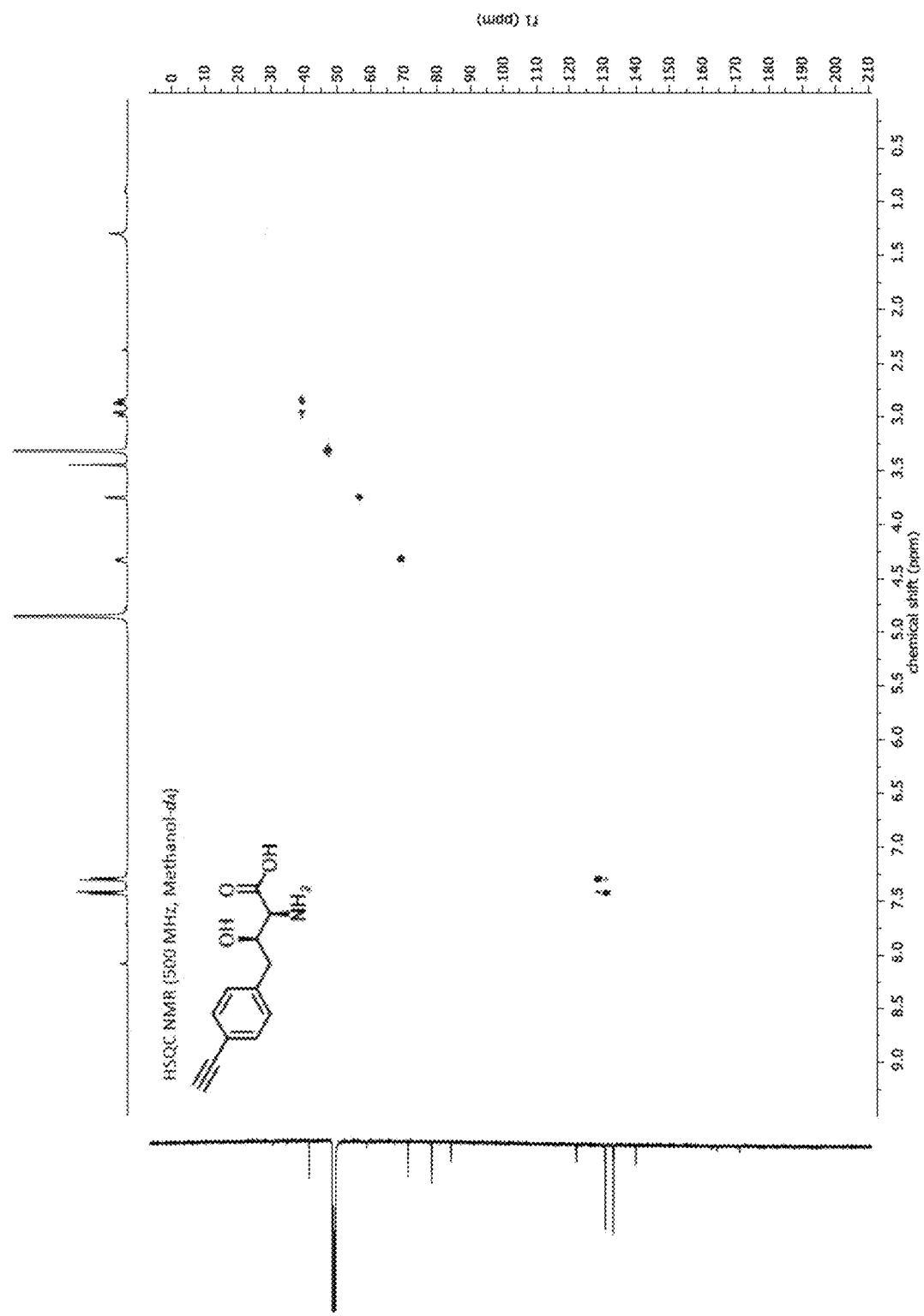

FIG. 88 is an $^1H$-$^{13}C$ HSQC spectrum obtained from a sample containing the alkyne-tagged ObiH product.

Figure 89:
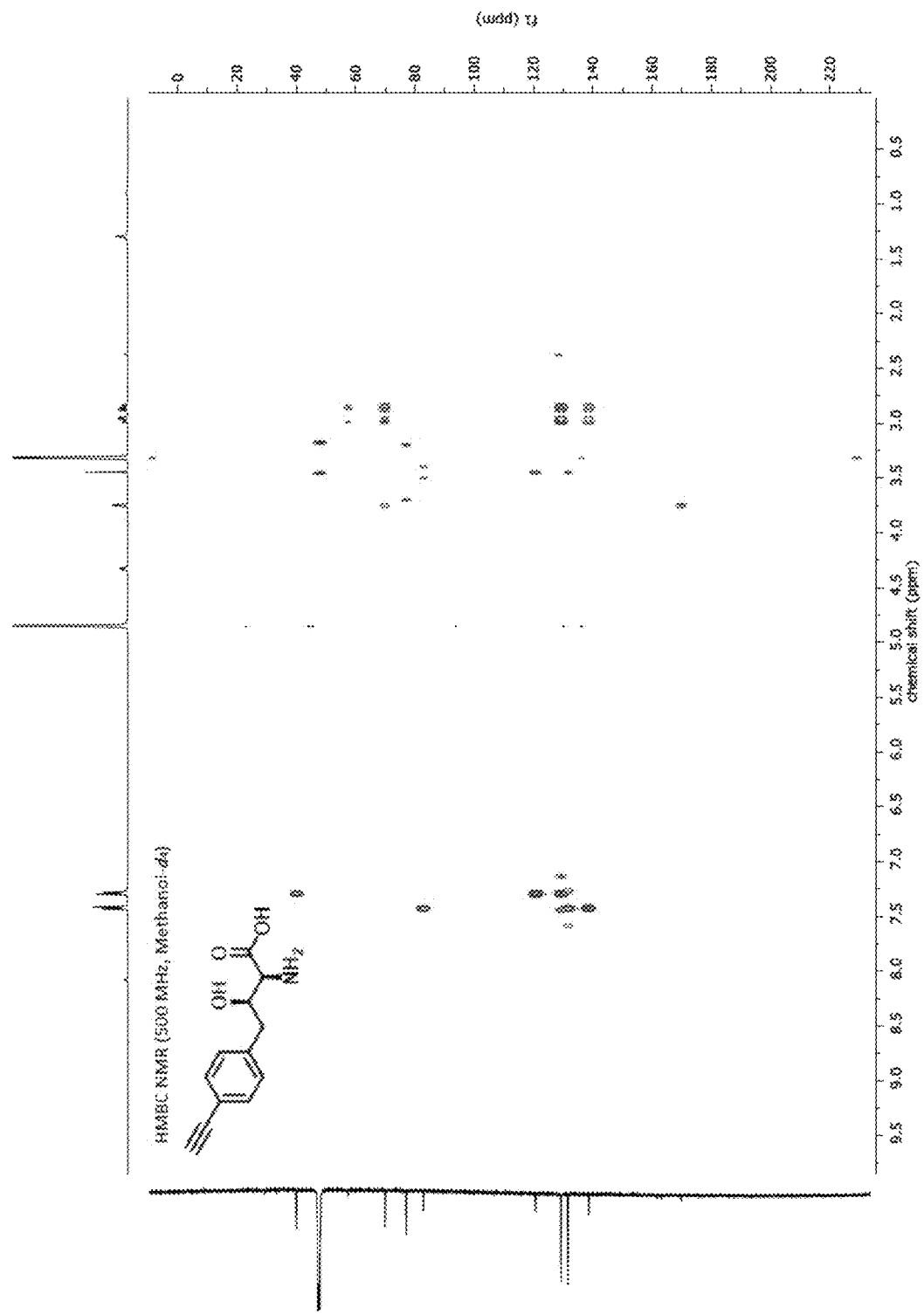

FIG. 89 is an $^1H$-$^{13}C$ HMBC spectrum obtained from a sample containing the alkyne-tagged ObiH product.

Figure 90:
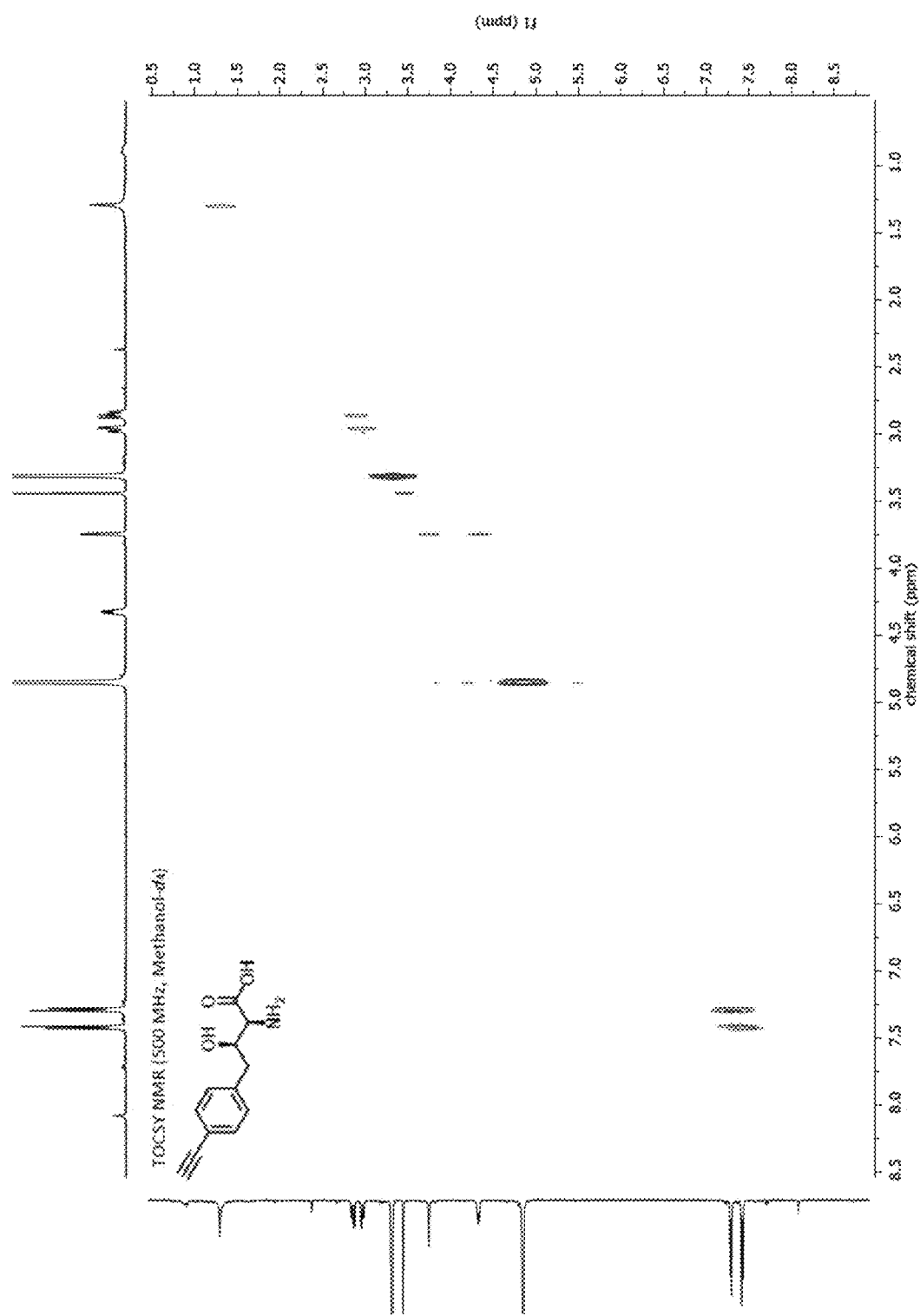

FIG. 90 is an $^1H$-$^{13}C$ TOCSY spectrum obtained from a sample containing the alkyne-tagged ObiH product.

Figure 91:
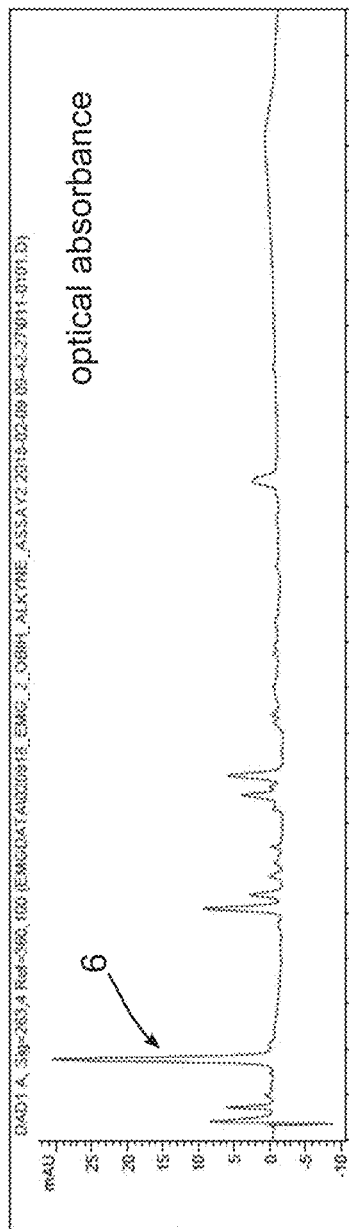

FIG. 91 is a graph of the ObiH reaction as depicted in FIG. 84 above as monitored using HPLC with detection by optical absorbance spectroscopy, showing a peak corresponding to the alkyne-tagged ObiH product 6.

Figure 92:
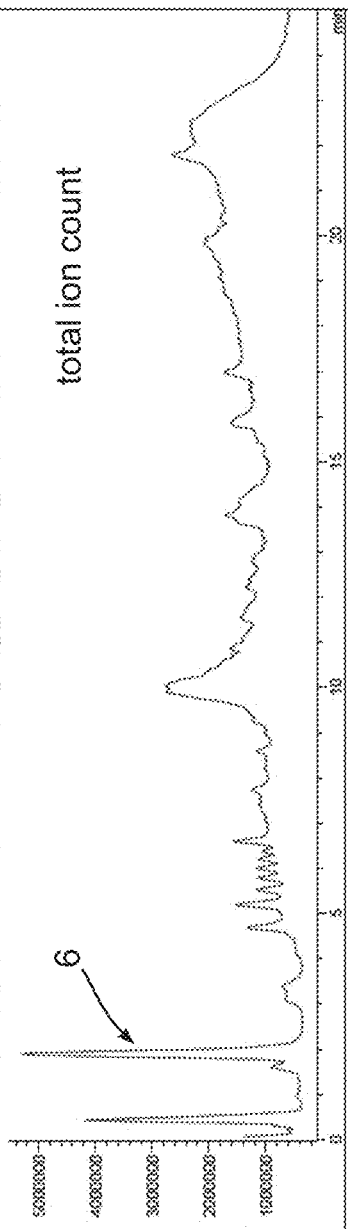

FIG. 92 is a graph showing a LC-MS chromatogram (total ion counts (y-axis) versus retention time (x-axis)) of the reaction mixture from the ObiH reaction as depicted in FIG. 84, showing a peak corresponding to the alkyne-tagged ObiH product 6.

Figure 93:
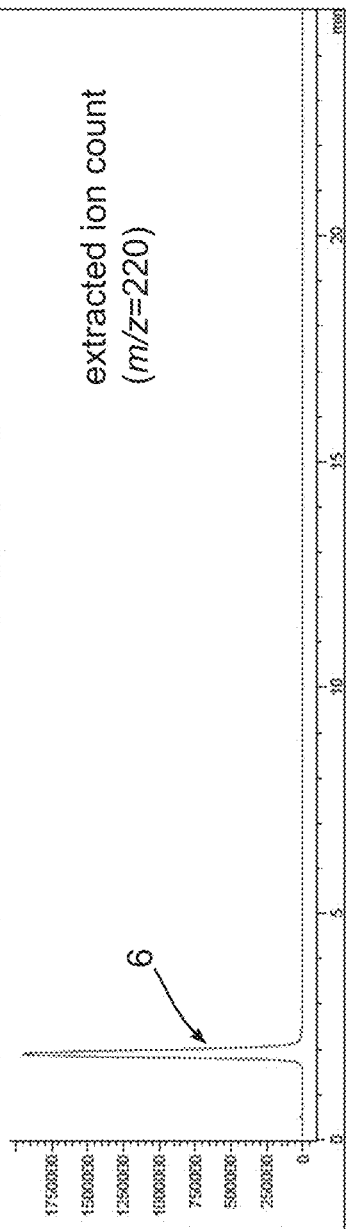

FIG. 93 is a graph showing a LC-MS chromatogram (extracted ion counts at m/z=220 (y-axis) versus retention time (x-axis)) of the reaction mixture from the ObiH reaction as depicted in FIG. 84, showing a peak corresponding to the alkyne-tagged ObiH product 6.

FIG. 94 is a graph of the ObiFD reaction as depicted in FIG. 84 above as monitored using HPLC with detection by optical absorbance spectroscopy, showing peaks corresponding to the alkyne-tagged ObiFD products 7 and 8.

FIG. 95 is a graph showing a LC-MS chromatogram (total ion counts (y-axis) versus retention time (x-axis)) of the reaction mixture from the ObiFD reaction as depicted in FIG. 84.

FIG. 96 is a graph showing a LC-MS chromatogram (extracted ion counts at m/z=356 (y-axis) versus retention time (x-axis)) of the reaction mixture from the ObiFD reaction as depicted in FIG. 84, showing a peak corresponding to the alkyne-tagged ObiFD product 8.

FIG. 97 is a graph showing a LC-MS chromatogram (extracted ion counts at m/z=338 (y-axis) versus retention time (x-axis)) of the reaction mixture from the ObiFD reaction as depicted in FIG. 84, showing peaks corresponding to the alkyne-tagged ObiFD products 7 and 8.

DETAILED DESCRIPTION OF THE DISCLOSURE

The present disclosure is directed to methods of producing peptide beta-lactones and peptide beta-hydroxy acids that include contacting a beta-hydroxy-alpha-amino acid, an aryl carrier protein (ObiD), and ATP with a non-ribosomal protein synthetase. A continuous flow reactor is also disclosed that includes an elongate conduit with at least one region that includes a first region with a non-ribosomal protein synthetase immobilized to a substrate. The non-ribosomal protein synthetase of the continuous flow reactor is configured to contact a flow of a reaction mixture that includes a beta-hydroxy-alpha-amino acid and an aryl carrier protein. The non-ribosomal protein synthetase is further configured to release a peptide beta-lactone into the flow of the reaction mixture.

Abbreviations

Definitions of various abbreviations used herein are provided as follows: A, adenylation; ACP, acyl carrier protein; 4-ADC, 4-aminodeoxychorismate synthase; AHL, acylhomoserine lactone; C, condensation; CDS, coding sequence;

cpm, counts per minute; DAHP, 3-Deoxy-D-arabinoheptulosonate 7-phosphate; 2,3-DHB, 2,3-dihydroxybenzoate; DTT, dithiothreitol; E. coli, Escherichia coli; gDNA, genomic DNA; β-OH-p-$NO_2$-homoPhe, β-hydroxy-para-nitro-homoPhenylalanine; LB, Luria broth; NRPS, non-ribosomal peptide synthetase; NRP, non-ribosomal peptide; RC-Obi, ring-closed obafluorin; ACP, acyl carrier protein: PAA, phenylacetaldehyde; PAPPA, para-aminophenylpyruvic acid; PCP, peptidyl carrier protein; PHPPA, para-hydroxyphenylpyruvic acid; PNPPA, para-nitrophenylpyruvic acid; PPA, phenylpyruvic acid; PPant, phosphopantetheinyl; PPTase, phosphopantetheinyl transferase; P. fluorescens, Pseudomonas fluorescens; PK, polyketide; PKS, polyketide synthase; PLP, pyridoxal 5'-phosphate; RO-Obi, ring-opened obafluorin; T, thiolation; TE, thioesterase; TFA, trifluoroacetic acid; and TPP, thiamine pyrophosphate.

Overview of Obi Biosynthesis

Figure 1A:
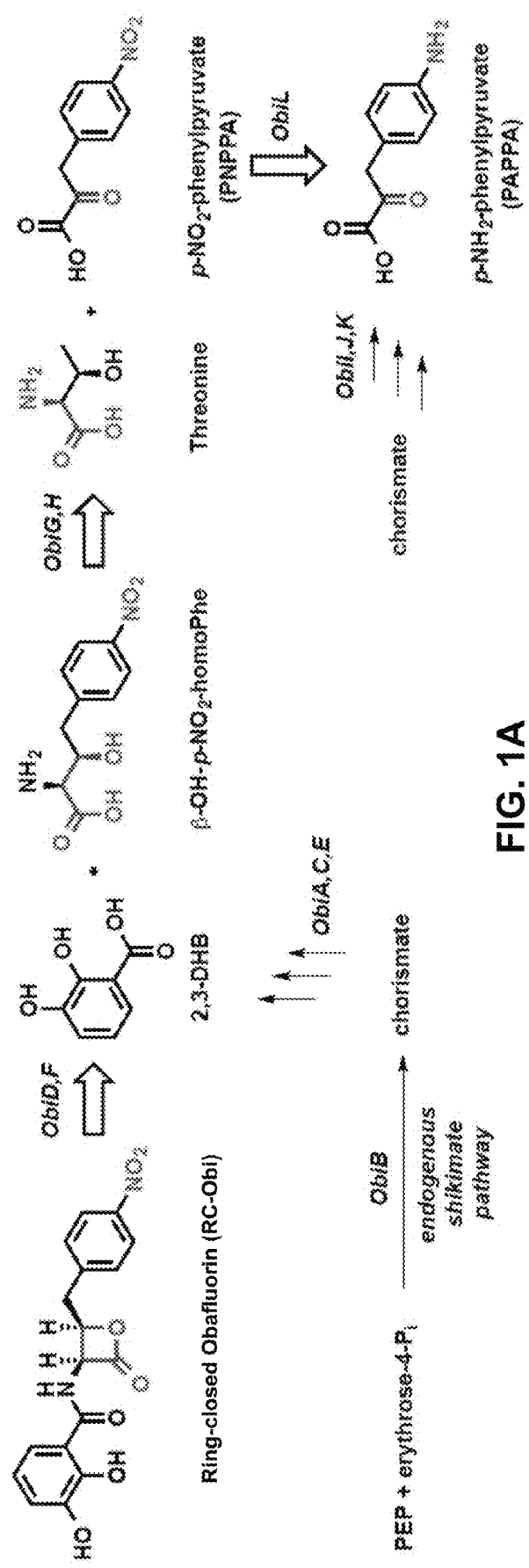
FIG. 1A is a schematic illustration of the retrobiosynthesis of ring-closed obafluorin (RC-Obi) from predicted protein homology and biochemical characterization in an aspect.

FIG. 1A is a schematic illustration of the retrobiosynthesis of ring-closed obafluorin (RC-Obi) derived using predicted protein homology and biochemical characterization as described in additional detail below. The RC-Obi β-lactone ring and related fragments in precursor molecules are shown in red for ease of tracing the fragments in precursor molecules. 2,3-DHB and PAPPA both originate from chorismate as the carbon source. PAPPA is converted to β-OH-p-$NO_2$-homoPhe by action of Fe(II) oxidase ObiL, decarboxylase ObiG, and aldolase ObiH. Amide coupling and β-lactone cyclization occur on the NRPS ObiF/ObiD to complete RC-Obi biosynthesis.

Figure 3A:
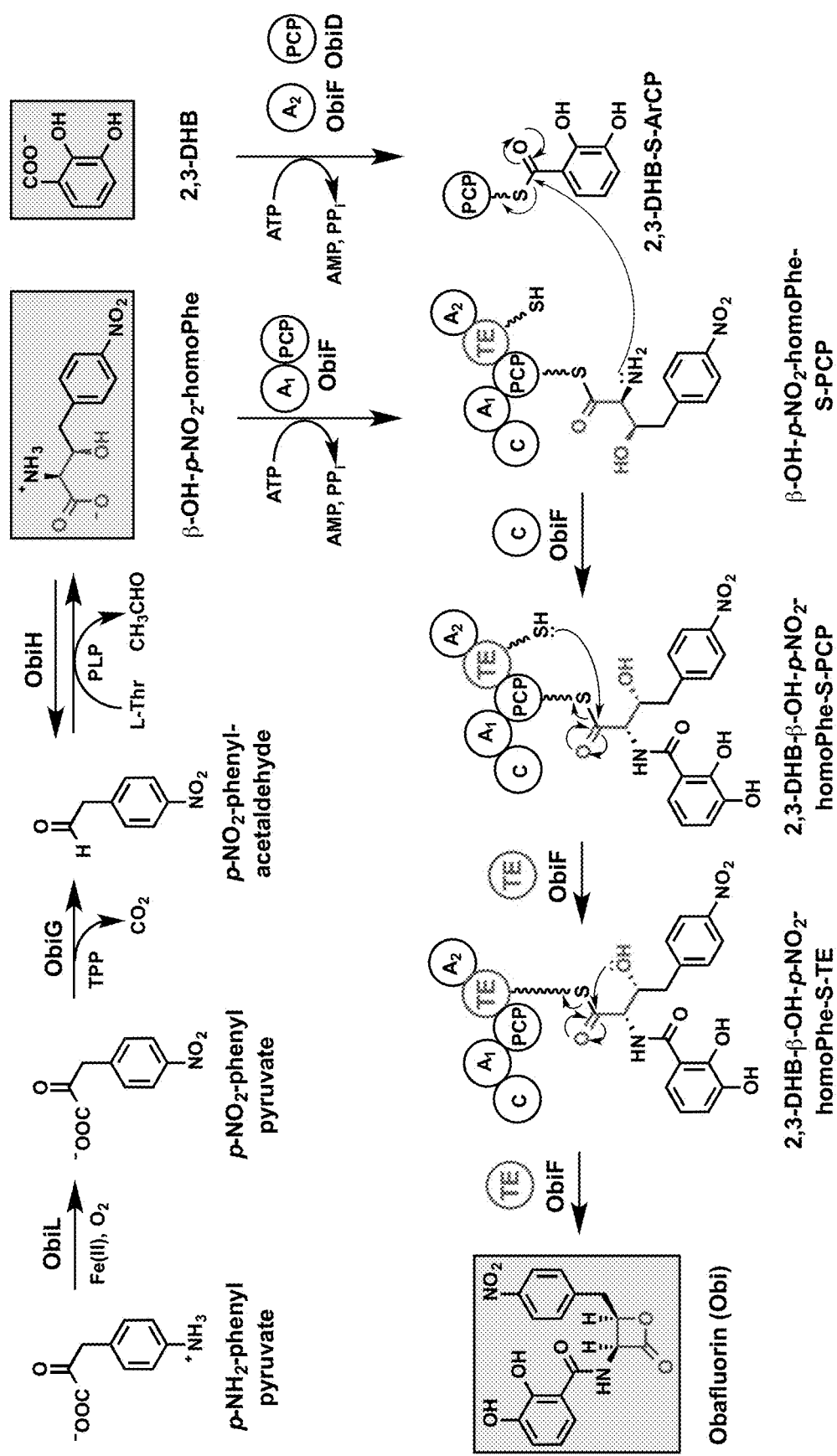
FIG. 3A is a schematic illustration showing an obafluorin β-lactone biosynthetic process.
Figure 3B:
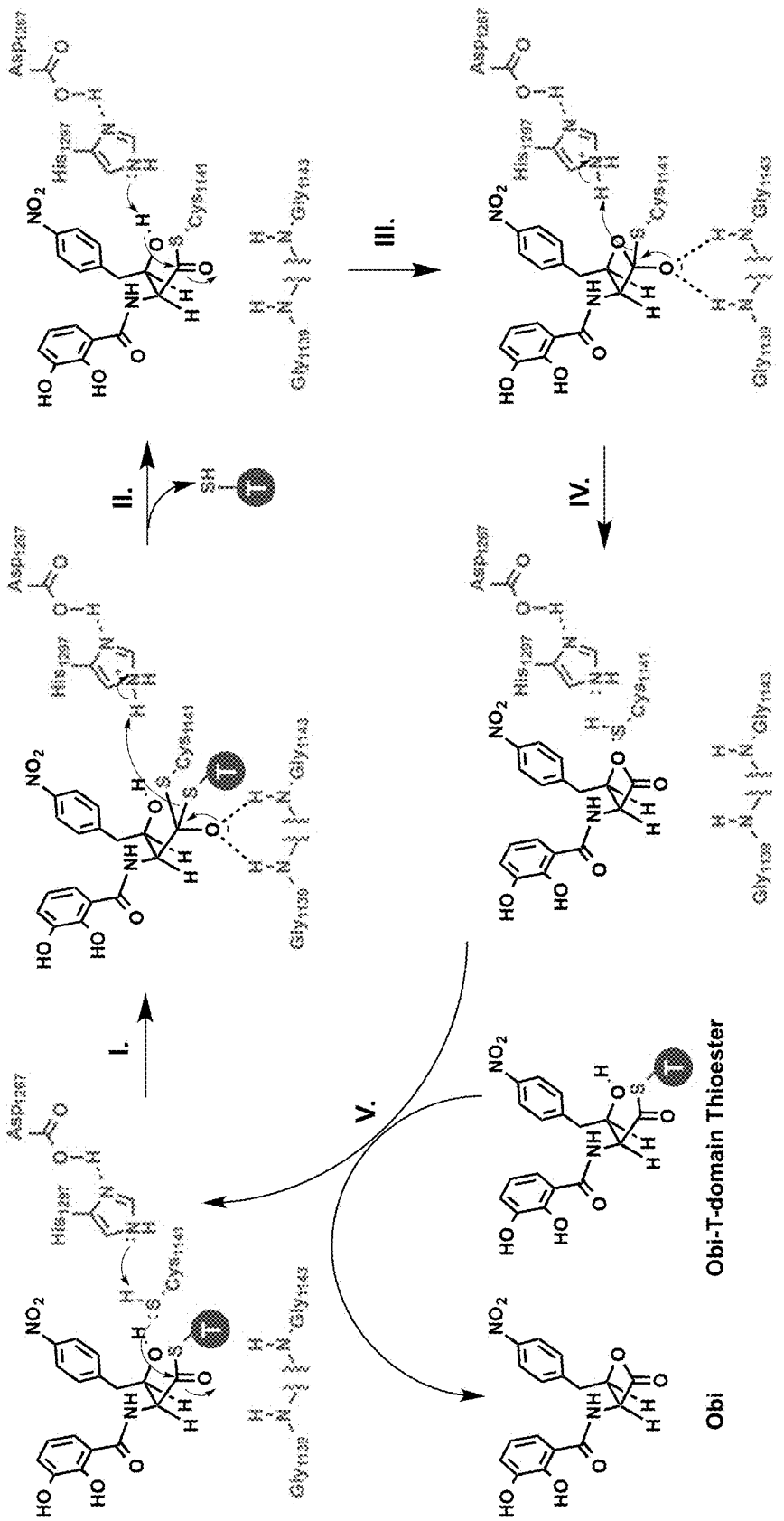
FIG. 3B is a schematic illustration showing a mechanistic model for β-lactone ring during antibiotic cleavage from the ObiF NRPS assembly line.
Figure 3C:
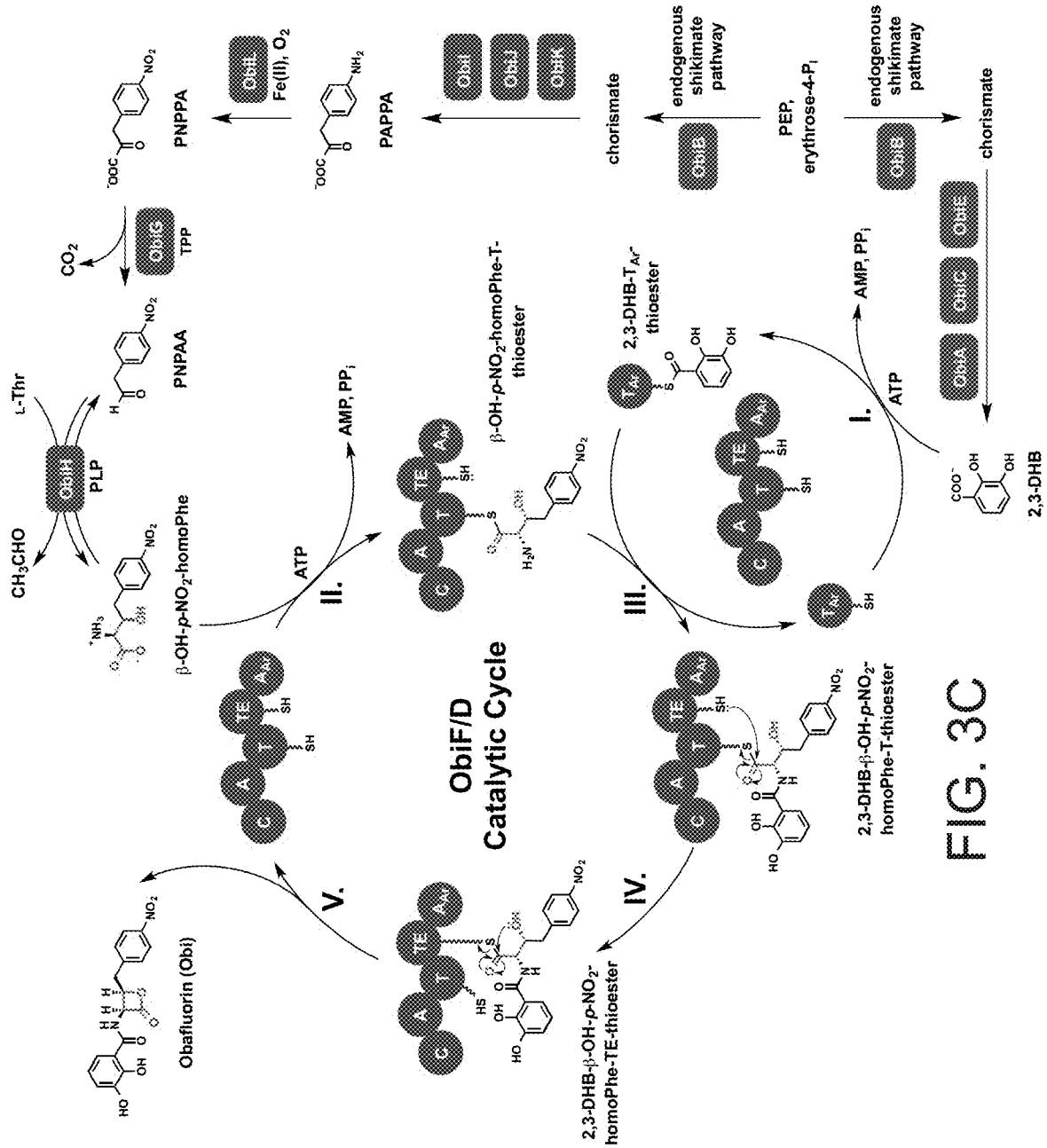
FIG. 3C is a schematic diagram showing a model for RC-Obi biosynthesis and the catalytic cycle of NRPS assembly line ObiF.

FIG. 3C is an illustration of RC-Obi biosynthesis as derived from in vitro characterization of ObiG, ObiH, ObiL, ObiF, and ObiD as described herein, computational prediction of the function of ObiA, ObiB, ObiC, ObiE, ObiI, ObiJ, and ObiK, as well as published isotope labeled precursor studies. FIG. 3C provides a summary of the enzymatically catalyzed biochemical pathways involved in RC-Obi biosynthesis and the catalytic cycle of NRPS assembly line ObiF. ObiB directs carbon flux from the primary metabolic pool to chorismate via the endogenous shikimate pathway. ObiA,C,E convert chorismate to 2,3-DHB. ObiI,J,K convert chorismate to PAPPA. ObiL is an aryl amine oxidase that converts PAPPA to PNPPA. ObiG is a decarboxylase that converts PNPPA to PNPAA. ObiH is a threonine aldolase that catalyzes a retro-aldol reaction with L-Thr and a crossed aldol with PNPAA generating acetaldehyde and β-OH-p-$NO_2$-homoPhe. ObiF and ObiD are the NRPS assembly line components that convert β-OH-p-$NO_2$-homoPhe and 2,3-DHB to RC-Obi at the cost of two ATP molecules. The NRPS catalytic cycle starts (1) with activation of 2,3-DHB as the acyl adenylate by $A_A$-domain followed by loading to the T, domain as the phosphopantetheinyl thioester. Similarly, β-OH-p-$NO_2$-homoPhe is activated and loaded as a phosphopantetheinyl thioester by the embedded A and T domains of ObiF (II). Amide bond formation giving the 2,3-DHB-β-OH-p-$NO_2$-homoPhe-T-thioester is catalyzed by the C domain (III). Transthioesterification to active site $Cys_{1141}$ of the TE domain (IV) leads to cyclization releasing RC-Obi J-lactone (V). Enzymes are color coded to match the genes shown in FIG. 1C.

As illustrated in FIG. 3C, carbon flux to RC-Obi biosynthesis starts from the primary metabolites erythrose-4-phosphate and PEP, which are converted to chorismate by the upregulated DAHP synthase ObiB and the endogenous shikimate pathway. Chorismate is converted to 2,3-DHB by ObiA, ObiC, and ObiE, and chorismate is also converted to PAPPA by ObiI, ObiJ, and ObiK.

Aryl amine oxidase (ObiL) converts PAPPA to PNPPA and ThDP-dependent decarboxylase ObiG converts PNPPA to PNPAA. Threonine aldolase (ObiH) establishes equilibrium between PNPAA, L-Thr, acetaldehyde, and β-OH-p-$NO_2$-homoPhe that is driven towards products by the ATP-consuming NRPS ObiF (see reaction II of FIG. 3C) that activates β-OH-p-$NO_2$-homoPhe as the acyl adenylate with the embedded A domain and covalently loads the amino acid as a phosphopantetheinyl thioester on the embedded T-domain. 2,3-DHB is similarly activated as the acyl adenylate by the C-terminal $A_{Ar}$-domain and loaded on the stand-alone $T_{Ar}$-domain as a phosphopantetheinyl thioester (see reaction I of FIG. 3C). The C domain is predicted to catalyze amide bond formation between the α-amino group of the β-OH-p-$NO_2$-homoPhe-T-thioester and the carbonyl of the 2,3-DHB-$T_{Ar}$-thioester, releasing free TAr (ObiD) and forming the 2,3-DHB-β-OH-p-$NO_2$-homoPhe-T-thioester (see reaction III of FIG. 3C). Transthioesterification to the active site Cys1141 of the TE-domain (see reaction IV of FIG. 3C) sets up the cyclization of the β-hydroxy thioester to the corresponding β-lactone releasing RC-Obi from the NRPS and turning over the ObiF assembly for another round of catalysis (see reaction V of FIG. 3C).

Chorismate Intake—Formation of 2,3-DHB and PAPPA

Figure 8A:
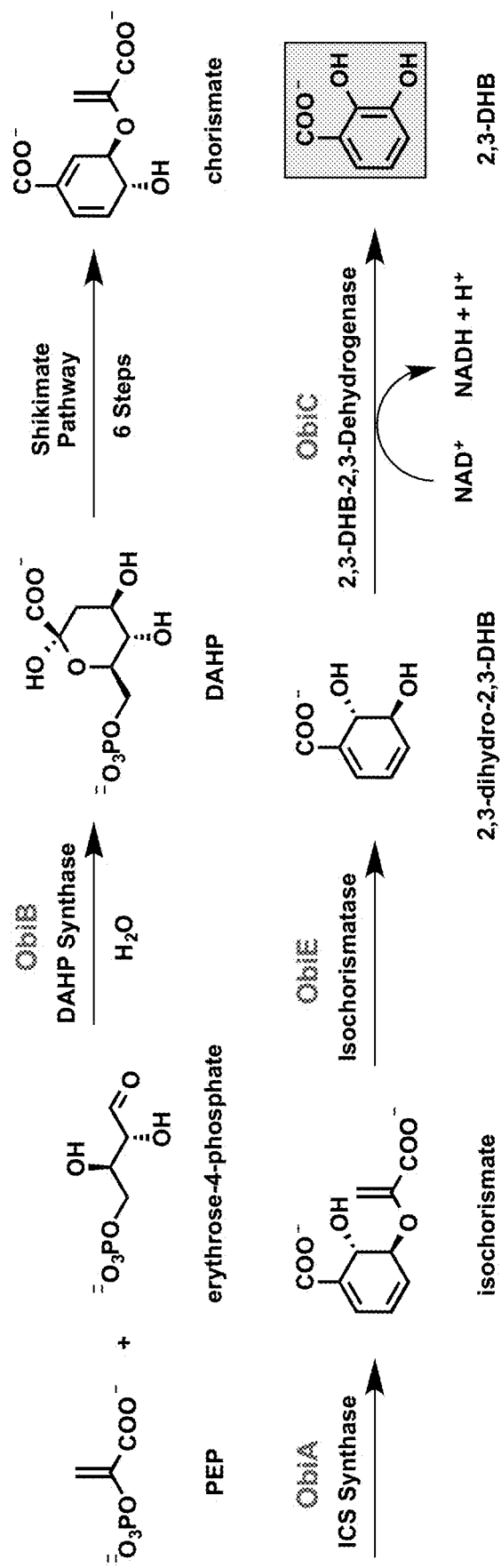
FIG. 8A is an illustration showing the biosynthesis of 2,3-DHB by the enzymes ObiA, ObiB, ObiC, and ObiE encoded in the obafluorin (Obi) biosynthetic gene cluster.

FIG. 8A is an illustration showing the biosynthesis of 2,3-DHB by the enzymes ObiA, ObiB, ObiC, and ObiE encoded in the obafluorin (Obi) biosynthetic gene cluster. Phosphoenolpyruvate (PEP) and erythrose-4-phosphate are converted to 3-deoxy-D-arabinoheptulosonate-7-phosphate (DAHP) by DAHP synthase ObiB. The native shikimate pathway in P. fluorescens is left to convert DAHP to chorismate, which is converted to 2,3-DHB by tandem action of isochorismate (ICS) synthase ObiA, isochorismatase ObiE, and dehydrogenase ObiC.

Figure 8B:
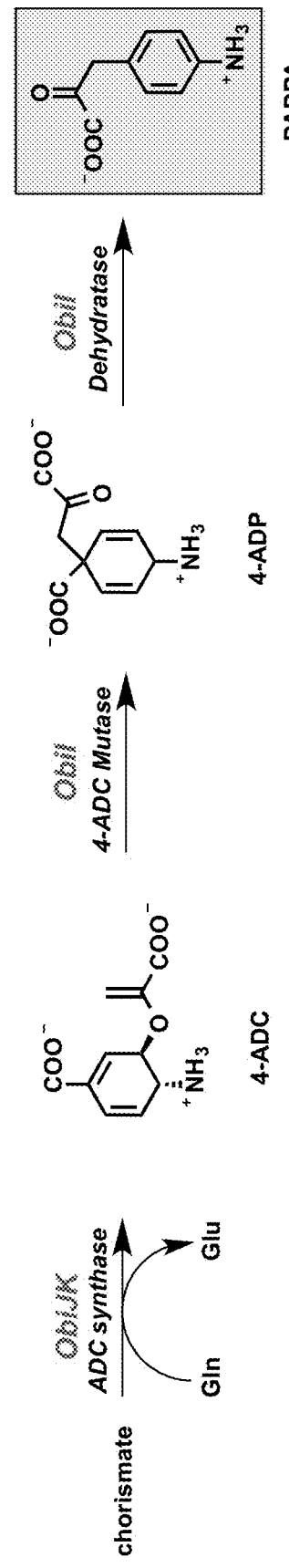
FIG. 8B is an illustration showing the biosynthesis of PAPPA by the enzymes ObiI, ObiJ, and ObiK encoded in the obafluorin (Obi) biosynthetic gene cluster.

FIG. 8B is an illustration showing the biosynthesis of PAPPA by the enzymes ObiI, ObiJ, and ObiK encoded in the obafluorin (Obi) biosynthetic gene cluster. The three enzymes, ObiI, ObiJ, and ObiK convert chorismate to p-$NH_2$-phenylpyruvate (PAPPA). Chorismate is first converted to 4-amino-deoxychorismate (4-ADC) by ADC synthase ObiJ/ObiK. The bifunctional 4-ADC mutase/dehydratase ObiI catalyzes the isomerization of 4-ADC to 4-amino-deoxyprephenate (4-ADP) and the aromatizing decarboxylation of 4-ADP to give PAPPA.

As illustrated in FIGS. 8A and 8B, chorismate is the primary carbon source of the Obi biosynthetic pathway. 2,3-DHB and PAPPA both originate from chorismate as the carbon source (shown in FIG. 1A). As shown in FIG. 8A, the gene obiB encodes an extra copy of the first biosynthetic enzyme from the shikimate pathway, DAHP synthase, which converts phosphoenol pyruvate (PEP) and erythrose-4-phosphate to chorismate. Presumably, upregulation of DAHP synthase increases carbon flux towards chorismate during RC-Obi production to provide a metabolic pool large enough to maintain required production levels of essential aromatic amino acids. Chorismate is converted to 2,3-DHB by action of isochorismate synthase (ObiA), isochorismatase (ObiE), and dehydrogenase (ObiC), which is analogous to the EntCBA set of enzymes involved in biosynthesis of the siderophore enterobactin. As illustrated in FIG. 8B, chorismate is also converted to PAPPA by the 4-amino-4-deoxy chorismate (4-ADC) synthase (ObiJ and ObiK) and 4-ADC mutase/dehydratase (ObiI) analogous to the CmlBCD and PapABC enzymes that lead to PAPPA in the chloramphenicol and pristinamycin biosynthetic pathways, respectively. Convert PAPPA to β-OH-p-$NO_2$-homoPhe (ObiL, ObiG, ObiH)

Three enzymes, Fe(II) oxidase ObiL, decarboxylase ObiG, and aldolase ObiH, convert PAPPA to β-OH-p-NO$_2$-homoPhe (FIGS. 1A and 3C). As shown in FIG. 3A, aryl amine oxidase ObiL converts PAPPA to PNPPA. Decarboxylase ObiG converts PNPPA to p-NO$_2$-phenylacetaldehyde (PNPAA) which is captured by threonine aldolase ObiH to establish an equilibrium between the β-OH-amino acids L-Thr and β-OH-p-NO$_2$-homoPhe which share the same (2S,3R) stereochemistry at C2 and C3.

FIG. 2F is a diagram illustrating the process of enzymatic conversion of PAPPA to β-OH-p-NO$_2$-homoPhe using recombinant oxidase ObiL, decarboxylase ObiG, and aldolase ObiH. The di-iron nonheme oxygenase ObiL converts the aryl amine PAPPA to the aryl nitro PNPPA in the presence of Fe(II) and O$_2$. The decarboxylase ObiG converts phenyl pyruvic acid PNPPA to phenyl acetaldehyde PNPAA using a TPP cofactor. The PLP-dependent aldolase ObiH establishes equilibrium between the starting materials PNPPA and L-Thr and the products acetaldehyde and β-OH-p-NO$_2$-homoPhe. The ObiH equilibrium is driven towards products by downstream coupling to the ATP-consuming NRPS ObiF.

ObiL is a non-heme diiron oxygenase that catalyzes the six-electron oxidation of the aryl amine PAPPA to the aryl nitro p-NO$_2$-phenylpyruvic acid (PNPPA), as illustrated in FIG. 2F. Related examples of arylamine oxidases are found in the biosynthetic pathways of aureothin (AurF; GenBank EJZ60582.1) and chloramphenicol (CmlI; PDB 5HYH_A).

Figure 20:
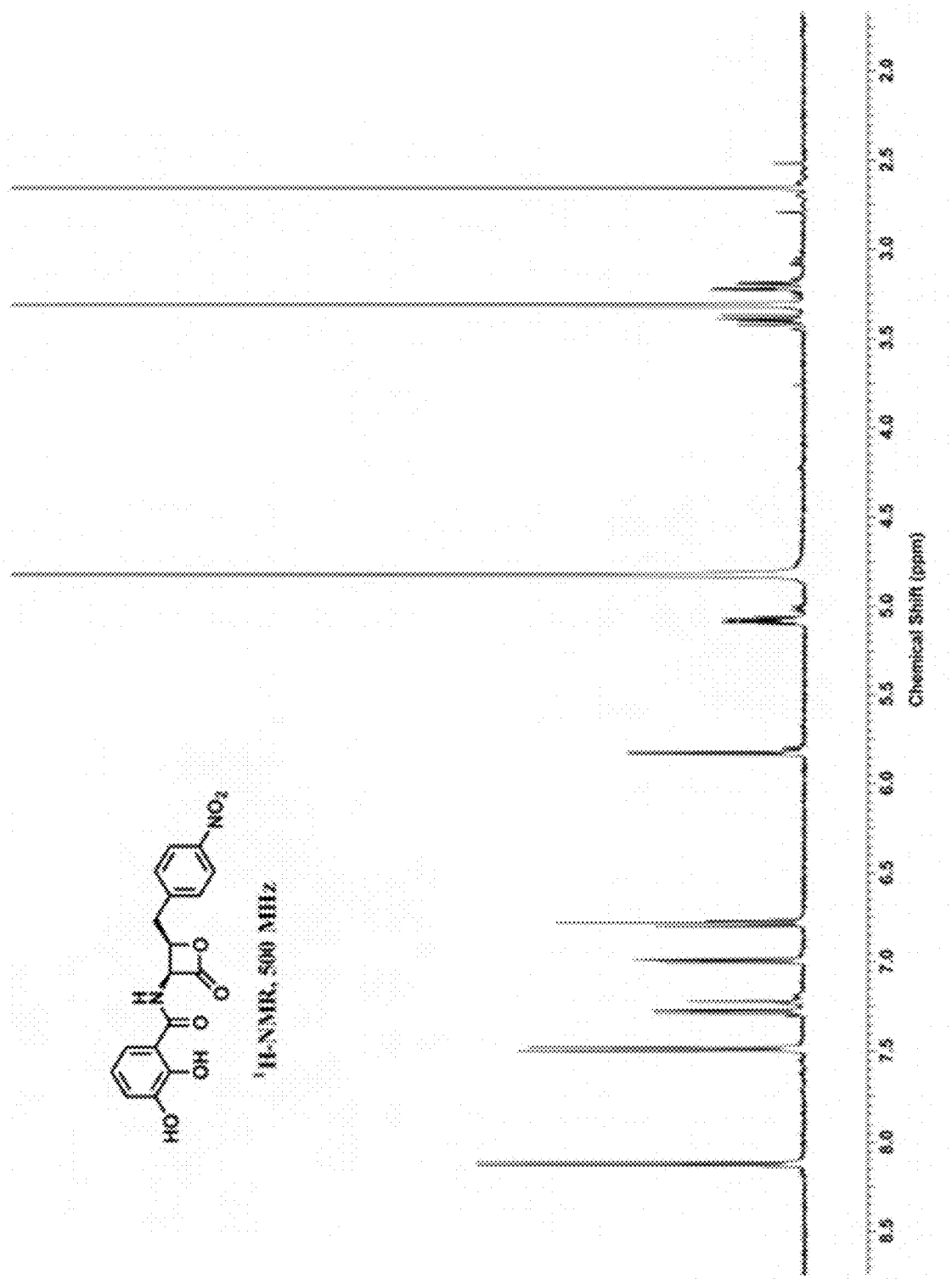
FIG. 20 is a $^1$H NMR spectrum obtained from a sample containing the closed-ring obafluorin protein (RC-Obi).
Figure 58:
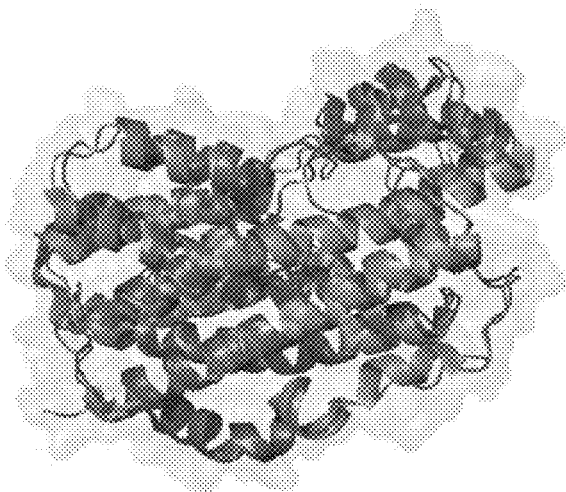
FIG. 58 is a structure homology model of ObiL modeled as a monomer to p-aminobenzoate N-oxygenase AurF (PDB 3cht). The p-nitrobenzoate ligand is shown as red sticks.

FIG. 58 illustrates a structure homology model of ObiL modeled as a monomer to p-aminobenzoate N-oxygenase AurF. ObiL shows 24% and 18% sequence homology to AurF and CmlI, respectively (see Table 1 below). AurF acts early in the biosynthetic pathway of aureothin to oxidize p-aminobenzoic acid (PABA) to p-nitrobenzoic acid (PNBA), and CmlI catalyzes the oxidation of the penultimate aniline intermediate to the aryl nitro as the final step of chloramphenicol biosynthesis. Subsequent treatment of an ObiL/PAPPA reaction mixture with recombinant ObiG and ObiH in the presence of thiamine diphosphate (ThDP), pyridoxal phosphate (PLP), and L-Thr gives direct detection of β-OH-p-NO2-homoPhe as detected by LC-MS (FIG. 20).

TABLE 1

Percent amino acid sequence identity of ObiL, AurF, and CmlI

| | ObiL[a] | AurF[b] | CmlI_A[c] |
|---|---|---|---|
| ObiL | | 24% | 18% |
| AurF | 24% | | 22% |
| CamlI_A | 18% | 22% | |

[a]GenBank KX134693.
[b]GenBank EJZ60582.1.
[c]PBD 5HYH_A.

Figure 57:
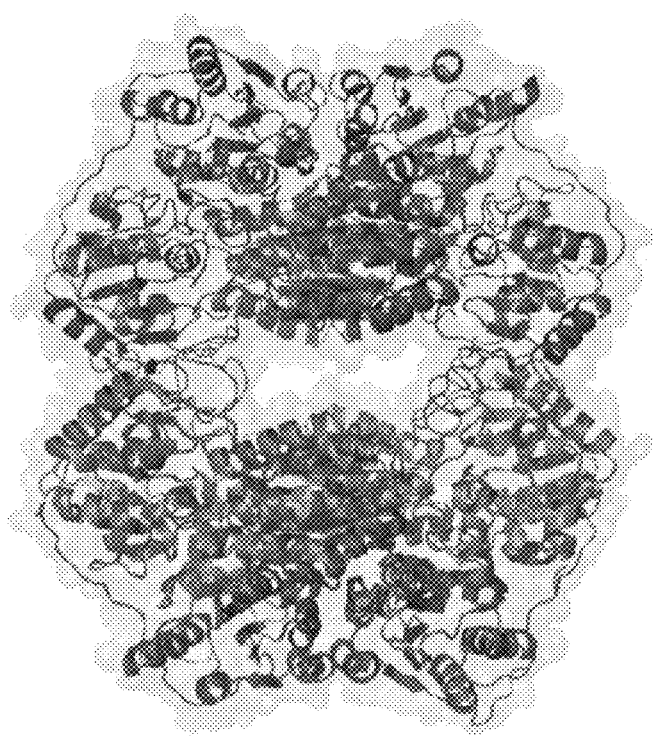
FIG. 57 is a structure homology model of ObiG modeled as a homotetramer to a homodimer of phenylpyruvate decarboxylase (PDB 2q5o). The 3-deaza-ThDP and 3-phenylpyruvic acid ligands are shown as red sticks.
Figure 61:
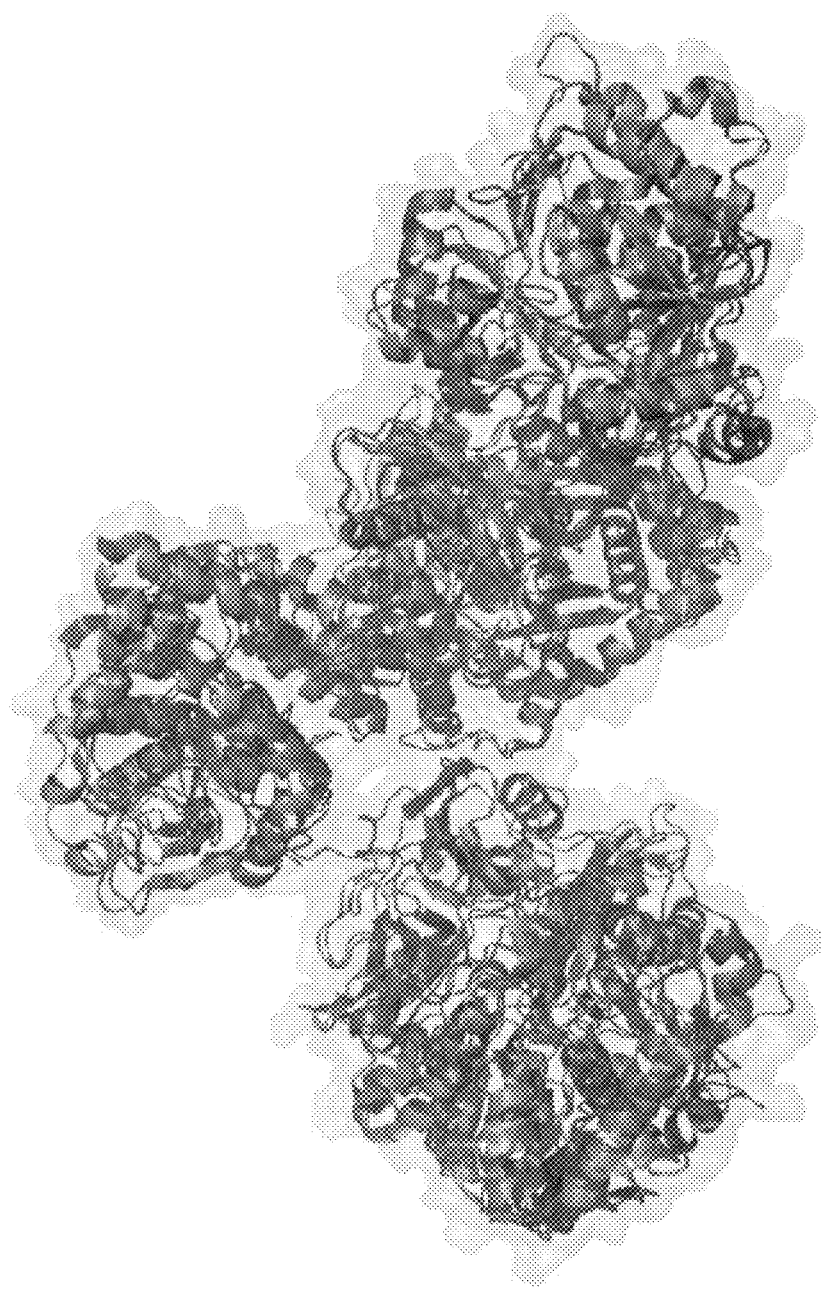

ObiG is a ThDP-dependent phenylpyruvate decarboxylase that catalyzes the conversion of PNPPA to PNPAA (FIG. 2F, FIG. 57 illustrates a structure homology model of ObiG modeled as a homotetramer to a homodimer of phenylpyruvate decarboxylase. ObiG preferentially decarboxylates p-nitro-phenyl pyruvic acid (PNPPA) to give the corresponding p-nitro-phenylacetaldehyde (FIG. 10A). A double enzyme reaction with ObiG and ObiH in the presence of ThDP, PLP, and L-Thr revealed that PNPPA is directly converted to β-OH-p-NO$_2$-homoPhe as detected by LC-MS (FIG. 2H) and $^1$H-NMR analysis of the reaction mixture (FIG. 2I). p-Amino-phenylpyruvic acid (PAPPA) was not accepted as a substrate by ObiG/ObiH suggesting that ObiL must oxidize PAPPA prior to ObiG,H catalysis (FIG. 2H and FIG. 2I). These results firmly establish that PAPPA acts as the substrate for oxygenase ObiL and decarboxylase ObiG acts on PNPPA to provide PNPAA aldehyde substrate for aldolase ObiH (FIG. 10B).

Figure 63:
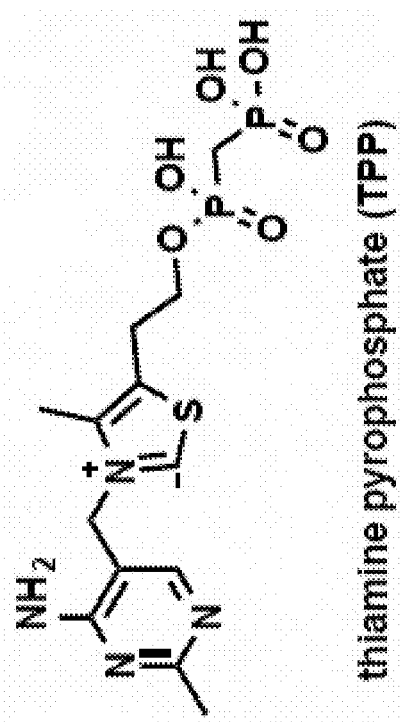
Figure 62:
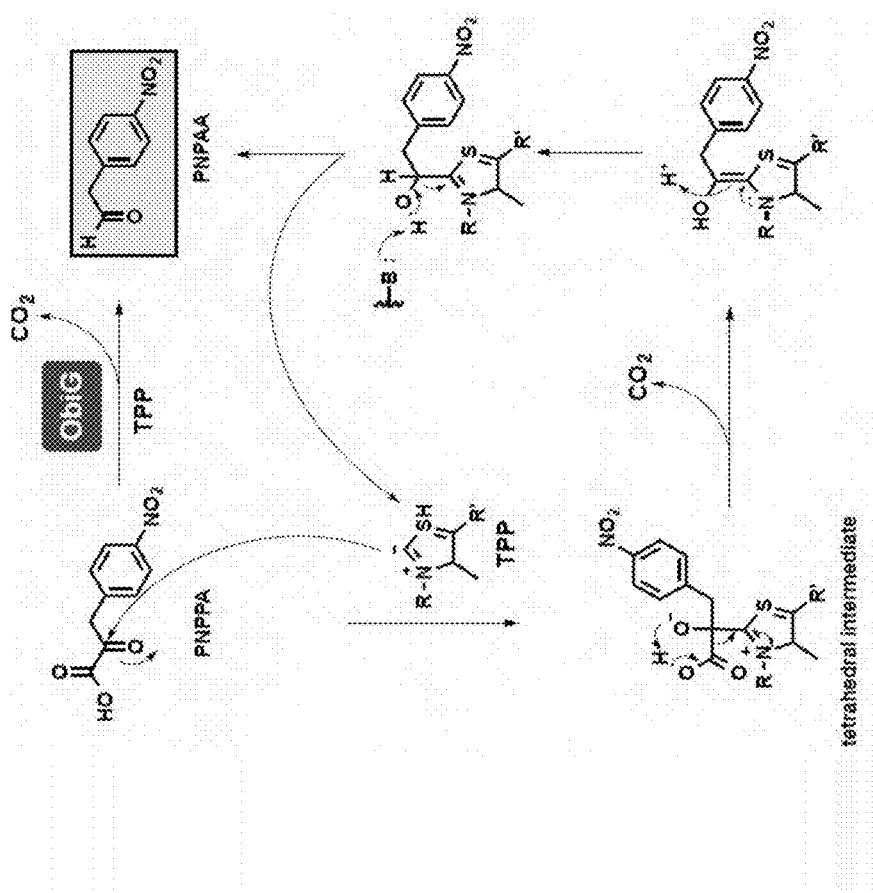

FIG. 62 is a chemical reaction diagram showing a mechanism of ObiG modeled after phenylpyruvate decarboxylase. ObiG is a ThDP decarboxylase that converts PNPPA to PNPAA. The proposed mechanism of the reaction is initiated by attack of the TPP-ylide on f-carbonyl of PNPPA, forming a tetrahedral intermediate. Decarboxylation, protonation, and elimination of catalytic TPP give PNPAA. FIG. 63 shows a chemical structural diagram of thiamine pyrophosphate (TPP).

The stereochemistry of the ObiH aldol product matches that of the preferred precursor L-Thr and the final biosynthetic product RC-Obi. Double enzyme reactions with decarboxylase ObiG and aldolase ObiH monitored by LCMS established that L-Thr is the preferred amino acid substrate and PNPPA is the preferred phenyl pyruvate substrate. p-Amino-phenylpyruvic acid (PAPPA) was not accepted as a substrate by ObiG/ObiH suggesting that ObiL must oxidize PAPPA prior to ObiGH catalysis. The timing and action of ObiL as an aryl amine oxidase was confirmed using a triple enzyme reaction of ObiGHL with L-Thr and PAPPA substrates which produced β-OH-p-NO$_2$-homoPhe.

Figure 60:
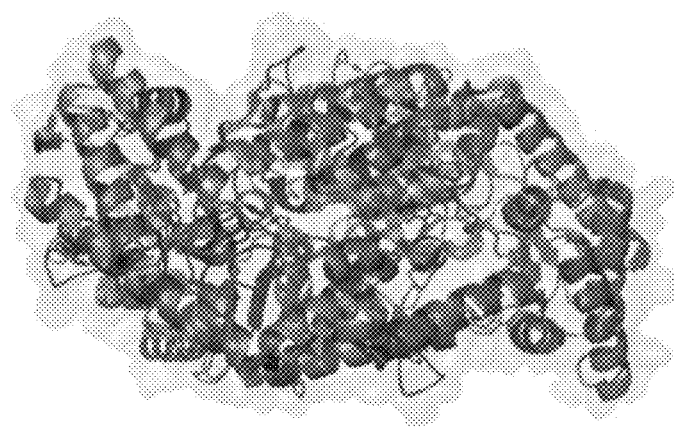

The reactive aldehyde resulting from the enzymatic conversion of PNPPA by ObiG is immediately captured by threonine aldolase ObiH. FIG. 60 illustrates a structure homology model of ObiH modeled as a homodimer to serine hydroxymethyltransferase from Burkholderia cenocepacia. ObiH catalyzes a retro aldol reaction on L-Thr and a forward crossed aldol reaction with p-nitro phenylacetaldehyde to yield (2S,3R)-β-OH-p-NO$_2$-homoPhe. ObiH is a threonine aldolase that catalyzes a retro-aldol reaction on L-Thr giving acetaldehyde and a PLP-stabilized glycine enolate that undergoes a crossed aldol reaction with PNPAA to yield (2S,3R)-β-OH-p-NO$_2$-homoPhe setting the final stereochemistry found in the Obi β-lactone scaffold (FIG. 2F). Threonine aldolases are PLP-dependent enzymes with homology to serine hydroxymethyl transferase and alanine racemase. Aldolases are involved in the biosynthesis of natural products containing β-hydroxy-α-amino acids including: the peptidyl nucleoside antibiotics A090289 A, caprazamycin A, and muramycin A135; the 4-methyl-oxazoline antibiotics JBIR-34 and BE-3203036; and the α-methyl-L-Ser antibiotics amicetin and bamicterin.

Figure 13A:
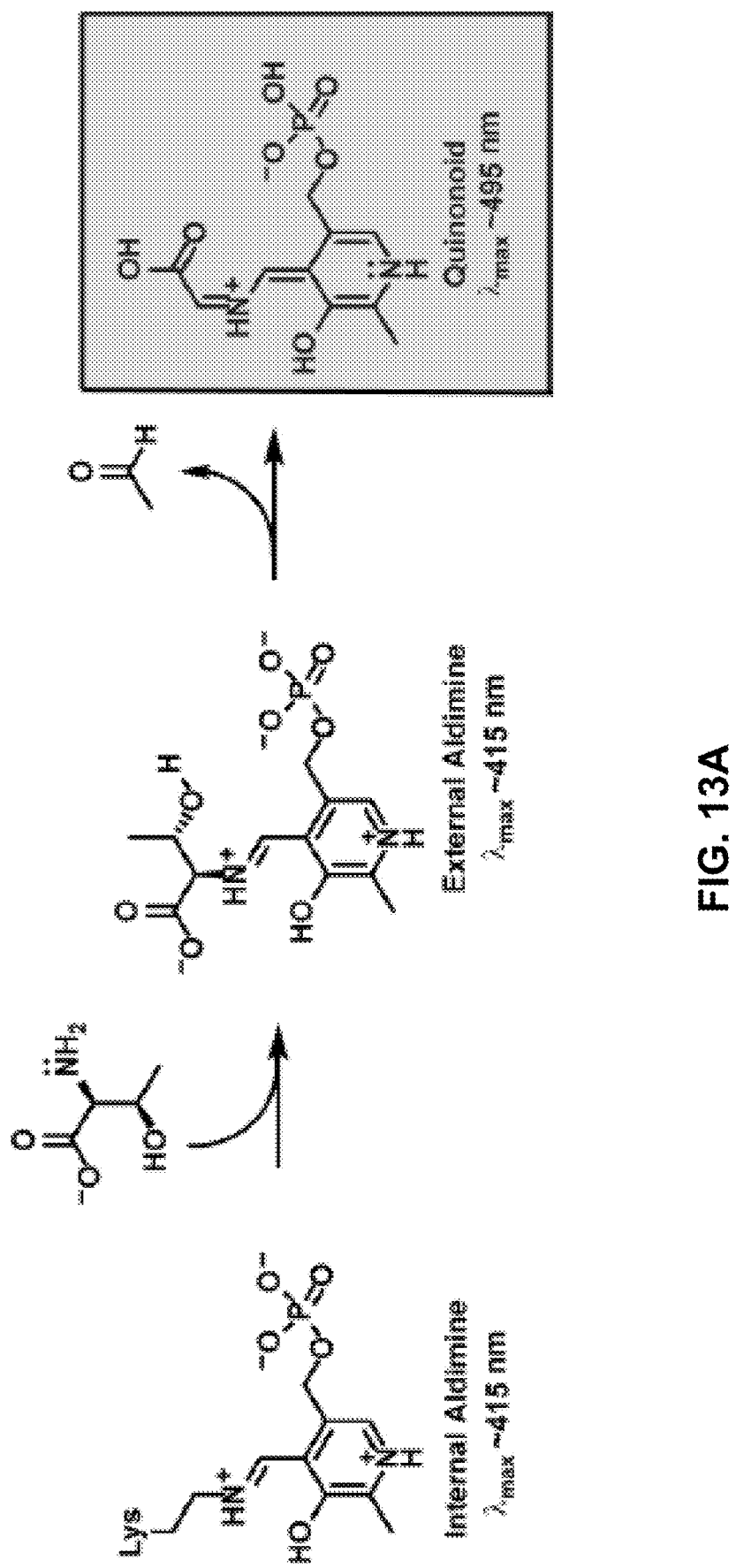
FIG. 13A is a schematic illustration showing formation of an ObiH quinonoid.
Figure 13B:
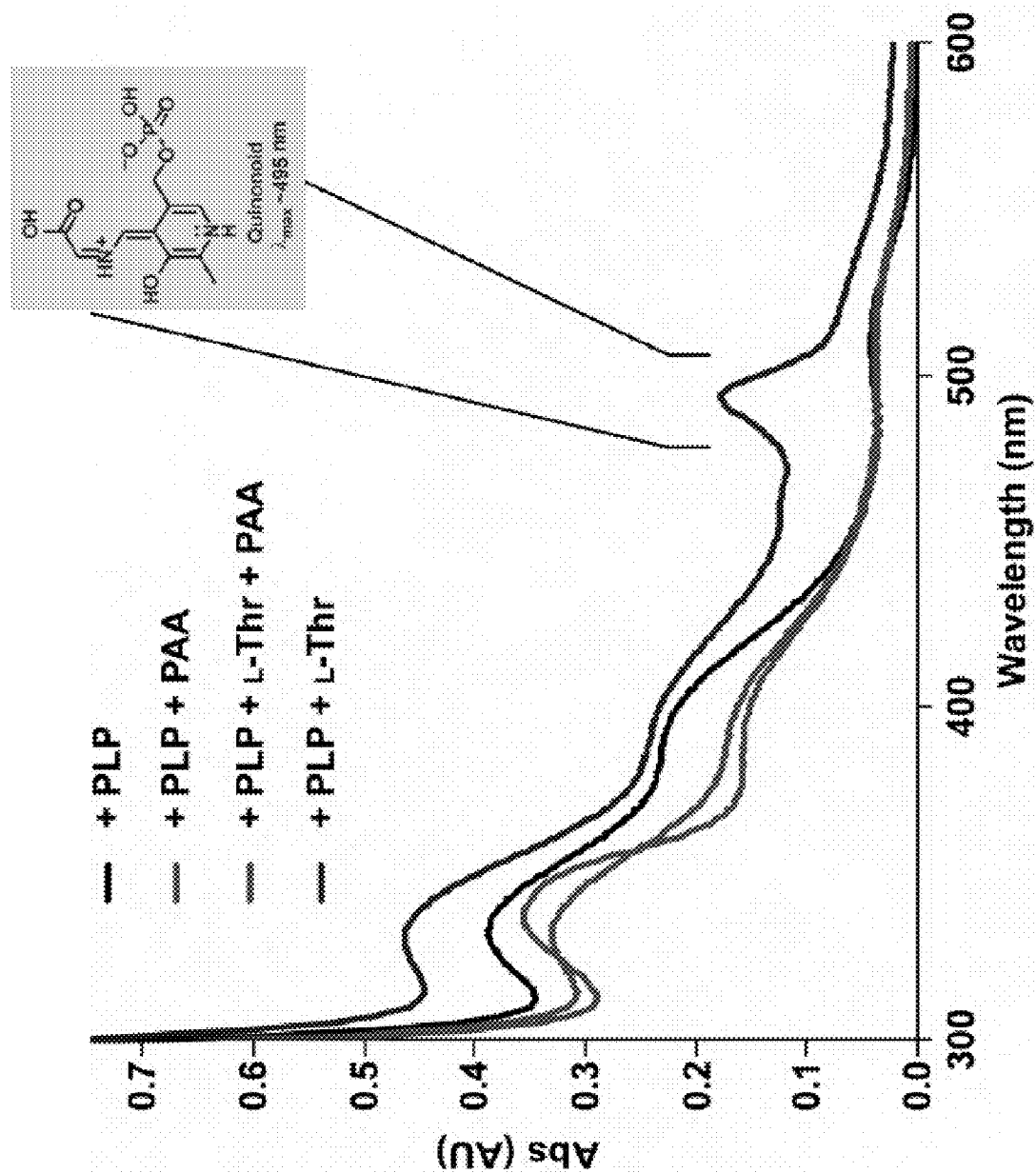
FIG. 13B is a graph of optical absorption spectrum of ObiH treated with: PLP and L-Thr (blue trace), PLP (black trace), PLP and phenylacetylaldehyde (PAA) (green trace), and PLP, PAA, and L-Thr (red trace).
Figure 13C:
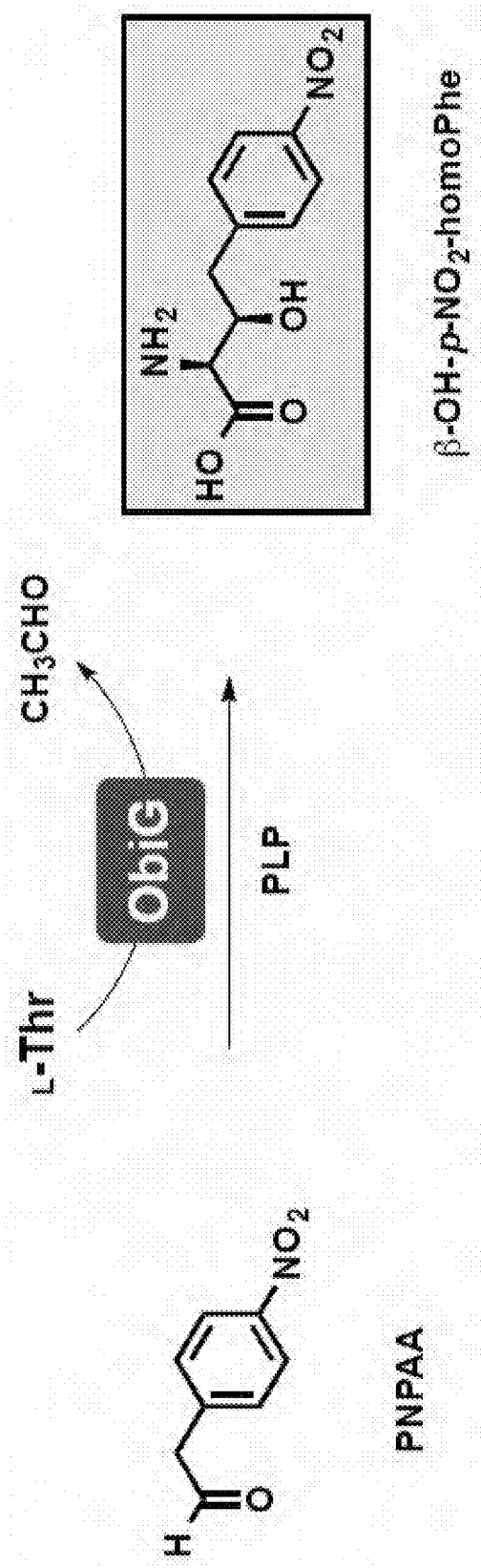
FIG. 13C is a chemical reaction diagram showing a mechanism of ObiG modeled after threonine aldolase. ObiG is a PLP-dependent L-Thr aldolase that converts L-Thr and PNPAA to β-OH-p-$NO_2$-homoPhe and acetaldehyde.
Figure 13D:
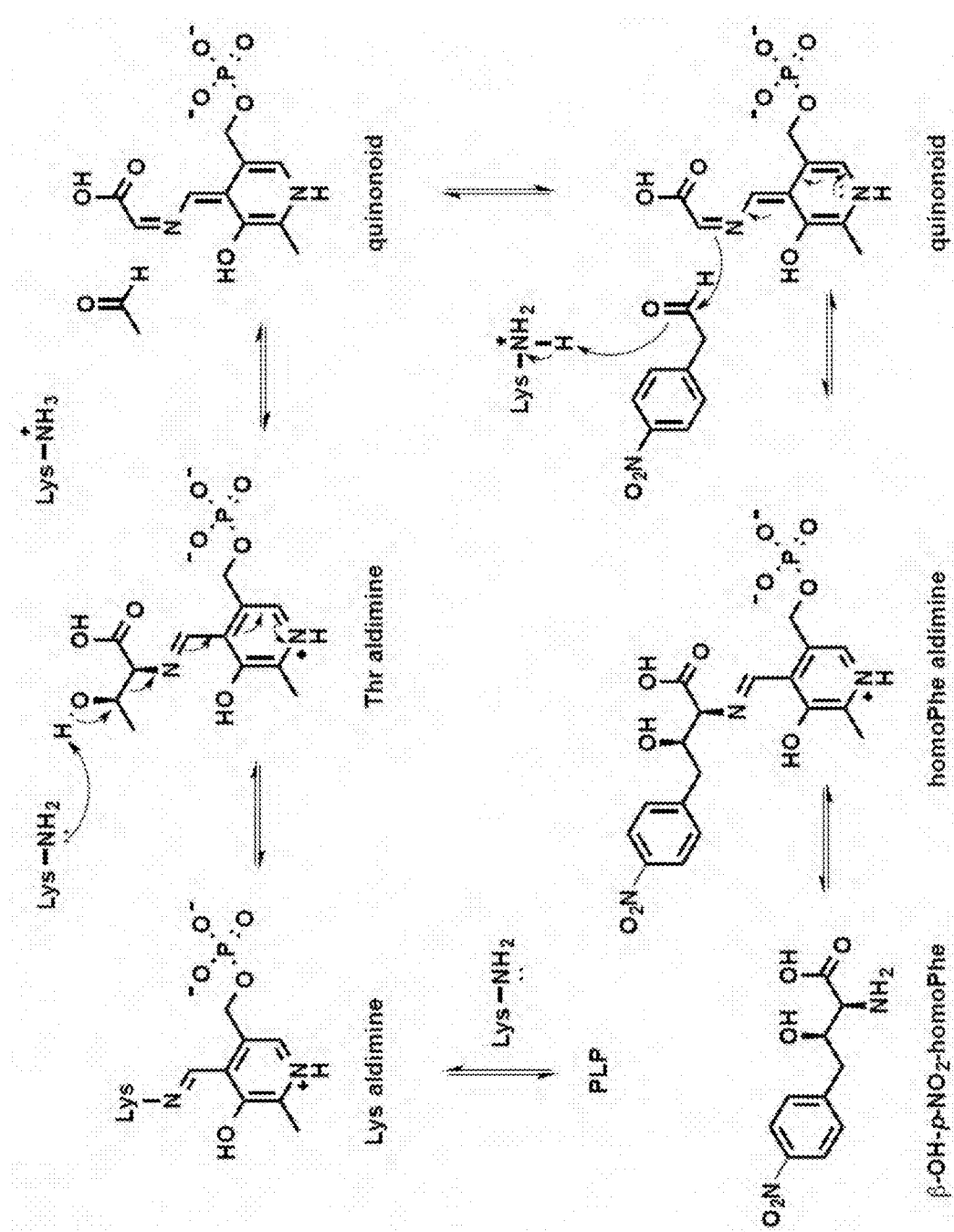
FIG. 13D is a chemical reaction diagram showing that the ObiG Lys-aldimine can equilibrate to the Thr aldimine.

FIGS. 13C and 13D illustrate a mechanism for ObiG conversion of L-Thr and PNPAA to β-OH-p-NO$_2$-homoPhe. As mentioned, ObiG is a PLP-dependent L-Thr aldolase that converts L-Thr and PNPAA to β-OH-p-NO$_2$-homoPhe and acetaldehyde. FIG. 13D illustrates a chemical reaction diagram showing that the ObiG Lys-aldimine can equilibrate to the Thr aldimine. A retro-adol reaction gives acetaldehyde and a stabilized glycine enolate (quinonoid). An aldol reaction with PNPAA gives the β-OH-p-NO$_2$-homoPhe-aladimine with stereochemistry matching that of L-Thr. The homoPhe-aldimine equilibrates with the Lys-aldimine releasing β-OH-p-NO$_2$-homoPhe.

Double enzyme reactions with decarboxylase ObiG and aldolase ObiH monitored by LCMS established that L-Thr is the preferred amino acid substrate (FIG. 2J). D-Thr, L-alloThr, D-alloThr, L-Ser, and D-Ser gave trace or no detectable aldol product from the ObiG,H double enzyme reaction with PNPAA. Given that the stereochemistry of the ObiH aldol product. (2S,3R)-β-OH-p-NO$_2$-homoPhe, matches that of L-Thr, it is probable that L-Thr leads to stereospecific enolate formation and subsequently stereospecific aldol reaction with PNPAA. The ObiH PLP cofactor forms an exceptionally stable glycine enolate quinonoid intermediate upon exposure to L-Thr that is observable by optical absorption spectroscopy (λ=495 nm) throughout the entire protein expression and purification process including dialysis. Addition of phenyl acetaldehyde (PAA) rapidly quenches the ObiH quinonoid and forms the aldol product. ObiH alone is not capable of driving the equilibrium of the aldol reaction completely to product. Kinetic analysis of the ObiH reaction by $^1$H-NMR and optical absorbance suggested strong product feedback inhibition, which is common for PLP-dependent enzymes (FIG. 2I). The equilibrium is driven in the direction of the β-OH-p-NO$_2$-homoPhe aldol product by downstream coupling to the ATP-consuming ObiD/ObiF NRPS machinery, which incorporates the ObiH product, β-OH-p-NO$_2$-homoPhe, into the final Obi NRP scaffold (NRPS). The ObiH equilibrium is driven towards RC-Obi by the ATP-consuming NRPS ObiF.

Convert β-OH-p-NO$_2$-homoPhe to Obi β-lactone (ObiD, ObiF)

Referring to FIG. 3A, the Obi NRPS (ObiF, ObiD) contains five domains encoded by ObiF (C-A$_1$-PCP-TE-A$_2$) and ObiD (aryl PCP). The ObiF NRPS module is loaded with β-OH-p-NO$_2$-homoPhe as a PCP-thioester with ATP activation by the A$_1$-domain. The A$_2$-domain of ObiF activates 2,3-DHB as the acyl adenylate before conversion of aryl PCP ObiD to the 2,3-DHB thioester. The ObiF C-domain catalyzes amide bond formation between the α-amino group of the β-OH-p-NO$_2$-homoPhe-PCP-thioester and the carbonyl of the 2,3-DHB-PCP-thioester. Transthioesterification by C1141 of the ObiF TE-domain is followed by release of the cyclized ring-closed RC-Obi β-lactone from the NRPS assembly line.

Amide coupling and β-lactone cyclization occur on the NRPS ObiF/ObiD to complete RC-Obi biosynthesis, as illustrated in FIG. 1A. The P. fluorescens ObiF NRPS is a single module, 209 kDa protein with C-A$_1$-T-TE-AAr catalytic domains (FIG. 39, FIG. 3D, FIG. 56, and FIG. 61).

Figure 3D:
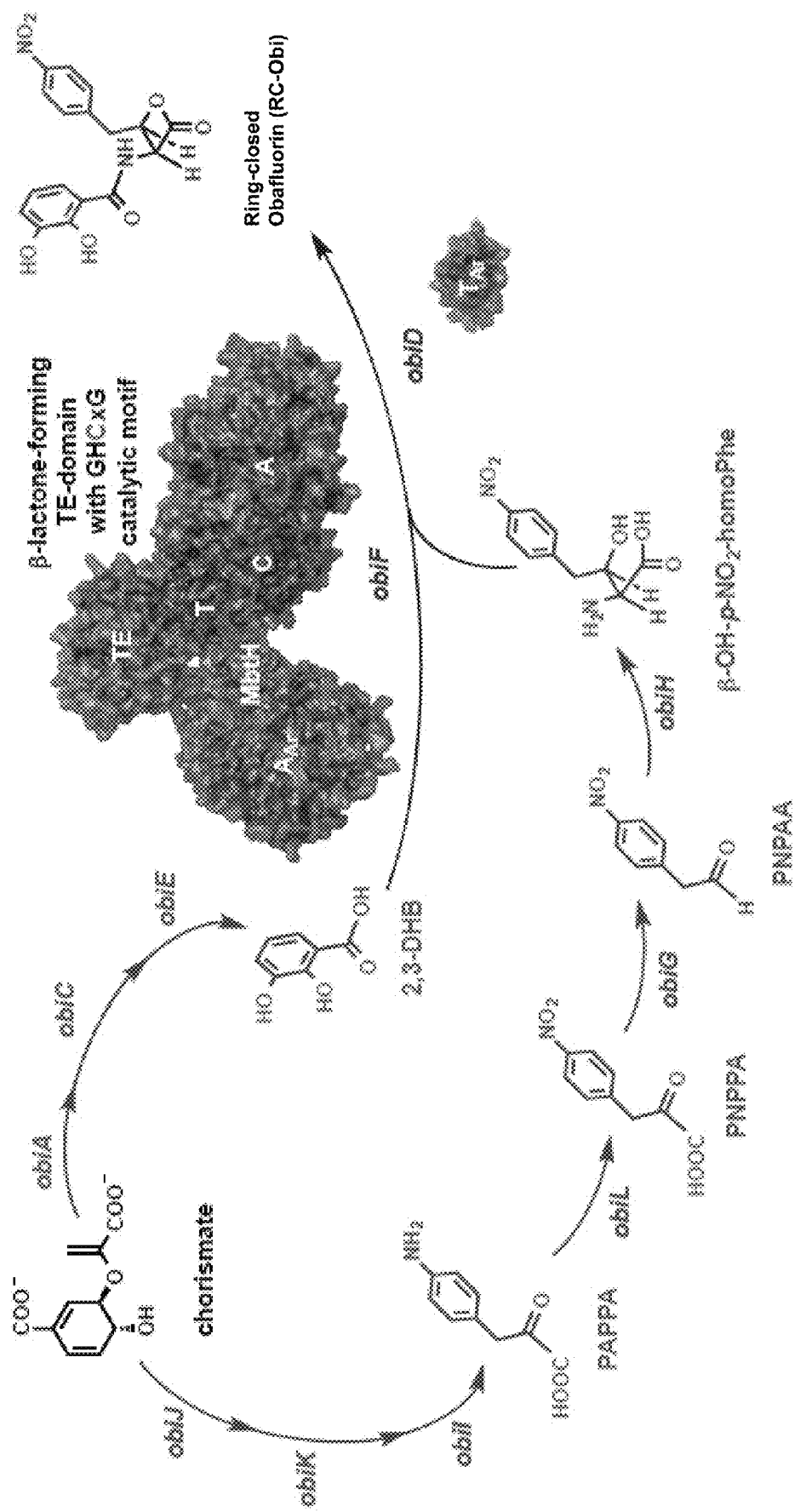
FIG. 3D is a schematic illustration showing an overview of the in vitro reconstitution of five enzymes (ObiL, ObiG, ObiH, ObiF, ObiD).
Figure 55:
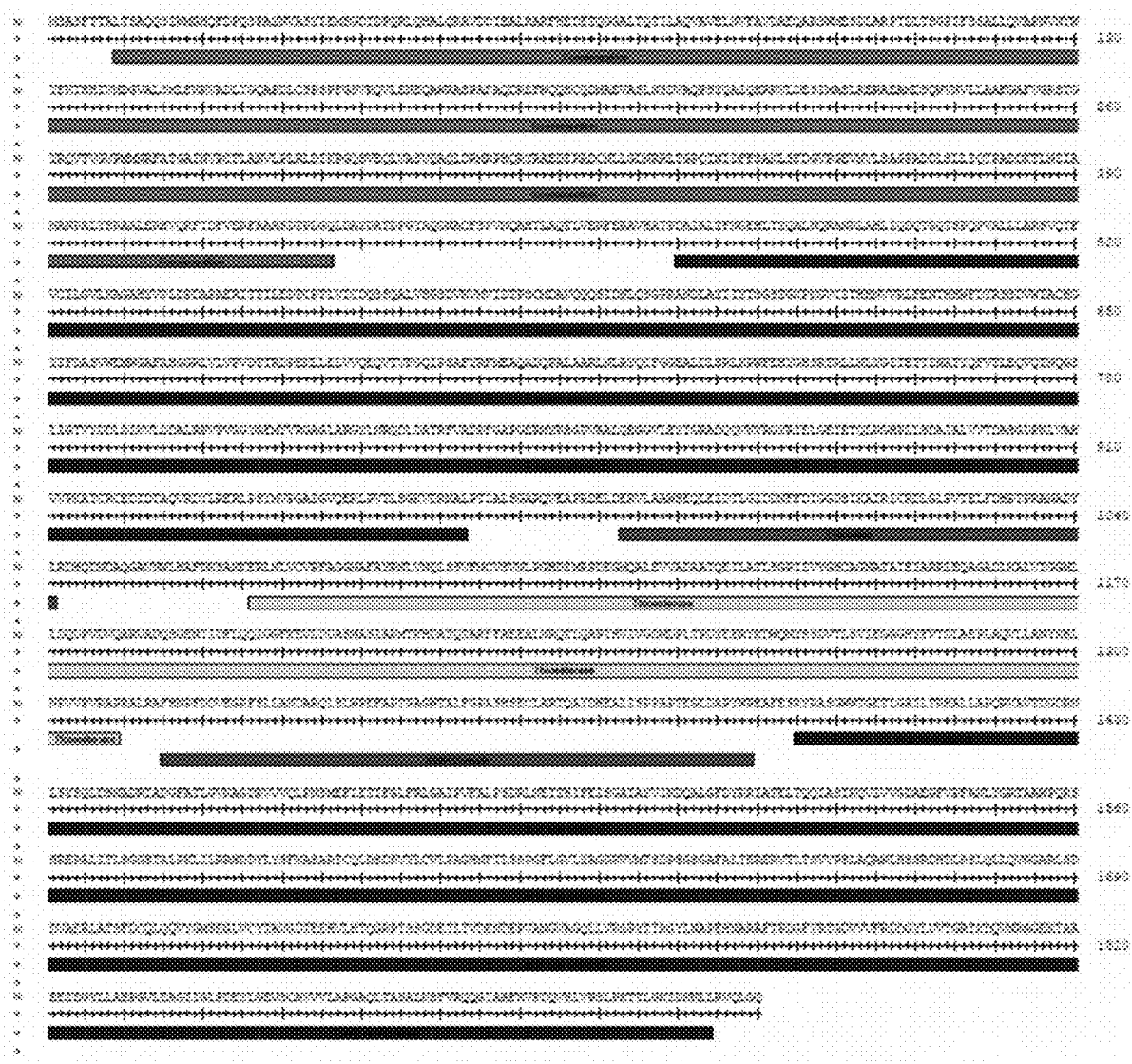
FIG. 55 is a primary protein sequence (GenBank KX134687, SEQ ID NO:2) in which the NRPS domains are highlighted with colors matching the ObiF homology model shown in FIG. 56.
Figure 56:
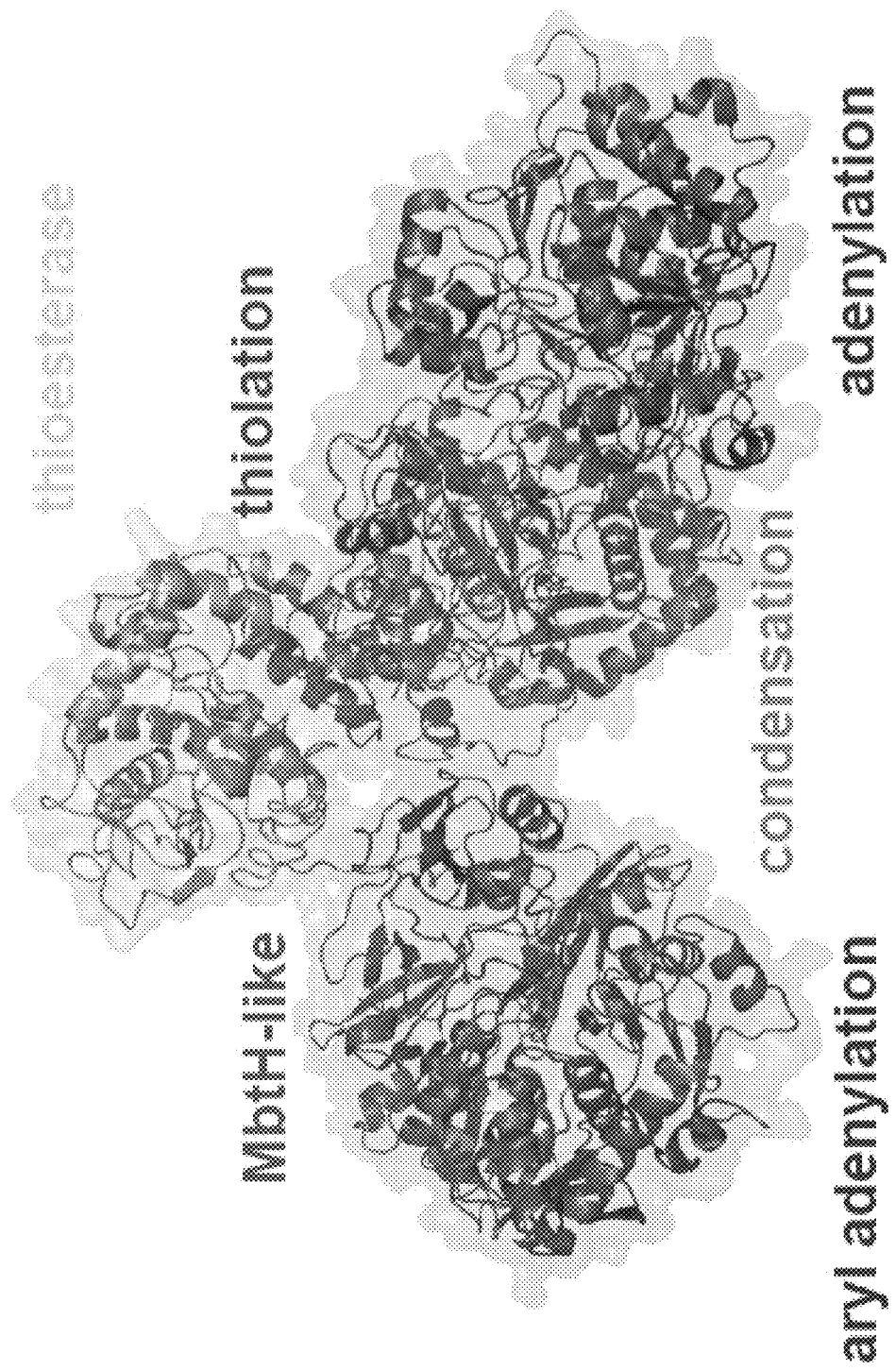
FIG. 56 is a structure homology model of the ObiF NRPS with the domains highlighted by color.

FIG. 56 is a structure homology model of the ObiF NRPS with the domains highlighted by color. The ObiF protein sequence is shown in FIG. 55 with protein domains highlighted in colors matching the ObiF homolog model. ObiL, ObiG, ObiH, ObiD, and ObiF are shown in green overlay with model structures from the PDB shown in orange. All homology models were generated using SWISS-MODEL (swissmodel.expasy.org) and images of secondary structure were generated using PyMOL v1.7 for Mac OS X. There is a small, ~70 amino acid MbtH-like domain between the TE and A$_{Ar}$ domains (FIG. 3D and FIG. 56).

Figure 40:
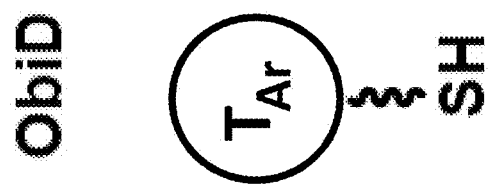
FIG. 40 is a schematic diagram showing an arrangement of domains within an ObiD enzyme.
Figure 39:
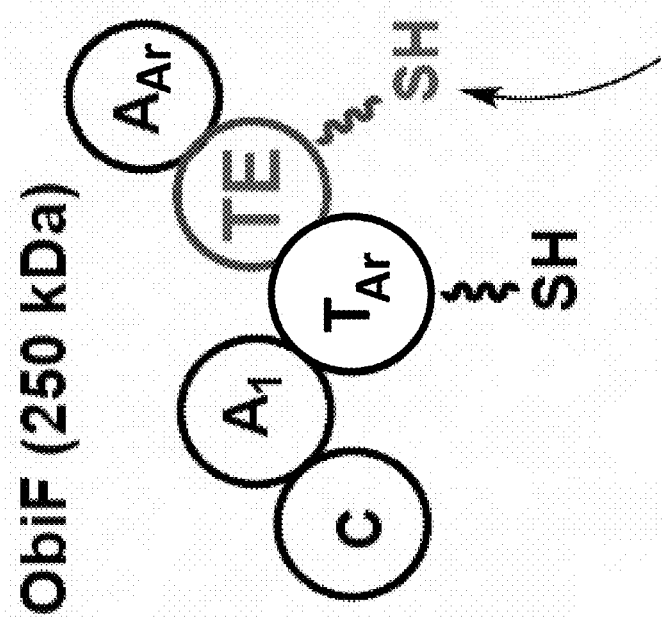
FIG. 39 is a schematic diagram showing an arrangement of domains within an ObiF enzyme.
Figure 59:
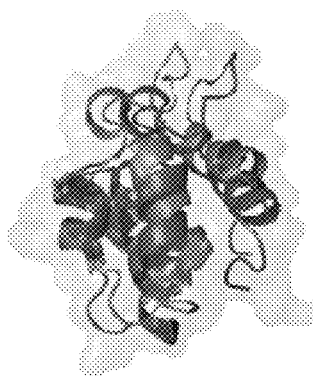

ObiD is a separate aryl acyl carrier protein (T$_{Ar}$), as illustrated in FIG. 40. FIG. 59 illustrates a structure homology model of ObiD modeled to the aryl carrier protein domain of EntB. The ObiF and ObiD domain organization resembles the well-studied enterobactin NRPS module EntF (GenBank AAB40785.1), which contains C-A-T-TE domains and separate aryl adenylation (A$_{Ar}$) (EntE, GenBank AAB40794.1) and aryl carrier (T$_{Ar}$) (EntB, GenBank AAB40795.1) domains. The ObiF homologue from C. shinanonensis SAY3 (GenBank WP_020608490.1) has the same domain organization as the P. fluorescens NRPS along with an ObiD homologue. (GenBank WP_018749564.1) The homologous proteins in B. difusa RF8-non_BP2 share an organization matching EntF (GenBank WP_059467198.1) with separate A$_{Ar}$ (GenBank WP_059467197.1) and T$_{Ar}$ (GenBank WP_059467195.1).

Figure 2B:
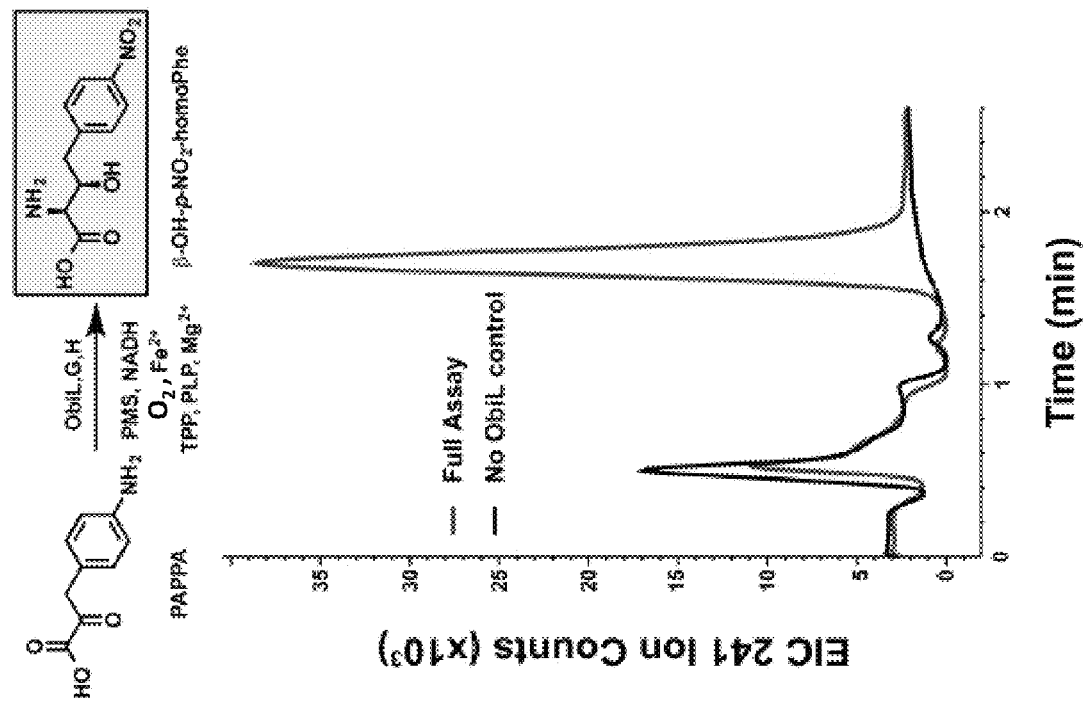
FIG. 2B is a graph summarizing the extracted ion chromatograms (EICs) vs retention time for the predicted products of a triple enzyme reaction with ObiL/ObiGiObiH.
Figure 2A:
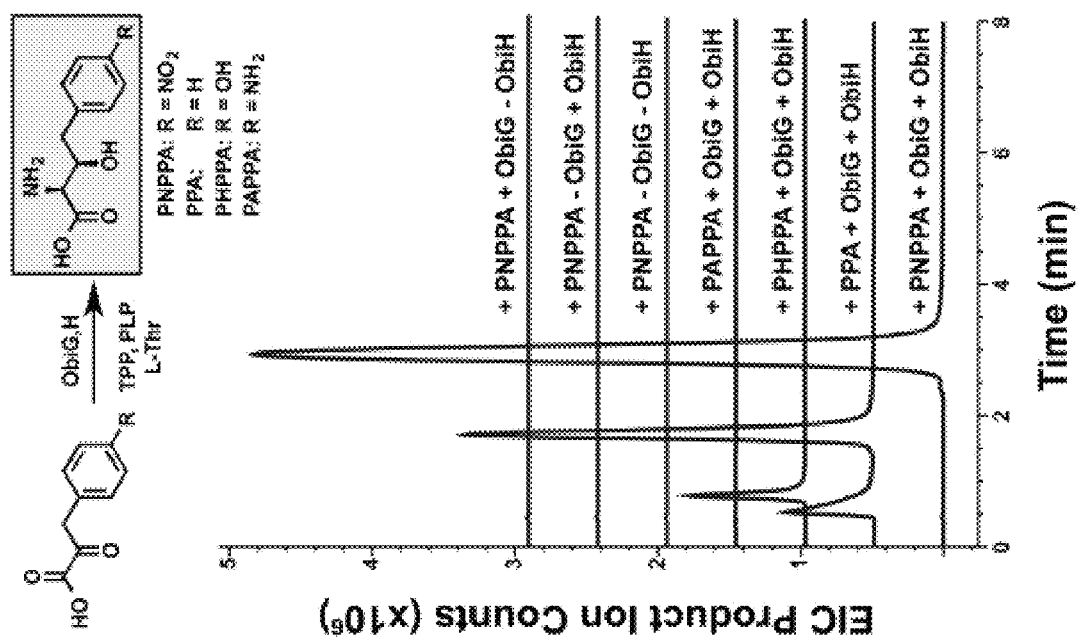
FIG. 2A is a graph summarizing the extracted ion chromatograms (EICs) vs retention time for the predicted products of a double enzyme reaction with ObiG and ObiH.
Figure 2C:
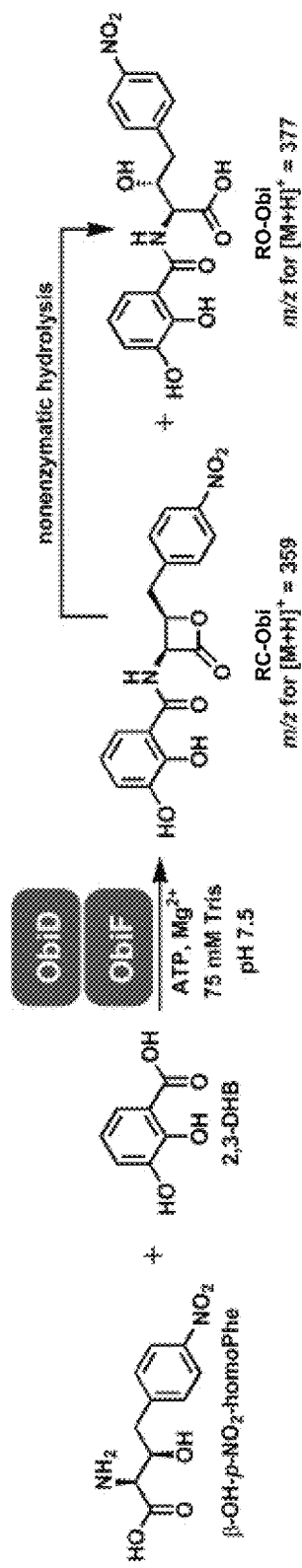
FIG. 2C is a diagram illustrating enzymatic conversion of β-OH-p-$NO_2$-homoPhe and 2,3-DHB to ring-closed obafluorin (RC-Obi, m/z=359 for [M+H]$^+$) and ring-opened obafluorin (RO-Obi, m/z=377 for [M+H]$^+$).

Recombinant NRPS ObiF and acyl carrier protein ObiD convert β-OH-p-NO$_2$-homoPhe and 2,3-DHB into the β-lactone Obi (FIG. 2C). Prior to in vitro enzyme reactions recombinant ObiD and ObiF were primed with 4'-phosphopantetheine transferase (Sfp) to install the phosphopantetheine post-translational modification on the T-domains. Treatment of β-OH-p-NO$_2$-homoPhe and 2,3-DHB with holo-ObiF and holo-ObiD in the presence of ATP/Mg$^{2+}$ gave clean conversion to RC-Obi β-lactone and the corresponding ring-opened hydrolysis product RO-Obi, presumably originating from the non-enzymatic hydrolysis of RC-Obi (see FIG. 2D, FIG. 2E, FIG. 6A, and FIG. 6B).

Figure 7A:
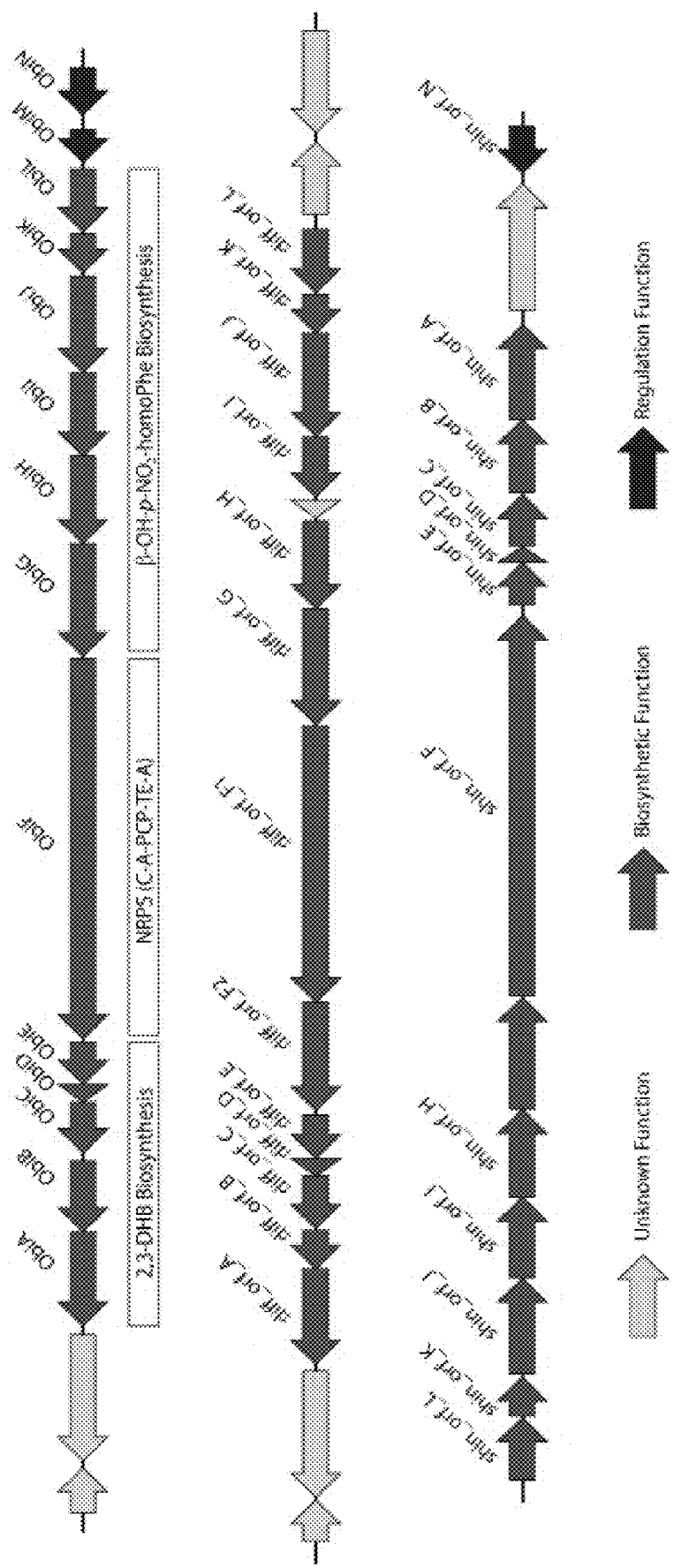
FIG. 7A is an illustration showing the transcriptional alignment of the Obi gene cluster with homologous clusters from environmental bacteria species *Chitinphilus shinanonensis* and the pathogenic bacteria species *Burkholderia diffusa*.
Figure 7B:
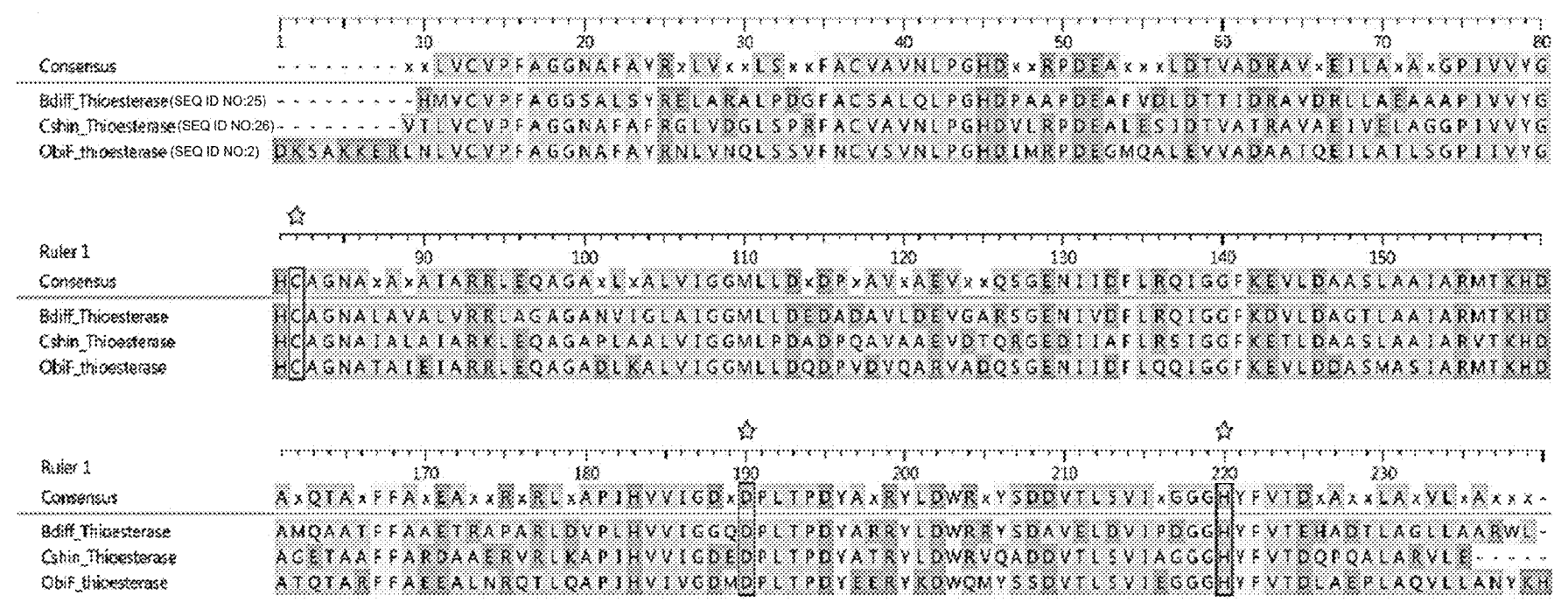

FIG. 7B is an illustration showing the primary amino acid sequence alignments of the NRPS TE domains from the three Obi clusters illustrated in FIG. 7A. TE sequences from P. fluorescens ATCC 39502 (ObiF_thioesterase; GenBank KX134687, SEQ ID NO:2), B. diffusa RF8-non_BP2 (GenBank WP 059467198.1, SEQ ID NO:25), and C. shinanonensis SAY3 (GenBank WP_020608490.1, SEQ ID NO:26) were aligned in MegAlignPro using ClustalW. Amino acid residues are color coded according to side chain chemistry (yellow=aromatic; red=acidic; blue=basic; orange=nonpolar, green=polar). Stars designate the proposed residues of the catalytic triad, which is conserved in all three sequences. The TE domain from ObiF NRPS in the strains Pseudomonas sp. 37 R 15 (GenBank WP 065949343.1) and 34 E 7 (GenBank WP_065936859.1) were identical to the sequence from P. fluorescens and are omitted for clarity.

It was discovered that the ObiF NRPS was the first β-lactone producing assembly line, PKS or NRPS, to include a TE domain in the termination module. Primary sequence analysis of the ObiF TE domain revealed that the expected catalytic serine of the conserved GXSXG motif is replaced by a cysteine at residue 1141 (see FIG. 7B). This mutation has been reported previously for type II TEs, but rarely reported for type I TEs. A GXCXG sequence is present in the pyochelin NRPS TE domain from P. aeruginosa (GenBank AAC83657.1) and the recently crystallized NRPS AB3403 from A. baumannii (GenBank WP_001060991.1; PDB 4ZXI).

FIG. 14A shows a primary sequence alignment of the ObiF (GenBank KX134687, SEQ ID NO:2), AB3403 (GenBank WP_001060991.1, SEQ ID NO:27), and EntF (GenBank AAB40785.1, SEQ ID NO:28) TE-domains generated using ClustalW in MegAlign software. Catalytic triad residues are colored green and conserved residues include black. All three TEs contain the conserved GXS(C)XG motif and the catalytic Ser(Cys)-His-Asp triad. AB3403 and EntF share conserved locations of the catalytic triad while ObiF moves the His-Asp residues to different loops of the protein.

A GXCXG motif in a type I TE-domain was also reported previously in an NRPS from Acinetobacter baumannii (see FIG. 14A) which produces an unknown metabolite implicated in motility, biofilm and pellicle formation which are associated with pathogen virulence. The structure of the A. baumannii NRPS (AB3403) was recently solved by X-ray crystallography and cryo-EM revealing molecular level details of the TE active site and global domain orientation.

A homology model of the ObiF TE domain is illustrated in FIG. 14B, and X-ray crystal structures of the AB3403 and EntF TE domains are illustrated in FIGS. 14C and 14D respectively. Alpha helices are colored cyan, beta-sheets are colored magenta, the lid domains are colored red, and the catalytics Asp-His-Cys(Ser) triads are shown as space filling spheres. ObiF, AB3403, and EntF have homologous secondary structures similar to the majority of type I TE-domains from PKS and NRPS termination modules. The lid domains of ObiF and AB3403 differ from the lid of EntF, but the active sites all orient the Ser(Cys)-His-Asp catalytic triad in a similar manner. The catalytic triad of ObiF is unique from AB3403 and EntF because it is predicted to move the His and Asp residues to unique loops while AB3403 and EntF conserve the locations of these residues.

Figure 14E:
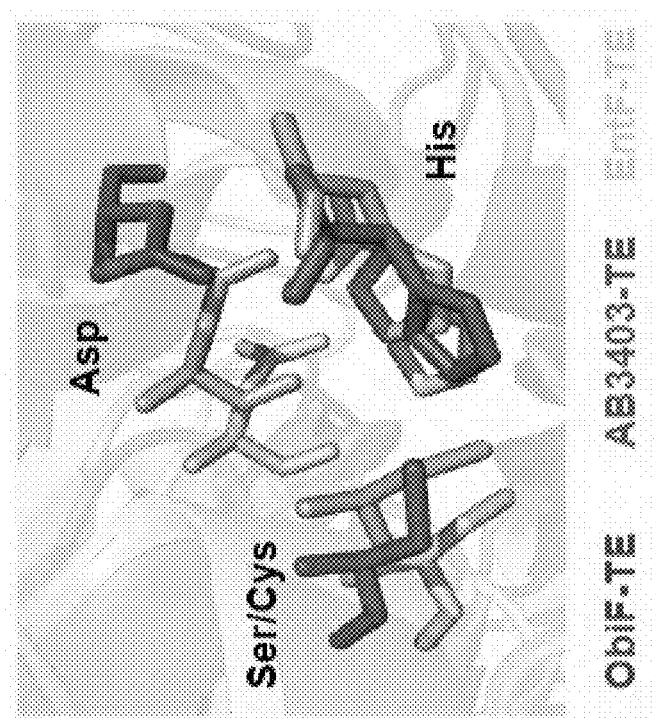
FIG. 14E is an overlay of the ObiF-TE homology model with the X-ray structures of AB3403-TE (PDB 4ZXI) and EntF-TE (PDB 3TEJ).

FIG. 14E illustrates an overlay of the ObiF-TE (FIG. 14B) homology model with the X-Ray structures of AB3403-TE (FIG. 14C) and EntF-TE (FIG. 14D). The catalytic triad of ObiF (red) is unique from AB3403 (light blue) and EntF (yellow). Homology modeling and comparative sequence analysis predicts that the His and Asp residues reside on unique loops of the secondary structure while AB3403 and EntF conserve the locations of these residues. Images of protein secondary structure were generated using PyMOL v1.7 for Mac OS X.

The ObiF, AB3403, and EntF TE-domains have low sequence similarity (FIG. 14A), but all contain a Ser(Cys)-Asp-His catalytic triad and the GXS(C)XG motif characteristic of the hydrolase superfamily. The lid domain of the ObiF TE-domain more closely matches the lid domain of AB3403 TE-domain and both domains possess the active site Cys residue. The catalytic triads of the AB3403 and EntF TEs are located in conserved loops of the secondary structure, while the conserved Asp residue of the ObiF TE is apparently moved from β-sheet 6 to β-sheet 7, but is still predicted to interact with the conserved active site His based on homology modeling.

Figure 2E:
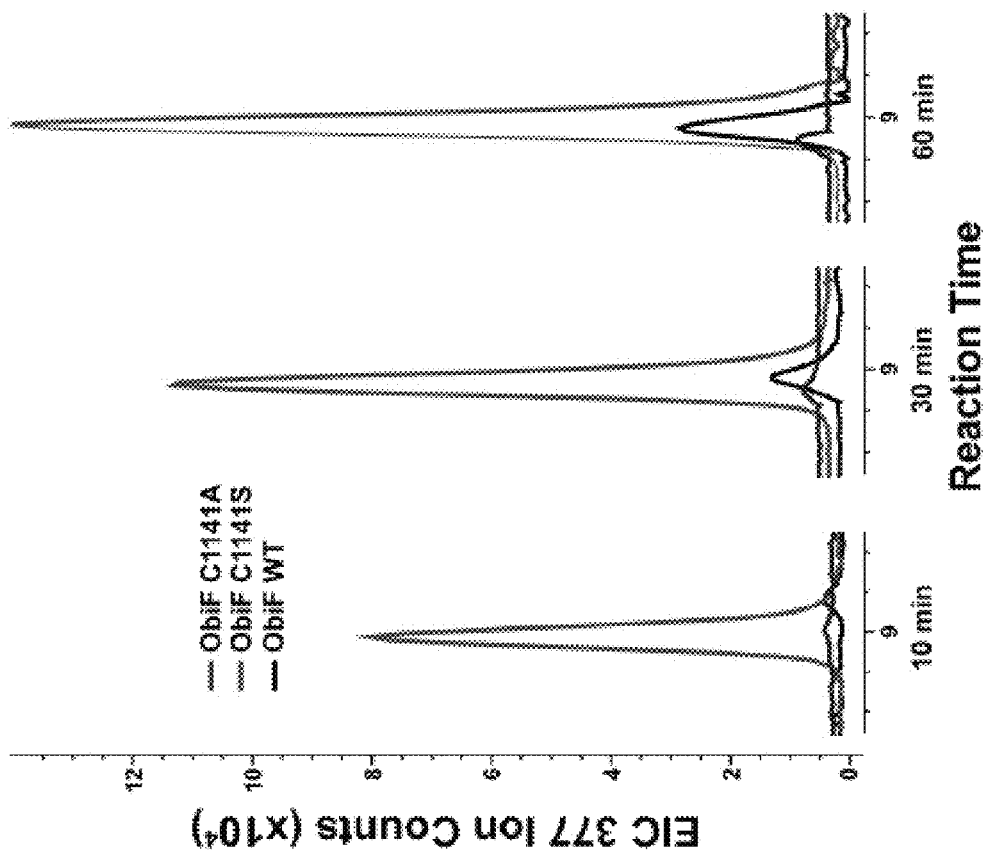
FIG. 2E is a graph summarizing the extracted ion chromatograms (EICs) vs retention time obtained for ring-opened obafluorin (RO-Obi, m/z=377) produced during the two-enzyme reaction summarized in FIG. 2C using three genetic variants of ObiF.
Figure 2D:
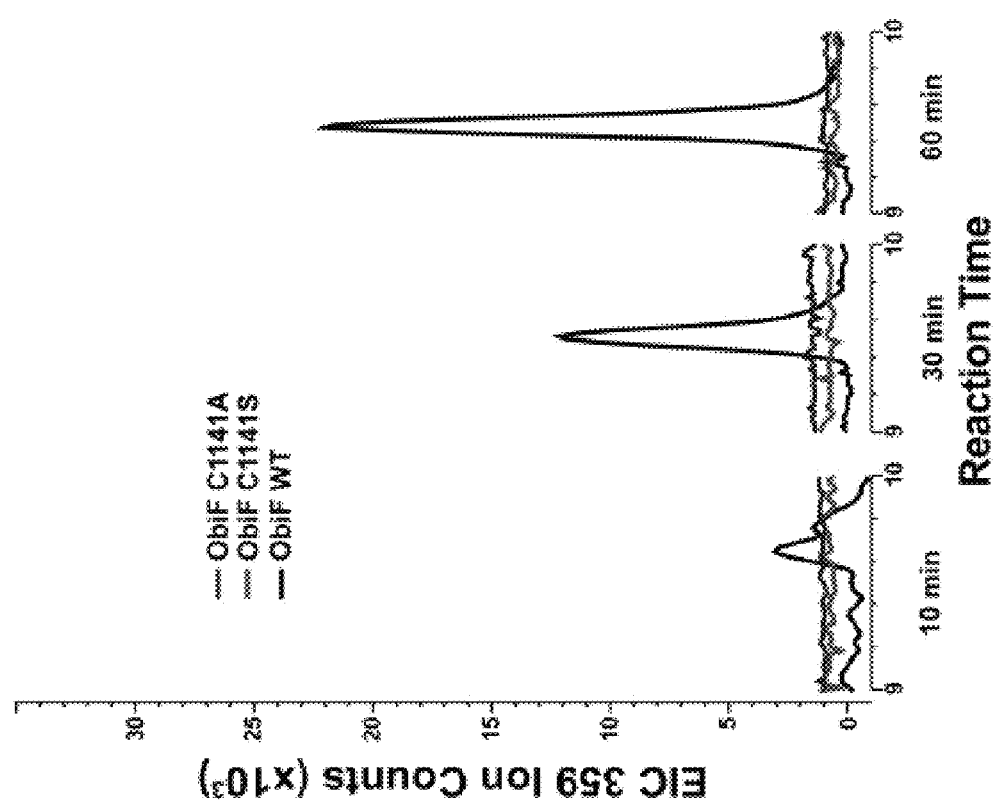
FIG. 2D is a graph summarizing the extracted ion chromatograms (EICs) vs retention time obtained for ring-closed obafluorin (RC-Obi, m/z=359) produced during the two-enzyme reaction summarized in FIG. 2C using three genetic variants of ObiF.

A C1141S mutation converted ObiF from a "β-lactone synthetase" to a hydrolase producing RO-Obi exclusively in the 3-hydroxy acid form (see FIG. 2D and FIG. 2E). A C1141A mutation brought the catalytic activity of ObiF to a near halt with only trace amounts of RO-Obi detected by LC-MS (see FIG. 2D and FIG. 2E). Presumably the penultimate 2,3-DHB-β-OH-p-$NO_2$-homoPhe thioester is stalled on the ObiF T domain since acyl transfer to the TE domain is blocked. The trace RO-Obi detected by LC-MS is predicted to form via slow hydrolysis of the T domain thioester (FIG. 2G). Prolonged exposure (24 hrs.) of the ObiF C1141A mutant gives a steady production of RO-Obi supporting that the NRPS module is functional, but requires slow non-enzymatic hydrolysis of the 2,3-DHB-β-OH-p-$NO_2$-homoPhe-T domain thioester for turnover.

Figure 64:
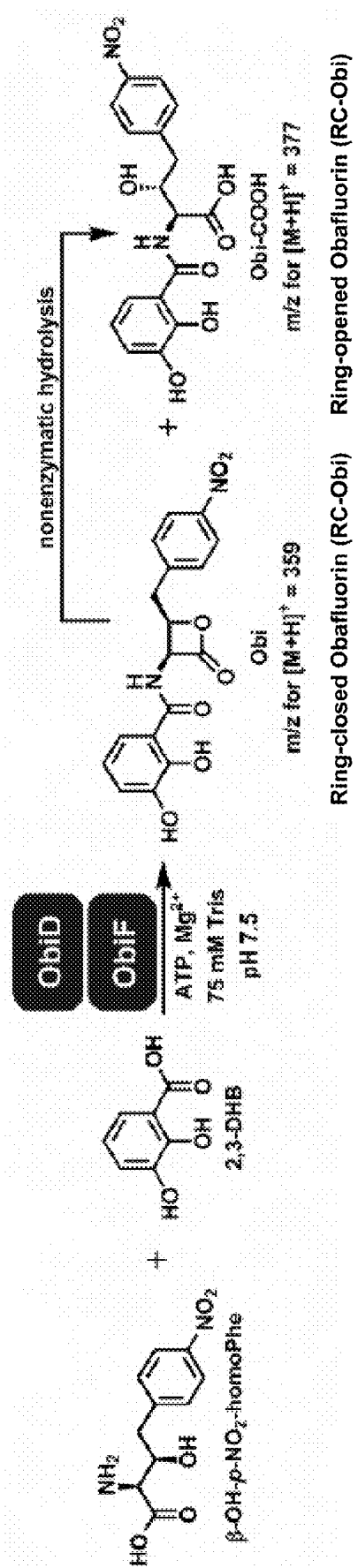

Recombinant ObiF containing a GHCAG motif (FIG. 7B) and ObiD homologues from *C. shinanonensis* SAY3 similarly catalyzed the in vitro conversion of β-OH-p-$NO_2$-homoPhe and 2,3-DHB to RC-Obi with similar efficiency as the *P. fluorescens* enzymes, suggesting that the NRPS module would be functional when expressed in *C. shinanonensis*. FIG. 64 is a chemical reaction diagram showing the production of RC-Obi and RO-Obi using recombinant ObiF and ObiD from *C. shinanonensis* genome. The illustrated scheme shows the conversion of starting materials 2,3-DHB and β-OH-p-NO2-homoPhe to product RC-Obi, which then non-enzymatically hydrolyzes to RO-Obi.

FIGS. 76, 77, 78, and 79 are schematic diagrams showing domain arrangements for ObiF and ObiD from several different sources: *P. fluorescens* ATCC 39502 (GenBank KX134687 and KX134685 (FIG. 76), *B. diffusa* RF8-non_BP2 (GenBank WP_059467198.1, WP_059467197.1, and WP_059467195.1) (FIG. 77), *C. shinanonensis* SAY3 (GenBank WP_020608490.1 and WP_018749564.1) (FIG. 78), and EntF (C-A-T-TE), EntE ($A_A$), and EntB ($T_Ar$) (PDB 5ja1 and 2fq1) (FIG. 79).

The four different NRPSs illustrated in FIG. 76, FIG. 77, FIG. 78, and FIG. 79 show strong homology but flexibility in domain orientation. The *P. fluorescens* and *C. shinanonensis* NRPSs have the $T_{Ar}$ domain responsible for 2,3-DHB transport untethered from the rest of the enzyme. For the NRPS (EntF) of *B. diffusa* and the *E. coli* enterobactin, both the $A_{Ar}$ and $T_{Ar}$ domains responsible for 2,3-DHB adenylation and thioester formation act transiently with respect to the NRPS module.

The ObiF A domains are highly selective for β-OH-p-$NO_2$-homoPhe and 2,3-DHB. Analysis of ObiF with NRPSPredictor2 software predicted that the embedded A-domain would adenylate L-Thr and that the terminal $A_{Ar}$ domain would adenylate 2,3-DHB, as summarized in Table 2 below. Table 2 provides ObiF A domain selectivity predictions using NRPSPredictor2, Stachelhaus code, Minowa, and SeqL algorithms. The specificity-conferring sequence of the embedded ObiF A domain (D/A/W/G/C/G/L/I/N/K) shows similarity to the signature sequences for A domains that activate L-Thr (D/F/W/N/I/G/M/V/H/K) and L-Phe (D/A/W/T/I/A/A/V/C/K), with some key differences that help rationalize selectivity for the sterically larger β-OH-p-$NO_2$-homoPhe substrate. In comparison to L-Phe A domains, Thr at position 4 is changed to a Gly, thereby extending the active site pocket to accommodate the chain extended homoPhe. In comparison to L-Thr A domains, Phe at position 2 is changed to Ala and Asn at position 4 is changed to Gly, which leaves room to accommodate the benzyl group. Both L-Phe and L-Thr A domains have Ile at position 5, which is changed to Cys in ObiF.

Figure 67:
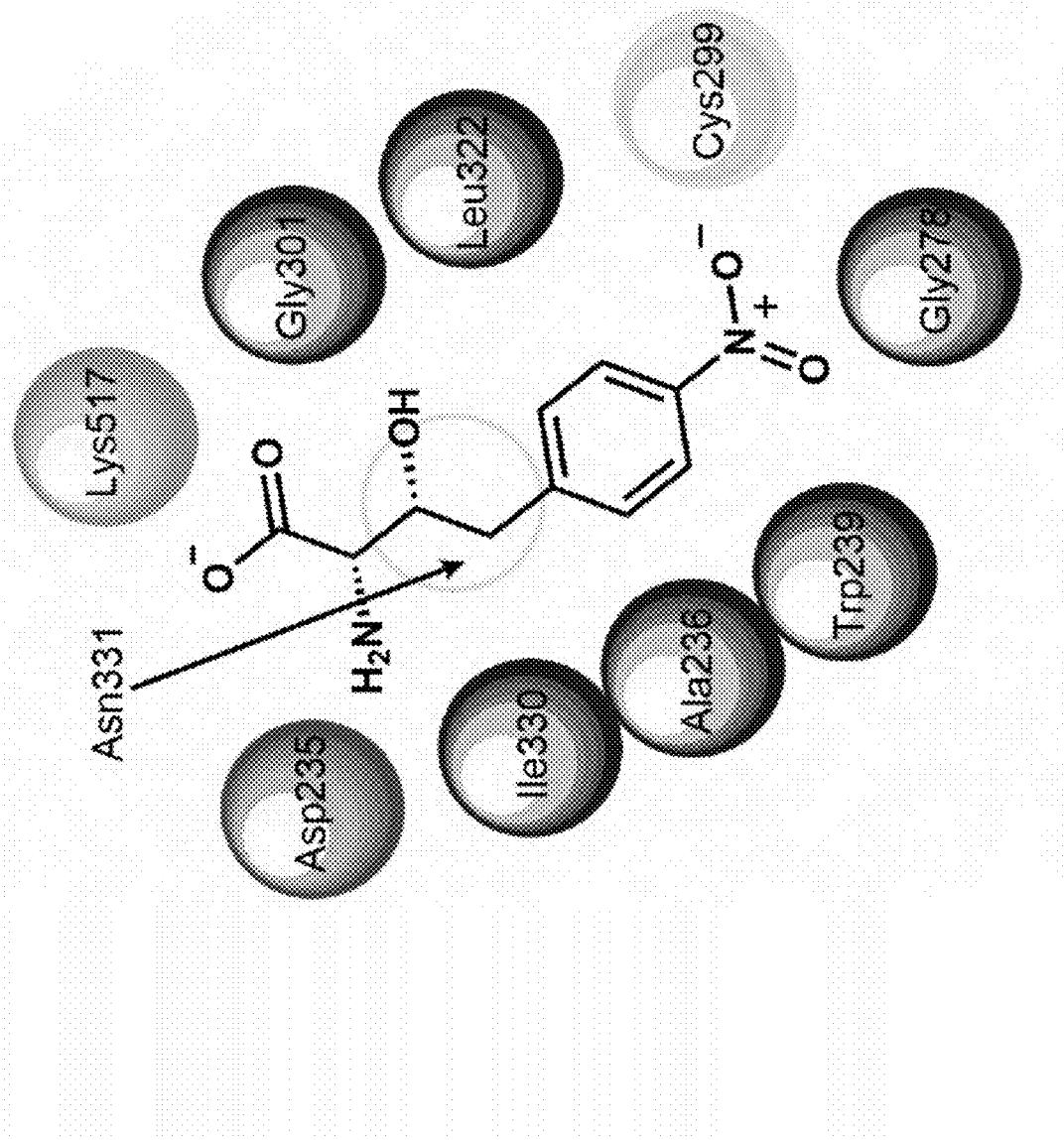

FIG. 67 is a schematic diagram showing a model for β-OH-p-$NO_2$-homoPhe selection by ObiF A domain specificity-conferring code. The ten letter specificity-conferring code for the ObiF-embedded A domain was determined and compared with a previously-published A domain sequence responsible for activating Phe. Several important differences were observed. Thr at position 278 is changed to a glycine, which would extend the pocket allowing added length of the homoPhe group. Additionally, Ile at position 299 is changed to a Cys, which is a potential hydrogen-bonding partner for the NO2 group and might interact with the electron-deficient aromatic ring. When compared to a previously-published A domain that activates Thr, Phe at position 236 is changed to an Ala residue which leaves room to accommodate the benzyl group of β-OH-p-$NO_2$-homoPhe that could occupy the space normally filled with the phenyl group of Phe236. The same I299C change is also a difference between the ObiF A domain and Thr adenylating A domain. β-OH-p-$NO_2$-homoPhe is a novel amino acid and the specificity-conferring code of the ObiF A domain could enhance future prediction of A domain selectivity for large amino acids.

TABLE 2

ObiF A domain substrate prediction

| Cluster[a] | NRPSPredictor2 | Stachelhaus | Minowa | SeqL |
| --- | --- | --- | --- | --- |
| *Burkholderia* | threonine | glutamine | threonine | N5-Hydroxyornithine |
| *Chitiniphilus* | threonine | alanine | threonine | N5-Hydroxyornithine |
| *Pseudomonas* | threonine | glutamine | threonine | N5-Hydroxyornithine |

[a]The full sequences for the *P. fluorescens*, *B. diffusa*, and *C. shinanonensis* obafluorin biosynthetic gene clusters were entered into antiSMASH (antismash.secondarymetabolites.org) for analysis. Adenylation domain selectivity was predicted using NRPSPredictor2[1,2], Stachelhaus code[3], Minowa[4], and SEQL-NRPS[5]. All methods predicted 2,3-DHB as substrate for $A_{Ar}$.

FIG. 67 is a schematic diagram showing a model for β-OH-p-$NO_2$-homoPhe selection by ObiF A domain specificity-conferring code. The ten letter specificity-conferring code for the ObiF-embedded A domain was determined and compared with a previously-published A domain sequence responsible for activating Phe. Several important differences were observed. Thr at position 278 is changed to a glycine, which would extend the pocket allowing added length of the homoPhe group. Additionally, Ile at position 299 is changed to a Cys, which is a potential hydrogen-bonding partner for the NO2 group and might interact with the electron-deficient aromatic ring. When compared to a previously-published A domain that activates Thr, Phe at position 236 is changed to an Ala residue which leaves room to accommodate the benzyl group of β-OH-p-NO$_2$-homoPhe that could occupy the space normally filled with the phenyl group of Phe236. The same I299C change is also a difference between the ObiF A domain and Thr adenylating A domain. β-OH-p-NO$_2$-homoPhe is a novel amino acid and the specificity-conferring code of the ObiF A domain could enhance future prediction of A domain selectivity for large amino acids.

Figure 2K:
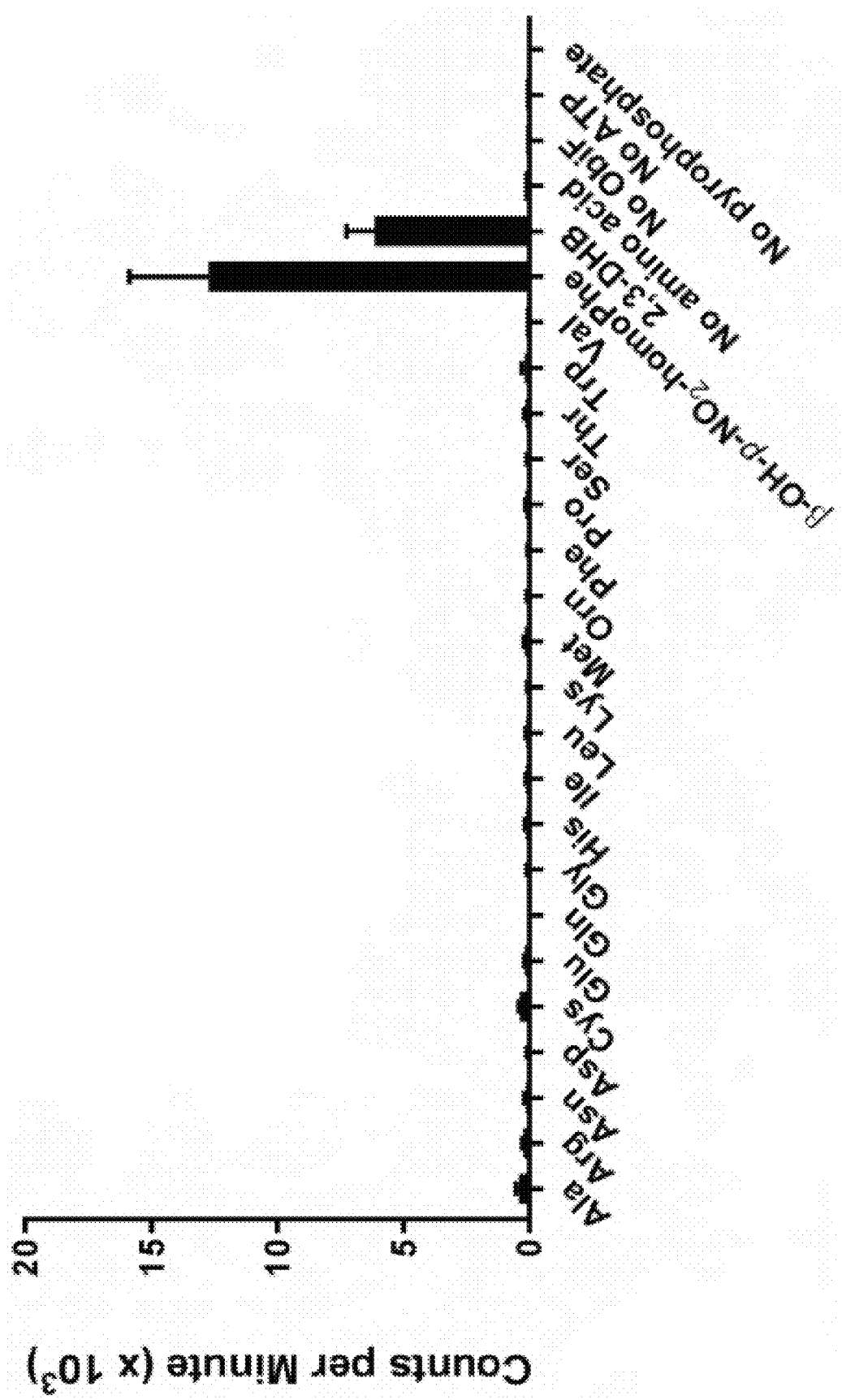
FIG. 2K is a bar graph summarizing ATP-[$^{32}$P]PP$_i$ exchange data for the incubation of recombinant ObiF (directly purified from *E. coli* cell lysates without treatment with Sfp) with [$^{32}$P]PP$_i$, unlabeled ATP, and carboxylate substrate followed by absorption onto activated charcoal.

Without being limited to any particular theory, the Cys in ObiF may interact favorably with the electron deficient nitro-phenyl group (FIG. 67). The ATP-[32P]PPi exchange assay, which tests for reversible acyl adenylate intermediate formation, was used in Example 11 to show that ObiF was highly selective for activating β-OH-p-NO$_2$-homoPhe and 2,3-DHB as acyl adenylates (FIG. 2K). Proteinogenic amino acids, including the β-hydroxy (L-Thr and L-Ser) and aromatic (L-Phe) amino acids, gave signals comparable to the control further supporting the high selectivity of the ObiF A domains for activating the non-proteinogenic amino acid β-OH-p-NO2-homoPhe and 2,3-DHB (FIG. 2K).

Role of Cys1141 of ObiF in β-lactone Biosynthesis

It was discovered that the ObiF TE-domain has a direct role in the formation of the Obi J-lactone ring as the final biosynthetic step releasing the mature cyclized product from the NRPS assembly line (FIG. 3B). The ObiF 2,3-DHB-β-OH-p-NO$_2$-homoPhe-T-thioester is shuttled from the T domain and loaded to the TE domain via transthioesterification where it resides as the C1141 thioester and undergoes C3-OH to C1 cyclization to release Obi β-lactone. Mutations of Ser to Cys have been previously reported to make deacylation of the TE active site rate limiting.

FIG. 3B is a schematic illustration showing a mechanistic model for β-lactone ring during antibiotic cleavage from the ObiF NRPS assembly line. The catalytic triad (Cys$_{1114}$-His$_{1297}$-Asp$_{1267}$) and oxyanion hole (Gly$_{1119}$-Gly$_{1141}$) of the ObiF TE domain are shown in red. His$_{1297}$ is predicted to assist in the deprotonation of Cys$_{1141}$ during attack of the thiolate on the Obi T-domain thioester to form the stabilized tetrahedral intermediate (I). Breakdown of the tetrahedral intermediate results in the Obi TE domain thioester of Cys$_{1141}$ and the free T domain thiol, completing the transthioesterification. His$_{1297}$ is predicted to assist in deprotonating the 3-hydroxyl group during nucleophilic addition to the C1-thioester carbonyl forming the stabilized 4-membered tetrahedral intermediate (III). Breakdown of the tetrahedral intermediate forms the RC-Obi β-lactone and regenerates the Cys$_{1141}$ thiol (IV). Release of RC-Obi completes turnover of ObiF and opens the TE domain for a new Obi T domain thioester for another round of transthioesterification and β-lactone ring formation (V).

Without being limited to any particular theory, in the case of β-lactone formation, the weaker C—S bond of the thioester compared to the C—O bond of an oxoester is likely required to make strained ring formation thermodynamically favorable. Further, slowing the rate of deacylation increases the dwell time of the C1141-thioester, which may play a role in making cyclization competitive with hydrolysis. Substrate preorganization has been reported previously to be an important factor in NRPS and PKS TE-mediated macrocyclizations, and influence the ring size tolerance of the cyclization.

Because the thermodynamic requirements for β-lactone formation are not met by the oxoester intermediate created by the ObiF-C1141S mutant, only the hydrolysis product RO-Obi accumulates (FIG. 2E). The ObiF-C1141A mutant also fails to generate detectable concentrations of RC-Obi β-lactone, which confirms the role of TE catalysis in β-lactone ring formation. As demonstrated in Example 14, the rate of hydrolysis of N-acetylcysteamine (SNAC) thioester (Obi-SNAC) was comparable to that of the ObiF-C1141A mutant (FIG. 2E and FIG. 38C), which further supports the role of the ObiF TE domain as a catalyst for β-lactone ring formation. TE domains have been used as autonomous catalysts on preparative scale for the cyclization of peptide substrates.

Modifications of Obi Biosynthesis Method

The "beta-lactone synthetase" identified in the Obi gene cluster is a type I α/β hydrolase TE domain that is part of an NRPS module (ObiF). TE Domains are a highly diverse family of α/β hydrolases that employ a variety of antibiotic release strategies including hydrolysis and macrocyclization. Without being limited to any particular theory, general features identified by the characterization of the Obi NRPS TE domain may be genetic and biochemical signatures associated with β-lactone biosynthesis. The presence of an active site Cys residue in the GXCXG motif of a type I TE is a feature associated with β-lactone ring formation that ensure a thermodynamically favorable scenario for strained ring formation proceeding through a more reactive thioester as compared to the traditional oxoester intermediate encountered during TE-mediated off-loading of NRPS products in other biosynthetic processes.

Amongst the type I TE domains, GXCXG motifs with an active site Cys instead of Ser are rare. Analysis of the thioesterase protein family (PF00975, European Bioinformatics Institute) revealed that 264 out of 3863 members (6.8%) contained a GXCXG, while the remaining 93.2% contained a GXSXG motif. Analysis of the top 20,000 hits from standard protein BLAST search of the full ObiF sequence against non-redundant protein sequences in the NCBI database revealed that 13,944 sequences possessed a GXSXG motif, 1,240 sequences contained a GXCXG motif, and 194 sequences contained a GHCXG motif. The ObiF TE domains from *P. fluorescens*, *C. shinanonesis*, and *B. diffusa* as reported all contain a GHCAG motif and show >50% total sequence homology (FIG. 7B). The ObiF TE domains are sequence unique compared to a diverse sampling of PKS and NRPS type I and type II TE domains including the TE-domains of the pyochelin and AB3403 NRPS modules that contain a GXCXG motif.

Homology modeling of the ObiF TE domain with the EntF (19% sequence similarity) and AB3403 (20% sequence similarity) TE-domains (see FIG. 14A) revealed similarities in the secondary structure with clear differences in the location of the Ser/Cys-His-Asp catalytic triads (see FIG. 14B, FIG. 14C, and FIG. 14D). The catalytic triads of the AB3403 and EntF TEs are located in conserved sites of the β-α-β repeat secondary structure consistent with canonical type I α/β hydrolases. The conserved Asp residue of the ObiF TE is apparently moved from β-strand 6 to β-strand 7, but is still predicted to interact with the conserved active site His in the catalytic triad.

Figure 41:
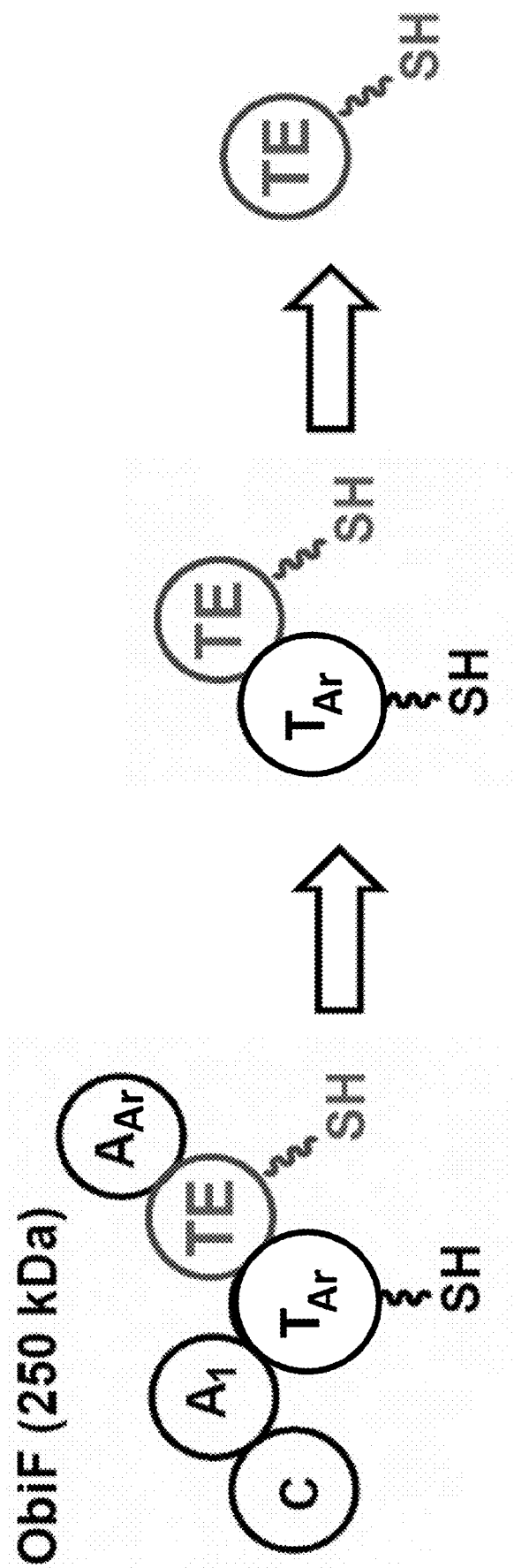
FIG. 41 is a schematic diagram showing a modification of the RC-Obi biosynthetic process by removal of domains from ObiF.

Inclusion of the 2,3-DHB-activating A$_{Ar}$ domain as part of the ObiF NRPS module (see FIG. 41) appears to be optional, as illustrated in FIGS. 76, 77, 78, and 79. In the *P. fluorescens* and *C. shinanonesis* ObiF NRPSs the A$_{Ar}$ domain is included in the primary sequence of the assembly as the last catalytic domain. In the *B. difusa* NRPS, the A$_{Ar}$ domain is predicted to be a stand-alone enzyme that activates 2,3-DHB as the acyl adenylate for transfer to the $T_{Ar}$ carrier protein in analogy to the enterobactin NRPS machinery (EntFEB). An MbtH domain is encoded in the ObiF primary sequence between the TE and $A_{Ar}$ domains (see FIG. 3D). The MbtH-like protein YbdZ is encoded in the enterobactin biosynthetic gene cluster and has been shown to enhance the adenylation activity of EntF44. The ObiF MbtH-like domain might play a similar role as YbdZ. Further, as illustrated in FIG. 3D, biosynthesis of the β-lactone antibiotic obafluorin proceeds through β-OH-p-$NO_2$-homoPhe and 2,3-DHB intermediates. Functional studies reveal that NRPS ObiF uses a type I thioesterase domain to catalyze cyclization of a β-hydroxy thioester to the corresponding β-lactone during antibiotic cleavage from the illustrated assembly line.

Recent published structural and biophysical studies of NRPS modules with C-A-T-TE domains have provided insight into the motions and dynamics of individual domains during coordinated catalysis by the enzyme assembly lines. The TE domain is predicted to be highly dynamic and distal from the T domain until invoked for final release of the antibiotic. In the case of ObiF, this would leave $A_{Ar}$ free to catalyze the formation of the 2,3-DHB acyl adenylate and keep the $T_{Ar}$ carrier protein loaded as a 2,3-DHB phosphopantetheinyl thioester. In the case of enterobactin biosynthesis, the $A_{Ar}$ and $T_{Ar}$ domains, EntE and EntB, respectively, are separate from the main NRPS module, EntF, which activates and loads Ser as a T domain phosphopantetheinyl thioester. The full length EntF is required for trimerization of Ser, amide bond formation with 2,3-DHB, and cyclization to the macrolactone. Thus, only $A_{Ar}$ and $T_{Ar}$ domains have been shown to be active in trans supporting the existence of ObiF NRPS modules with and without the $A_{Ar}$ domain as part of the main NRPS module (see FIG. 41).

Without being limited to any particular theory, other catalytic domains with active site Cys residues might be capable of catalyzing the cyclization of β-hydroxy thioesters to β-lactones. For example, it was previously reported that an uncharacterized ketosynthase (KS) domain resides at the C-terminus of the ebelactone PKS termination module. KS-Domains are reported to undergo transthioesterification reactions with T-domain thioesters to form an intermediate KS Cys thioester that is part of a conserved Cys-His-His triad. The KS Cys-His-His triad typically catalyzes thio-Claisen condensation with a malonyl T domain thioester, but might also be capable of β-lactone ring formation. The termination module of the hybrid PKS-NRPS assembly line for oxazolomycin features a C-terminal C domain of unknown function. Condensation domains typically catalyze amide bond formation between two T domain thioesters, but there are previously documented cases of C domains catalyzing cyclization during product release such as in cyclosporin A and enniatin biosynthesis. The terminal C-domain of the oxazolomycin assembly line might catalyze the intramolecular condensation of a T domain thioester to the spirocyclic β-lactone. The salinosporamide biosynthetic gene cluster encodes for several uncharacterized enzymes including a stand-alone KS domain, SalC, and a type 11 thioesterase, SalF4. SalF contains a GXSXG catalytic motif and has been proposed to be involved in proofreading, which might indicate a role as a classic hydrolase. The KS domain SalC could be involved in formation of the cis-fused bicyclic β-lactone or the salinosporamides might experience the same fate as the closely related lactacystin, which is cleaved from the assembly line as an N-acetylcystein thioester and non-enzymatically equilibrates with the β-lactone in solution.

The presence of genes encoding for a pyruvate decarboxylase and threonine aldolase simultaneously in a biosynthetic gene cluster may also serve as a genetic signature for β-hydroxy-α-amino acid production. Fe(II)/α-KG-dependent oxygenases and non-heme di-iron oxygenases are known to produce β-hydroxy-α-amino acids via direct C—H bond activation chemistry. The direct hydroxylation of amino acid side chains take place while loaded as phosphopantetheinyl thioesters on NRPS T domains. This makes A domain substrate prediction insufficient for the potential incorporation of β-hydroxy-α-amino acids into NRP scaffolds.

The Obi β-lactone scaffold represents a novel structural class of β-lactone antibiotics from nature's chemical inventory. The Obi biosynthetic machinery characterized in this study offers a versatile platform for the chemoenzymatic synthesis of β-lactones from β-hydroxy α-amino acid precursors. Here, the novel amino acid β-OH-p-$NO_2$-homoPhe was produced by the tandem action of arylamine oxidase ObiL, phenylpyruvate decarboxylase ObiG, and threonine aldolase ObiH, which might represent a general strategy for producing β-hydroxy-α-amino acid precursors to peptide β-lactones. The Obi NRPS biosynthetic machinery, ObiF and ObiD, contains a sequence novel TE domain with a rare catalytic Cys residue that plays a direct role in β-lactone ring formation.

In an aspect, β-hydroxy-α-amino acids may be directly incorporated into peptide scaffolds on an NRPS assembly line leading to peptides capped at the C-terminus with a β-lactone warhead. The genetic and biochemical characterization of the Obi biosynthetic pathway in *P. fluorescens* described herein serves as a basis for expanding the known chemistry of NRPS and PKS product release mechanisms to include strained ring formation. In various aspects, the chemoenzymatic approach to the biosynthesis of C-terminal β-lactone peptides may be modified as described above to enable precursor-directed process modifications and NRPS engineering to develop biosynthetic methods for producing a variety of targeted peptide i-lactone inhibitors of proteases for the treatment of diseases associated with microbial and viral infections, cancer, and/or obesity.

Methods of Producing of i-Lactone Peptides

In various aspects, at least one of the isolated and purified enzymes encoded by the Obi gene cluster may be incorporated into a method for producing a peptide beta-lactone from one or more precursor compounds. The method makes use of the biosynthetic pathways and enzymes disclosed herein associated with the production of RC-Obi (see FIG. 3C). In an aspect, the method for producing a peptide beta-lactone is implemented in vitro using existing devices and/or systems. Non-limiting examples of suitable devices and/or systems include single batch reactors including stirred batch reactors, semi-batch reactors, a series of two or more connected batch reactors, a continuous flow reactor, a trickle-bed reactor, and any other suitable device and/or system known in the art.

In various aspects, the isolated and purified enzymes incorporated into the method of producing peptide beta-lactones may be any one or more enzymes encoded by the Obi gene cluster of *Pseudomonas fluorescens* as well as variants of the one or more enzymes including, but not limited to, homologous enzymes from other *Pseudomonad* species including the environmental chitin-degrading bacterium *Chitiniphilus shinanonensis* and the plant growth-promoting rhizobacterium *Burkholderia diffusa*. In another aspect, the enzymes used in various aspects of the method may be modified to enhance enzyme activity for a particular substrate and/or to maintain activity for a wider variety of substrates.

The number of enzymes incorporated into the method in various aspects may vary depending on one or more of at least several factors including, but not limited to, the precursor compounds used to produce the peptide beta-lactones using the method and/or any modifications to the enzymes used in the method. In one aspect, the method of producing a peptide beta-lactone may include a number of enzymes encoded by the Obi gene cluster ranging from one enzyme to about 11 enzymes or more.

In various aspects, the enzymes incorporated into the method of producing peptide beta-lactones may be isolated and purified enzymes obtained by isolation from one or more cell cultures that contain cells that express one or more of the enzymes used in the method. In one aspect, the cell cultures may contain cells that express the one or more enzymes as describe herein above including, but not limited to *Pseudomonas fluorescens* cells, *Chitiniphilus shinanonensis* cells, and *Burkholderia diffusa* cells. In another aspect, the cell cultures may include transgenic cells including, but not limited to, transgenic *E. coli* and yeast cells in which at least a portion of the Obi gene cluster expressing one or more of the enzymes associated with RC-Obi biosynthesis forms have been introduced. In an aspect, at least a portion of the Obi gene cluster introduced into the transgenic cell may be modified using known methods in order to enhance the efficiency of enzyme expression.

In one aspect, the isolated enzymes may be one or more enzymes encoded by at least a portion of the Obi gene cluster. Suitable enzymes may include the enzymes associated with biosynthesis as listed in Table 3 below:

TABLE 3

Sequences of RC-Obi Biosynthesis Enzymes

| Gene | Protein | Protein sequence |
|---|---|---|
| obiD (SEQ ID NO: 1) | Aryl carrier protein (ArCP) (EntB) | MTQGKLIYDKADFYAEIAAILRIPTEELAELE SPQEAGVDSVRLLTLSEKWRKRGIDVSFMELA ERPGFTAWWELLSARMPVTECEQP |
| obiF (SEQ ID NO: 2) | NRPS w/ C-A-T-TE-A domains (EntF + EntE) | MSASFTTALTSAQQSIWMGHQFDPQSPAYNVA SYIEMSGDIDPQRLQHALQRAVDDIEALRARF HEDETQGGALTQTILAQVAVELNVFAVDAEQA RSWMESDLARPTDLTSGPIFSSALLQVAPNVN YWYFKTHHIVMDGVALSMLFKRVADLYGQAPD ALCSPSPFGSVRQVLENEQAWRASPFAQDREF WQQHCQDMAEVASLNSDVAQPSYQAIQHRRVL DESIMASLRERAEAMDSQWVNVLLAAFGAFVG RSTGYRQVTVGVPMMNRFATGAINVPCTLANV LPLRLDIKPGQSVEQLVASVQAQLDRMRPHQR YRAEDIRRDCNLLGDNRRLTGPQINIDFFSAK LSFDGVPGEVNVLSAGPADDLSLLIQTPADDK TLNIIAMANPALYSRAALERHVQRFIDFVERF AAASDTPLGQLDAYDATDPGYAQGNACFSPVN QAHTLAQTLVERFERAVHATPDAIALTFNGEH LTYQALNQRANRLAHLIQDQTGQTSPQPVALL LARSVQTFVCILGVLKAGAHYVPLDPDAPAER ITTILEDTCPTLVICDQSSQALVSGSDVKVMV IDTPSCMDAVQQQSIDNLQSGPRANDLAYIIY TSGSTGKPKGVCITHHNVVRLFENTHHWFDYR SSDVWTACHGYIFDASVWEMWGAFAHGGRLVL VPVDTTRDPEKLLELVVQEQVTVFGQIPSAFY RFMEAQADQPALAARLNLRYQCFGGEALDLSR LKPWFEHYGHSRTRLLNLYGITETTINATYQF VTLEQVQTNQGSLIGTVYDDLDIKVLDDALRP VPVGGYGEMYVRGAGLARGYLNRQDLDATRFV ADPFGAPGERMYRSGDVAALQEGGVLEYIGRA DQQVKVRGYRIELGEIETQLRGHPLLSDAIAL VVTDASGDPKLVAHVVPKATCRCEDIDTAQVR DYLRERLPSYMVPGAIGVQERLPVTLSGKVDR KALPTIALSGARQVEAPRDELDERVLAAWSEQ LEIDTLGIDDNFFDIGGDSIKAIRICRDLGLP VTELFDHPTPRANADYLRDHQDNDAQGAVNWL HAFDKSAKKERLNLVCVPFAGGNAFAYRNLVN QLSSVFNCVSVNLPGHDIMRPDEGMQALEVVA DAATQEILATLSGPIIVYGHCAGNATAIEIAR RLEQAGADLKALVIGGMLLDQDPVDVQARVAD QSGENIIDFLQQIGGFKEVLDDASMASIARMT KHDATQTARFFAEEALNRQTLQAPIHVIVGDM DPLTPDYEERYKDWQMYSSDVTLSVIEGGGHY FVTDLAEPLAQVLLANYKHLNPVVPVRAPRAL RAFHNPFDDVEGRFSLLANDARQLSLWPEFAP TPAGWTALFGPASHSECLARTQAYDHEALISP PAPTEGLDAPYWPEAFESRYRASGWWTGETLG AILTRHALLAPQRVAVTDGDRNLSYSQLDSNA DRIADGFATLGVKAGDRVVVQLPNSMEFIETI FGLFRLGAIPVFALPSDRLNEITHIFEISGAI AYVIKDQALGFDYRRIATELTQQIASIKQVIV VGDAEGFVPFANLYGRTAAWPQRSSREPALIT LSGGSTALPKLILRRHDDYLYSFKASARICQL DSDSVYLCVLPAGHNFTLSSPGFLGVLYAGGR VVMTSDPSGSGAFALIERERVTLTSVVPSLAQ AWLHSSRDHDLSSLQLLQVGGARLSDDVAERL ATSFDCQLQQVYGMSEGLVCYTAVGDTEEHVL HTQGRPISSGDEILIVDENDEPVANGVAGQLL VRGPYTIRGYLNAPEHNARAFTPDGFYRTGDV VVFRDDGYLVVTGRIKDQVNRGGEKIAAEEIE GYLLAHPGVLEAGIIGLPDEYLGEVSCAVVVL APGAQLTASALKSFVRQQGIAAFKVPDQVHLV PSLPKTTLGKIDKKLLRVQLGQ |
| obiF-C1141A (SEQ ID NO: 6) | NRPS w/ C-A-T-TE-A domains (EntF + EntE) | MSASFTTALTSAQQSIWMGHQFDPQSPAYNVA SYIEMSGDIDPQRLQHALQRAVDDIEALRARF HEDETQGGALTQTILAQVAVELNVFAVDAEQA RSWMESDLARPTDLTSGPIFSSALLQVAPNVN YWYFKTHHIVMDGVALSMLFKRVADLYGQAPD LCSPSPFGSVRQVLENEQAWRASPAFAQDREF WQQHCQDMAEVASLNSDVAQPSYQAIQHRRVL DESIMASLRERAEAMDSQWVNVLLAAFGAFVG RSTGYRQVTVGVPMMNRFATGAINVPCTLANV LPLRLDIKPGQSVEQLVASVQAQLDRMRPHQR YRAEDIRRDCNLLGDNRRLTGPQINIDFFSAK LSFDGVPGEVNVLSAGPADDLSLLIQTPADDK TLNIIAMANPALYSRAALERHVQRFIDFVERF AAASDTPLGQLDAYDATDPGYAQGNACFSPVN QAHTLAQTLVERFERAVHATPDAIALTFNGEH LTYQALNQRANRLAHLIQDQTGQTSPQPVALL LARSVQTFVCILGVLKAGAHYVPLDPDAPAER ITTILEDTCPTLVICDQSSQALVSGSDVKVMV IDTPSCMDAVQQQSIDNLQSGPRANDLAYIIY TSGSTGKPKGVCITHHNVVRLFENTHHWFDYR SSDVWTACHGYIFDASVWEMWGAFAHGGRLVL VPVDTTRDPEKLLELVVQEQVTVFGQIPSAFY RFMEAQADQPALAARLNLRYQCFGGEALDLSR LKPWFEHYGHSRTRLLNLYGITETTINATYQF VTLEQVQTNQGSLIGTVYDDLDIKVLDDALRP VPVGGYGEMYVRGAGLARGYLNRQDLDATRFV ADPFGAPGERMYRSGDVAALQEGGVLEYIGRA DQQVKVRGYRIELGEIETQLRGHPLLSDAIAL VVTDASGDPKLVAHVVPKATCRCEDIDTAQVR DYLRERLPSYMVPGAIGVQERLPVTLSGKVDR KALPTIALSGARQVEAPRDELDERVLAAWSEQ LEIDTLGIDDNFFDIGGDSIKAIRICRDLGLP VTELFDHPTPRANADYLRDHQDNDAQGAVNWL HAFDKSAKKERLNLVCVPFAGGNAFAYRNLVN QLSSVFNCVSVNLPGHDIMRPDEGMQALEVVA DAATQEILATLSGPIIVYGHAAGNATAIEIAR RLEQAGADLKALVIGGMLLDQDPVDVQARVAD QSGENIIDFLQQIGGFKEVLDDASMASIARMT KHDATQTARFFAEEALNRQTLQAPIHVIVGDM DPLTPDYEERYKDWQMYSSDVTLSVIEGGGHY FVTDLAEPLAQVLLANYKHLNPVVPVRAPRAL RAFHNPFDDVEGRFSLLANDARQLSLWPEFAP |

TABLE 3-continued

Sequences of RC-Obi Biosynthesis Enzymes

| Gene | Protein | Protein sequence |
|---|---|---|
| | | TPAGWTALFGPASHSECLARTQAYDHEALISP PAPTEGLDAPYWPEAFESRYRASGWWTGETLG AILTRHALLAPQRVAVTDGDRNLSYSQLDSNA DRIADGFATLGVKAGDRVVVQLPNSMEFIETI FGLFRLGAIPVFALPSDRLNEITHIFEISGAI AYVIKDQALGFDYRRIATELTQQIASIKQVIV VGDAEGFVPFANLYGRTAAWPQRSSREPALIT LSGGSTALPKLILRRHDDYLYSFKASARICQL DSDSVYLCVLPAGHNFTLSSPGFLGVLYAGGR VVMTSDPSGSGAFALIERERVTLTSVVPSLAQ AWLHSSRDHDLSSLQLLQVGGARLSDDVAERL ATSFDCQLQQVYGMSEGLVCYTAVGDTEEHVL HTQGRPISSGDEILIVDENDEPVANGVAGQLL VRGPYTIRGYLNAPEHNARAFTPDGFYRTGDV VVFRDDGYLVVTGRIKDQVNRGGEKIAAEEIE GYLLAHPGVLEAGIIGLPDEYLGEVSCAVVVL APGAQLTASALKSFVRQQGIAAFKVPDQVHLV PSLPKTTLGKIDKKLLRVQLGQ |
| obiF-C1141S (SEQ ID NO: 7) | NRPS w/ C-A-T-TE-A domains (EntF + EntE) | MSASFTTALTSAQQSIWMGHQFDPQSPAYNVA SYIEMSGDIDPQRLQHALQVAPKQDIEALRARF HEDETQGGALTQTILAQVAVELNVFAVDAEQA RSWMESDLARPTDLTSGPIFSSALLQVAPNVN YWYFKTHHIVMDGVALSMLFKRVADLYGQAPD LCSPSPFGSVRQVLENEQAWRASPAFAQDREF WQQHCQDMAEVASLNSDVAQPSYQAIQHRRVL DESIMASLRERAEAMDSQWVNVLLAAFGAFVG RSTGYRQVTVGVPMMNRFATGAINVPCTLANV LPLRLDIKPGQSVEQLVASVQAQLDRMRPHQR YRAEDIRRDCNLLGDNRRLTGPQINIDFFSAK LSFDGVPGEVNVLSAGPADDLSLLIQTPADDK TLNIIAMANPALYSRAALERHVQRFIDFVERF AAASDTPLGQLDAYDATDPGYAQGNACFSPVN QAHTLAQTLVERFERAVHATPDAIALTFNGEH LTYQALNQRANRLAHLIQDQTGQTSPQPVALL LARSVQTFVCILGVLKAGAHYVPLDPDAPAER ITTILEDTCPTLVICDQSSQALVSGSDVKVMV IDTPSCMDAVQQQSIDNLQSGPRANDLAYIIY TSGSTGKPKGVCITHHNVVRLFENTHHWFDYR SSDVWTACHGYIFDASVWEMWGAFAHGGRLVL VPVDTTRDPEKLLELVVQEQVTVFGQIPSAFY RFMEAQADQPALAARLNLRYQCFGGEALDLSR LKPWFEHYGHSRTRLLNLYGITETTINATYQF VTLEQVQTNQGSLIGTVYDDLDIKVLDDALRP VPVGGYGEMYVRGAGLARGYLNRQDLDATRFV ADPFGAPGERMYRSGDVAAELGQVLEYIGRA DQQVKVRGYRIELGEIETQLRGHPLLSDAIAL VVTDASGDPKLVAHVVPKATCRCEDIDTAQVR DYLRERLPSYMVPGAIGVQERLPVTLSGKVDR KALPTIALSGARQVEAPRDELDERVLAAWSEQ LEIDTLGIDDNFFDIGGDSIKAIRICRDLGLP VTELFDHPTPRANADYLRDHQDNDAQGAVNWL HAFDKSAKKERLNLVCVPFAGGNAFAYRNLVN QLSSVFNCVSVNLPGHDIMRPDEGMQALEVVA DAATQEILATLSGPIIVYGHSAGNATAIEIAR RLEQAGADLKALVIGGMLLDQDPVDVQARVAD QSGENIIDFLQQIGGFKEVLDDASMASIARMT KHDATQTARFFAEEALNRQTLQAPIHVIVGDM DPLTPDYEERYKDWQMYSSDVTLSVIEGGGHY FVTDLAEPLAQVLLANYKHLNPVVPVRAPRAL RAFHNPFDDVEGRFSLLANDARQLSLWPEFAP TPAGWTALFGPASHSECLARTQAYDHEALISP PAPTEGLDAPYWPEAFESRYRASGWWTGETLG AILTRHALLAPQRVAVTDGDRNLSYSQLDSNA DRIADGFATLGVKAGDRVVVQLPNSMEFIETI FGLFRLGAIPVFALPSDRLNEITHIFEISGAI AYVIKDQALGFDYRRIATELTQQIASIKQVIV VGDAEGFVPFANLYGRTAAWPQRSSREPALIT LSGGSTALPKLILRRHDDYLYSFKASARICQL DSDSVYLCVLPAGHNFTLSSPGFLGVLYAGGR VVMTSDPSGSGAFALIERERVTLTSVVPSLAQ AWLHSSRDHDLSSLQLLQVGGARLSDDVAERL ATSFDCQLQQVYGMSEGLVCYTAVGDTEEHVL HTQGRPISSGDEILIVDENDEPVANGVAGQLL VRGPYTIRGYLNAPEHNARAFTPDGFYRTGDV VVFRDDGYLVVTGRIKDQVNRGGEKIAAEEIE |

TABLE 3-continued

Sequences of RC-Obi Biosynthesis Enzymes

| Gene | Protein | Protein sequence |
|---|---|---|
| | | GYLLAHPGVLEAGIIGLPDEYLGEVSCAVVVL APGAQLTASALKSFVRQQGIAAFKVPDQVHLV PSLPKTTLGKIDKKLLRVQLGQ |
| obiH (SEQ ID NO: 3) | serine hydroxy-methyl-trans-ferase/threonine aldolase | MSNVKQQTAQIVDWLSSTLGKDHQYREDSLSL TANENYPSALVRLTSGSTAGAFYHCSFPFEVP AGEWHFPEPGHMNAIADQVRDLGKTLIGAQAF DWRPNGGSTAEQALMLAACKPGEGFVHFAHRD GGHFALESLAQKMGIEIFHLPVNPTSLLIDVA KLDEMVRRNPHIRIVILDQSFKLRWQPLAEIR SVLPDSCTLTYDMSHDGGLIMGGVFDSPLSCG ADIVHGNTHKTIPGPQKGYIGFKSAQHPLLVD TSLWVCPHLQSNCHAEQLPPMWVAFKEMELFG RDYAAQIVSNAKTLARHLHELGLDVTGESFGF TQTHQVHFAVGDLQKALDLCVNSLHAGGIRST NIEIPGKPGVHGIRLGVQAMTRRGMKEKDFEV VARFIADLYFKKTEPAKVAQQIKEFLQAFPLA PLAYSFDNYLDEELLAAVYQGAQR |
| obiG (SEQ ID NO: 4) | Thiamine-dependent pyruvate decarbox-ylase | MTNLPSTHINLTSEEVSLGDLVGRVLVESGID DLFCIPGDFTMQLSRELLTTPGLALRTMSHEY GTTLAALGYAVGKGVPGAVCFTYGVGVLNATN AIAQAYVERVPLLVFSGSPGTRERQAPLFLHH TIVDHQTQYRIMKEITVHQVCVTDPHQVLEQL REAVALAVLHSRPVYIEIPRDLFQARVRYSPA RRVPLEPSTRYSQAARQAAELAYALVRKARDP VFVPGLDLKRRGLTDLAMRVCERLAMPWVATP MSRGGIPVSHPNYRGIYAGPASPSRVTRELLA KCDVLMLIGEPNSDVNMGIASHIAKGRLIHAD DGKISVGRQHFNASTAEFLIAFSDVIHNAKTP LAPLTETQKDFIVPTPASLYPSEESPLTPFDI INELNRHFVTQPDTQLVVDCGDVFFMSLGMFP ADVLTSPLYMSMGIAVPGAMGYQLGTGKRPIV LVGDGAFHMTGNELMRAAKFGLSPIVIVLNNQ RWASLSSDAADIALTEQMPMSFSAAGQFLQVQ AFTATTGRELRQHLEEALNMDRPVLIDAQVDP SKRSYLCERFFDAVKGQQHLPKA |
| obiL (SEQ ID NO: 5) | p-amino-benzoate N-oxygenase (AurF) | MPESQLLNKITDTWYAKATVRSTPRILVPDYS SEQLIYPVARCSICEHPLVLELGPQVRSYILT QAAYQFLYGVGLLETKFVIQCCLDMLHNNIKD ISDAAKLQALTVIVDEGYHAHVALDYIIQMKK KSAIEPLEVPQTNRKLDATARAYASLPESMRM DFQLLAVTLAENVLTDEVANLGRERELAQSFT TLMMDHVRDEGRHSRFFADLMKERWPQLPRAT QEHFGLMLPAYLDDFLGADLSRGFERKILAHC GLTEAQAEQVIHESDPHFSTDQARMKKSILQR IYRLLNQIGVLELDSVKDAFSDRNYVTT |

In an aspect, the one or more enzymes may be isolated and purified from the one or more cell cultures using any known method including, but not limited to, chromatographic separation methods similar to the isolation and purification methods described in the Examples herein. In one aspect, for those enzymes produced by transgenic cells, the enzymes may be further treated after isolation and purification in order to activate the enzyme prior to use. By way of non-limiting example, recombinant ObiF and ObiD enzymes may be treated with phosphopantetheinyl transferase (Sfp) enzyme in order to add the required phosphopantetheinyl post-translational modification to the PCP domains that is required for activity prior to use.

Figure 42:
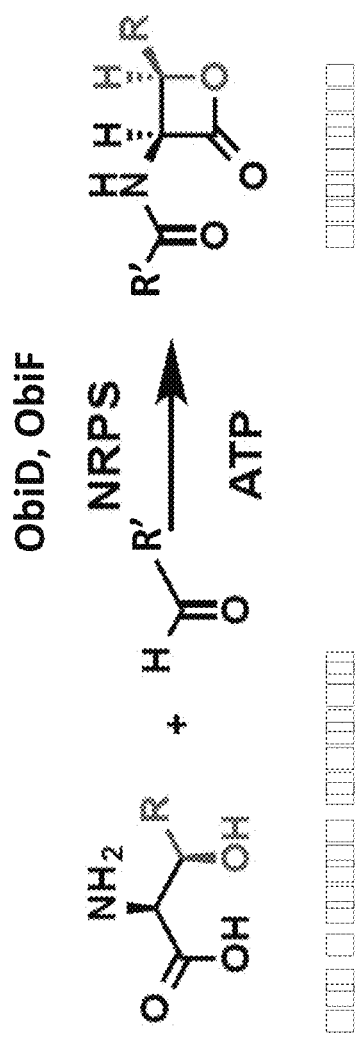
FIG. 42 is a schematic diagram showing a method of producing a peptide beta-lactone from a beta-hydroxy-alpha-amino acid in one aspect.

FIG. 42 is a schematic diagram showing a method of producing a peptide beta-lactone from a beta-hydroxy-alpha-amino acid in one aspect. As illustrated in FIG. 42, the beta-hydroxy-alpha-amino acid and a benzoic acid derivative with an aryl carrier protein including, but not limited to, ObiD and a non-ribosomal protein synthetase including, but not limited to, ObiF, produces a closed beta-lactone ring.

Figure 45:
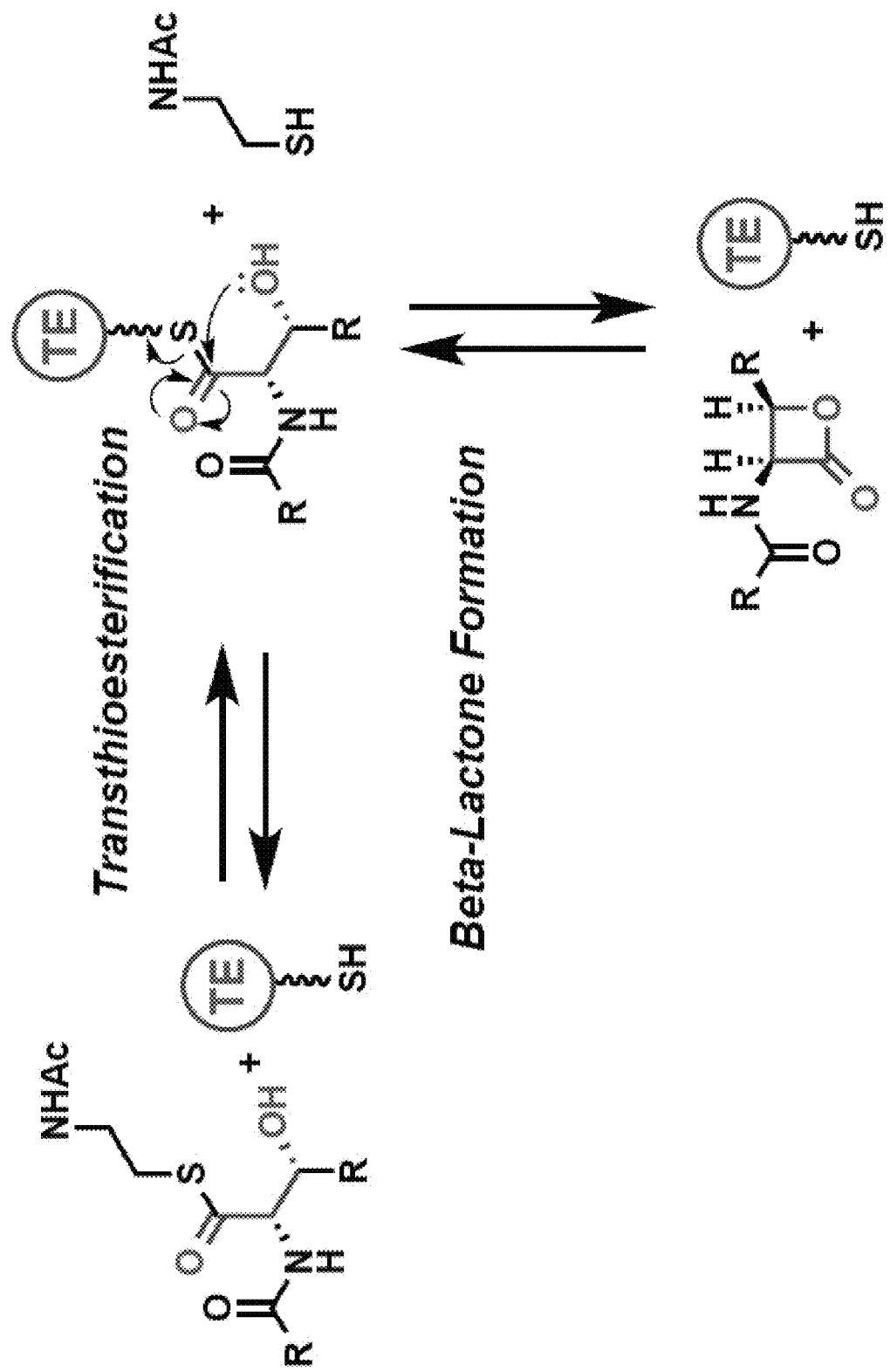
FIG. 45 is a schematic diagram showing transthioesterification and beta-lactone formation by a TE domain of an ObiF enzyme in an aspect.

In one aspect, the method illustrated in FIG. 42 may make use of a modified form of a non-ribosomal protein synthetase that is optimized to function without need for an aryl carrier protein. In one aspect, the non-ribosomal protein synthetase used in the method may be ObiF, a homolog of ObiF, recombinant ObiF, and any variation thereof comprising the amino acid sequence of SEQ ID NO:2 or fragment thereof. The ObiF performs transthioesterification of the beta-hydroxy-alpha-amino acid and benzoic acid derivative, as well as the formation of the peptide beta-lactone, as illustrated in FIG. 45.

In one aspect, the aryl carrier protein used in the method may be ObiD, a homolog of ObiD, recombinant ObiD, and any variation thereof comprising the amino acid sequence of SEQ ID NO:1 or fragment thereof. The ObiD positions the activated benzoic acid derivative at the C domain of ObiF for subsequent transthioesterification of the beta-hydroxy-alpha-amino acid and benzoic acid derivative, as well as the formation of the peptide beta-lactone, as illustrated in FIG. 3C.

In various aspects, the method may produce any peptide beta-lactone without limitation with suitable modification of the ObiF and/or ObiD enzymes. In one aspect, the peptide beta-lactone produced by the method may be obafluorin (RC-Obi), as illustrated in FIG. 3C. In another aspect, the method peptide beta-lactone produced by the method may be an obafluorin analog including, but not limited to any compound with one of the chemical structures as described below:

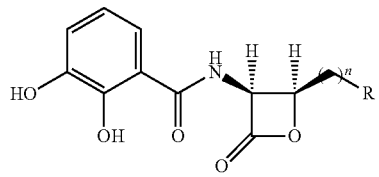

wherein n=1, 2, or 3, and

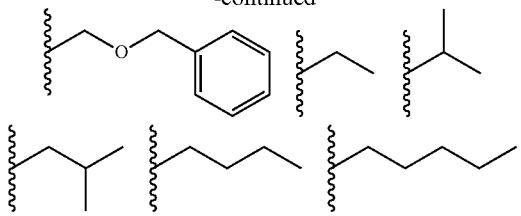

In another aspect, the method may further include hydrolyzing the peptide beta-lactone produced by the method to produce a peptide beta-hydroxy acid, including, but not limited to, any compound with any one of the chemical structure as described herein below:

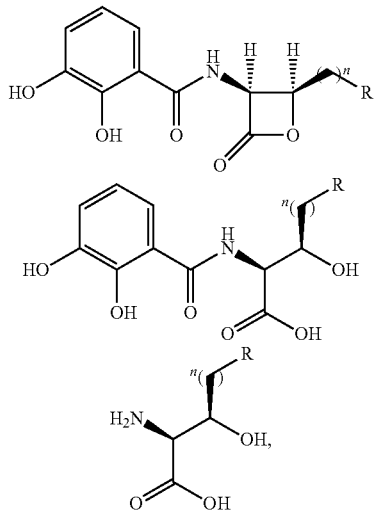

wherein n=0, 1, 2; and

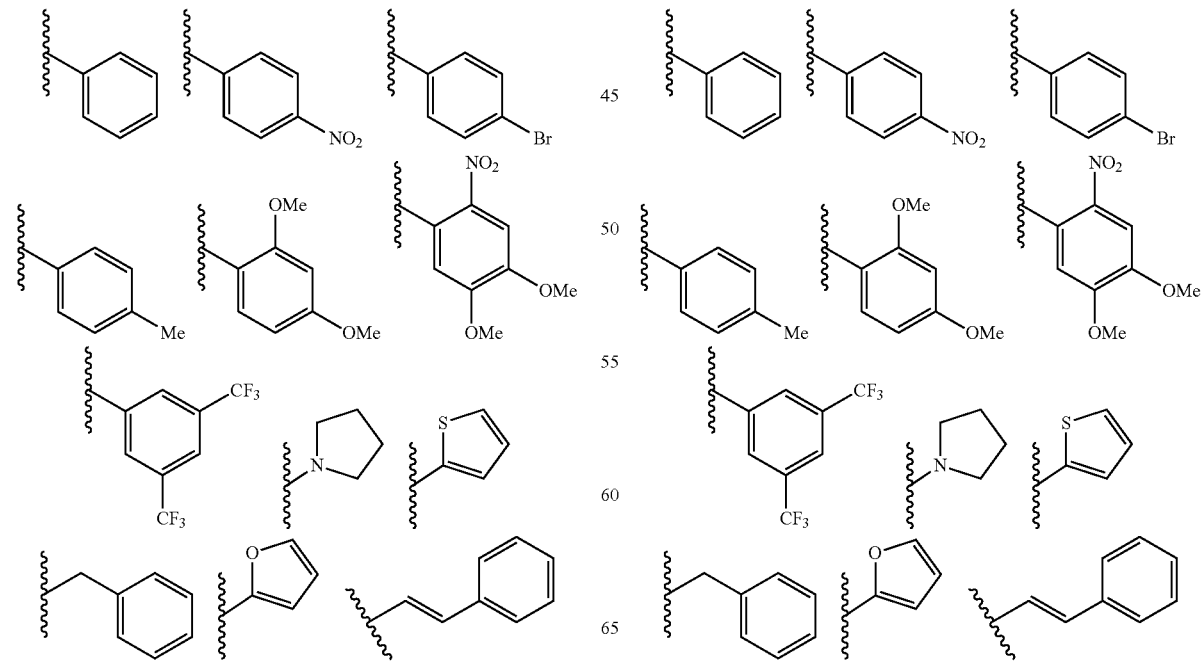

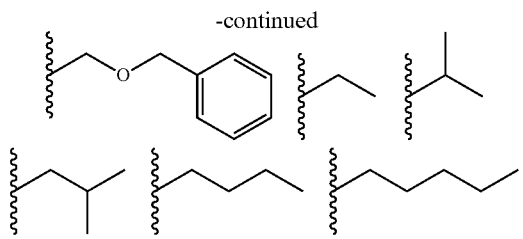

In various aspects, any benzoic acid derivative may be contacted with the ObiF and ObiD enzymes or variations thereof without limitation. Non-limiting examples of suitable benzoic acid derivatives include 2,3-dihydroxoybenzoic acid, as described herein previously (see FIG. 3C). In one aspect, the benzoic acid derivative may be obtained commercially. In another aspect, the benzoic acid derivative may be synthesized in a separate process using any method known in the art without limitation. In an additional aspect, the benzoic acid derivative may be synthesized as part of a method of producing a peptide beta-lactone in another aspect described herein below.

In various aspects, any beta-hydroxy-alpha-amino acid may be contacted with the ObiF enzyme or variations thereof without limitation. Non-limiting examples of suitable beta-hydroxy-alpha-amino acid include beta-OH-p-$NO_2$-homoPhe and beta-OH-homoPhe, as described herein previously (see FIG. 3C). In one aspect, the beta-hydroxy-alpha-amino acid may be obtained commercially. In another aspect, the beta-hydroxy-alpha-amino acid may be synthesized in a separate process using any method known in the art without limitation. In an additional aspect, the beta-hydroxy-alpha-amino acid may be synthesized as part of a method of producing a peptide beta-lactone in another aspect described herein below.

In another aspect, the method may also include forming the beta-hydroxy-alpha-amino acid by contacting an aliphatic or aryl aldehyde or derivative thereof, an amino acid, and a pyridoxyl phosphate (PLP) cofactor with a serine hydroxymethyltransferaseithreonine aldoloase.

In an aspect, the serine hydroxymethyltransferase/threonine aldoloase used in the method may be ObiH, a homolog of ObiH, and any variation thereof comprising the amino acid sequence of SEQ ID NO:3 or fragment thereof. The ObiH catalyzes the synthesis of the beta-hydroxy-alpha-amino acid from the aliphatic or aryl aldehyde or derivative thereof and the amino acid in conjunction with the PLP cofactor as illustrated in FIG. 3C.

In various aspects, any amino acid may be contacted with the ObiH or variations thereof without limitation. Non-limiting examples of suitable amino acids include: threonine and any isomer thereof, serine and any isomer thereof, and glycine and any isomer thereof. In one aspect, the amino acid may be L-threonine (L-Thr) as described herein previously (see FIG. 3C). In an aspect, the amino acids may be obtained commercially.

In various aspects, any aliphatic or aryl aldehyde or derivative may be contacted with the ObiH or variations thereof without limitation. Non-limiting examples of suitable aliphatic or aryl aldehydes or derivatives include: aliphatic aldehydes, aromatic benzaldehydes, aromatic phenylacetaldehydes, and aromatic cinnamaldehydes. In one aspect, the aliphatic or aryl aldehydes may be p-$NO_2$-phenylacetaldehyde (PNPAA) as described herein previously (see FIG. 3C). In one aspect, the aliphatic or aryl aldehydes or derivatives may be obtained commercially. In another aspect, the aliphatic or aryl aldehydes or derivatives may be synthesized in a separate process using any method known in the art without limitation. In an additional aspect, the aliphatic or aryl aldehydes or derivatives may be synthesized as part of a method of producing a peptide beta-lactone in another aspect described herein below.

In another aspect, the method may also include forming the aliphatic or aryl aldehyde or derivative thereof by contacting an aliphatic or aryl pyruvate or derivative thereof and thiamine pyrophosphate (TPP) with a thiamine dependent pyruvate decarboxylase.

In an aspect, the thiamine dependent pyruvate decarboxylase used in the method may be ObiG, a homolog of ObiG, and any variation thereof comprising the amino acid sequence of SEQ ID NO:4 or a fragment thereof. The ObiG catalyzes the conversion of the phenyl pyruvate or derivative thereof to the aliphatic or aryl aldehyde or derivative in conjunction with the TPP cofactor as illustrated in FIG. 3C.

In various aspects, any phenyl pyruvate or derivative may be contacted with the ObiG or variations thereof without limitation. Non-limiting examples of suitable phenyl pyruvates or derivatives include: p-nitrophenylpyruvate, p-hydroxyphenylpyruvate, and phenylpyruvate. In one aspect, the phenyl pyruvate or derivative may be p-nitrophenylpyruvate (PNPPA) as described herein previously (see FIG. 3C). In one aspect, the phenyl pyruvate or derivative may be obtained commercially. In another aspect, the phenyl pyruvate or derivative may be synthesized in a separate process using any method known in the art without limitation. In an additional aspect, the phenyl pyruvate or derivative may be synthesized as part of a method of producing a peptide beta-lactone in another aspect described herein below.

In another aspect, the method may also include forming the aliphatic or aryl pyruvate derivative consisting of p-nitrophenylpyruvate (PNPPA) by contacting p-aminophenylpyruvate (PAPPA), oxygen, and Fe(II) with a p-aminobenzoate N-oxygenase.

In an aspect, the p-aminobenzoate N-oxygenase used in the method may be ObiL, a homolog of ObiL, and any variation thereof comprising the amino acid sequence of SEQ ID NO:5 or fragment thereof. The ObiL catalyzes the conversion of PAPPA to PNPPA in conjunction with the Fe(II) cofactor as illustrated in FIG. 3C.

Figure 43:
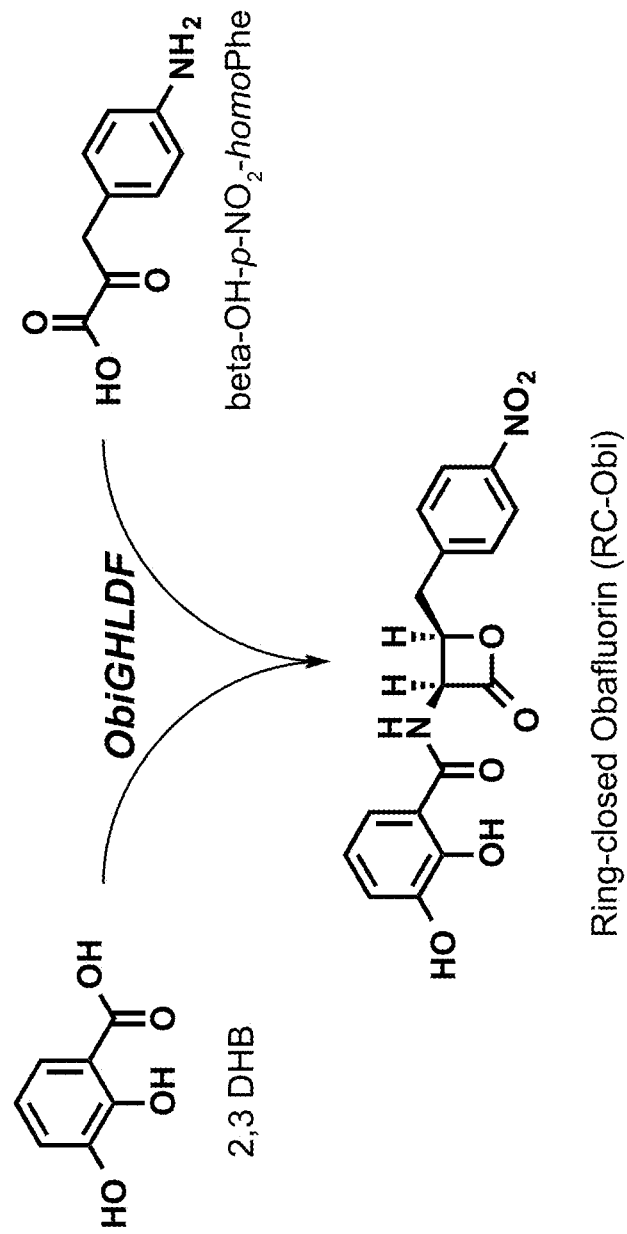
FIG. 43 is a schematic diagram showing an overview of the enzymatic biosynthesis of RC-Obi from 2,3-dihydroxybenzoic acid (2,3-DHB) and β-OH-p-NO$_2$-homoPhenylalanine precursors using the enzymes ObiG, ObiH, ObiL, ObiF, and ObiD in one aspect.
Figure 44:
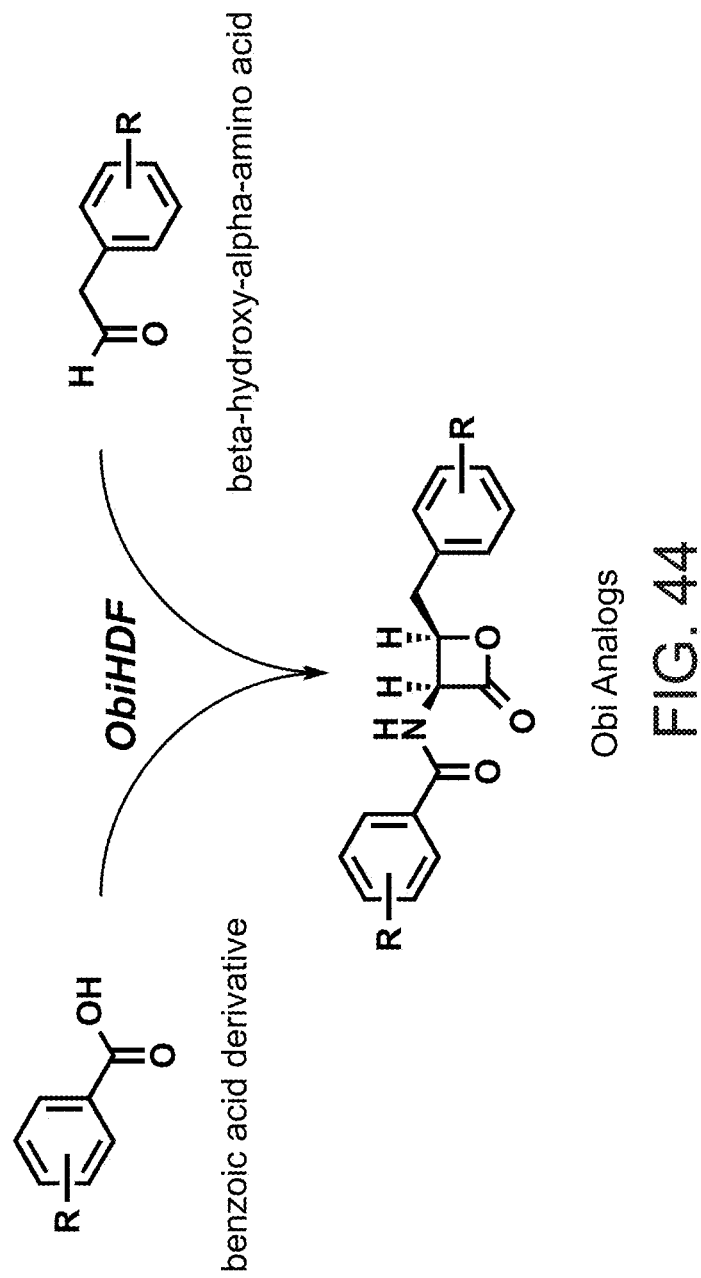
FIG. 44 is a schematic diagram showing an overview of the enzymatic biosynthesis of an RC-Obi analog from benzoic acid derivative and beta-hydroxy-alpha-amino acid precursors using the enzymes ObiH, ObiF, and ObiD in one aspect.

FIG. 43 is a schematic diagram summarizing one aspect of a method (shown in detail in FIG. 3C) that incorporates all of the aspects described herein above that include the ObiG, ObiH, ObiL, ObiD, and ObiF enzymes encoded by the Obi gene cluster. As illustrated in FIG. 43, 2,3-DHB (a benzoic acid derivative) and beta-OH-p-$NO_2$-homoPhe (a beta-hydroxy-alpha-amino acid) precursors are modified and combined to produce obafluorin (a peptide beta-lactone). FIG. 44 is a schematic diagram summarizing another aspect of a method for producing an RC-Obi analog that incorporates all of the aspects described herein above that include the ObiH, ObiD, and ObiF enzymes encoded by the Obi gene cluster. As illustrated in FIG. 44, a benzoic acid derivative and a beta-hydroxy-alpha-amino acid precursor to produce the RC-Obi analog (a peptide beta-lactone). As illustrated in FIG. 44, the R groups attached to the beta-hydroxy-alpha-amino acid precursor may include the R-groups defined herein above for non-limiting examples of RC-Obi analogs.

In another aspect, the method may be further modified to produce an N-acyl-beta-hydroxy-alpha-amino acid by hydrolyzing the peptide beta-lactone produced using any of the previous methods described herein above. Any suitable known method of hydrolysis may be used to hydrolyze the peptide beta-lactone without limitation. By way of non-limiting example, the peptide beta-lactone may be contacted with a hydrolyzing agent including, but not limited to, MES buffer.

EXAMPLES

Example 1: Sequencing of *Pseudomonas fluorescens* Genome

The genome of the known RC-Obi producer *Pseudomonas fluorescens* ATCC 39502 was sequenced to search for a putative Obi biosynthetic gene cluster. *P. fluorescens* ATCC 39502 was purchased from ATCC and glycerol stocks were made from cells grown in Bennet's media and stored at −80° C.

The *P. fluorescens* ATCC 39502 gDNA was isolated using a Qiagen DNeasy Blood & Tissue kit following the provided instructions. The gDNA was sequenced by Ambry Genetics (Aliso Viejo, Calif.) using Illumnia MiSeq. Contigs containing ORFs were assembled, annotated, and deposited in GenBank (Accession #s KX134682-KX134695) with assistance from Cofactor Genomics (St. Louis, Mo.).

Figure 1B:
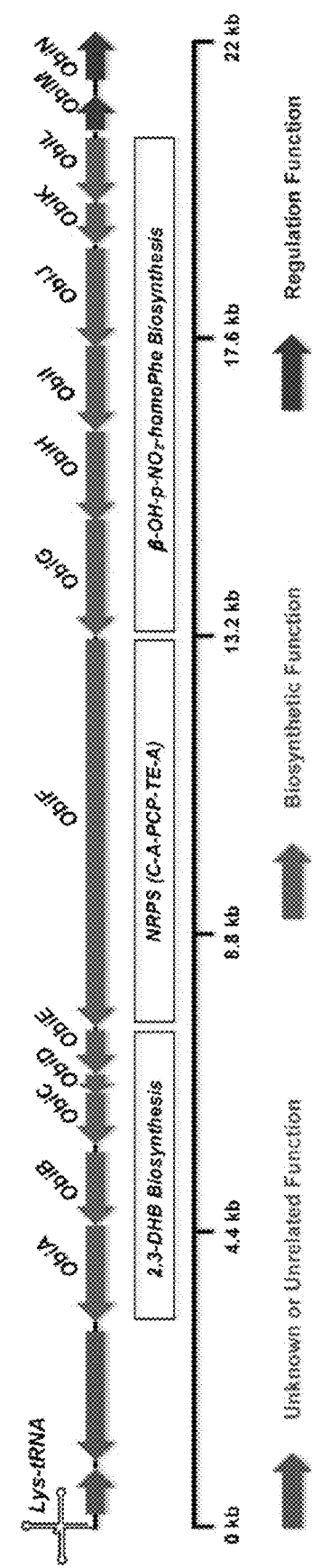
FIG. 1B is an annotated biosynthetic gene cluster of Obi identified from whole genome sequencing of P. fluorescens ATCC 39502.

A gene cluster of approximately 20 kb with 14 candidate coding sequences (CDSs) was identified, including one encoding an AurF di-iron non-heme arylamine oxygenase homolog (ObiL) predicted to install the aryl nitro functional group via oxidation of the precursor aniline, as illustrated in FIG. 1B and FIG. 2F and listed in Table 4 below. Table 4 includes a summary of the predicted functions of ORFs in the RC-Obi biosynthetic gene cluster in *P. fluorescens* ATCC 39502 and GenBank accession numbers. Table 5 includes a summary of the GenBank accession numbers of the homologous genes in *Chitinphilus shinanonensis* (SAY3), *Burkholderia diffusa* (RF8-non_BP2), and *Pseudomonas* sp. (37_R_15 and 34_E_7) cross-referenced to the corresponding genes in the Obi gene cluster of *P. fluorescens*.

TABLE 4

Putative functional assignments of genes in the *P. fluorescens* ATCC 39502 Obi biosynthetic cluster.

| Gene | # AAs | Predicted Function from BLAST Search[1] | GenBank Accession # |
|---|---|---|---|
| obiA | 473 | Isochorismate synthase (EntC) | KX134682 |
| obiB | 358 | DAHP synthase | KX134683 |
| obiC | 257 | 2,3-DHB-2,3-dehydrogenase (EntA) | KX134684 |
| obiD | 88 | Aryl carrier protein ($T_{Ar}$) (EntB) | KX134685 |
| obiE | 215 | Isochrismatase (EntB) | KX134686 |
| obiF | 1911 | NRPS w/ C-A-T-TE-$A_{Ar}$ catalytic domains (EntF + EntE) | KX134687 |
| obiG | 568 | TPP dependent phenylpyruvate decarboxylase | KX134688 |
| obiH | 441 | Serine hydroxymethyl transferase/threonine aldolase | KX134689 |
| obiI | 421 | Bifunctional chorismate mutase/dehydratase (TyrA) | KX134690 |
| obiJ | 487 | p-aminobenzoate synthase (PabA) | KX134691 |
| obiK | 200 | 4-amino-4-deoxychorismate synthase (PabA) | KX134692 |
| obiL | 317 | p-aminobenzoate N-oxygenase (AurF) | KX134693 |
| obiM | 170 | Autoinducer synthesis protein (LuxI) | KX134694 |
| obiN | 237 | Quorum-sensing control repressor (LuxR) | KX134695 |

[1]Functions were predicted from NCBI protein BLAST searches against the non-redundant protein database. Homologous protein names are shown in parentheses.

TABLE 5

Homologous Obi biosynthetic gene clusters in the NCBI database.

| | | | GenBank Accession Numbers | | |
|---|---|---|---|---|---|
| Gene[1] | *P. fluorescens* ATC 39502 | *C. shinanonensis* SAY3 | *B. diffusa* RF8-non_BP2 | *Pseudomonas* sp. 37_R_15 | *Pseudomonas* sp. 34_E_7 |
| obiA | KX134682 | WP_051083264.1 | WP_059467192.1 | WP_065949338.1 | WP_065936864.1 |
| obiB | KX134683 | WP_018749566.1 | WP_060322869.1 | WP_065949339.1 | WP_065936863.1 |
| obiC | KX134684 | WP_018749565.1 | WP_059467194.1 | WP_065949340.1 | WP_065936862.1 |
| obiD | KX134685 | WP_018749564.1 | WP_059467195.1 | WP_065949341.1 | WP_065936861.1 |
| obiE | KX134686 | WP_018749563.1 | WP_059467196.1 | WP_065949342.1 | WP_065936860.1 |
| obiF | KX134687 | WP_020608490.1 | WP_059467198.1[2] WP_059467197.1[3] | WP_065949343.1 | WP_065936859.1 |
| obiG | KX134688 | WP_018749562.1 | WP_060322856.1 | WP_065949344.1 | WP_065936858.1 |
| obiH | KX134689 | WP_018749561.1 | WP_059467200.1 | WP_065949345.1 | WP_065936857.1 |
| obiI | KX134690 | WP_018749560.1 | WP_059467202.1 | WP_065949346.1 | WP_065936856.1 |
| obiJ | KX134691 | WP_051083263.1 | WP_059467203.1 | CRM14833.1 | CRN02515.1[d] |
| obiK | KX134692 | WP_051083262.1 | WP_059467204.1 | CRM14850.1 | No number |
| obiL | KX134693 | WP_026263186.1 | WP_059467205.1 | WP_065949347.1 | WP_065936855.1 |
| obiM | KX134694 | No Homologue | No Homologue | WP_065949348.1 | WP_065936854.1 |
| obiN | KX134695 | WP_018749568.1 | No Homologue | WP_065949349.1 | WP_065936853.1 |

[a]Predicted gene functions are provided in Supplementary Table 1.
[b]Domains = C-A-T-TE.
[c]Domain = $A_{Ar}$.
[d]There is a frame with an internal stop codon. The gene shows homology to WP_015032126.1, a predicted amino-deoxychorismate synthase, component I.

The sequenced Obi gene cluster was found to encode for putative enzymes required for the biosynthesis of 2,3-DHB (ObiA, ObiB, ObiC, and ObiE) and the non-proteinogenic amino acid β-OH-p-$NO_2$-homoPhe (ObiG, ObiI, ObiJ, ObiK, and ObiL), as summarized in FIG. 1B. CDSs encoding for an aryl acyl-carrier protein (ObiD) and an NRPS module (ObiF) with condensation (C), adenylation (A), thiolation (T), and thioesterase (TE) domains (see FIG. 1C) make up the remaining biosynthetic genes. The sequenced Obi gene cluster was not found to contain any obvious antibiotic resistance genes. Referring to FIG. 1B, the Lys-tRNA at the start of the Obi gene cluster is indicated by a hairpin structure. Genes representing ORFs of unknown/unrelated function are colored green, those of biosynthetic function are colored red, and those of regulatory function are colored blue. Three blocks of biosynthetic ORFs are arranged for transcription in the same direction: (I) 2,3-DHB biosynthesis, (II) nonribosomal peptide synthetase (NRPS) with C-$A_1$-PCP-TE-$A_2$ domains, and (III) β-OH-p-$NO_2$-homoPhe biosynthesis.

Figure 1C:
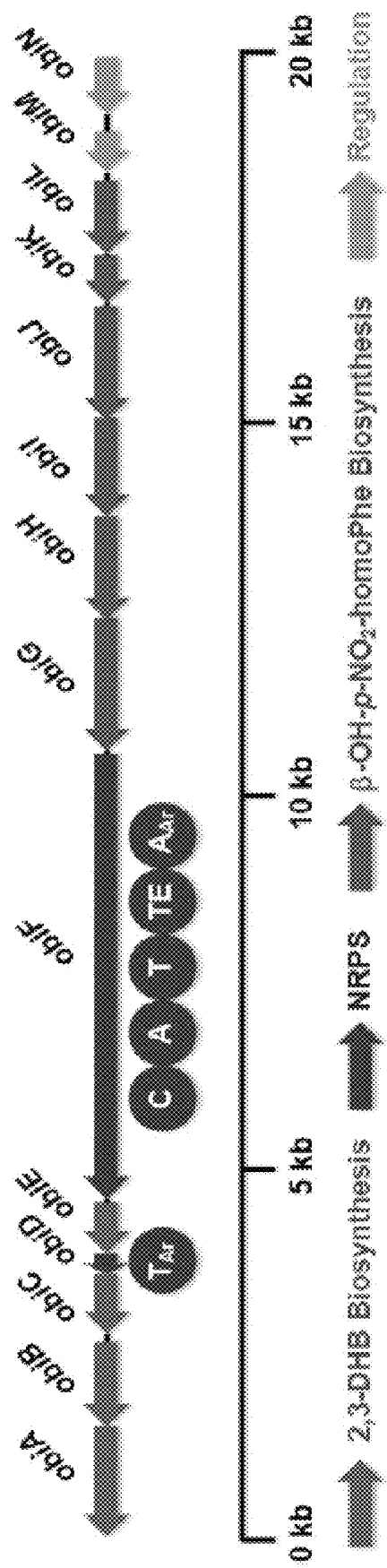
FIG. 1C is an annotated biosynthetic gene cluster of Obi identified from whole genome sequencing of P. fluorescens ATCC 39502.
Figure 1D:
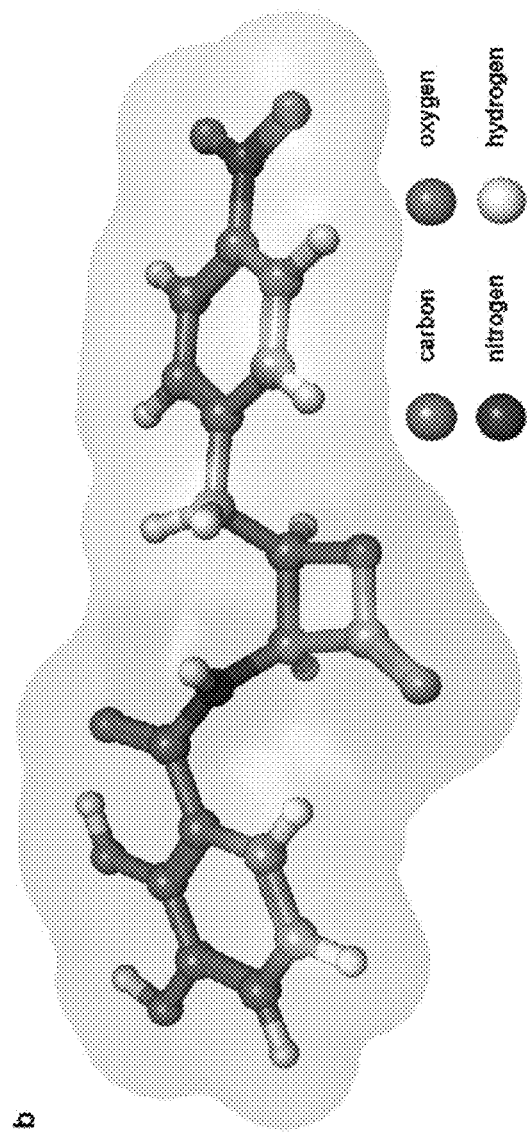
FIG. 1D is a chemical structure diagram illustrating the arrangement of atoms within a 3D model of the RC-Obi structure with color-coded surfaces corresponding to CDSs involved in fragment biosynthesis.
Figure 1E:
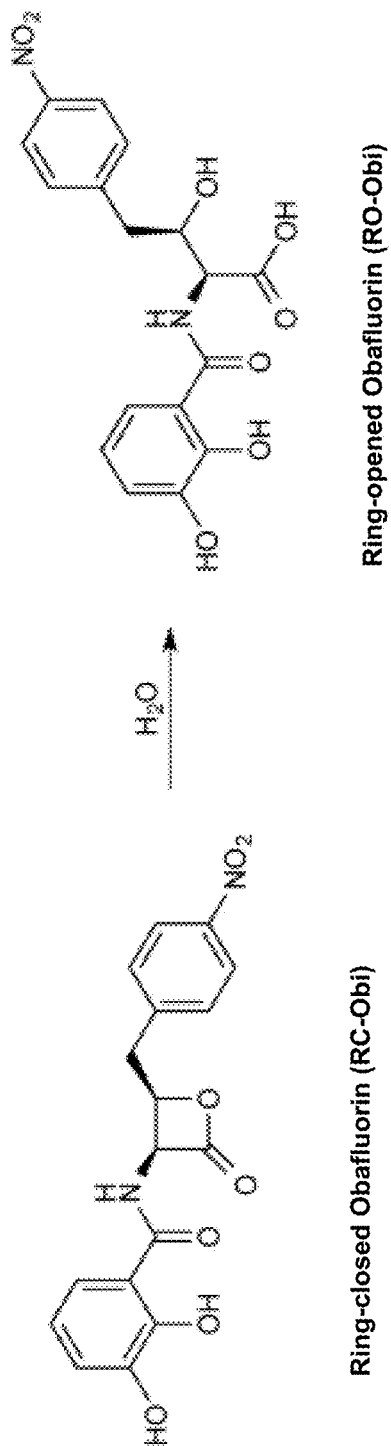
FIG. 1E is a schematic diagram illustrating the non-enzymatic hydrolysis of obafluorin β-lactone (RC-Obi) to form a β-hydroxy carboxylic acid, the open-ring form of obafluorin (RO-Obi).

FIG. 1C shows an annotated biosynthetic gene cluster of Obi identified from whole genome sequencing of *P. fluorescens* ATCC 39502. Arrows representing CDSs for enzymes involved in the biosynthesis of 2,3-DHB and β-OH-p-$NO_2$-homoPhe are colored red and respectively. The NRPS CDSs are colored blue and abbreviations of catalytic domains are shown as blue spheres: A, adenylation; C, condensation; T, thiolation; and TE, thioesterase. CDSs proposed to have a role in regulation are colored orange.

Referring again to Table 4, genes obiM and obiN were determined to encode for proteins with strong homology to acylhomoserine lactone (AHL) synthase LuxI and AHL-binding transcriptional regulator LuxR, respectively. The LuxI/LuxR pair is known to be a common quorum sensing system found in many Pseudomonads. A BLAST search of the NCBI database using the NCBI BLAST analysis of the Obi biosynthetic gene cluster from *P. fluorescens* ATCC 39502 revealed homologous gene clusters in the environmental chitin-degrading bacteria *Chitiniphilus shinanonensis* SAY3 and the rhizobacterium *Burkholderia diffusa* RF8-non_BP2. Two additional clusters were found in *Pseudomonas* sp. 37_R_15 and *Pseudomonas* sp. 34_E_7 that were virtually identical in sequence identity (>95% for all protein sequences) and direction of gene transcription compared to the gene cluster found in *P. fluorescens* ATCC 39502. GenBank accession numbers are shown in Table 4 above. Gene function predictions, also shown in Table 4, revealed homologous Obi clusters in other Pseudomonads including *Pseudomonas* sp. 37_R_15 and 34E_7, the environmental chitin-degrading bacterium *Chitiniphilus shinanonensis* SAY3 (see FIG. 7A and FIG. 7B), and the plant growth-promoting rhizobacterium *Burkholderia diffusa* RF8-non_BP2 (see FIG. 7A and FIG. 7B), which is also an opportunistic human pathogen.

FIG. 64 is a chemical reaction diagram showing the production of RC-Obi and RO-Obi using recombinant ObiF and ObiD from *C. shinanonensis* genome. The illustrated scheme shows the conversion of starting materials 2,3-DHB and β-OH-p-$NO_2$-homoPhe to product RC-Obi, which then non-enzymatically hydrolyzes to RO-Obi.

Figure 65:
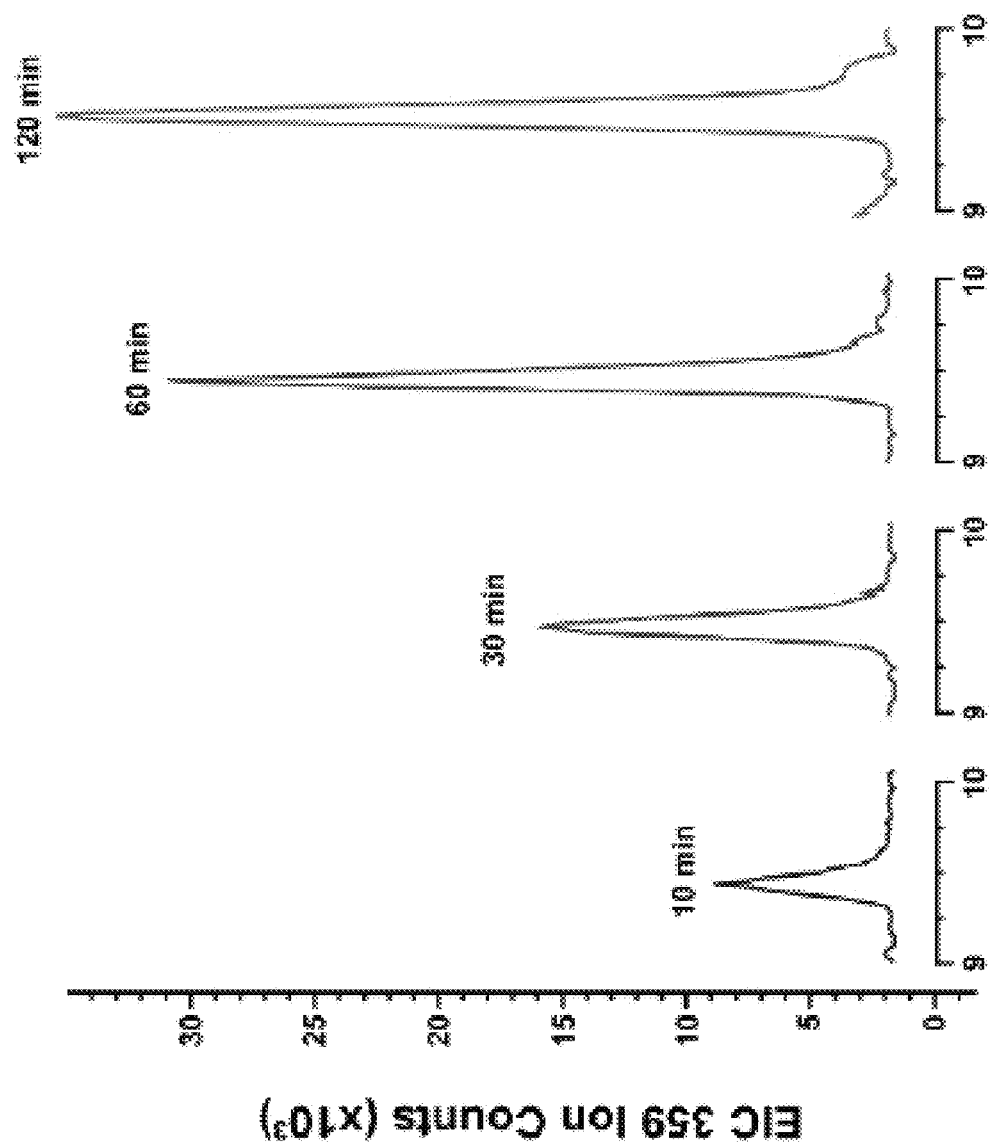

FIG. 65 is a graph showing LC-MS traces from samples of a reaction mixture obtained at various times of the reaction illustrated in FIG. 64, characterizing a time-dependent buildup of the RC-Obi peak (rt=0.5 min; m/z for [M+H]+=359).

Figure 66:
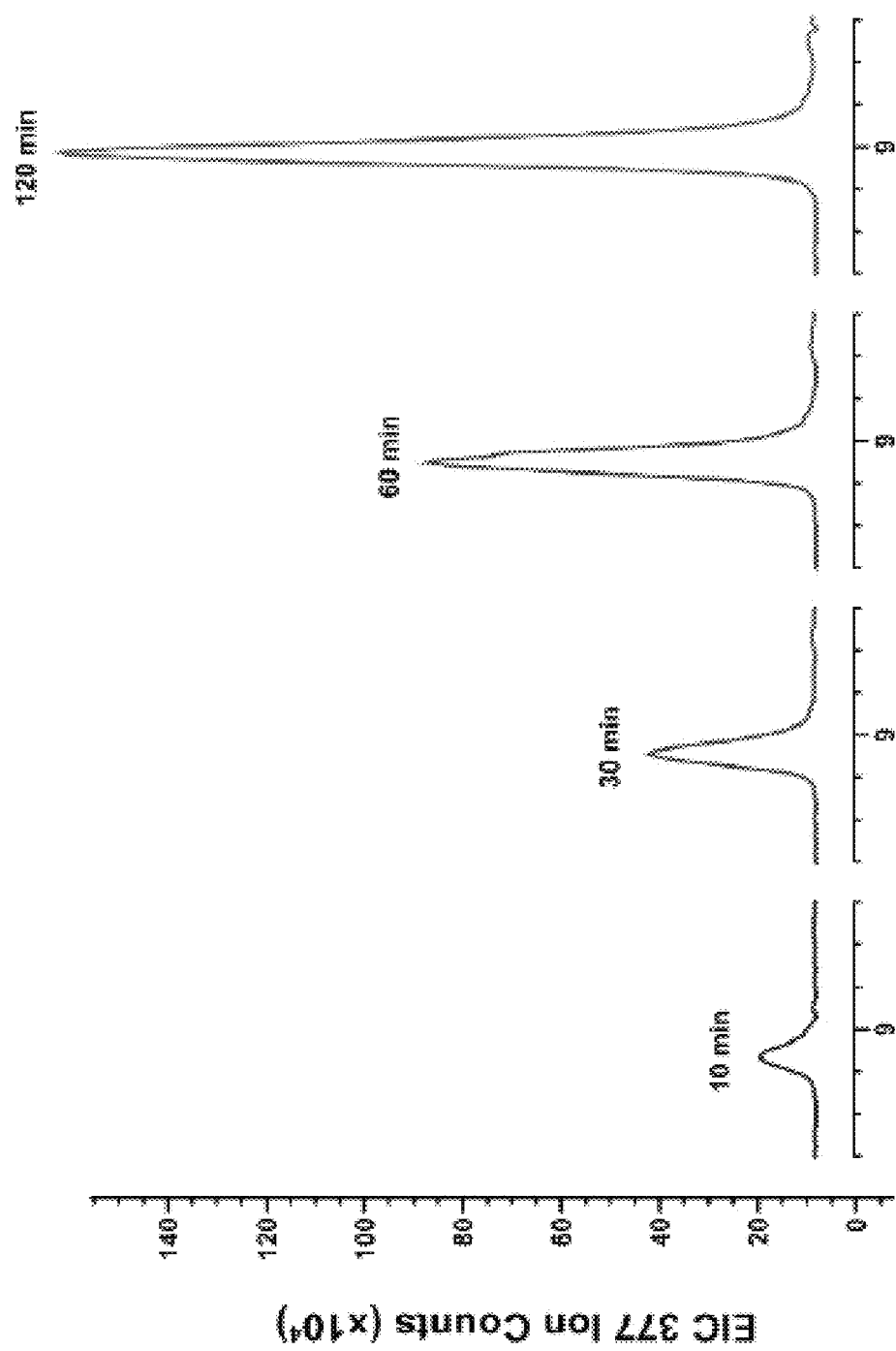

FIG. 66 is a graph showing LC-MS traces from samples of a reaction mixture obtained at various times of the reaction illustrated in FIG. 64, characterizing a time-dependent buildup of the RO-Obi peak (rt=9.0 min; m/z for [M+H]+=377).

Figure 17:
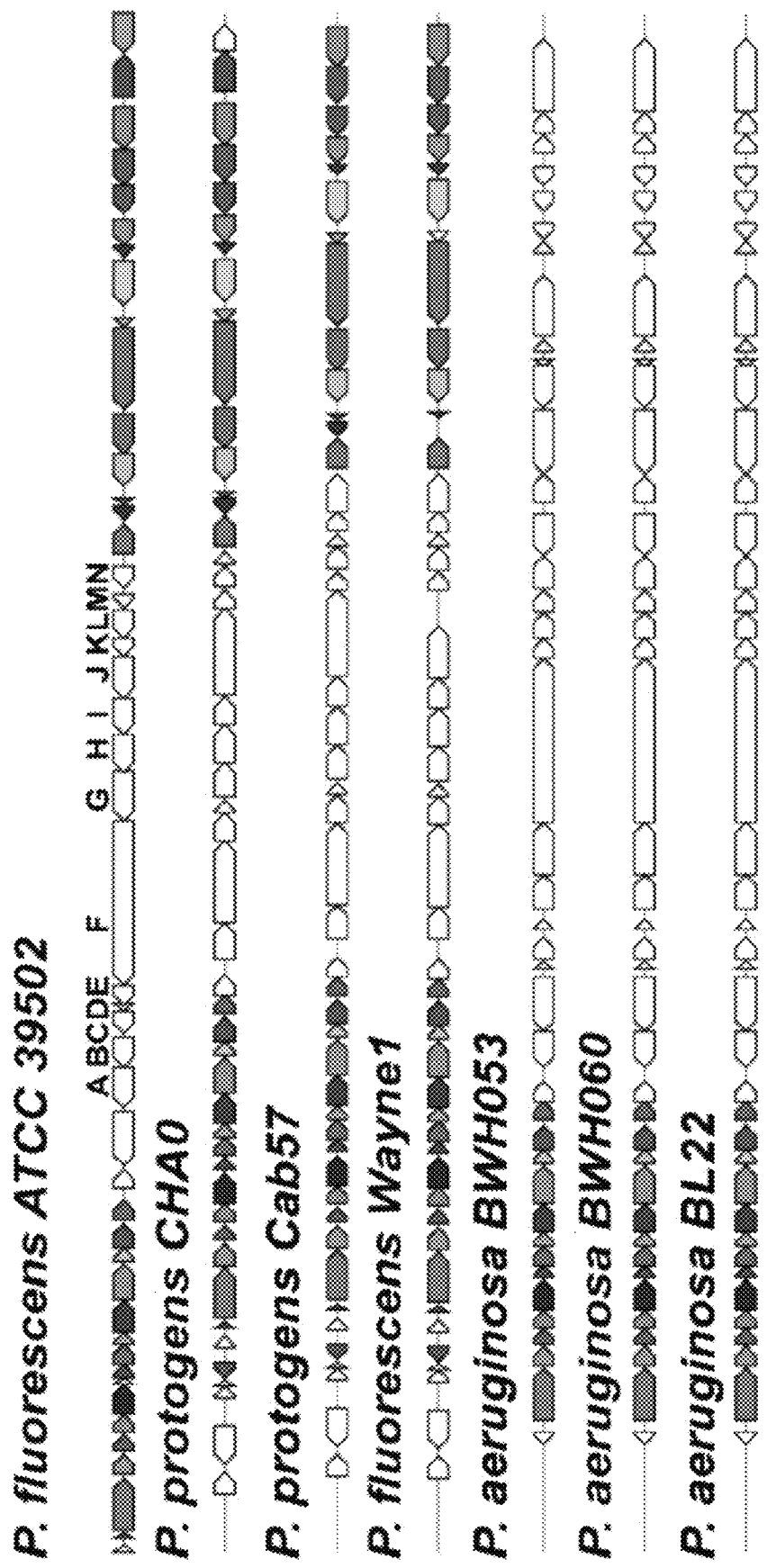
FIG. 17 is a schematic illustration showing a comparison of the *P. fluorescens* ATCC 39502 genome with the genomes of other Pseudomonads.

FIG. 17 is a schematic illustration showing a comparison of the *P. fluorescens* ATCC 39502 genome with the genomes of other Pseudomonads. Analysis of the obafluorin biosynthetic gene cluster with the antiSMASH algorithm (http://antismash.secondarymetabolites.org/) supports the defined genomic region dedicated to obafluorin biosynthesis in *P. fluorescens* ATCC 39502. Homology is shown by colored genes where white gene arrows indicate no homology. The top row shows the proposed obafluorin gene cluster in white with annotated genes flanked on the left by the Holliday Junction Resolution System and on the right by the Glycine Cleavage System. Analysis of the genomes of other Pseudomonads showed that this site was commonly used for the insertion of a biosynthetic gene cluster obtained from horizontal gene transfer. Other white regions indicated biosynthetic gene clusters for other secondary metabolites, not obafluorin.

The results of these experiments identified a gene cluster of approximately 20 kb with 14 candidate coding sequences (CDSs) within the genome of the known RC-Obi producer *Pseudomonas fluorescens* ATCC 39502.

Example 2: Cloning of ObiG, ObiH, ObiI, ObiD, ObiF ObiF-C1141S, ObiF-C1141A, CS-ObiD and CS-ObiF To demonstrate the cloning of various enzymes associated with the biosynthesis of RC-Obi, the following experiments were conducted.

Gene sequences were amplified from either *P. fluorescens* ATCC 39502 gDNA or *C. shinanonensis* DSM 23277 gDNA (isolated using Qiagen DNeasy Blood & tissue kit following provided instructions) using forward and reverse primers designed for each gene (see Tables 6 and 7 below) and a Herculase II Fusion DNA Polymerase kit.

TABLE 6

PCR Primers

| Primer | SEQ ID NO: | Nucleotide Sequence (5' to 3')* |
|---|---|---|
| ObiD_F | 8 | GAACTGGGGAAGGC<u>CATATG</u>ACCCAG |
| ObiD_RC | 9 | TCGAA<u>AAGCTT</u>CATGGCTGCTCGCACTC |
| ObiF_F | 10 | GTTAAACT<u>CATATG</u>TCAGCCTCATTCAC |
| ObiF_RC | 11 | CCAGTT<u>AAGCTT</u>TGGGTTTATTGG |
| ObiF_C1141S_F | 12 | GTCTACGGGCACAGCGCCGGTAAC |
| ObiF_C1141A_F | 13 | GTCTACGGGCACGCAGCCGGTAAC |
| ObiF_Mut_RC | 14 | GATAATCGGCCCGCTCAACG |
| ObiG_F | 15 | GGTGTATCA<u>GCTAGC</u>CCAACGATG |
| ObiG_RC | 16 | GGTAAATGA<u>AAGCTT</u>GGTCATGCCTTG |
| ObiH_F | 17 | GCAGAGAAAC<u>CATATG</u>AGCAATGTC |
| ObiH_RC | 18 | GGG<u>AAGCTT</u>GACCATCGTTG |
| ObiL_F | 19 | CATGTAATGCC<u>CATATG</u>CCTGAATC |
| ObiL_RC | 20 | CGTATATCG<u>AAGCTT</u>AACGCTCAAG |

TABLE 6-continued

PCR Primers

| Primer | SEQ ID NO: | Nucleotide Sequence (5' to 3')* |
|---|---|---|
| CS_obiD_F | 21 | GCGCTGGC<u>CATATG</u>AACGC |
| CS_obiD_RC | 22 | GTCCATGC<u>AAGCTT</u>CCGTCAAAG |
| CS_obiF_F | 23 | GCGCCC<u>CATATG</u>CCCCAC |
| CS_obiF_RC | 24 | GTCA<u>AAGCTTT</u>CATTCGGTCAGG |

Note:
Restriction enzyme sites are underlined, and mutant codons are in bold

TABLE 7

PCR Primer Pairs

| Construct | 5'Primer | 3'Primer | Template |
|---|---|---|---|
| ObiD | ObiD_F | ObiD_RC | *P. fluorescens* gDNA |
| ObiF | ObiF_F | ObiF_RC | *P. fluorencens* gDNA |
| ObiF C1141S | ObiF_C1141S_F | ObiF_Mut_RC | WT-ObiF in pET28 |
| ObiF C1141A | ObiF_C1141A_F | ObiF_Mut_RC | WT-ObiF in pET28 |
| ObiG | ObiG_F | ObiG_RC | *P. fluorescens* gDNA |
| ObiH | ObiH_F | ObiH_RC | *P. fluorescens* gDNA |
| ObiL | ObiL_F | ObiL_RC | *P. fluorescens* gDNA |
| CS_obiD | CS_obiD_F | CS_obiD_RC | *C. shinanonensis* gDNA |
| CS_obiF | CS_obiF_F | CS_obiF_RC | *C. shinanonensis* gDNA |

The resulting PCR fragments were purified by gel electrophoresis. PCR products and pET28a vectors were separately digested with either FD-NdeI and FD-HindIII or NheI and FDHindIII. Cut DNA was purified using a QIAquick Gel Extraction Kit without running an agarose gel. Ligation reactions were carried out overnight at 16° C. using T4 DNA Ligase. Ligation mixtures were purified and transformed into electrocompetent *E. coli* TOP10 cells. Clones were selected for on LB agar containing 50 μg/mL kanamycin. Sequencing of selected colonies revealed clones containing the desired constructs. Plasmids were purified and used to transform electrocompetent *E. coli* BL21 (DE3) cells.

The organism strains and plasmids described above are summarized in Table 8 below:

TABLE 8

Strains and Plasmids Used for Enzyme Cloning

| Strain | Plasmid | Inducible Gene/Marker | Origin/ Reference |
|---|---|---|---|
| *Pseudomonas Fluorescens* ATCC 39502 | None | Obafluorin producer | ATCC |
| *Chitiniphilus shinanonensis* SAY3 (DSM 23277) | None | Obafluorin biosynthetic gene cluster present in gDNA sequence | DSMZ |
| *E. coli* TOP10 | None | Cloning strain | Agilent |
| *E. coli* BL21 (DE3) | None | Protein expression strain | Agilent |
| *E. coli* BL21 (DE3) | pET29 | Sfp | C. T. Walsh |
| *E. coli* BL21 (DE3) | pET28a | ObiD | This work |
| *E. coli* BL21 (DE3) | pET28a | ObiF | This work |
| *E. coli* BL21 (DE3) | pET28a | ObiF C1141S | This work |
| *E. coli* BL21 (DE3) | pET28a | ObiF C1141A | This work |
| *E. coli* BL21 (DE3) | pET28a | ObiG | This work |
| *E. coli* BL21 (DE3) | pET28a | ObiH | This work |
| *E. coli* BL21 (DE3) | pET28a | ObiL | This work |
| *E. coli* BL21 (DE3) | pET28a | CS_ObiD | This work |
| *E. coli* BL21 (DE3) | pET28a | CS_ObiF | This work |

The experiments described above resulted in the successful cloning of various enzymes associated with the biosynthesis of RC-Obi.

Example 3: Expression and Purification of ObiG, ObiH, ObiL, ObiD, ObiF, ObiF-C1141S, ObiF-C1141A, CS-ObiD and CS-ObiF To demonstrate the expression and purification of various enzymes associated with the biosynthesis of RC-Obi, the following experiments were conducted.

For protein expression, a 5 mL culture of *E. coli* BL21 harboring the appropriate plasmid (see Table 8 above) was grown overnight in LB containing 50 μg/mL kanamycin with agitation at 37° C. A 200 μL aliquot of this culture was used to inoculate 500 mL of terrific broth (12 g/L tryptone, 24 g/L yeast extract, 5 g/L glycerol, 17 mM KH$_2$PO$_4$, 72 mM K$_2$HPO$_4$) containing 50 μg/mL kanamycin. The culture was grown at 37° C. with agitation until OD$_{600}$ reached approximately 0.4. The culture was cooled in an ice bath for 20 min, then 500 μL of a sterile 0.5 M IPTG solution was added. The culture was then incubated with agitation for 18 hrs. (at 15° C. for ObiG/ObiF/CS-ObiF, and at 20° C. for ObiD/CS-ObiD/ObiH/ObiL).

All subsequent protein purification steps were performed at 4° C. Cells were harvested by centrifugation of the cultures at 5,000 rpm for 20 minutes. Supernatant was discarded, and cell pellets were each suspended in 40 mL cold lysis buffer (50 mM K2HPO4 pH 8.0, 500 mM NaCl, 5 mM β-mercaptoethanol, 20 mM imidazole, 10% glycerol). Cell suspensions were transferred to 50 mL falcon tubes and flash frozen in liquid nitrogen. Frozen cells were thawed and gently rocked for 30 minutes before being mechanically lysed using an Avestin EmulsiFlex-C5 cell disruptor. Cell lysate was centrifuged at 45,000 rpm for 35 min and supernatant was incubated with pre-washed Ni-NTA resin for 30 min. Resin was washed twice with 40 mL lysis buffer then eluted five times with 10 mL elution buffer (50 mM K2HPO4 pH 8.0, 500 mM NaCl, 5 mM β-mercaptoethanol, 300 mM imidazole, 10% glycerol). Fractions containing the majority of protein, as judged by SDS-PAGE with Coomassie blue visualization (see FIGS. 18A, 18B, 18C, and 18D), were combined in 10,000 MWCO SnakeSkin dialysis tubing from Thermo Scientific and soaked overnight in 1.8 L phosphate buffer (50 mM $K_2HPO_4$ pH 8.0, 150 mM NaCl, and 1 mM DTT). Dialyzed protein solution was concentrated using an appropriately sized spin filter (EMD Millipore Amicon® Ultra 15 mL Centrifugal Filters). Concentrated protein solutions were flash frozen in liquid nitrogen and stored at −80° C.

Figure 18A:
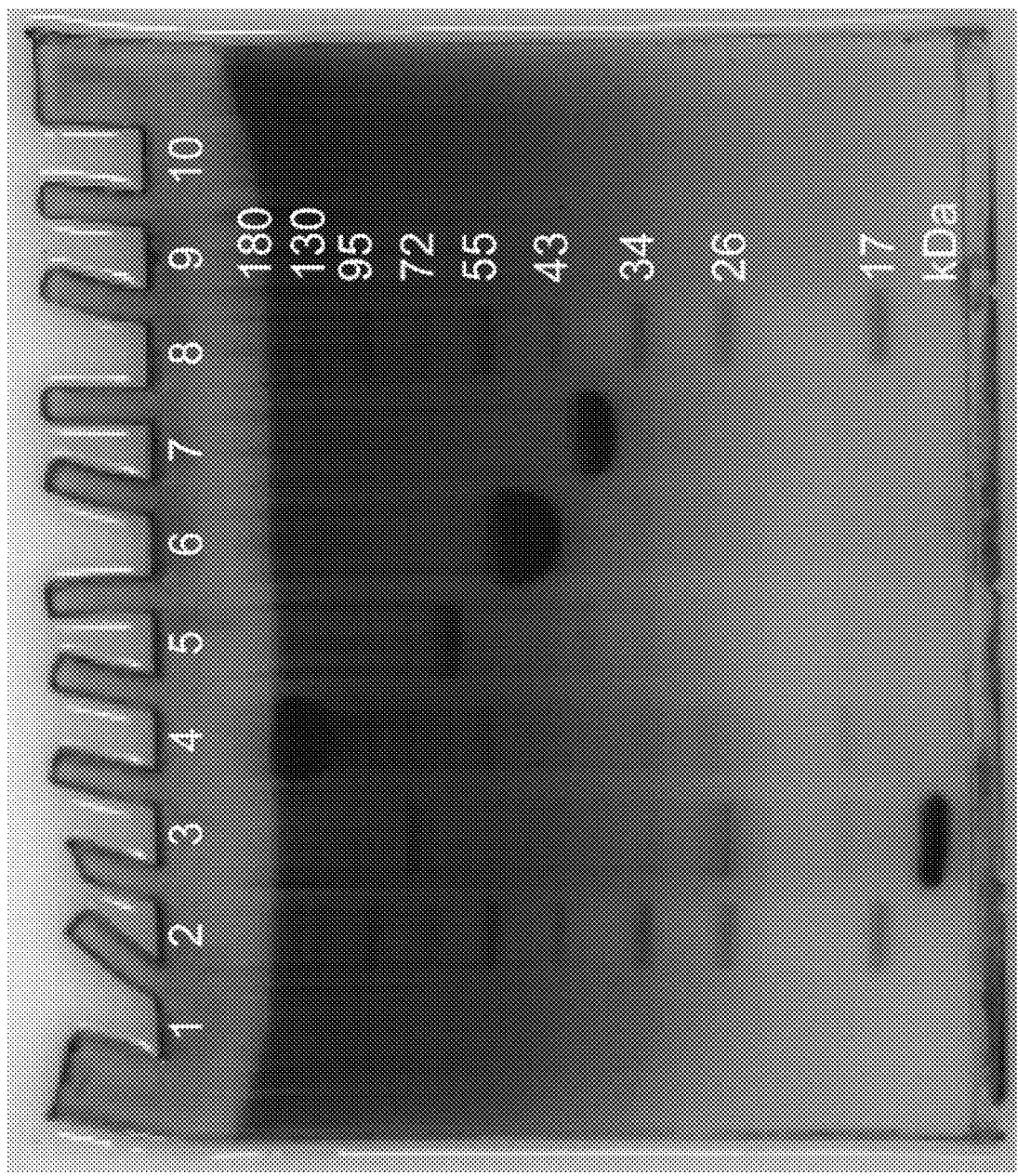
FIG. 18A is an image of a gel showing purified proteins associated with the biosynthesis of RC-Obi, shown separated on SDS-PAGE gels (any kD, Bio-Rad) and stained with Coomassie blue.

FIG. 18A is an image showing purified proteins associated with the biosynthesis of RC-Obi, shown separated on SDS-PAGE gels (any kD, Bio-Rad) and stained with Coomassie blue. Proteins include (from left to right lane): 1) empty; 2) ladder, 3) ObiD (10.0 kDa); 4) ObiF(209.3 kDa); 5) ObiG(62.1 kDa); 6) ObiH(48.6 kDa); 7) ObiL(36.0 kDa); 8) ladder; 9) empty; and 10) empty. All proteins have an N-terminal His-tag.

Figure 18B:
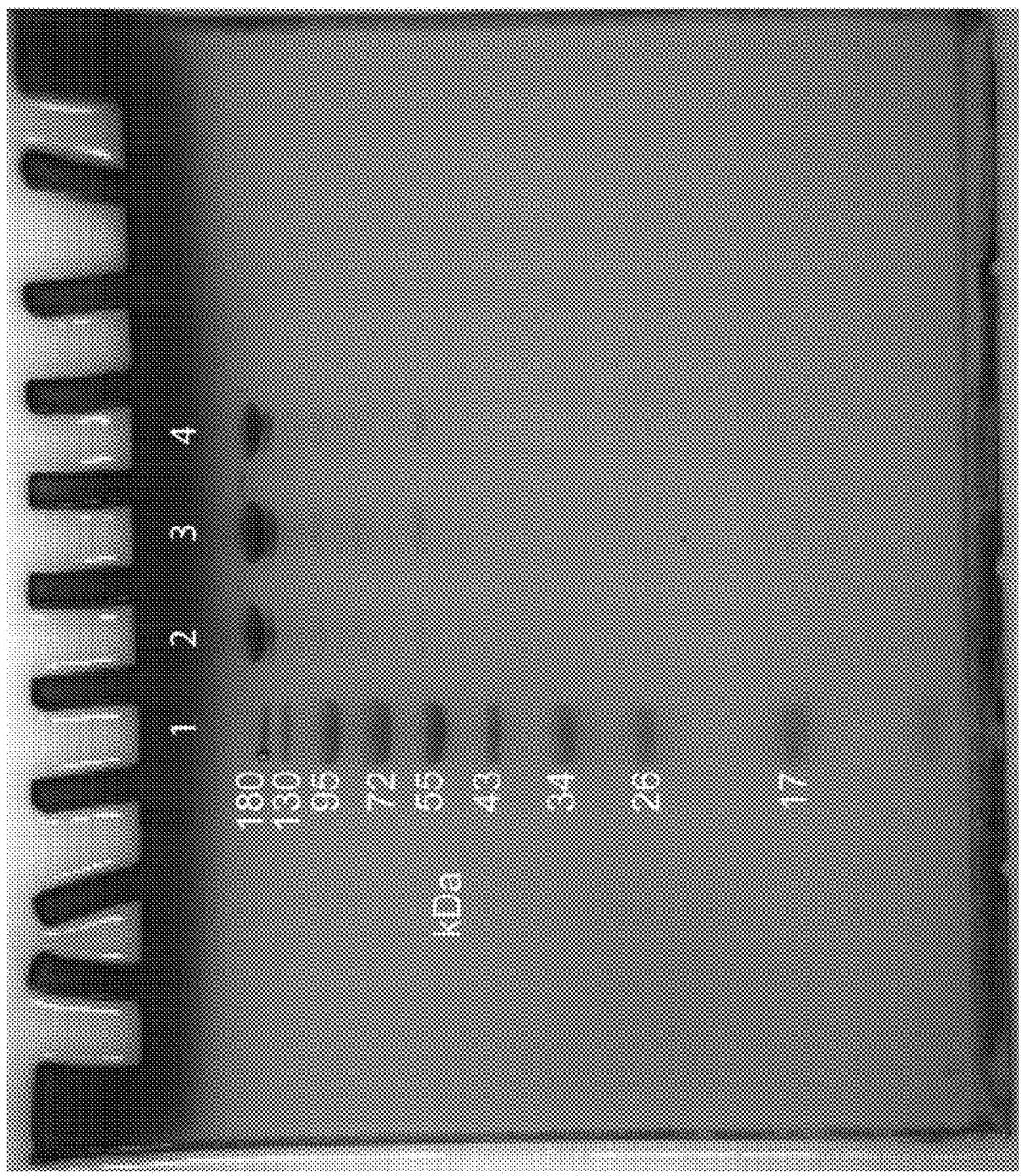
FIG. 18B is an image of a gel showing purified proteins associated with the biosynthesis of RC-Obi, shown separated on SDS-PAGE gels (any kD, Bio-Rad) and stained with Coomassie blue.

FIG. 18B is an image showing purified proteins associated with the biosynthesis of RC-Obi, shown separated on SDS-PAGE gels (any kD, Bio-Rad) and stained with Coomassie blue. Proteins include (from left to right lane): 1) ladder, 2) ObiF-WT; 3) ObiF-C1141S; 4) ObiF-C1141A. All proteins have an N-terminal His-tag.

Figure 18C:
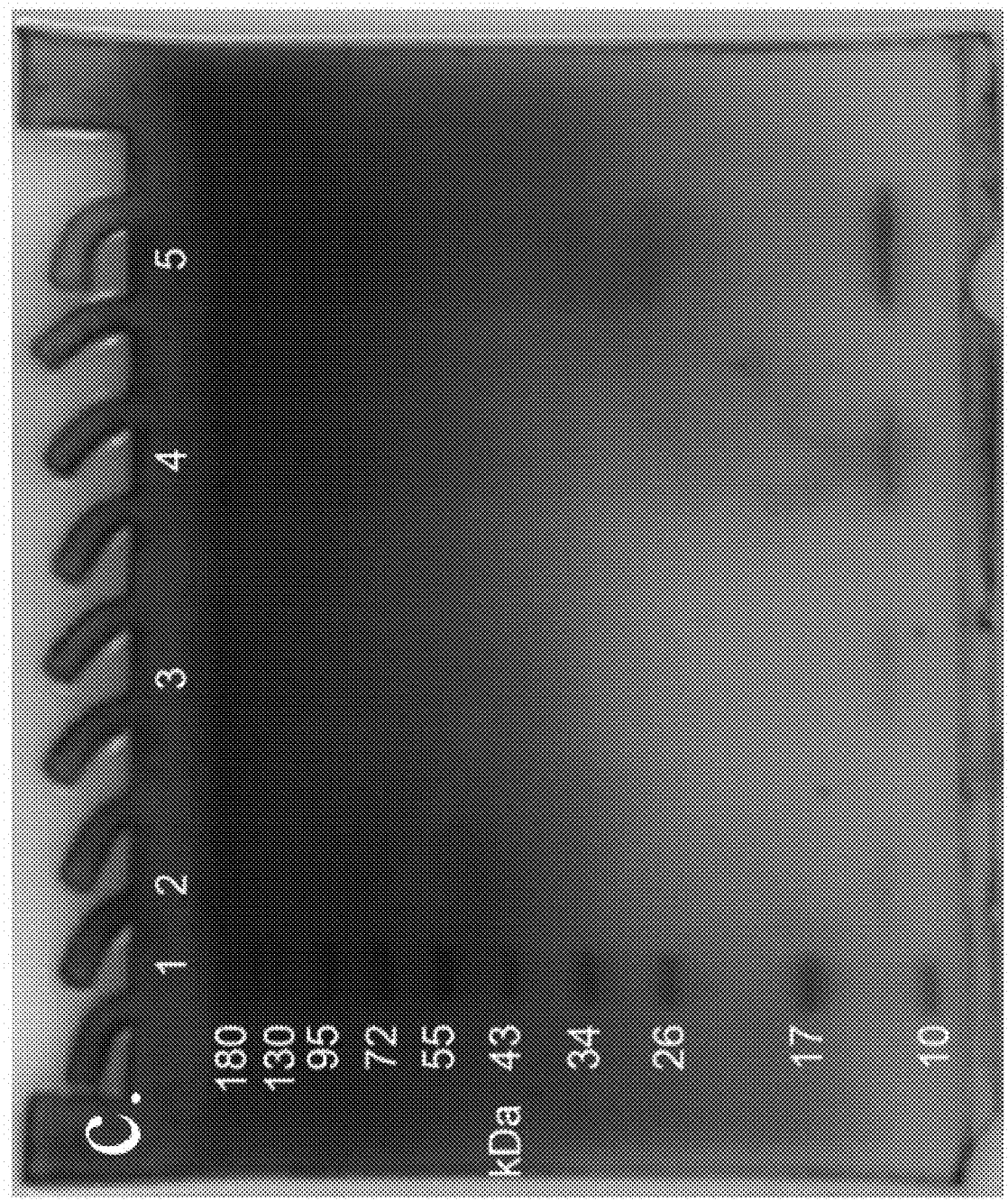
FIG. 18C is an image of a gel showing purified proteins associated with the biosynthesis of RC-Obi, shown separated on SDS-PAGE gels (any kD, Bio-Rad) and stained with Coomassie blue.

FIG. 18C is an image showing purified proteins associated with the biosynthesis of RC-Obi, shown separated on SDS-PAGE gels (any kD, Bio-Rad) and stained with Coomassie blue. Proteins include (from left to right lane): 1) ladder, 2) 830 ng CS_ObiD, 3) 1.6 µg CS_ObiD, 4) 3.2 µg CS_ObiD 5) 6.5 µg CS_ObiD. All proteins have an N-terminal His-tag.

Figure 18D:
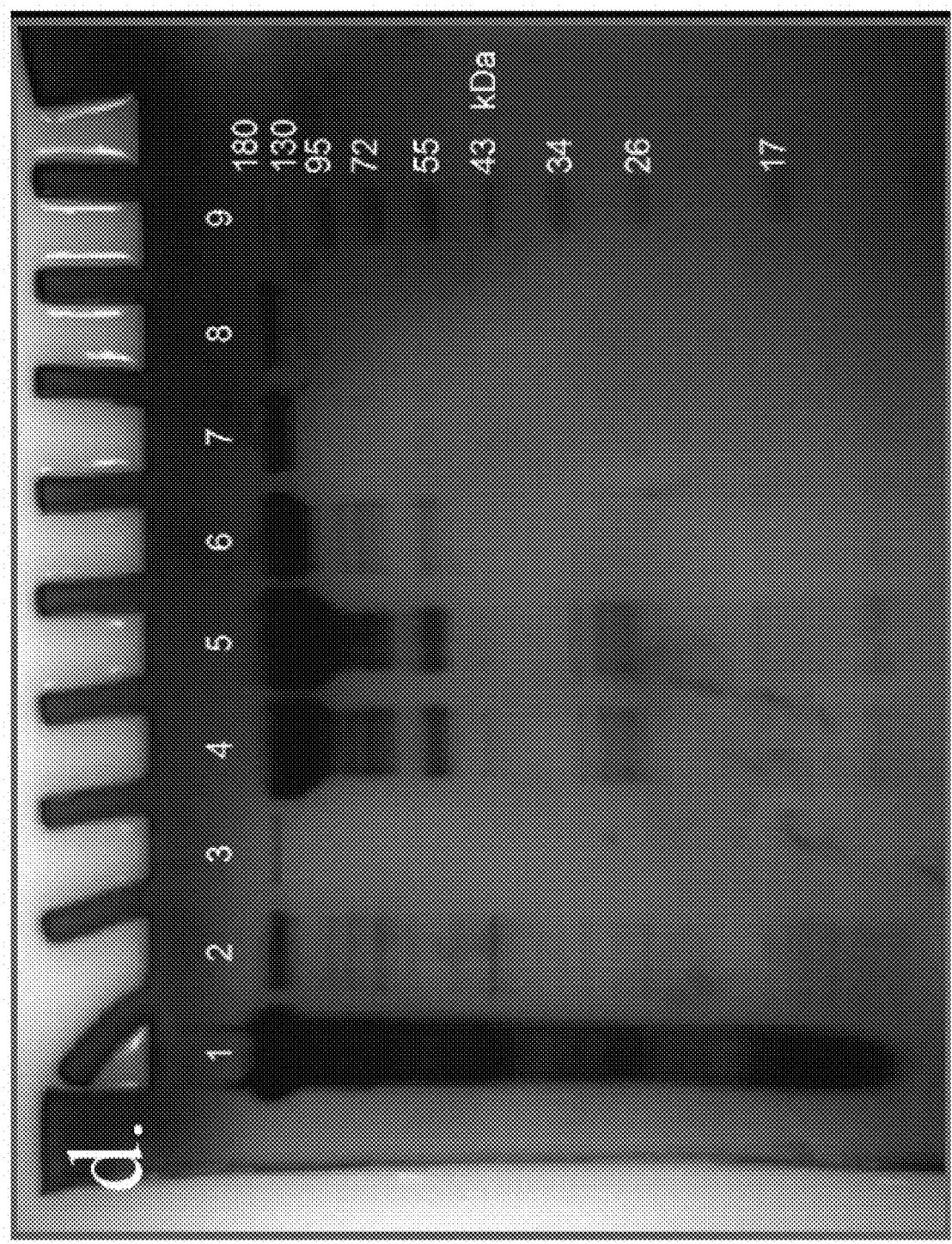
FIG. 18D is an image of a gel showing purified proteins from a Ni-NTA purification column of CS_ObiF, shown separated on SDS-PAGE gels (any kD, Bio-Rad) and stained with Coomassie blue.
Figure 19C:
FIG. 19C is an image showing a cell lysate of the resuspended cell pellet of FIG. 19B.
Figure 19B:
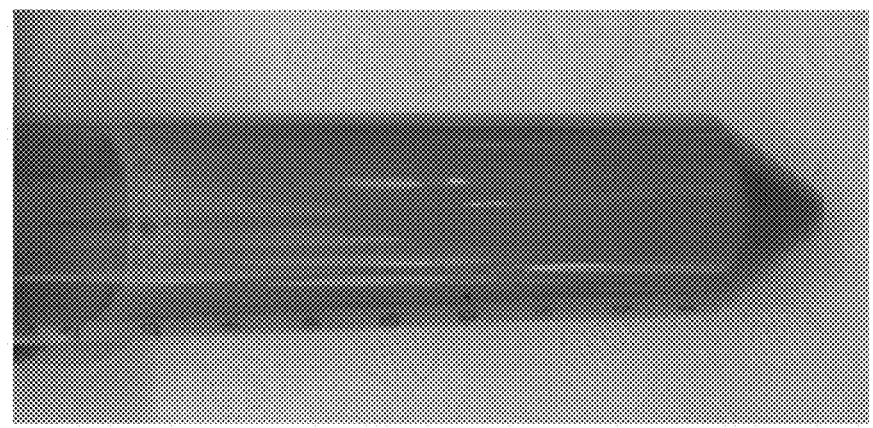
FIG. 19B is an image showing the resuspended cell pellet of FIG. 19A in lysis buffer.
Figure 19A:
FIG. 19A is an image showing an *E. coli* BL21 cell pellet after an induced growth period, in which the *E. coli* BL21 cells were induced to overexpress ObiH.
Figure 19E:
FIG. 19E is an image showing an Ni-agarose resin prior to loading the lysate of FIG. 19D.
Figure 19D:
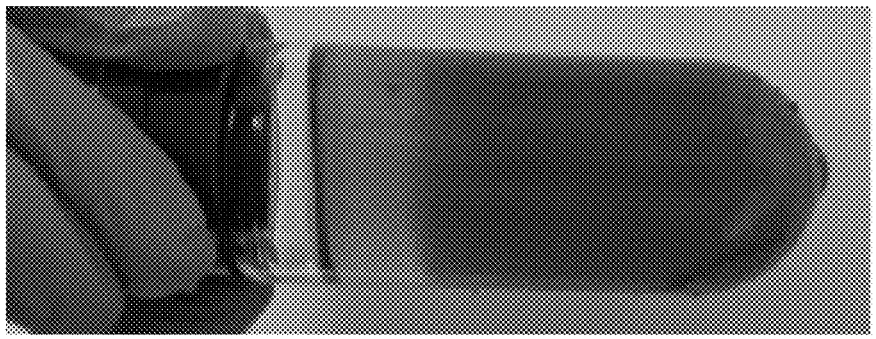
FIG. 19D is an image showing a pellet and lysate after ultracentrifugation of the cell lysate of FIG. 19C.
Figure 19G:
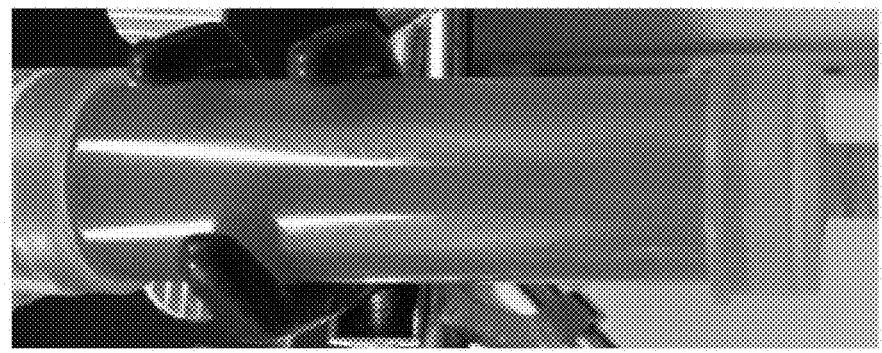
FIG. 19G is an image showing the Ni-agarose resin of FIG. 19F in a column suspension.
Figure 19F:
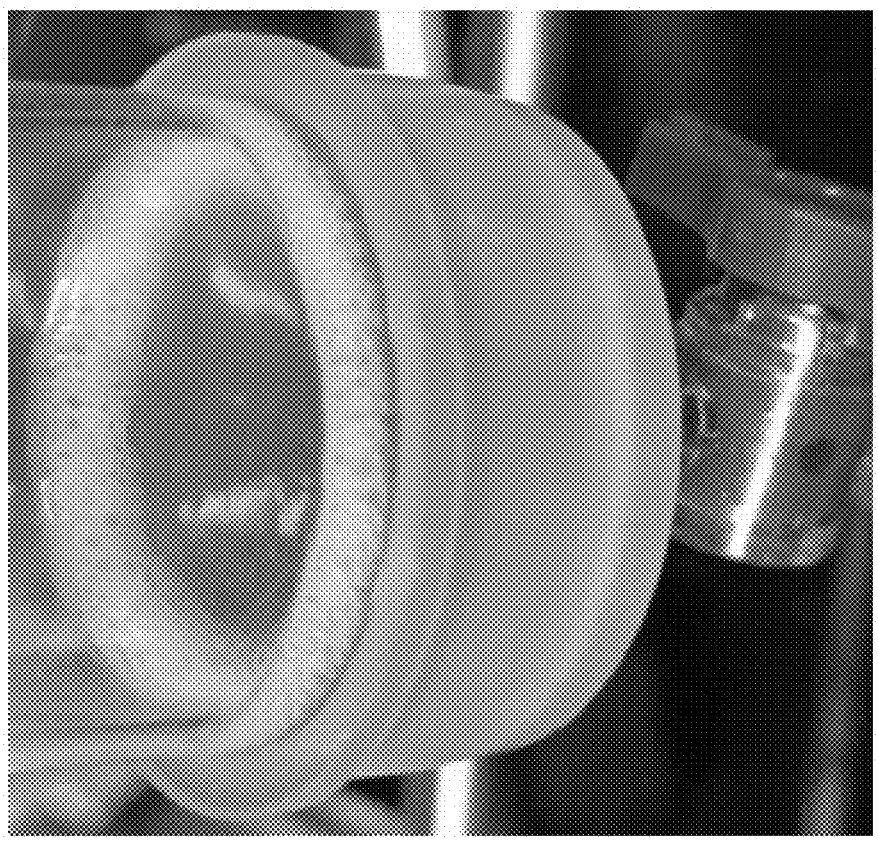
FIG. 19F is an image showing the Ni-agarose resin of FIG. 19E after loading the lysate of FIG. 19D.
Figure 19H:
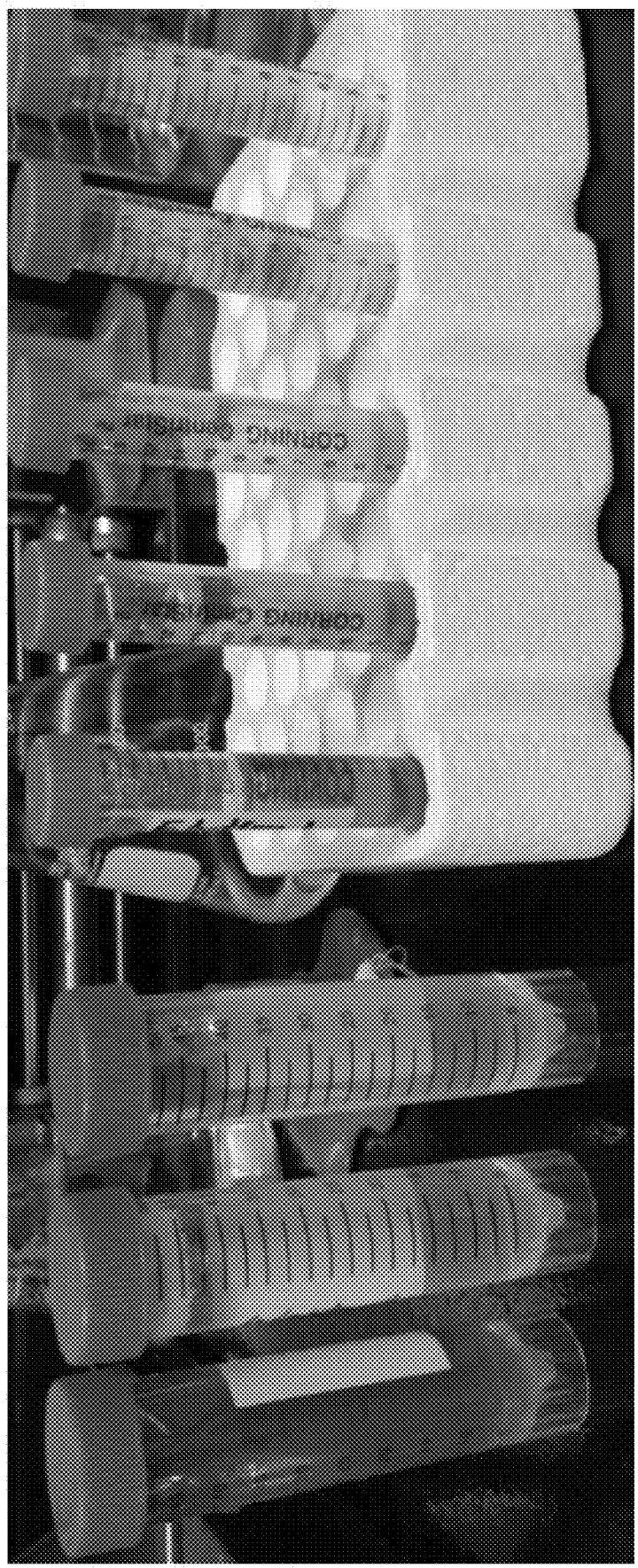
FIG. 19H is an image showing the fractions from Ni-agarose resin purification, from left to right: column flowthrough, wash 1, wash 2, elution 1, elution 2, elution 3, elution 4, and elution 5.
Figure 19I:
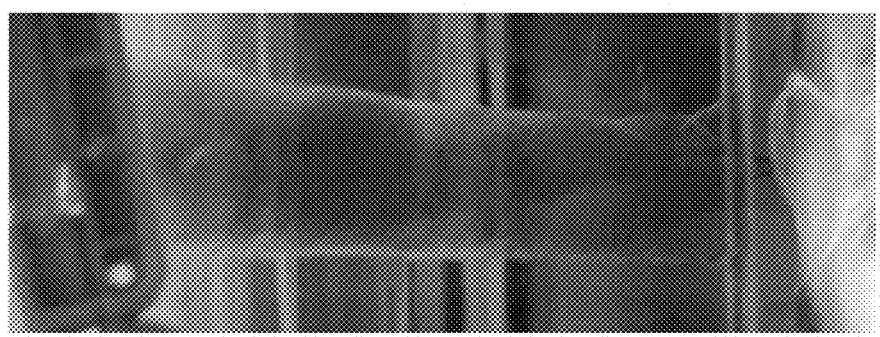
FIG. 19I is an image showing an ObiH protein solution from FIG. 19H in the dialysis tubing suspended in 1.8 L of size-exclusion buffer.

FIG. 18D is an image showing purified proteins from a Ni-NTA purification column of CS_ObiF, shown separated on SDS-PAGE gels (any kD, Bio-Rad) and stained with Coomassie blue. Proteins include (from left to right lane): 1) Flowthrough, 2) Wash 1, 3) Wash 2, 4) Elution 1, 5) Elution 2, 6) Elution 3, 7) Elution 4, 8) Elution 5, 9) ladder. All proteins have an N-terminal His-tag.

The experiments described above resulted in the successful expression and purification of various proteins serving as enzymes in the biosynthesis of RC-Obi.

Example 4: Mutagenesis of WT-ObiF to ObiF-CH1141S and ObiF-C1141A

To produce mutated analogs of wild-type ObiF, the following experiments were conducted.

Mutagenesis primers (see Table 6 and Table 7 above) were phosphorylated using T4 Polynucleotide Kinase according to product instructions. Primers were taken directly from phosphorylation mixture for use in PCR amplification. PCR was carried out using a Herculase II Fusion DNA Polymerase kit. After amplification, 1 µL FastDigest DpnI was added to PCR reaction mixture to digest template plasmid with wild type gene. Reaction was incubated at 37° C. for 60 min, then plasmids were purified using gel electrophoresis methods similar to those described in Example 3 above. Purified plasmids were ligated overnight at 16° C. using T4 DNA ligase, then transformed into electrocompetent *E. coli* TOP10 cells. Plasmids were sequenced using methods similar to those described in Example 1 to confirm the desired mutations.

The experiments described above resulted in the production of plasmids used to produce two mutated analogs of wild-type ObiF, ObiF-C1141S and ObiF-C1141A.

Example 5: Effect of Pyruvic Acid Substrates on ObiG Activity

To determine the sensitivity of ObiG activity with respect to different pyruvic acid substrates, the following experiments were conducted.

FIG. 10A is a schematic illustration showing the enzymatic biosynthesis of various phenylacetaldehydes via an enzyme (ObiG) reaction and the subsequent treatment of the phenylacetaldehydes with Purpald® to enable a colorimetric assay used to assess the products of the enzymatic reaction.

Purpald® indicator was used to estimate the activity of ObiG enzyme for four different pyruvic acid substrates according to the reaction scheme illustrated in FIG. 10A. A pre-incubation solution was made with 10 µM ThDP, 10 µM $MgCl_2$, 25 mM MES buffer pH 7.5, and 10 µM ObiG from a freshly thawed frozen stock. The enzyme pre-incubation solution incubated at room temperature for 5 min. In a separate 1.5 mL Eppendorf tube, the pyruvic acid substrate (PAPPA, PNPPA, PHPPA, or PPA) was diluted to 1 mM in 25 mM MES pH 7.5 buffer. The substrate mix was transferred in one aliquot into the pre-incubation solution. The final concentrations of reagents were 10 µM ObiG, 5 µM ThDP, 5 µM $MgCl_2$, 1 mM pyruvic acid substrate, and 25 mM Mes buffer pH 7.5. Aliquots of the enzyme solution were added to an equal volume of a 20 mg/mL solution of Purpald® in 1 M aqueous NaOH at various time points. The resulting solution was mixed and then left open to air to develop the purple color. All reactions and time points were single trials.

FIG. 10B is a photograph of reaction tubes containing reaction products resulting from the ObiG reaction illustrated in FIG. 10A that were treated with Purpald®. Each column of reaction tubes within the image corresponds to the substitution at the para-position of the phenylpyruvic acid (see FIG. 10A) and each row within the image corresponds to the reaction time at which each reaction aliquot was quenched with the Purpald® solution. The dark orange color for the PNPPA (R=$NO_2$) substrate is due in part to the starting material, which forms an orange anion at basic pH (the pH of the Purpald® solution is ~15). The legend on the bottom of the image shows the substitution at the para-position of the phenylpyruvic acid and the time points on the right of the image show when reaction aliquots were quenched with the Purpald® solution. The dark orange color for the PNPPA (R=$NO_2$) substrate is due in part to the starting material, which forms an orange anion at basic pH (the pH of the Purpald®; solution is ~14).

The results of this experiment demonstrated varying levels of ObiG activity depending on the substitution at the para-position of the phenylpyruvic acid.

Example 6: Detection of ObiH Quinonoid by Optical Absorption Spectroscopy

To characterize the formation of a stable quinonoid by ObiH, the following experiments were conducted.

FIG. 13A is an illustration showing a reaction scheme for the formation of an ObiH quinonoid starting with an internal Lys-aldimine which undergoes imine exchange with L-Thr to form an external aldimine. Referring again to FIG. 13A, a retro-aldol reaction may form acetaldehyde which may leave the active site and the stable quinonoid (λ~495 nm) poised to react with p-$NO_2$-phenylacetaldehyde in the forward aldol reaction to produce β-OH-p-$NO_2$-homoPhe.

In a 1.5 mL Eppendorf tube, a master mix of 50 µM ObiH from a freshly thawed frozen stock, 50 µM PLP, and 25 mM MES buffer was prepared and analyzed by optical absorption spectroscopy scanning from 200-600 nm. Three solutions at a final volume of 500 μL were analyzed as single trials: 1) L-Thr was added to the master mix a 1 mM final concentration; 2) PAA was added to the master mix at 1 mM final concentration; and 3) L-Thr and PAA were added to the master mix at 1 mM final concentration each. All samples were then analyzed by optical absorption spectroscopy scanning from 200-600 nm in order to observe the quinonoid peak which absorbs at ~495 nm.

FIG. 13B is a graph showing the absorption spectra obtained from all samples. The ObiH quinonoid was observable by optical absorption spectroscopy with a characteristic absorbance at ~495 nm when the ObiH was treated with PLP and L-Thr (blue trace). ObiH treated with PLP alone (black trace), ObiH treated with PLP and phenylacetylaldehyde (PAA) (green trace), and ObiH treated with PLP, PAA, and L-Thr (red trace) exhibited no absorbance peak at 495 nm, indicating that no quinonoid was formed.

FIGS. 19A, 19B, 19C, 19D, 19E, 19F, 19G, 19H, and 19I illustrate the stability of the ObiH quinonoid throughout an enzyme purification process. The enduring presence of the quinonoid, indicated by a magenta color, is clearly visible throughout the purification process.

The results of these experiments demonstrated that when ObiH was contacted with PLP and L-Thr, a quinonoid was formed.

Example 7: Effect of Pyruvic Acid Substrates on Combined ObiG/ObiH Double Enzyme Reactions To characterize the bioconversion of PNPPA to β-OH-p-NO$_2$-homoPhe by the enzymes ObiG and ObiH, the following experiments were conducted.

Three solutions were prepared using individual Eppendorf tubes. First, an ObiG solution containing 10 μM ThDP, 10 μM MgCl$_2$, and 10 μM ObiG was adjusted to 333 μL final volume using 25 mM MES buffer pH 7.5 and allowed to pre-incubate for 5 min. Second, a pyruvic acid solution containing 1 mM final concentration of PNPPA, PAPPA, PHPPA, and PPA, was adjusted to 333 μL with 25 mM MES buffer pH 7.5. Third, an ObiH solution containing 10 μM PLP, 1 mM amino acid (L-Thr), and 10 μM ObiH was adjusted to 333 μL final volume. After the pre-incubation time was complete, the three solutions were combined in a single Eppendorf tube and allowed rest for 3 hrs. at room temperature before quenching with MeCN to crash the enzyme. The mixtures were centrifuged and the supernatants were analyzed by LC-MS using a gradient of 0% B held for 5 minutes then 0% B to 95% B over 10 min using single ion monitoring for the expected ions in positive ion mode (retention times and observed product ions (see FIG. 2A): β-OH-homoPhe, 1.7 min, [M+H]$^+$ m/z=196; β-OH-p-OH-homoPhe, 0.8 min, [M+H]$^+$ m/z=212; β-OH-p-NO$_2$-homoPhe, 2.9 min, [M+H]$^+$ m/z=241; β-OH-p-NH$_2$-homoPhe, not observed. Product masses were confirmed by high-resolution LC-MS analysis.

FIG. 2A is a graph summarizing the extracted ion chromatograms (EICs) vs retention time for the predicted products of a double enzyme reaction with ObiG and ObiH. EICs were generated by LC-MS using single ion monitoring (SIM) for the predicted [M+H]$^+$ ion m/z values: 211, 212, 196, and 241 for PAPPA (R=NH$_2$), PHPPA (R=OH), PPA (R=H), and PNPPA (R=NO$_2$), respectively. Control experiments demonstrated that both ObiG and ObiH are needed to convert p-NO$_2$-phenylpyruvate (PNPPA) and L-Thr to β-OH-p-NO$_2$-homoPhe. d FIG. 2H is an extracted ion chromatogram (EIC) showing EIC product concentrations resulting from the double enzyme reaction with ObiG and ObiH. PNPPA was a substrate and PAPPA was not a substrate in the double enzyme reaction. EICs were generated by LC-MS using single ion monitoring (SIM) for the predicted product [M+H]$^+$ ion m/z values: m/z=211 for PAPPA and m/z=241 for PNPPA. Control experiments demonstrate the strict requirement for both enzymes, decarboxylase ObiG and aldolase ObiH, to convert p-NO$_2$-phenylpyruvate and L-Thr to β-OH-p-NO$_2$-homoPhe.

For NMR analysis the same samples were prepared using fully deuterated MES buffer. After equilibration for 3 hrs., the reactions were quenched with TFA to a pH ~2. The samples were then flash frozen in liquid nitrogen, lyophilized to dryness, resuspended in 750 μL of D$_2$O, and centrifuged to pellet any insoluble particulate. The soluble supernatants were then transferred to NMR tubes and analyzed. All reactions were performed in triplicate.

Figure 21:
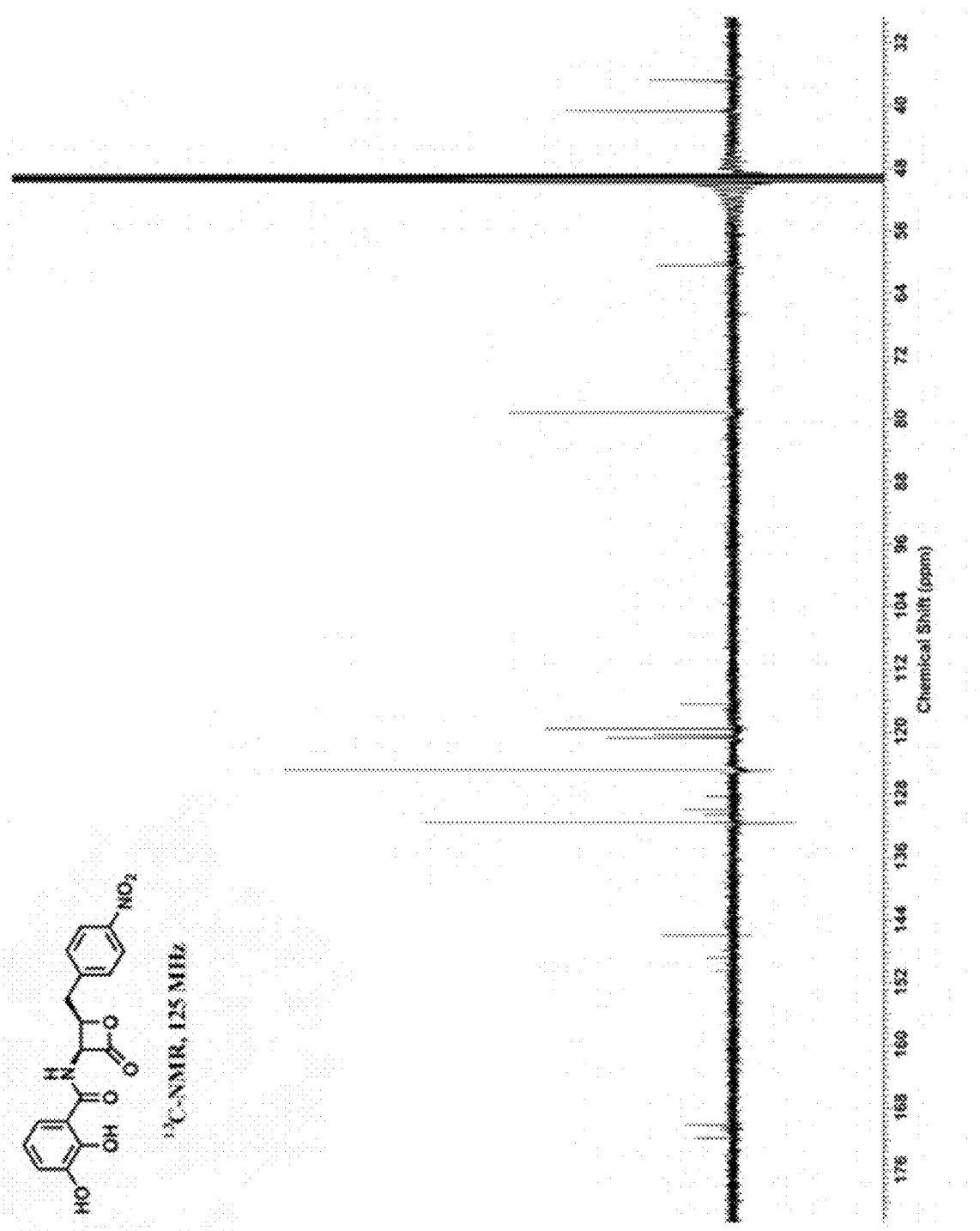
FIG. 21 is a $^{13}$C NMR spectrum obtained from a sample containing the closed-ring obafluorin protein (RC-Obi).

FIG. 21 is a bar graph showing the relative amount of L-Thr consumed during the ObiG/ObiH double enzyme reactions with L-Thr and either PAPPA or PNPPA. The double enzyme reactions were conducted in fully deuterated MES buffer and analyzed by $^1$H-NMR after 3 hrs. of equilibration. The product β-OH-homoPhe gives a diagnostic ddd-splitting pattern for H, with a chemical shift of ~4.4 ppm in the $^1$H-NMR spectrum (see inset graph of FIG. 2I), which is detectable only when PNPPA is the substrate of the reaction. The methyl group of L-Thr gives a characteristic doublet at ~1.2 ppm in the $^1$H-NMR spectrum. The intensity of this signal decreased noticeably when PNPPA was the substrate. Error bars represent standard deviations for three independent trials.

Figure 11A:
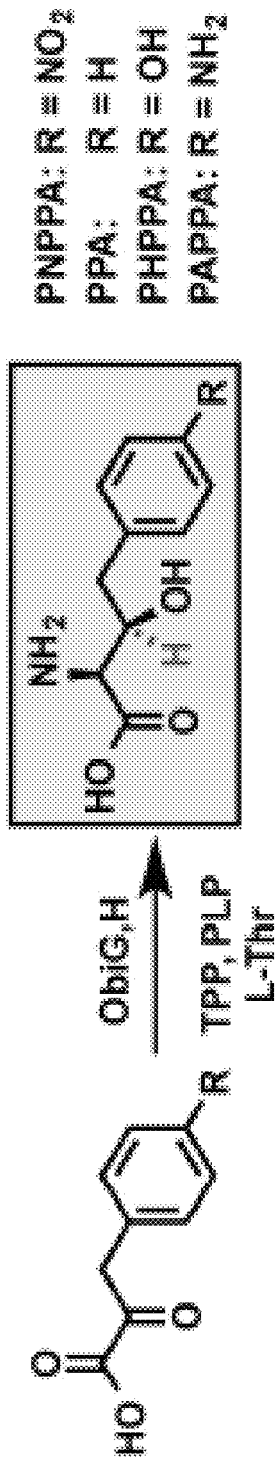
FIG. 11A is a schematic illustration showing the ObiG/ObiH double enzyme reactions with L-Thr and a panel of phenyl pyruvic acids (PNPPA, PPA, PHPPA, and PAPPA).
Figure 11B:
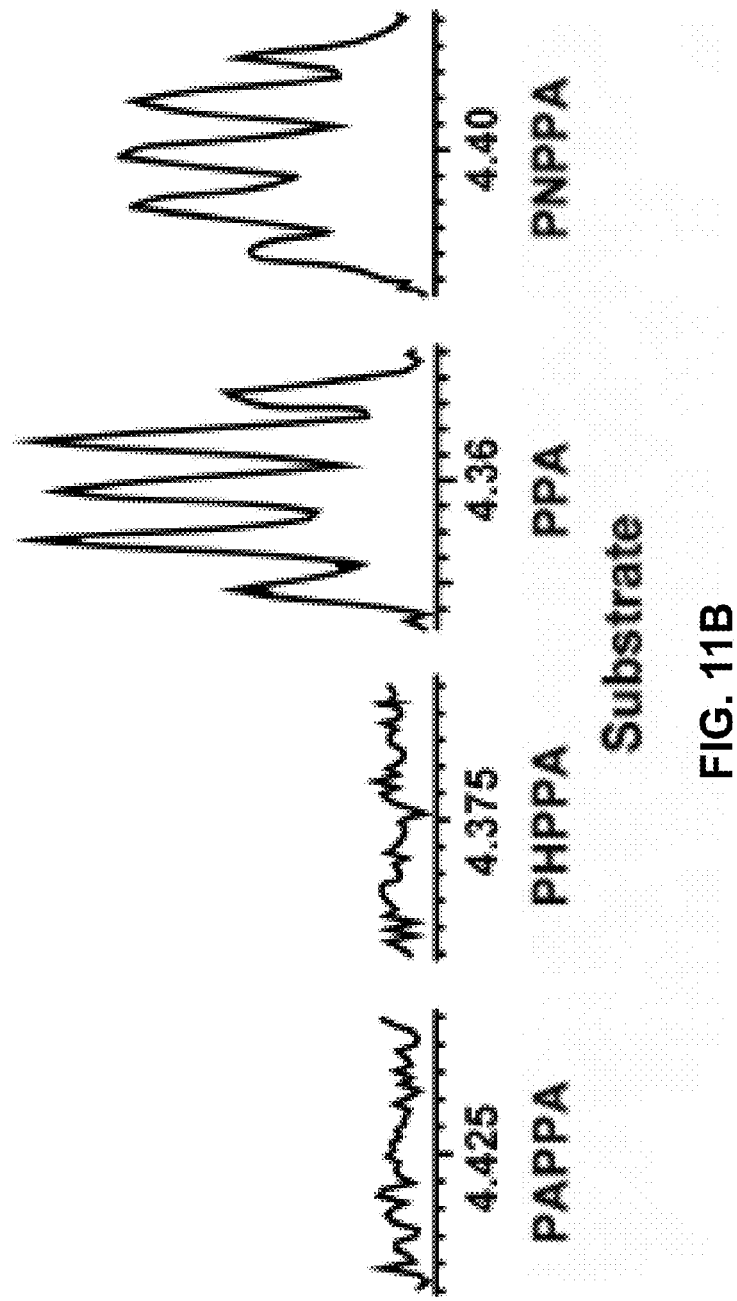
FIG. 11B contains extracted ion chromatograms (EIC) generated for the predicted product [M+H]$^+$ ion (m/z=241) of the four β-OH-p-$NO_2$-homoPhe produced by the ObiG/ObiH double enzyme reaction illustrated in FIG. 11A.

FIG. 11B contains extracted ion chromatograms (EIC) generated for the predicted product [M+H]$^+$ ion (m/z=241) of the four β-OH-p-NO$_2$-homoPhe produced by the ObiG/ObiH double enzyme reaction illustrated in FIG. 11A with four pyruvic acid substrates: PNPPA, PPA, PHPPA, and PAPPA. PNPPA was the preferred ObiG and ObiH substrate on the path to obafluorin. The ObiGiObiH double enzyme reactions with L-Thr and a panel of phenyl pyruvic acids (PNPPA, PPA, PHPPA, and PAPPA) were analyzed by 1H-NMR after 3 hrs. of equilibration. The product β-OH-homoPhe gave a diagnostic multiplet with a chemical shift of ~4.4 ppm in the 1H-NMR spectrum (proton highlighted in red in FIG. 11A), which is observed only for PNPPA and PPA. The methyl group of L-Thr gave a characteristic doublet at ~1.2 ppm in the 1H-NMR spectrum. The intensity of this signal decreased noticeably when PNPPA and PPA were the substrates.

Example 8: Effect of Amino Acid Substrates on Combined ObiG/ObiH Double Enzyme Reactions To characterize the bioconversion of PNPPA to β-OH-p-NO$_2$-homoPhe by the enzymes ObiG and ObiH, the following experiments were conducted.

Three solutions were prepared using individual Eppendorf tubes. First, an ObiG solution containing 10 μM TPP, 10 μM MgCl$_2$, and 10 μM ObiG was adjusted to 333 μL final volume using 25 mM MES buffer pH 7.5 and allowed to pre-incubate for 5 min. Second, a pyruvic acid solution containing 1 mM final concentration of PNPPA, was adjusted to 333 μL with 25 mM MES buffer pH 7.5. Third, an ObiH solution containing 10 μM PLP, 1 mM amino acid (L-Thr, D-Thr, L-Ser, D-Ser, Gly, L-alloThr, or D-alloThr), and 10 μM ObiH was adjusted to 333 μL final volume. After the pre-incubation time was complete, the three solutions were combined in a single Eppendorf tube and allowed rest for 3 hrs. at room temperature before quenching with MeCN to crash the enzyme. The mixtures were centrifuged and the supernatants were analyzed by LC-MS using a gradient of 0% B held for 5 minutes then 0% B to 95% B over 10 min using single ion monitoring for the expected ions in positive ion mode. Product masses were confirmed by high-resolution LC-MS analysis.

Figure 12:
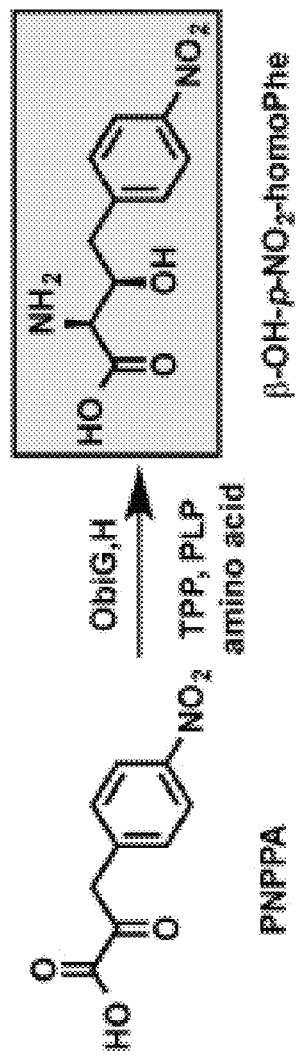
FIG. 12 is a schematic illustration of an ObiG and ObiH double enzyme reactions using PNPPA and a panel of amino acid substrates to enzymatically transform PNPPA into β-OH-p-$NO_2$-homoPhe.

After 3 hrs. of reaction time, the EICs were obtained for the product $[M+H]^+$ ion (m/z=241) of the β-OH-p-$NO_2$-homoPhe as predicted by the reaction diagram illustrated in FIG. 12. FIG. 2J is an extracted ion chromatogram (EIC) showing the β-OH-p-$NO_2$-homoPhe product concentrations resulting from the double enzyme reaction with ObiG and ObiH using PNPPA and a panel of amino acid substrates. The reaction including L-Thr resulted in the highest β-OH-p-$NO_2$-homoPhe product concentration.

A double enzyme reaction with ObiG and ObiH in the presence of TPP, PLP, and L-Thr revealed that PNPPA is directly converted to β-OH-p-$NO_2$-homoPhe as detected by LC-MS (FIG. 2H) and $^1$H-NMR analysis of the reaction mixture (FIG. 2I). p-Amino-phenylpyruvic acid (PAPPA) was not accepted as a substrate by ObiG/ObiH suggesting that ObiL must oxidize PAPPA prior to ObiG,H catalysis (FIG. 2H and FIG. 2I). These results firmly establish that PAPPA is the true substrate for oxygenase ObiL and decarboxylase ObiG acts on PNPPA to provide PNPAA aldehyde substrate for aldolase ObiH (FIG. 10B).

Example 9: NMR Analysis of β-OH-p-$NO_2$-homoPhe from the ObiG/ObiI Reaction

To characterize the structure of the β-OH-p-$NO_2$-homoPhe product resulting from the ObiG/ObiH double enzyme reaction described above (see FIG. 2A), the following experiments were conducted.

The ObiG/ObiH double enzyme reaction described above was scaled up with respect to the substrates to produce enough material for NMR analysis. The concentrations of reaction components were 10 μM ObiG, 10 μM ThDP, 10 μM $MgCl_2$, 10 μM ObiH, 10 μM PLP, 5 mM L-Thr, 5 mM PNPPA, and 25 mM pH 7.5 MES buffer, with a final reaction volume of 1 mL. After 3 hrs., the reaction was quenched with TFA to a pH ~2, centrifuged at 13,000 rpm for 2 min, flash frozen in liquid nitrogen, and lyophilized to dryness. The resulting solid was dissolved in 1:10 MeCN:H2O, filtered, and purified by preparatory HPLC using a solvent gradient of 0% B held for 5 min then 0% B to 100% B over 10 min (β-OH-p-$NO_2$-homoPhe retention time=14.3 min). The desired TFA salt of β-OH-p-$NO_2$-homoPhe product was isolated as a white powder.

Figure 32:
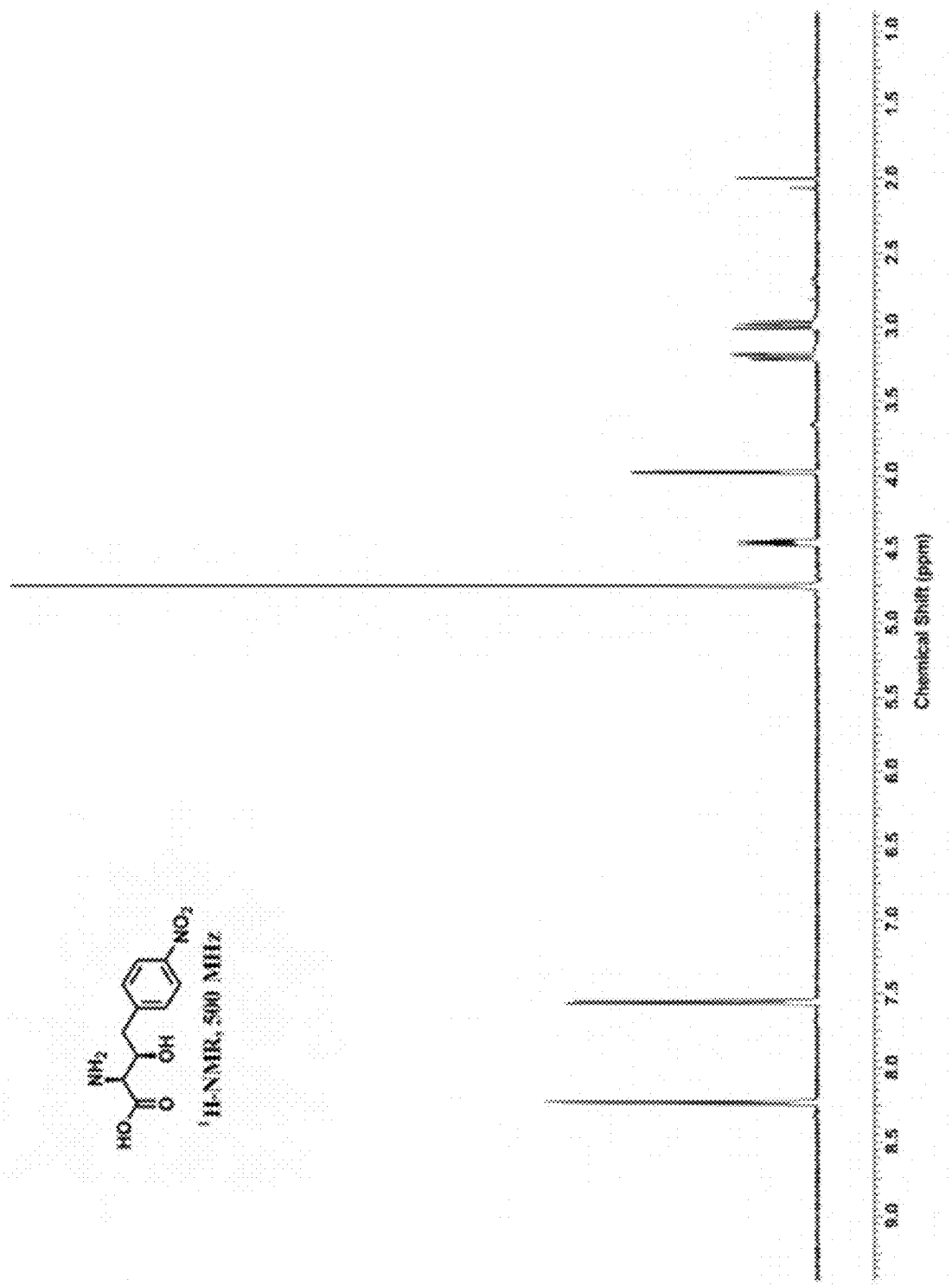
FIG. 32 is a $^1$H NMR spectrum obtained from a sample containing β-OH-p-NO$_2$-homoPhe.
Figure 33:
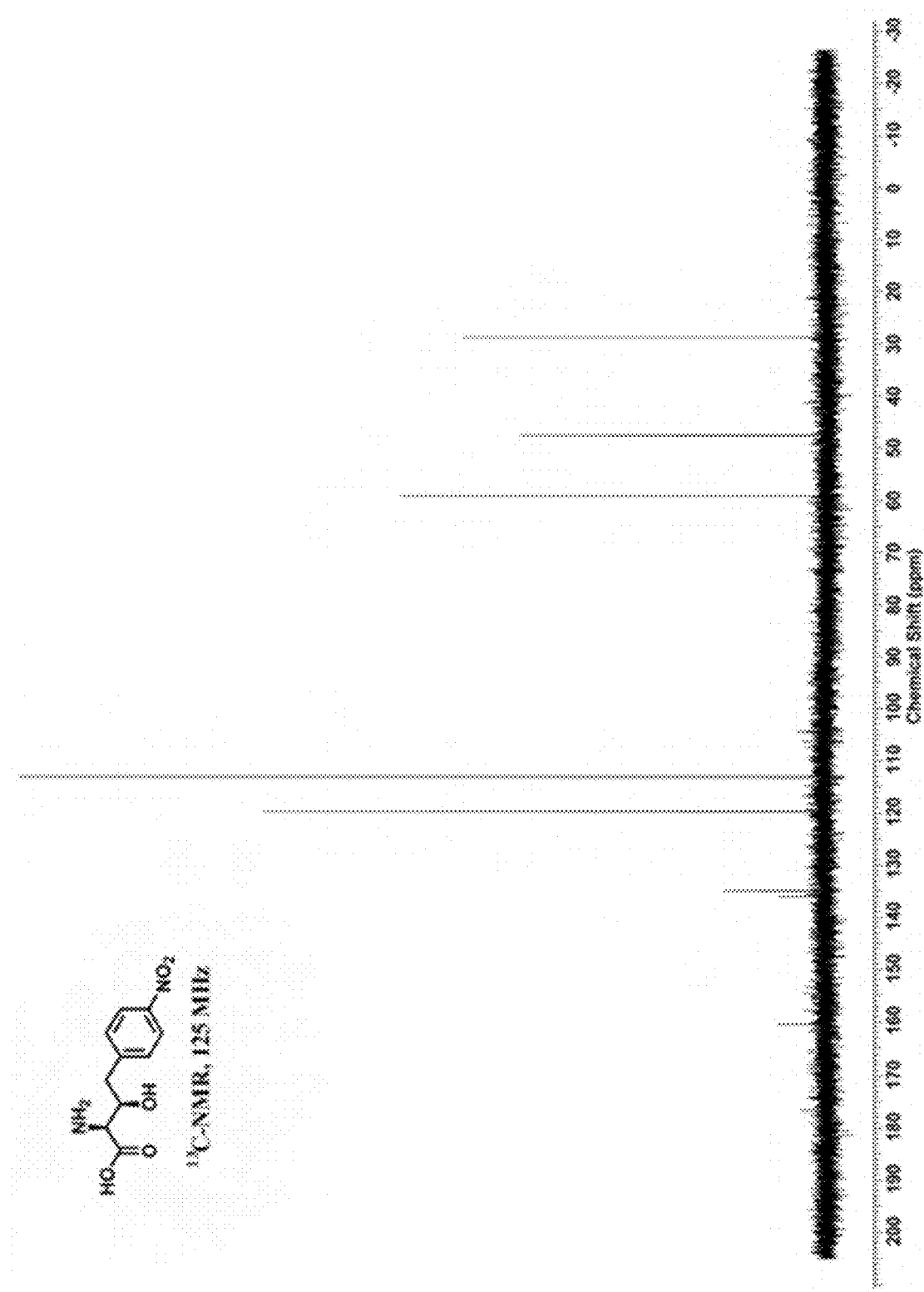
FIG. 33 is a $^{13}$C NMR spectrum obtained from a sample containing β-OH-p-NO$_2$-homoPhe.
Figure 34:
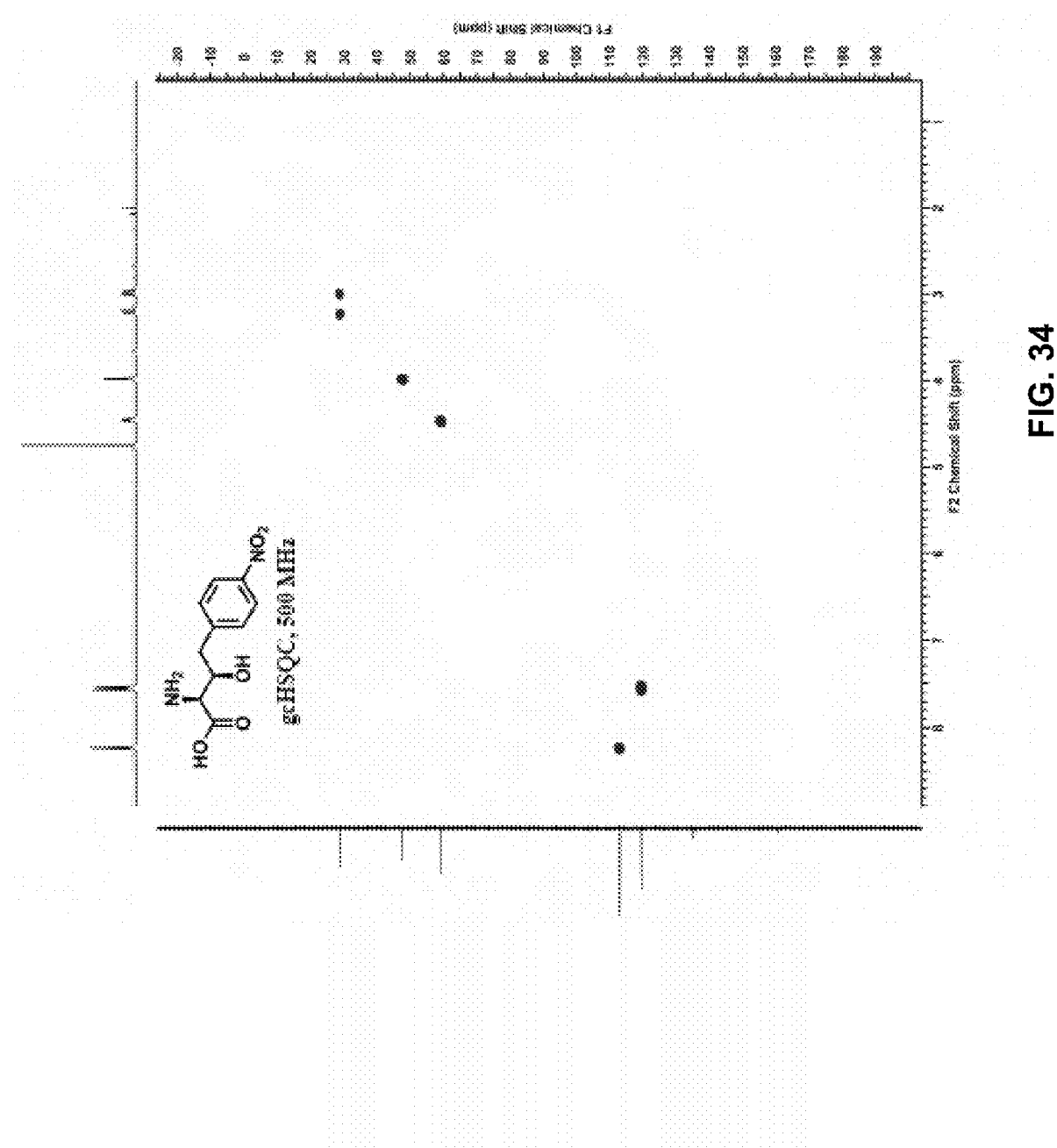
FIG. 34 is a $^1$H-$^{13}$C HSQC spectrum obtained from a sample containing p-OH-p-NO$_2$-homoPhe.
Figure 35:
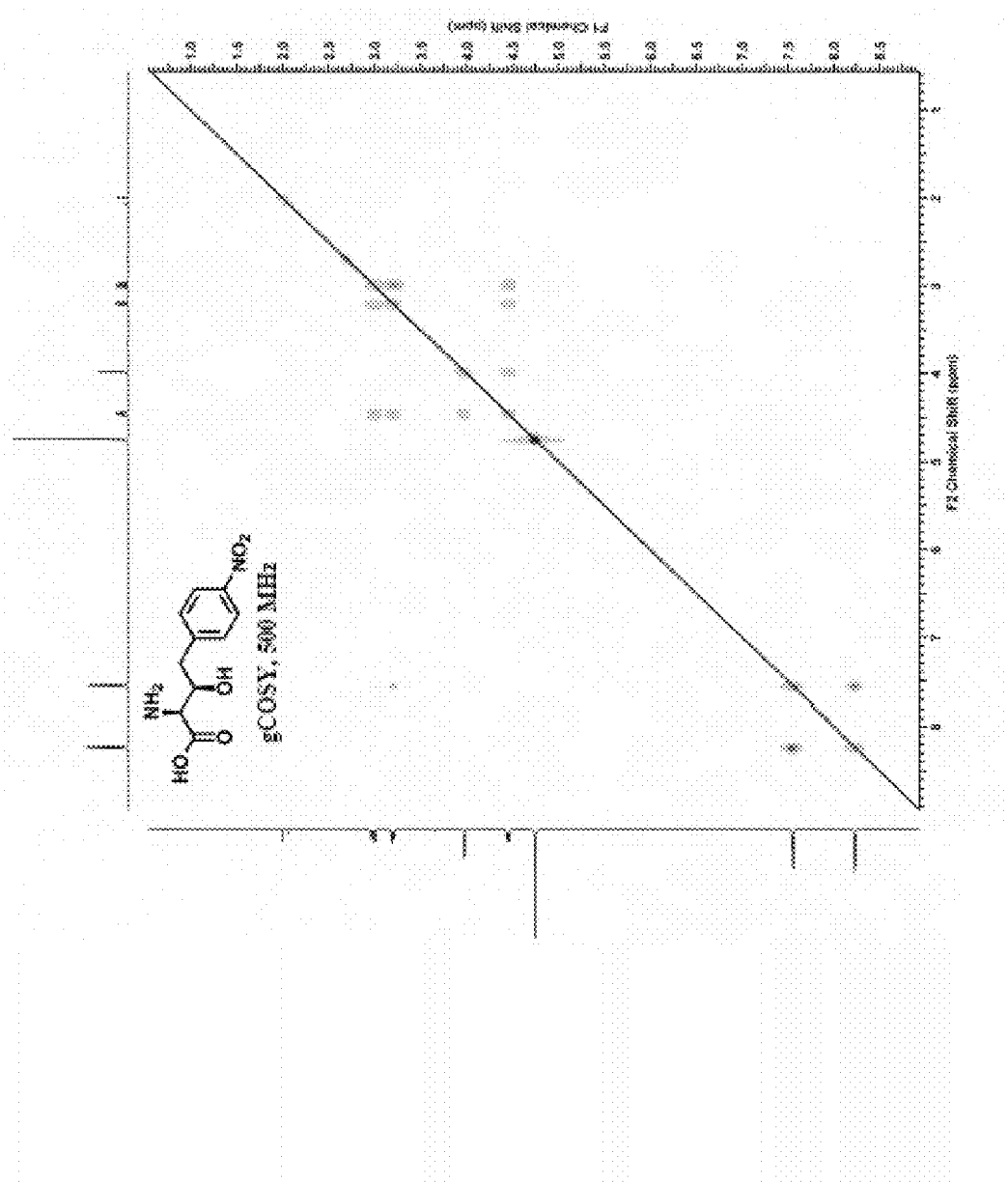
FIG. 35 is a $^1$H-$^{13}$C COSY spectrum obtained from a sample containing β-OH-p-NO$_2$-homoPhe.
Figure 36:
FIG. 36 is a $^1$H-$^{13}$C HMBC spectrum obtained from a sample containing β-OH-p-NO$_2$-homoPhe.
Figure 37:
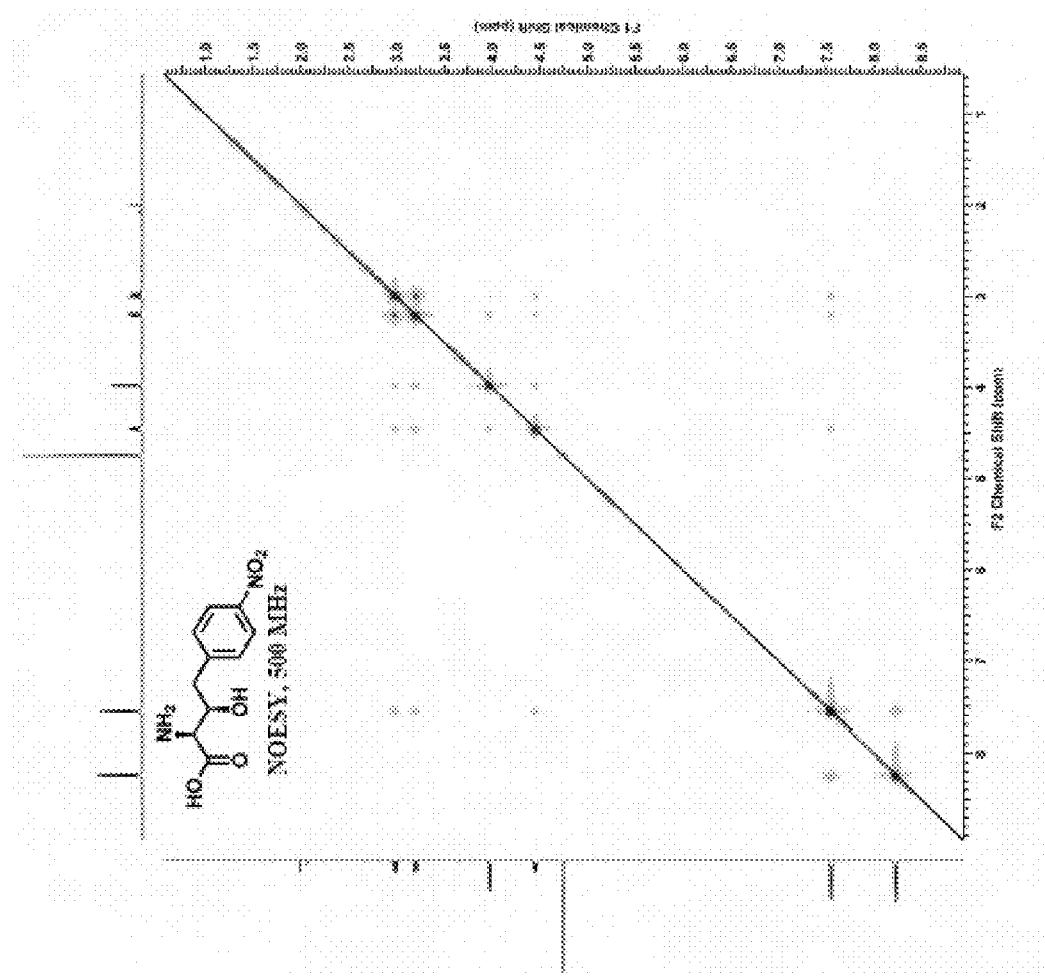
FIG. 37 is a $^1$H-$^{13}$C NOESY spectrum obtained from a sample containing β-OH-p-NO$_2$-homoPhe.

Table 9 is a summary of the NMR data obtained from a sample of the β-OH-p-$NO_2$-homoPhe product described above. NMR spectra obtained from the β-OH-p-$NO_2$-homoPhe product are provided as FIG. 32 ($^1$H NMR spectrum), FIG. 33 ($^{13}$C NMR spectrum), FIG. 34 ($^1$H-$^{13}$C HSQC spectrum), FIG. 35 ($^1$H-$^{13}$C COSY), FIG. 36 ($^1$H-$^{13}$C HMBC), and FIG. 37 ($^1$H-$^{13}$C NOESY spectrum). A summary of the NMR data obtained for this experiment are summarized in Table 9 below.

TABLE 9

NMR characterization data of β-hydroxy-p-$NO_2$-homoPhe TFA salt in $D_2O$.

| Atom | $^{13}$C (ppm) unreferenced | $^1$H (ppm), multiplets in Hz | gCOSY $^1$H-$^1$H 3 bond | HMBC $^1$H-$^{13}$C 2-3 bond | NOESY $^1$H-$^1$H through space, 4 Å |
|---|---|---|---|---|---|
| 1 | 160.56 | | | 2, 3 | |
| 2 | 47.54 | 3.98 (d, J = 4.8 Hz, 1H) | 3 | 1, 3, 4 | 3, 4a, 4b |
| 3 | 59.15 | 4.49-4.43 (m, 1H) | 2, 4a, 4b | 1, 4, 5 | 2, 4a, 4b, 6 |
| 4 | 28.86 | a) 3.20 (dd, $J_{4b}$ = 14.0 Hz, $J_3$ = 3.6 Hz, 1H) b) 2.99 (dd, $J_{4b}$ = 14.0 Hz, $J_3$ = 10.2 Hz, 1H) | 3, 4a, 4b | 2, 3, 5, 6 | 2, 3, 6 |
| 5 | 134.95 | | | 3, 4, 7 | |
| 6 | 119.73 | 7.55 (d, J = 9.0 Hz, 2H) | 7 | 4, 8 | 3, 4a, 4b, 7 |
| 7 | 113.17 | 8.24 (d, J = 8.4 Hz, 2H) | 6 | 5, 6 | 6 |
| 8 | 136.03 | | | 6 | |

The results of these experiments characterized the structure of the β-OH-p-$NO_2$-homoPhe product resulting from the ObiG/ObiH double enzyme reaction described above.

Example 10: Combined OhiG, ObiH, and ObiL Triple Enzyme Reaction

Figure 9A:
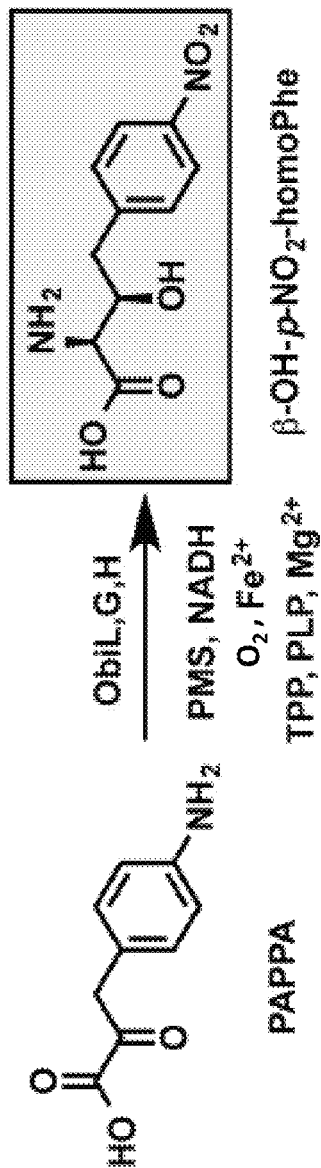
FIG. 9A is a schematic illustration showing the enzymatic biosynthesis of β-OH-p-NO$_2$-homoPhe from PAPPA via a triple enzyme ObiL/ObiG/ObiH reaction with additional reagents to enable a colorimetric assay as illustrated in FIG. 9B.

FIGS. 2F and 9A illustrate a conversion of PAPPA to β-OH-p-$NO_2$-homoPhe through the ObiG, ObiH, and ObiL Triple Enzyme Reaction. To characterize the role of ObiL enzyme in the enzymatic conversion of PAPPA to β-OH-p-$NO_2$-homoPhe using the reaction illustrated schematically in FIG. 2F, the following experiments were conducted.

A solution of 100 μM ObiL from a freshly thawed frozen stock, 3 mM phenazine methosulfate, 1 mM PAPPA, 100 μM iron(II) sulfate, and 25 mM NADH was prepared in 25 mM MES buffer at pH 5.5 at a final volume of 500 μL. NADH was added last to initiate the reaction and the mixture was incubated at room temperature for 1 hr. Upon addition of NADH, the color of the reaction changed from light yellow to sky blue to indicate the conversion of PAPPA to PNPPA by the reaction.

In a separate Eppendorf tube a 500 μL solution was prepared containing 10 μM ObiG, 10 μM ThDP, 10 μM $MgCl_2$, 10 μM ObiH, 10 μM PLP, 1 mM L-Thr, and 25 mM MES buffer at pH 7. The ObiG/ObiH solution was added directly to the ObiL solution formed above and the mixture was allowed to react for 2 hrs. at room temperature. The reaction mixture was quenched with MeCN to crash the enzyme. The pH of the ObiL solution changed from 5.5 to 7.0 over the course of the reaction. The control assay (i.e. no ObiL) reached an end pH of 6.0 and was adjusted to a pH of 7 using 1 M NaOH prior to addition of the ObiG/ObiH solution.

Figure 9B:
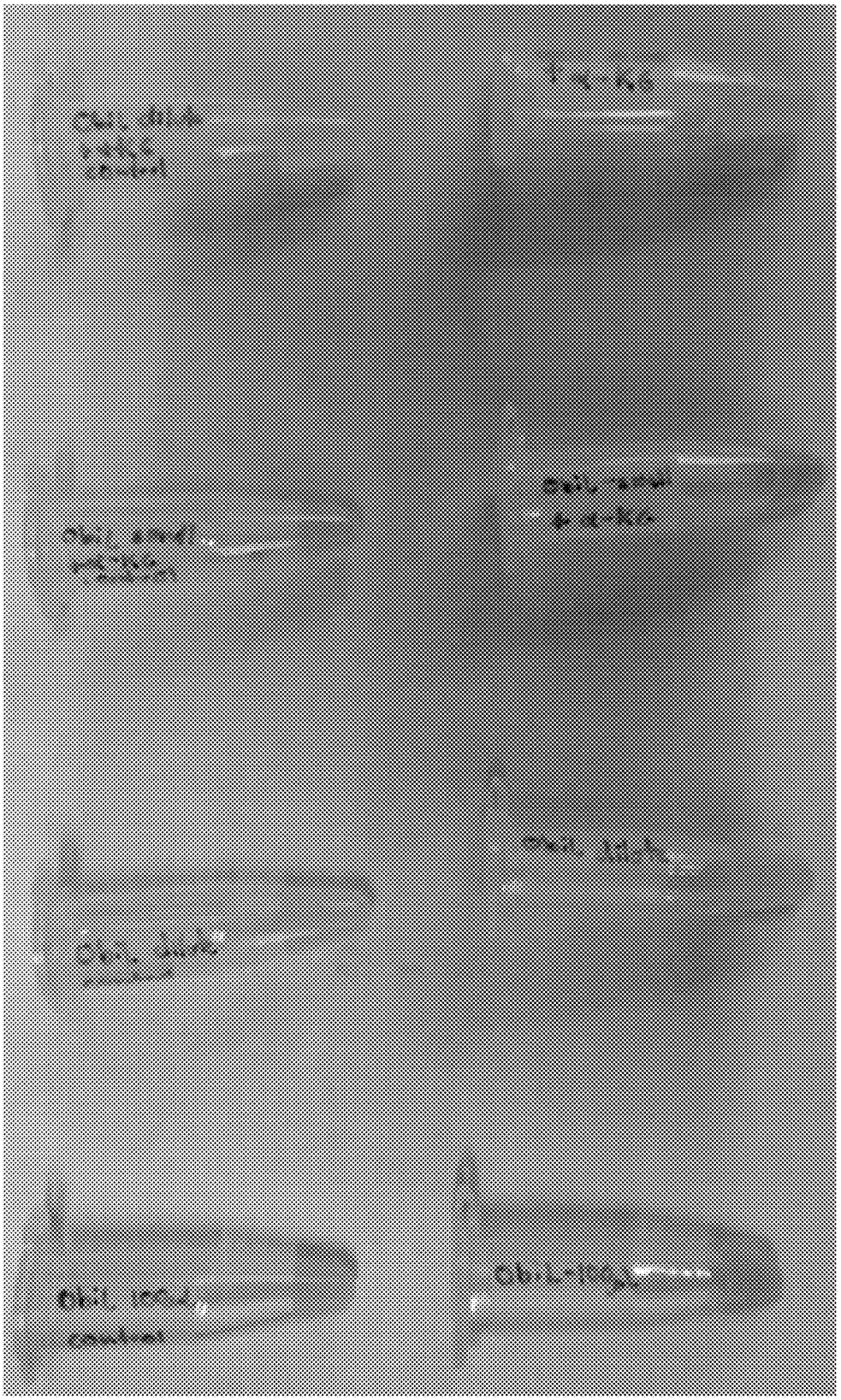
FIG. 9B is a photograph of two rows of reaction tubes containing the products of the triple enzyme ObiL/ObiG/ObiH reaction with PAPPA at the 1 hr. time point.

FIG. 9B is a photograph of two rows of reaction tubes containing the products of the triple enzyme ObiL/ObiGiObiH reaction with PAPPA at the 1 hr. time point. The tubes in the bottom row (sky blue) contain the products of the full colorimetric assay and the tubes in the bottom row (clear) are no-ObiL enzyme controls. The full assay mixture turned a sky blue color indicative of redox chemistry occurring.

The resulting mixtures were centrifuged and the supernatants were analyzed by LC-MS using a gradient of 0% B held for 5 min then 0% B to 95% B over 10 min. Ion counts for expected products were extracted from total ion chromatograms in positive ion mode. FIG. 2B is an extracted ion chromatogram (EIC) showing the β-OH-p-$NO_2$-homoPhe product concentration ($[M+H]^+$=241) resulting from the triple enzyme reaction with ObiG, ObiH, and ObiL. The EICs show formation of β-OH-p-$NO_2$-homoPh $[M+H]^+$ ion (m/z=241) starting from a PAPPA reactant when all three enzymes (ObiL/ObiGiObiH) and necessary cofactors and cosubstrates are present, thereby revealing the timing of aniline oxidation by ObiL. FIG. 2G is an extracted ion chromatogram (EIC) showing the β-OH-p-$NO_2$-homoPhe product concentration ($[M+H]^+$=241), indicating a similar dependence of the reaction on the inclusion of ObiL to enable the reaction.

Example 11: Combined ObiF and ObiD Double Enzyme Reaction

To characterize the formation of β-lactone analogs of RC-Obi using the obafluorin NRPS ObiF/ObiD reaction scheme (see FIG. 2C), the following experiments were conducted.

Phosphopantetheinylation of apo-ObiD and apo-ObiF (wild type, C1141S/C1141A mutants, and *C. shinanonensis* homologues) was carried out in separate 500 μL solutions containing 180 μM CoASH, 5 mM DTT, 10 mM $MgCl_2$, 400 nM Sfp, 25 μM apo-enzyme, and 75 mM tris-HCl at pH 7.552. The C1141S/C1141A mutant enzymes were produced using the methods described in Example 4 above. Reactions were left at room temperature for 2 hrs., and then used directly as the source of holo-ObiD and holo-ObiF. Reactions were performed in duplicate at 500 μL total volume. Full reactions contained 5 mM ATP, 5 mM DTT, 1 mM 2,3-DHB, 1 mM β-OH-p-$NO_2$-homoPhe, 1 μM holo-ObiF (ObiF, CS-ObiF, ObiF-C1141A, or ObiF-C1141S), 1 μM holo-ObiD, and 75 mM tris-HCl at pH 7.5. Control reactions were also prepared by replacing various components with an equivalent volume of 75 mM tris-HCl buffer. Three control experiments were performed for the ObiF (see Table 10), ObiF-C1141S (see Table 11), ObiF-C1141A (see Table 12), CS-ObiF reactions: (−) ObiD; (−) 2,3-DHB/(−) β-OH-p-$NO_2$-homoPhe; and (−) ATP (see Table 13). Two additional controls were prepared as either (−) ObiF or (−) ObiF/(−) ObiD. Reactions were performed at room temperature.

TABLE 10

Control reactions for ObiF.[a]

| Trial | Reagents | | | | | Products[b] | |
|---|---|---|---|---|---|---|---|
| | 2,3-DHB | β-hydroxy-p-$NO_2$-homoPhe | ATP | ObiF | ObiD | RC-Obi | RO-Obi |
| Full Assay | + | + | + | + | + | ++ | + |
| No substrates | − | − | + | + | + | − | − |
| No enzymes | + | + | + | − | − | − | − |
| No ObiF | + | + | + | − | + | − | − |
| No ObiD | + | + | + | + | − | − | − |
| No ATP | + | + | − | + | + | − | − |

[a]Reactions were conducted as described in the Online Methods.
[b]Presence (+) or absence (−) of products was judged by LC-MS analysis.

TABLE 11

Control reactions for ObiF-C1141S mutant.[a]

| Trial | Reagents | | | | | Products[b] | |
|---|---|---|---|---|---|---|---|
| | 2,3-DHB | β-hydroxy-p-$NO_2$-homoPhe | ATP | ObiF | ObiD | RC-Obi | RO-Obi |
| Full Assay | + | + | + | + | + | ++ | + |
| No substrates | − | − | + | + | + | − | − |
| No enzymes | + | + | + | − | − | − | − |
| No CS ObiF | + | + | + | − | + | − | − |
| No CS ObiD | + | + | + | + | − | − | − |
| No ATP | + | + | − | + | + | − | − |

[a]Reactions were conducted as described in the Online Methods.
[b]Presence (+) or absence ( ) of products was judged by LC-MS analysis.

TABLE 12

Control reactions for ObiF-C1141A mutant.[a]

| | Reagents | | | | | Products[b] | |
|---|---|---|---|---|---|---|---|
| Trial | 2,3-DHB | β-hydroxy-p-NO$_2$-homoPhe | ATP | ObiF-C1141S | ObiD | RC-Obi | RO-Obi |
| Full Assay | + | + | + | + | + | − | +++ |
| No substrates | − | − | + | + | + | − | − |
| No enzymes | + | + | + | − | − | − | − |
| No ObiF | + | + | + | − | + | − | − |
| No ObiD | + | + | + | + | − | − | − |
| No ATP | + | + | − | + | + | − | − |

[a]Reactions were conducted as described in the Online Methods.
[b]Presence (+) or absence ( ) of products was judged by LC-MS analysis.

TABLE 13

Control reactions for CS ObiF and CS ObiD.[a]

| | Reagents | | | | | Products[b] | |
|---|---|---|---|---|---|---|---|
| Trial | 2,3-DHB | β-hydroxy-p-NO$_2$-homoPhe | ATP | ObiF-C1141A | ObiD | RC-Obi | RO-Obi |
| Full Assay | + | + | + | + | + | − | + |
| No substrates | − | − | + | + | + | − | − |
| No enzymes | + | + | + | − | − | − | − |
| No ObiF | + | + | + | − | + | − | − |
| No ObiD | + | + | + | + | − | − | − |
| No ATP | + | + | − | + | + | − | − |

[a]Reactions were conducted as described in the Online Methods.
[b]Presence (+) or absence ( ) of products was judged by LC-MS analysis.

At 10, 30, and 60 min time points a 50 μL aliquot from each reaction was quenched with 50 μL acidic McCN (acidified with HCl) to give a final pH of approximately 3.5. Mixtures were centrifuged for 2 min at 13,000 rpm to remove precipitated enzyme and the supernatants were analyzed by LC-MS using a gradient of 5% solvent B to 95% solvent B over 20 min. Ion counts for the closed-ring obafluorin RC-Obi and open-ring obafluorin RO-Obi were extracted from total ion chromatograms in positive ion mode. Reaction mixtures were also analyzed by HPLC using a gradient of 5% B to 95% B over 20 min, 95% B to 100% B over 3 min, and 100% B to 5% B over 2 min at a flow rate of 1 mL/min with optical absorbance detection at 270 nm. Product ions and retention times were confirmed using purified standards of RC-Obi and RO-Obi isolated from *P. fluorescens* ATCC 39502 fermentations.

FIG. 2D is a summary of the EIC spectra showing the amount of RC-Obi ([M+H]$^+$ m/z=359) obtained for reactions that included wild-type ObiF (ObiF WT) as well as the C1141S/C1141A ObiF mutants. The retention time for the RC-Obi product was about 9.5 min. Referring again to FIG. 2D, only the wild-type ObiF enzyme enabled the production of the closed-ring obafluorin RC-Obi product. The low concentration of RC-Obi product resulting from the two-enzyme enzymatic conversion of β-OH-p-NO$_2$-homoPhe and 2,3-DHB using the holo-ObiF mutants C1141S and C1141A demonstrated that the active site cysteine residue in the TE domain of ObiF may influence the formation of the β-lactone ring.

FIG. 2E is a summary of the EIC spectra showing the amount of open-ring obafluorin RO-Obi ([M+H]$^+$ m/z=377) obtained for reactions that included wild-type ObiF (ObiF WT) as well as the C1141S/C1141A ObiF mutants. The retention time for the RO-Obi product was about 9 min. Referring again to FIG. 2E, the C1141S mutation of ObiF resulted in exclusive production of RO-Obi carboxylate while the wild-type ObiF and the C1141A mutation of ObiF resulted in slow accumulation of RO-Obi.

Figure 51:
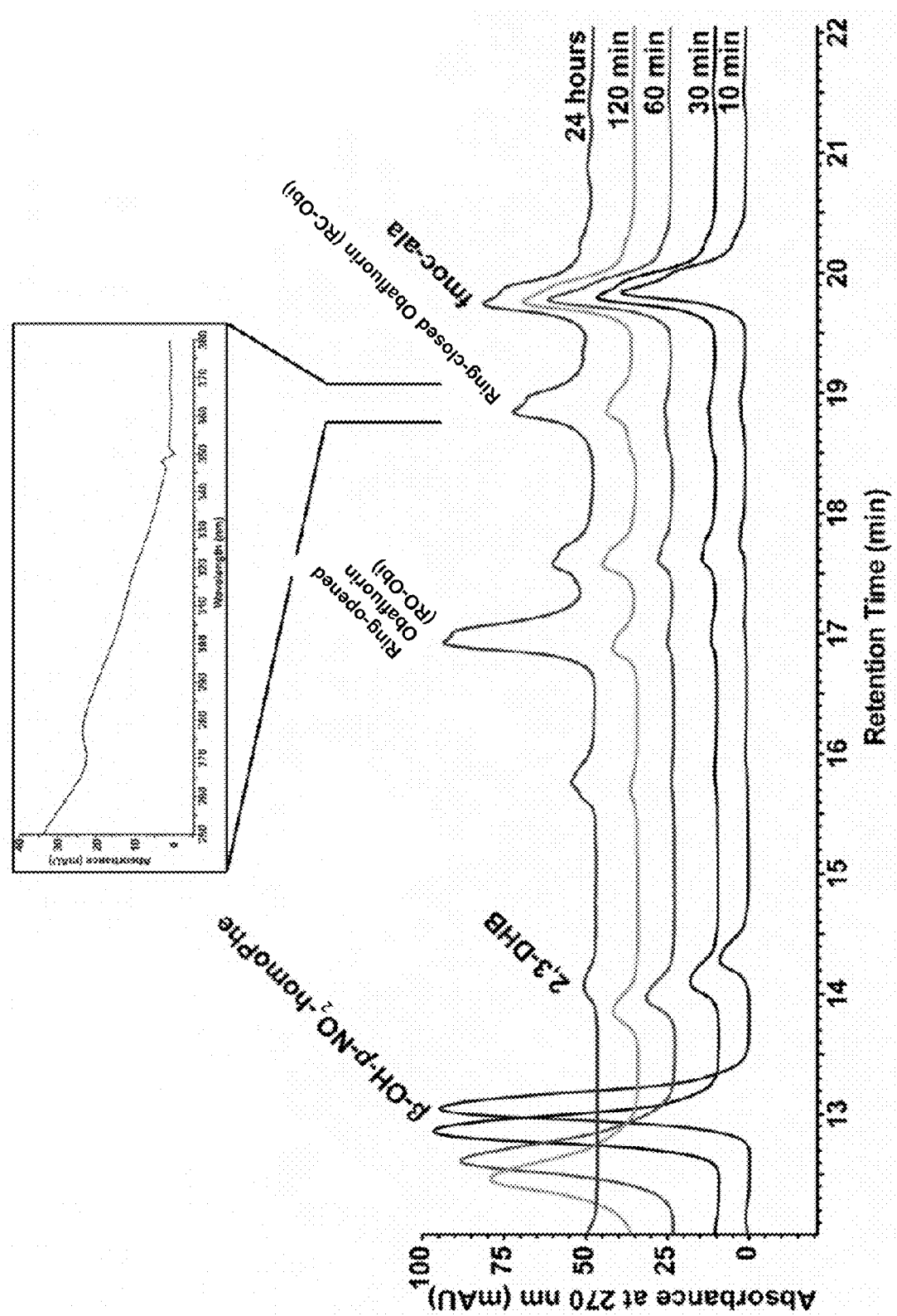
FIG. 51 is a graph showing a series of HPLC elution profiles for holo-ObiF-catalyzed conversion of 2,3-DHB and β-OH-p-NO$_2$-homoPhe to RC-Obi.
Figure 52:
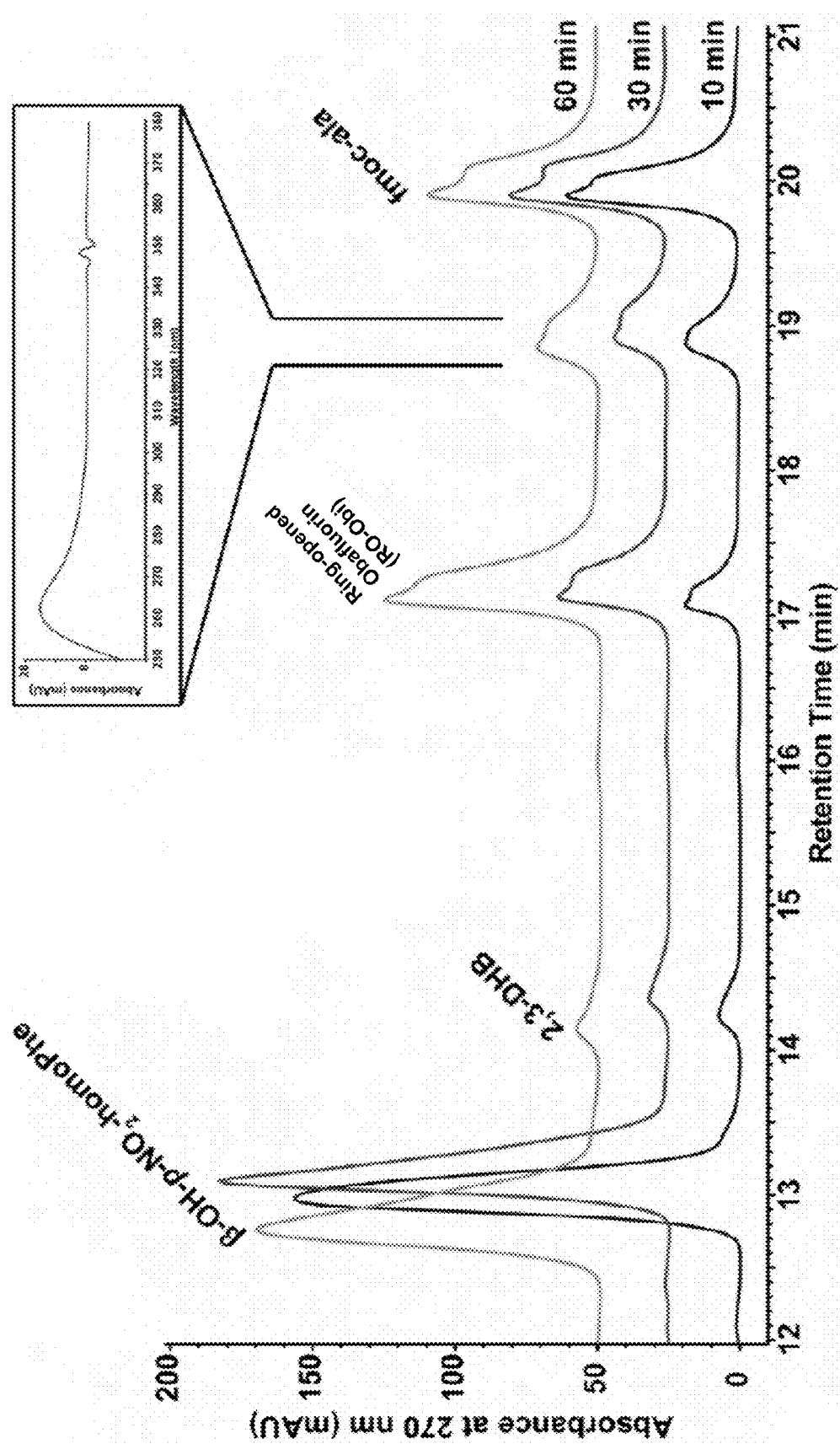
FIG. 52 is a graph showing a series of HPLC elution profiles for the holo-ObiF mutant C1141S-catalyzed conversion of 2,3-DHB and β-OH-p-NO$_2$-homoPhe to RC-Obi.
Figure 53:
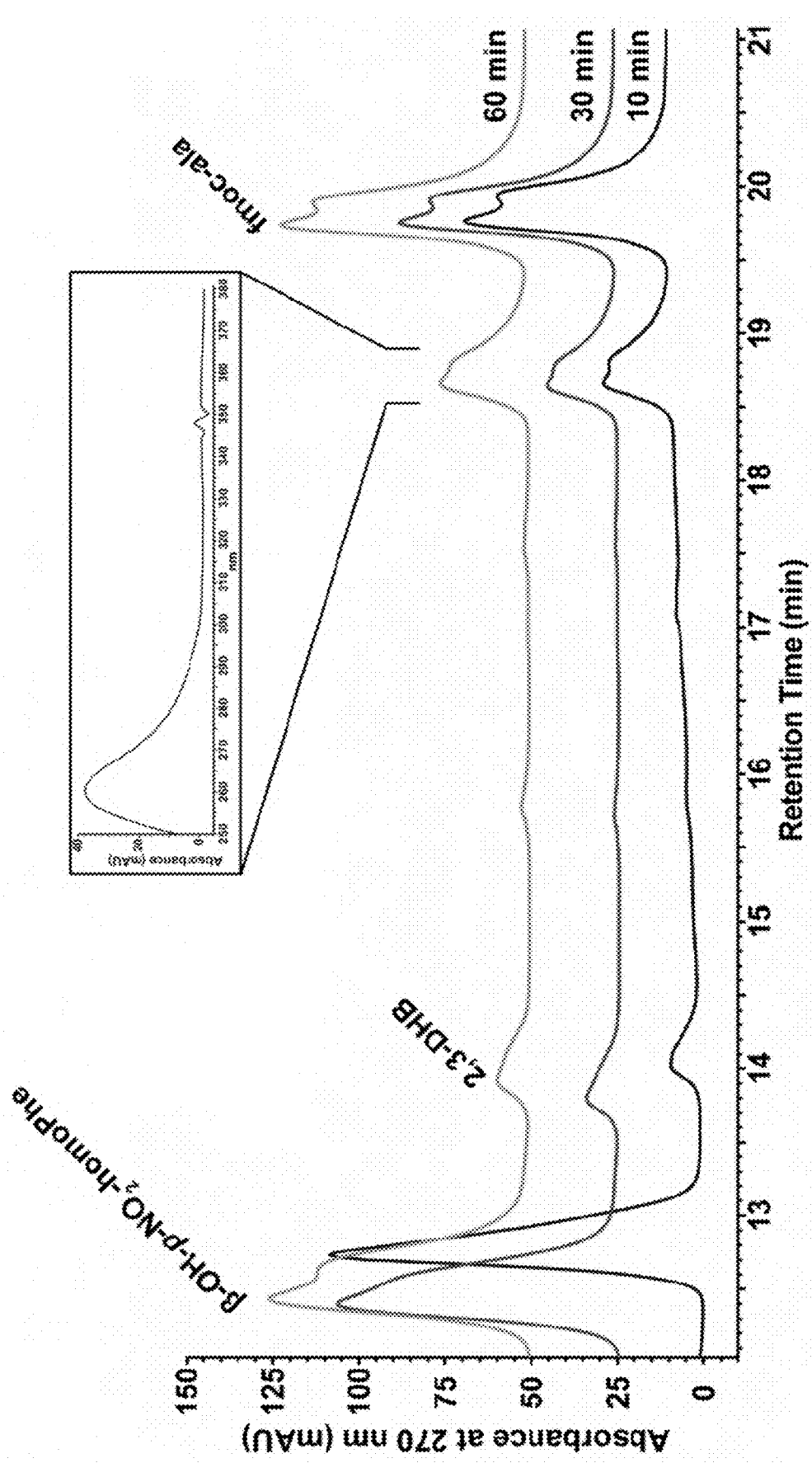
FIG. 53 is a graph showing a series of HPLC elution profiles for the holo-ObiF mutant C1141A-catalyzed conversion of 2,3-DHB and β-OH-p-NO$_2$-homoPhe to RC-Obi.

The reaction mixture of the ObiFiObiD-catalyzed conversion of 2,3-DHB and β-OH-p-NO2-homoPhe as monitored by HPLC with detection by optical absorbance is shown in FIGS. 51, 52, and 53 for reaction mixtures containing holo-ObiF, holo-ObiF mutant C1141S, and holo-ObiF mutant C1141A, respectively. The ObiF,D reaction was carried out in an identical manner for each variation of the ObiF enzyme. All HPLC chromatograms are shown for absorbance at 270 nm with retention times and peak heights normalized to an Fmoc-Ala internal standard.

FIGS. 51, 52, and 53 are graphs showing a series of HPLC elution profiles as monitored by absorbance at 270 nm with retention times and peak heights normalized to an Fmoc-Ala internal standard summarizing the concentrations of various reactants and reaction products for the holo-ObiF-catalyzed conversion of 2,3-DHB and β-OH-p-NO$_2$-homoPhe to RC-Obi (FIG. 51), the holo-ObiF mutant C1141S-catalyzed conversion of 2,3-DHB and β-OH-p-NO$_2$-homoPhe to RC-Obi (FIG. 52), and the holo-ObiF mutant C1141A-catalyzed conversion of 2,3-DHB and β-OH-p-NO$_2$-homoPhe to RC-Obi (FIG. 53); the inset graph shows the UV-vis spectrum of the RC-Obi peak.

As illustrated in FIG. 51, holo-ObiF converts β-OH-p-NO$_2$-homoPhe and 2,3-DHB to RC-Obi over time. The UV-vis spectrum (250-380 nm) of the Obi peak, shown illustrated in the inset graph of FIG. 51, is characterized by an absorbance signal detected at spectral wavelengths of up to ~350 nm due to the extended conjugation of the aryl-nitro group.

As illustrated in FIG. 52, the holo-ObiF mutant C1141S enzyme exclusively produces RO-Obi (open-ring obafluorin) from β-OH-p-NO$_2$-homoPhe and 2,3-DHB. The spectral peak shown at ~19 min in FIG. 52 is associated with an unknown impurity from the reaction. The UV-vis spectrum (250-380 nm) of the unknown peak, shown in the inset graph of FIG. 52, is not associated with RC-Obi, due to the absence of an absorbance signal beyond about 300 nm and as concluded from subsequent LC-MS analysis (data not shown).

As illustrated in FIG. 53, the holo-ObiF mutant C1141A enzyme had no detectable product formation within the reaction mixture, although the unknown peak at ~19 min was again observed.

Figure 54:
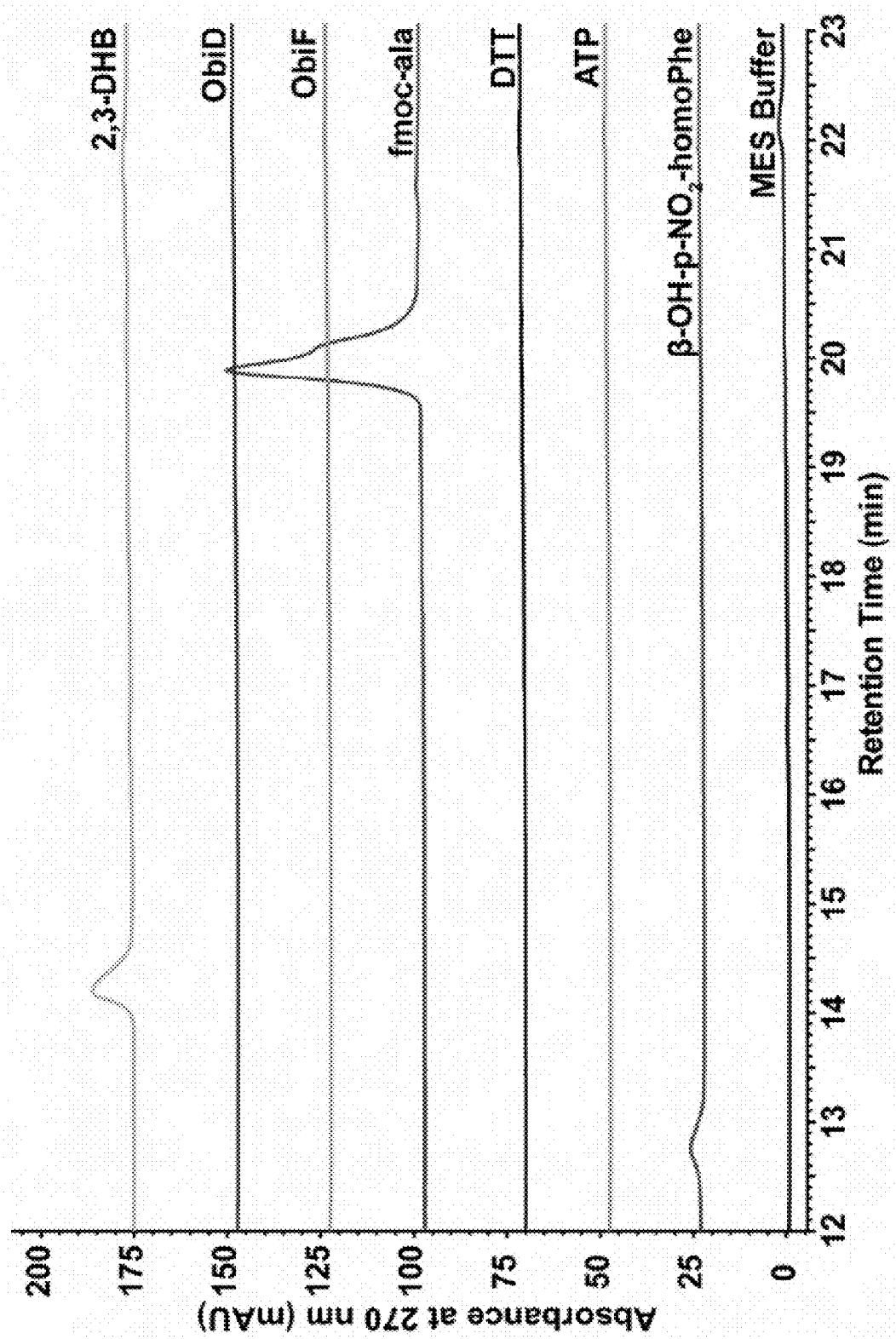
FIG. 54 is a graph showing a series of HPLC elution profiles of pure analytical standards corresponding to various reactants and intermediate products associated with the relevant to catalyzed conversion of 2,3-DHB and β-OH-p-NO$_2$-homoPhe to RC-Obi.

FIG. 54 is a graph showing HPLC chromatograms of pure analytical standards for compounds associated with the ObiF,D reaction. FIG. 54 shows a series of HPLC elution profiles as monitored by absorbance at 270 nm with retention times and peak heights normalized to an Fmoc-Ala internal standard summarizing the concentrations of pure analytical standards corresponding to various reactants and intermediate products associated with the relevant to catalyzed conversion of 2,3-DHB and β-OH-p-NO$_2$-homoPhe to RC-Obi.

Figure 15A:
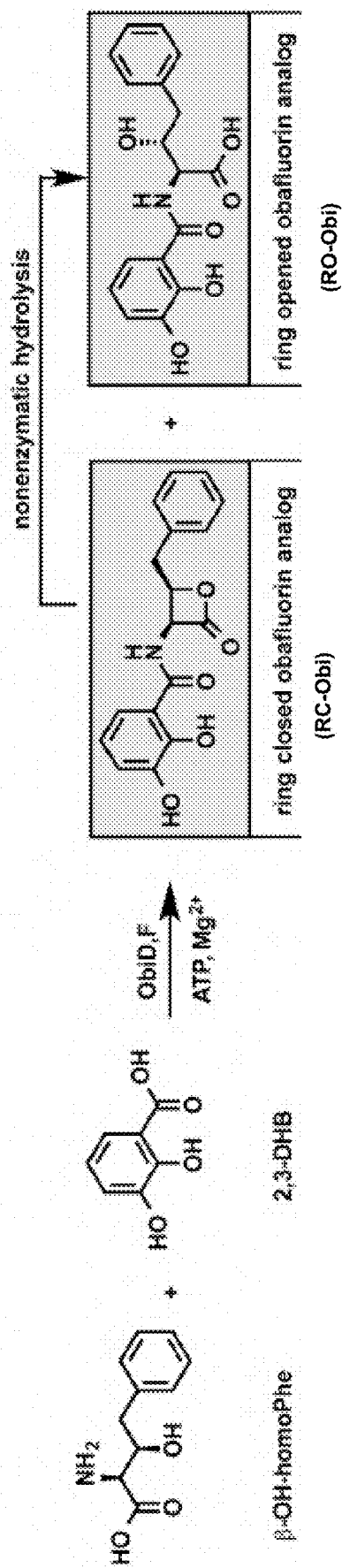
FIG. 15A is a schematic diagram illustrating the enzymatic synthesis of β-lactone analogs of RC-Obi using obafluorin NRPS enzymes ObiF and ObiH machinery.

To assess the effect of different substrates on the ObiFiO-biD-catalyzed formation of RC-Obi, the reaction and analysis described above was repeated for the ObiF/ObiD reactions with β-OH-p-NO$_2$-homoPhe and 2,3-DHB, with β-OH-homoPhe substituted for β-OH-p-NO$_2$-homoPhe, as illustrated schematically in FIG. 15A.

Figure 15C:
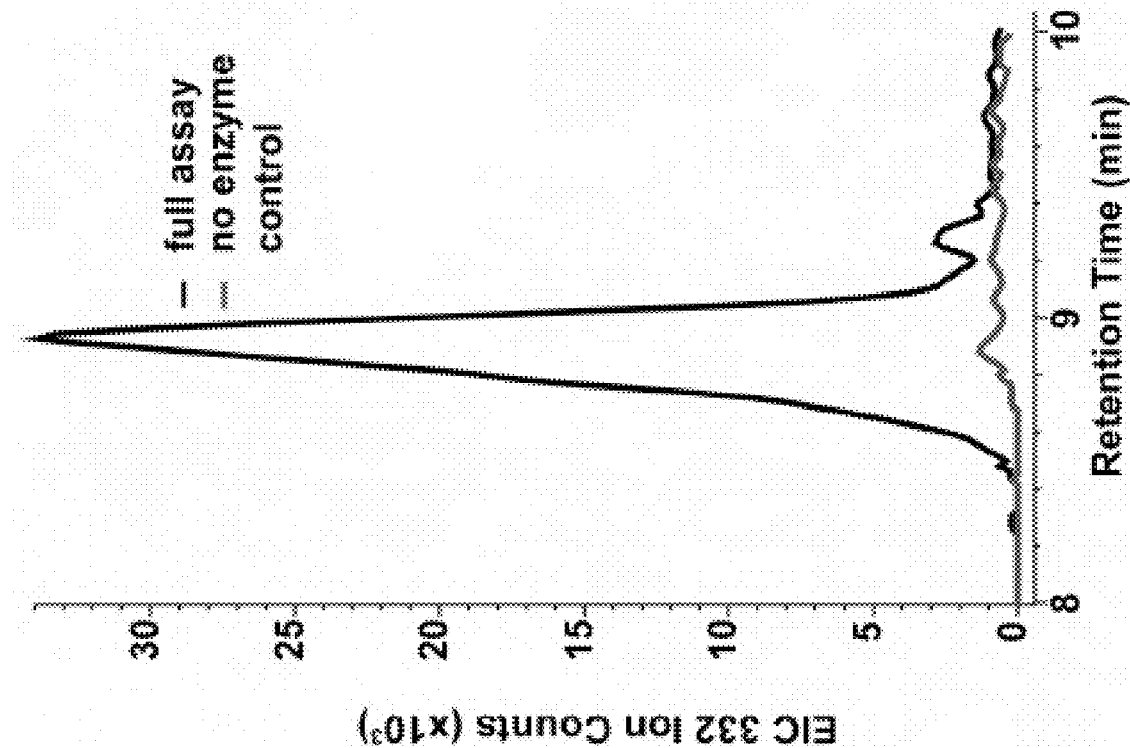
FIG. 15C is an EIC spectrum showing the amount of hydrolyzed ring-opened obafluorin analog product ([M+H]$^+$ m/z=332) produced by the reaction illustrated in FIG. 15A.
Figure 15B:
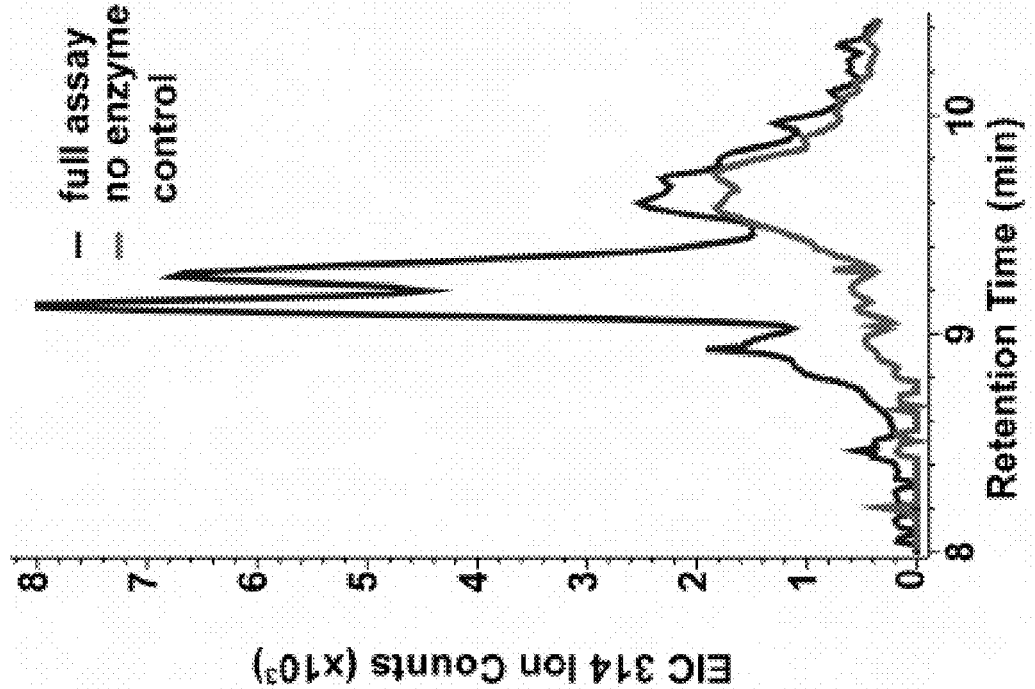
FIG. 15B is an EIC spectrum showing the amount of Δ-$NO_2$—Obi β-lactone analog ([M+H]$^+$ m/z=314) produced by the reaction illustrated in FIG. 15A.

FIG. 15B and FIG. 15C include graphs showing the EIC spectra of the holo-ObiF/holo-ObiD reaction of D-OH-homoPhe (from the ObiG/ObiH reaction with PPA) showing production of the Δ-NO$_2$-Obi β-lactone analog, [M+H]$^+$ (m/z=314), and the corresponding hydrolysis product, [M+H]$^+$ (m/z=332).

FIG. 15B is an EIC spectrum showing the amount of Δ-NO$_2$—Obi β-lactone analog ([M+H]$^+$ m/z=314) produced by the reaction illustrated in FIG. 15A. LC-MS analysis of the holo-ObiF/holo-ObiD reaction of β-OH-homoPhe (from the ObiG/ObiH reaction with PPA) shows production of the Δ-NO$_2$—Obi β-lactone analog, ([M+H]; m/z=314). FIG. 15C is an EIC spectrum showing the amount of hydrolyzed ring-opened obafluorin analog product ([M+H]m/z=332) produced by the reaction illustrated in FIG. 15A, showing production of the hydrolyzed Δ-NO$_2$—Obi β-lactone analog.

The results of these experiments demonstrated the production of Obi and Obi analogs using enzymatic synthesis with ObiD and ObiF.

Example 11: Activity of ObiF Measured Using [$^{32}$P] PPi Exchange Assay

To characterize the activity of the ObiF enzyme exposed to various amino acid and carboxylate substrates, the following experiments were conducted.

Reaction mixtures (650 µL) were formed that contained 2 µM ObiF, 5 mM of an amino acid, 1 mM ATP, 1 mM MgCl$_2$, 40 mM KCl, 1 mM DTT, 5 mM Na[$^{32}$P]PPi (3.3×10$^5$ cpm/mL), and 50 mM Tris-HCl (pH 8). The reaction mixtures were incubated at room temperature for 30 min, then three 200 µL aliquots of each reaction mixture were removed and quenched with 500 µL of a charcoal suspension (100 mM NaPPi, 350 mM HClO$_4$, and 16 g/L powdered charcoal). The reaction mixture samples were shaken and then centrifuged at 13,000 rpm for three minutes. The resulting charcoal pellets were washed with 750 µL of wash solution (100 mM NaPPi, 350 mM HClO$_4$) and centrifuged again for three min. This washing step was repeated once more, followed by suspension of the charcoal pellets in 1.5 mL EcoLite(+) scintillation fluid from MP Biomedicals. Charcoal-bound radioactivity was measured on a Beckman Coulter LS 6500 scintillation counter.

FIG. 2K is a bar graph summarizing ATP-[$^{32}$P]PP$_i$ exchange data for the incubation of recombinant ObiF (directly purified from E. coli cell lysates without treatment with Sfp) with [$^{32}$P]PP$_i$, unlabeled ATP, and carboxylate substrate followed by absorption onto activated charcoal. The bar graph shows counts per minute (cpm) for each of the carboxylate substrates. β-OH-p-NO$_2$-homoPhe and 2,3-DHB substrates produced signals greater than any of the control experiments. All proteinogenic amino acids shown in this graph were L-versions of the respective amino acids. Error bars represent standard deviations for three independent trials.

The results of these experiments demonstrated that the recombinant ObiF was most active upon contact with one of the carboxylate substrates β-OH-p-NO$_2$-homoPhe and 2,3-DHB.

Example 12: Isolation of RC-Obi and RO-Obi

To isolate the closed-ring isoform of obafluorin (RC-Obi) and the ring-opened obafluorin hydrolysis product (RO-Obi), the following experiments were conducted.

RC-Obi and RO-Obi were isolated from *Pseudomonas fluorescens* ATCC 39502 fermentations. Bennet's Agar slants (1 g/L yeast extract, 1 g/L beef extract, 2 g/L NZ amine, 10 g/L glucose, 15 g/L agar) were inoculated with streaks of *P. fluorescens* ATCC 39502 from a frozen glycerol stock. The slants were incubated at 25° C. for 48 hrs. 5 mL of sterile saline was added to the top of the slant and shaken gently. Inoculated saline (1 mL) was transferred to 100 mL of sterile media (5 g/L yeast extract, 5 g/L glucose, 0.1 g/L MgSO$_4$-7H$_2$O, 0.1 g/L FeSO$_4$-7H$_2$O, 200 mL local soil filtrate extract, and 800 mL tap water, autoclaved) to form a starter culture.

The starter culture was incubated with shaking at 225 rpm at 25° C. for 24 hrs. 5 mL samples of the starter culture were transferred to 3 L baffled flasks containing 500 mL of the same media, and the resulting cultures were incubated with shaking at 225 rpm at 25° C. for 17 hrs. The cultures were pooled and centrifuged at 5000 rpm at 4° C. for 25 min to pellet the cultured cells. The supernatant of the pooled cultures was acidified to pH 3 with IM aqueous HCl. The pooled supernatant was saturated with EtOAc then extracted with three 100 mL volumes of EtOAc. Extractions were pooled and dried using rotary evaporation to yield a grey-brown solid. The solid was dissolved in 10 mL acetonitrile, filtered, and concentrated by rotary evaporation under reduced pressure to yield 221 mg of clear, brown oil.

The oil was dissolved in 10 mL of acetonitrile, filtered, and purified with Prep HPLC with a gradient of 5% solvent B to 95% solvent B over 20 min. The two largest peaks were isolated which upon NMR analysis proved to be RC-Obi (retention time=23.0 min) and RO-Obi (retention time=20.5 min), both isolated as brown oils.

Figure 22:
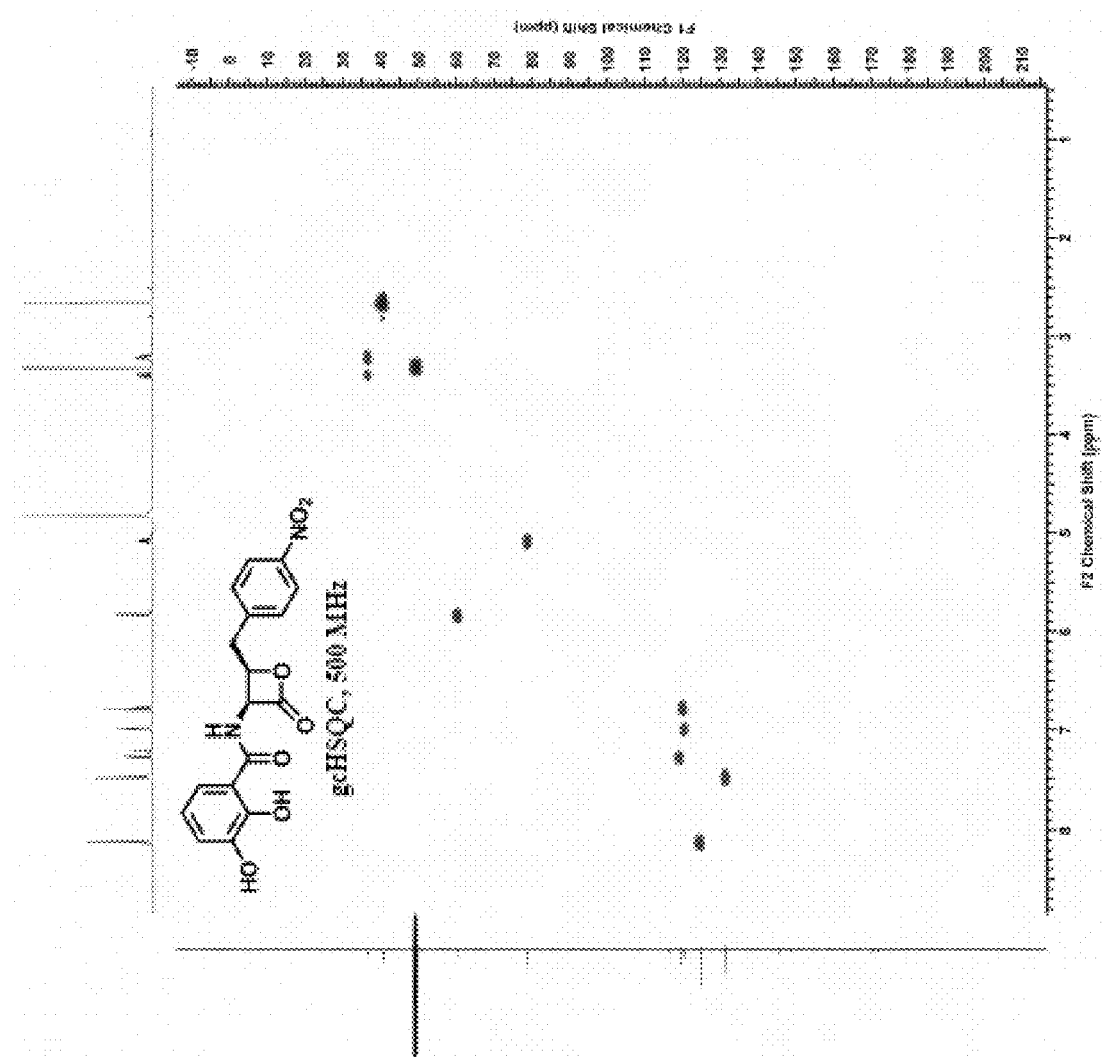
FIG. 22 is a $^1$H-$^{13}$C HSQC spectrum obtained from a sample containing the closed-ring obafluorin protein (RC-Obi).
Figure 23:
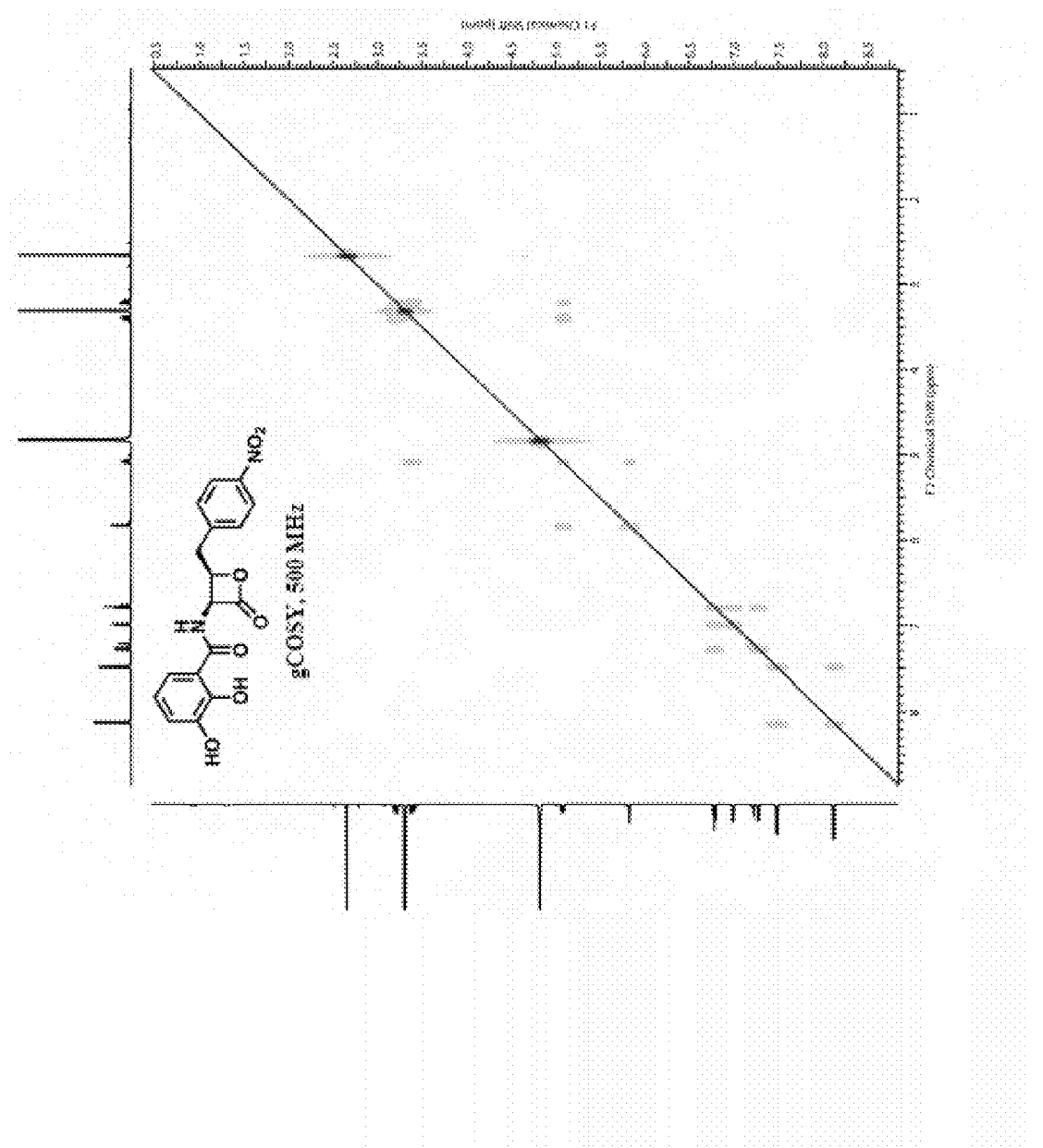
FIG. 23 is a $^1$H-$^{13}$C COSY spectrum obtained from a sample containing the closed-ring obafluorin protein (RC-Obi).
Figure 24:
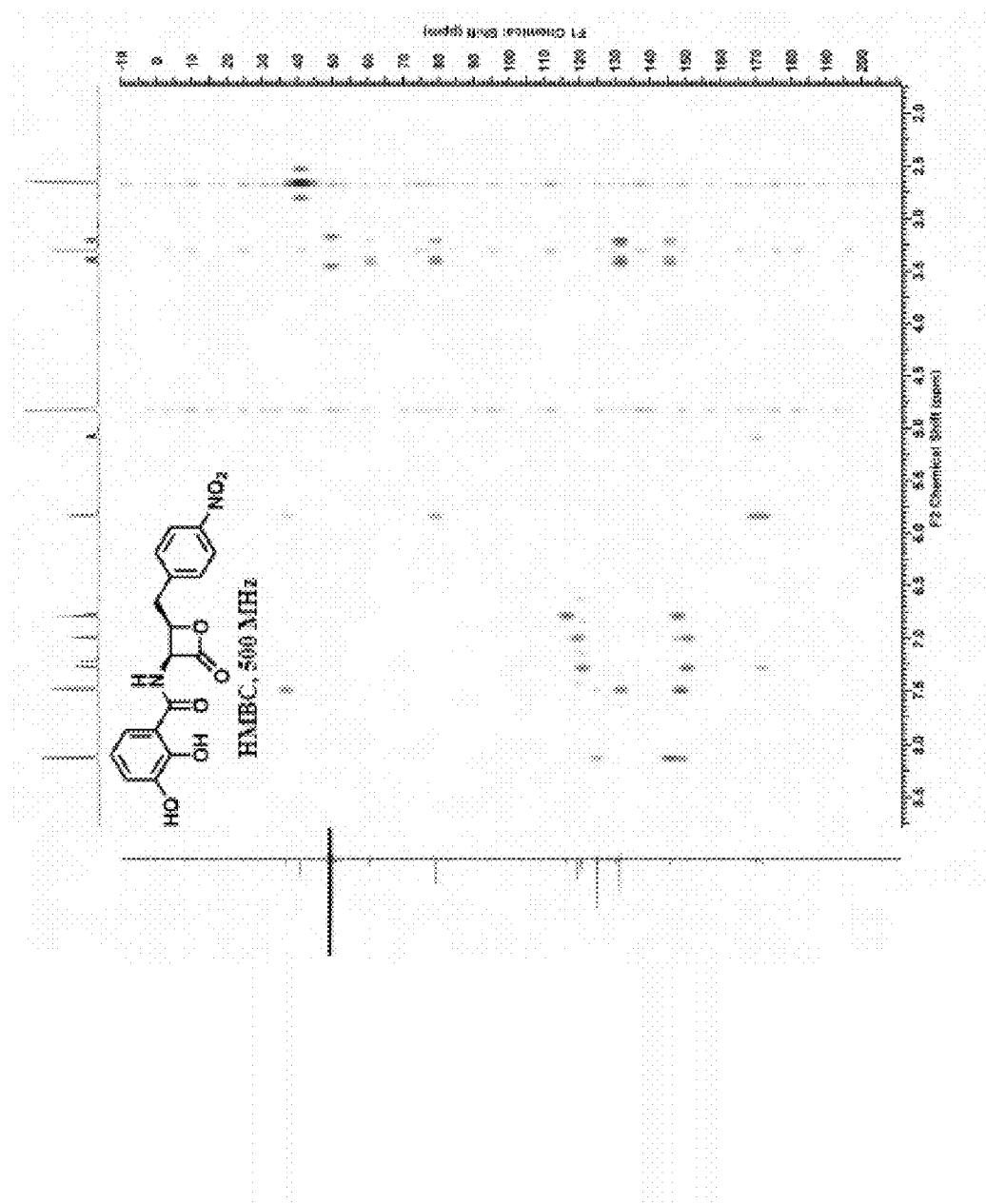
FIG. 24 is a $^1$H-$^{13}$C HMBC spectrum obtained from a sample containing the closed-ring obafluorin protein (RC-Obi).
Figure 25:
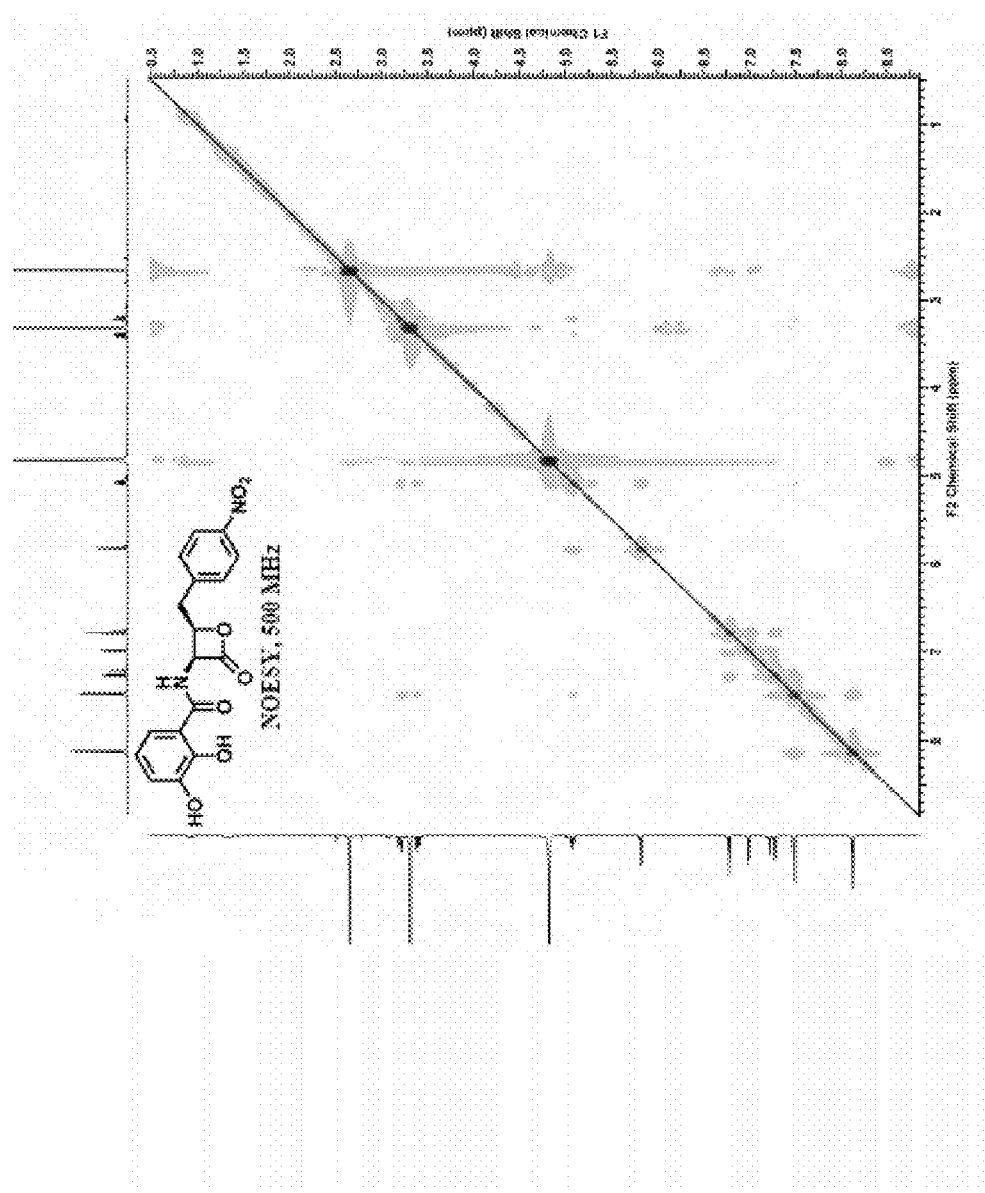
FIG. 25 is a $^1$H-$^{13}$C NOESY spectrum obtained from a sample containing the closed-ring obafluorin protein (RC-Obi).

Table 14 is a summary of the NMR data obtained from the RC-Obi fraction of the oil. NMR spectra obtained from the RC-Obi fraction of the oil are provided as FIG. 20 ($^1$H NMR spectrum), FIG. 21 ($^{13}$C NMR spectrum), FIG. 22 ($^1$H-$^{13}$C HSQC spectrum), FIG. 23 ($^1$H-$^{13}$C COSY), FIG. 24 ($^1$H-$^{13}$C HMBC), and FIG. 25 ($^1$H-$^{13}$C NOESY spectrum).

TABLE 14

Summary of NMR Data for Closed-Ring Obafluorin (RC-Obi)

| Atom | $^{13}C$ (ppm) | $^1H$ (ppm), multiplets in Hz | gCOSY $^1H$-$^1H$ 3 bond | HMBC $^1H$-$^{13}C$ 2-3 bond | NOESY $^1H$-$^1H$ Through space, 4 Å |
|---|---|---|---|---|---|
| 1 | 116.41 | | | 5 | |
| 2 | 150.47 | | | 4, 6 | |
| 3 | 147.81 | | | 4, 5 | |
| 4 | 120.77 | 6.99 (d, J = 6.6 Hz, 1H) | 5 | 2, 3 | 5 |
| 5 | 120.37 | 6.78 (t, J = 1.0 Hz, 1H) | 4, 6 | 1, 3 | 4, 6 |
| 6 | 119.50 | 7.28 (d, J = 9.6 Hz, 1H) | 5 | 7, 2, 4 | 5 |
| 7 | 171.77 | | | 9, 6 | |
| 8 | | | | | |
| 9 | 60.53 | 5.83 (d, J = 6.0 Hz, 1H) | 11 | 7, 10, 11, 12 | 11 |
| 10 | 170.19 | | | 9, 11 | |
| 11 | 79.17 | 5.08 (td, J = 5.7, 9.0 Hz, 1H) | 9, 12 | 10, 13 | 9, 12a, 12b |
| 12 | 36.81 | 3.40 (dd, J = 9.0, 15.0 Hz, 1H) 3.21 (dd, J = 5.1, 14.7 Hz, 1H) | 11 | 9, 11, 13, 14 | 11, 12a, 12b, 14 |
| 13 | 145.5 | | | 12, 15 | |
| 14 | 131.61 | 7.49 (d, J = 8.4 Hz, 2H) | 15 | 12, 15, 16 | 12a, 12b, 15 |
| 15 | 124.91 | 8.12 (d, J = 9.0 Hz, 2H) | 14 | 13, 16 | 14 |
| 16 | 148.70 | | | 14, 15 | |

Figure 26:
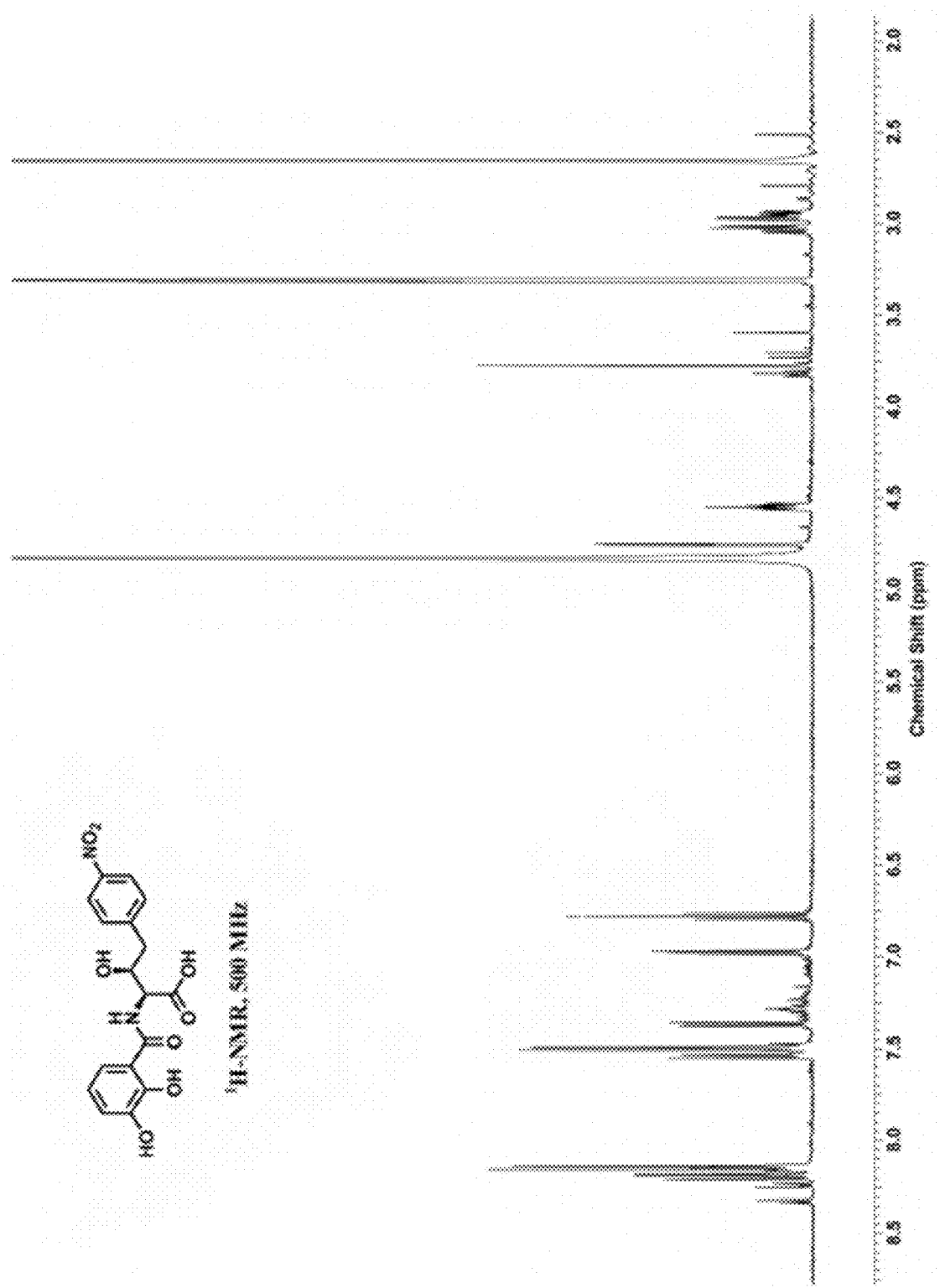
FIG. 26 is a $^1$H NMR spectrum obtained from a sample containing the opened-ring obafluorin protein (RO-Obi).
Figure 27:
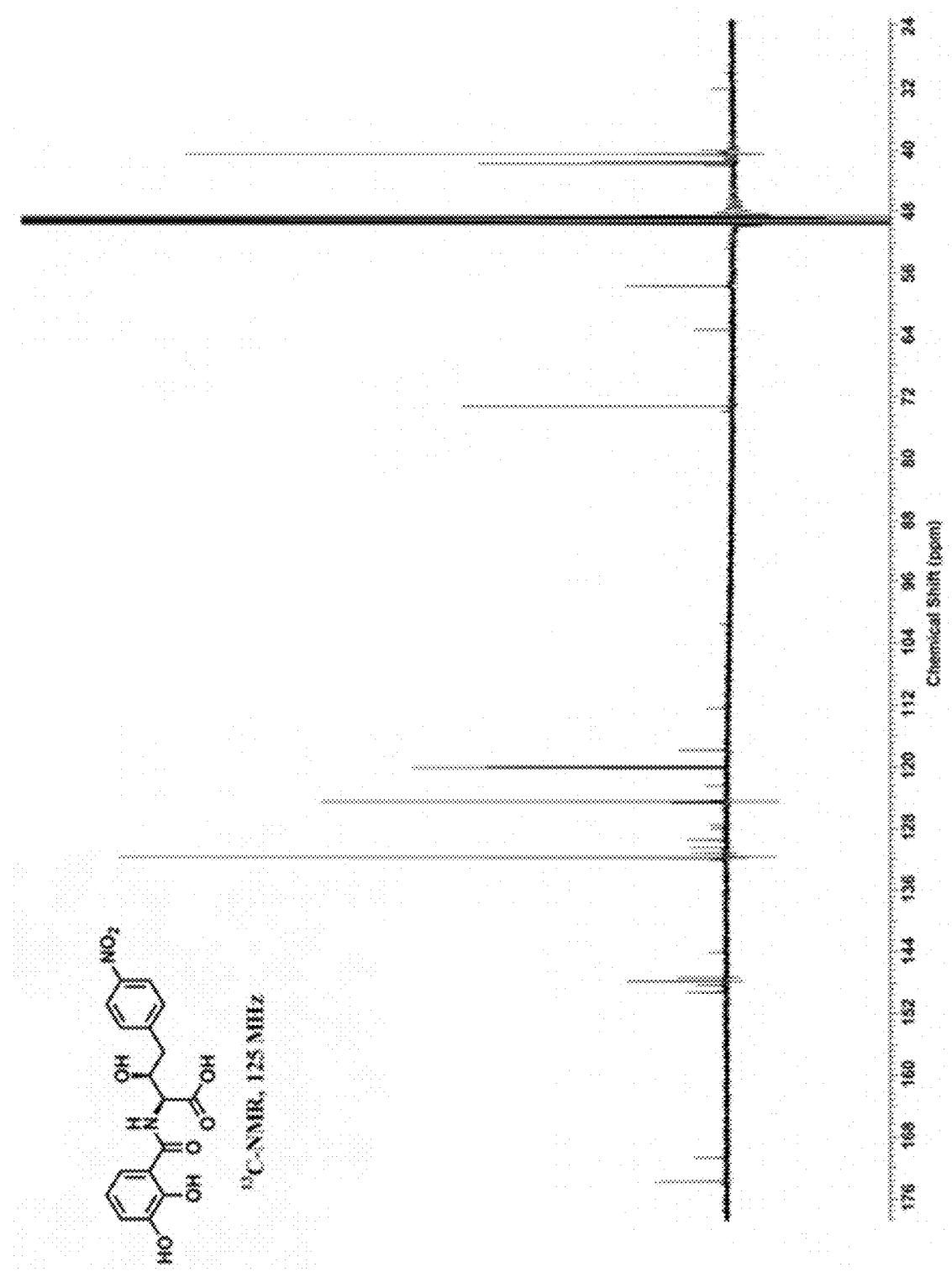
FIG. 27 is a $^{13}$C NMR spectrum obtained from a sample containing the opened-ring obafluorin protein (RO-Obi).
Figure 28:
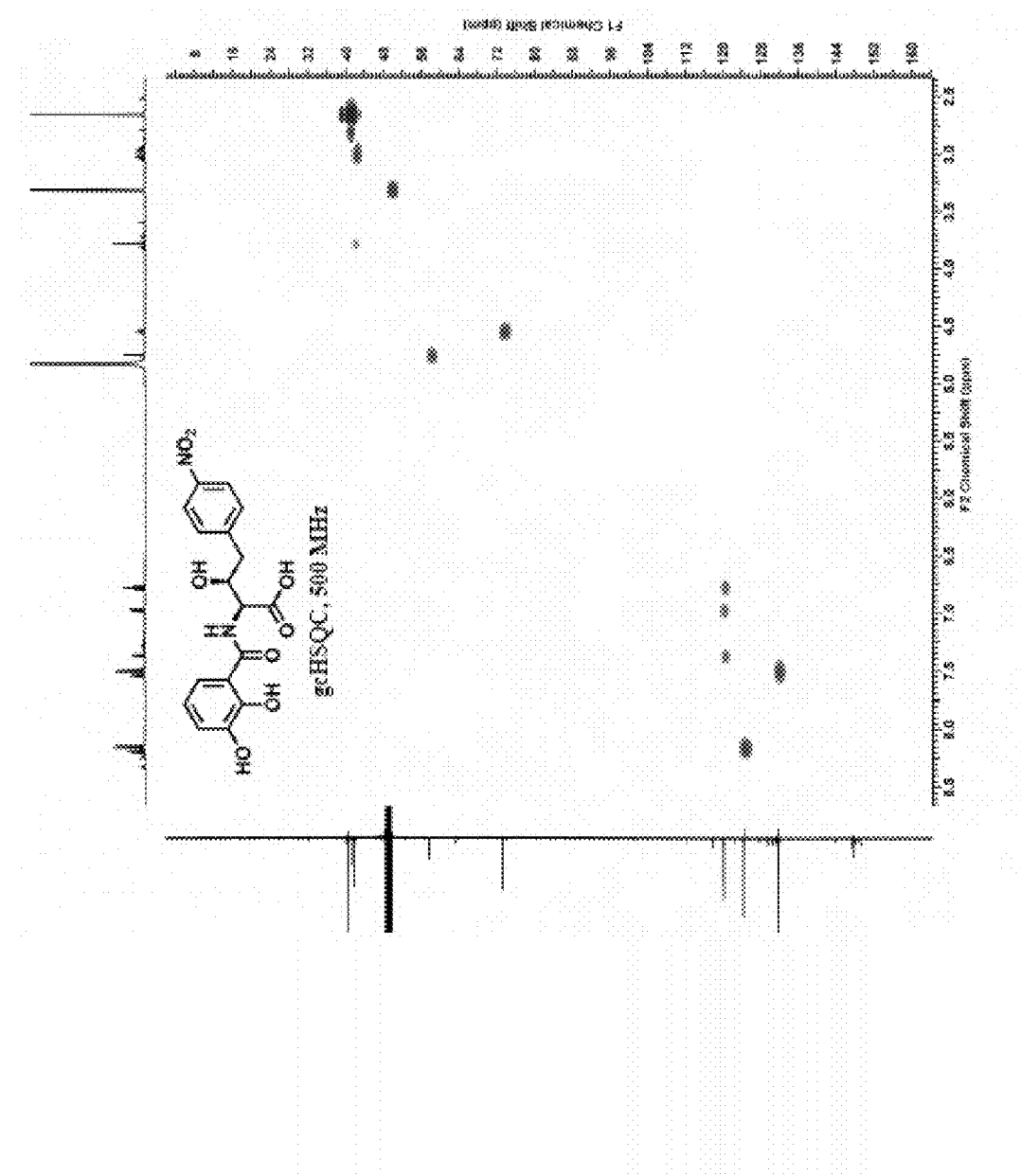
FIG. 28 is a $^1$H-$^{13}$C HSQC spectrum obtained from a sample containing the opened-ring obafluorin protein (RO-Obi).
Figure 29:
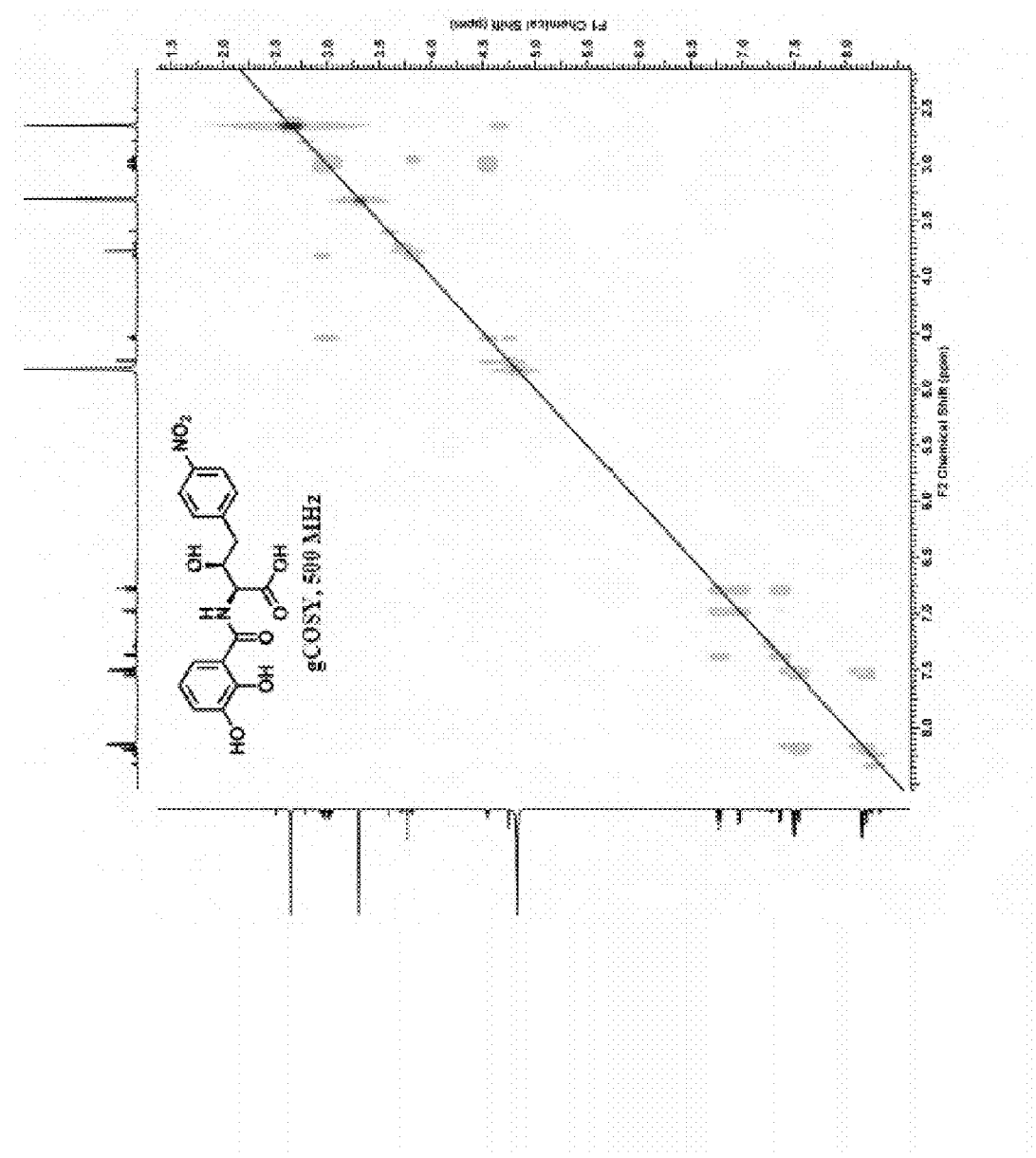
FIG. 29 is a $^1$H-$^{13}$C COSY spectrum obtained from a sample containing the opened-ring obafluorin protein (RO-Obi).
Figure 30:
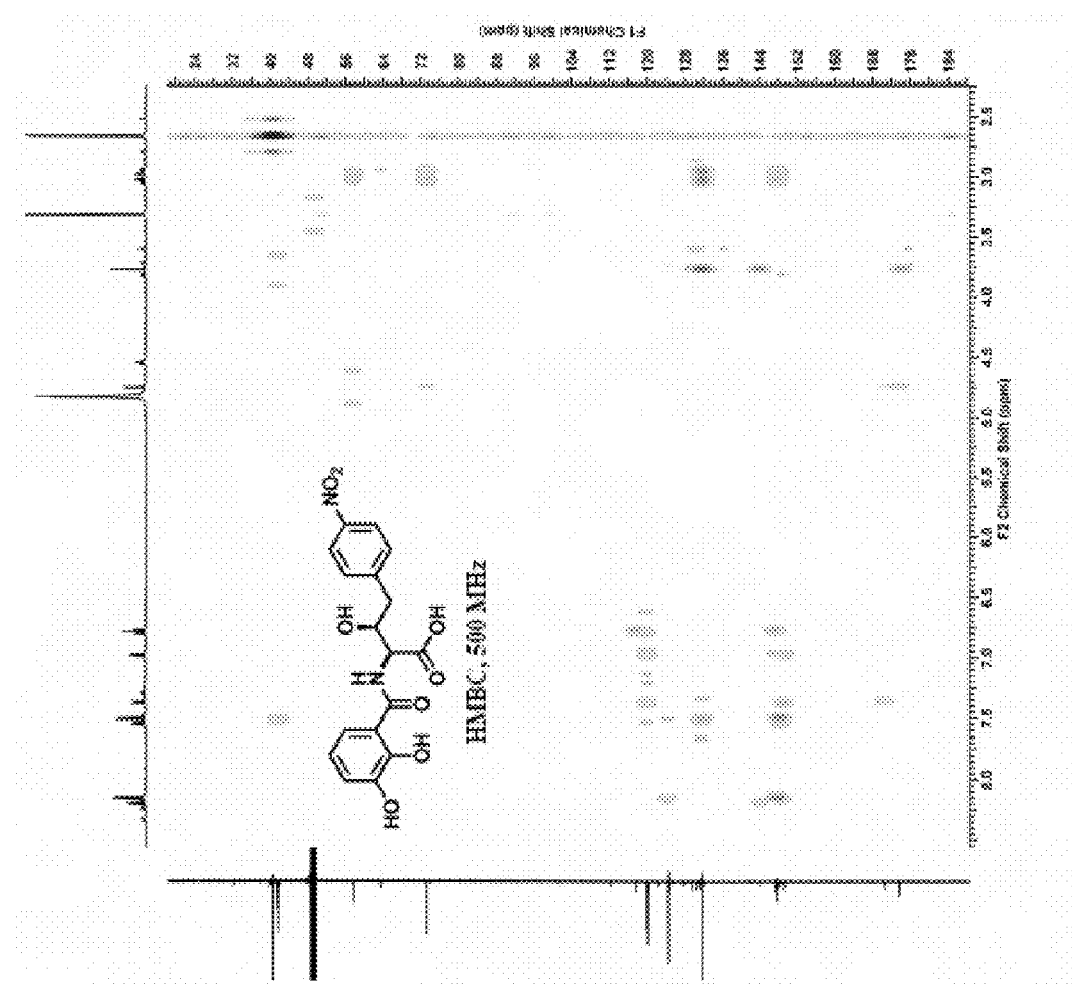
FIG. 30 is a $^1$H-$^{13}$C HMBC spectrum obtained from a sample containing the opened-ring obafluorin protein (RO-Obi).
Figure 31:
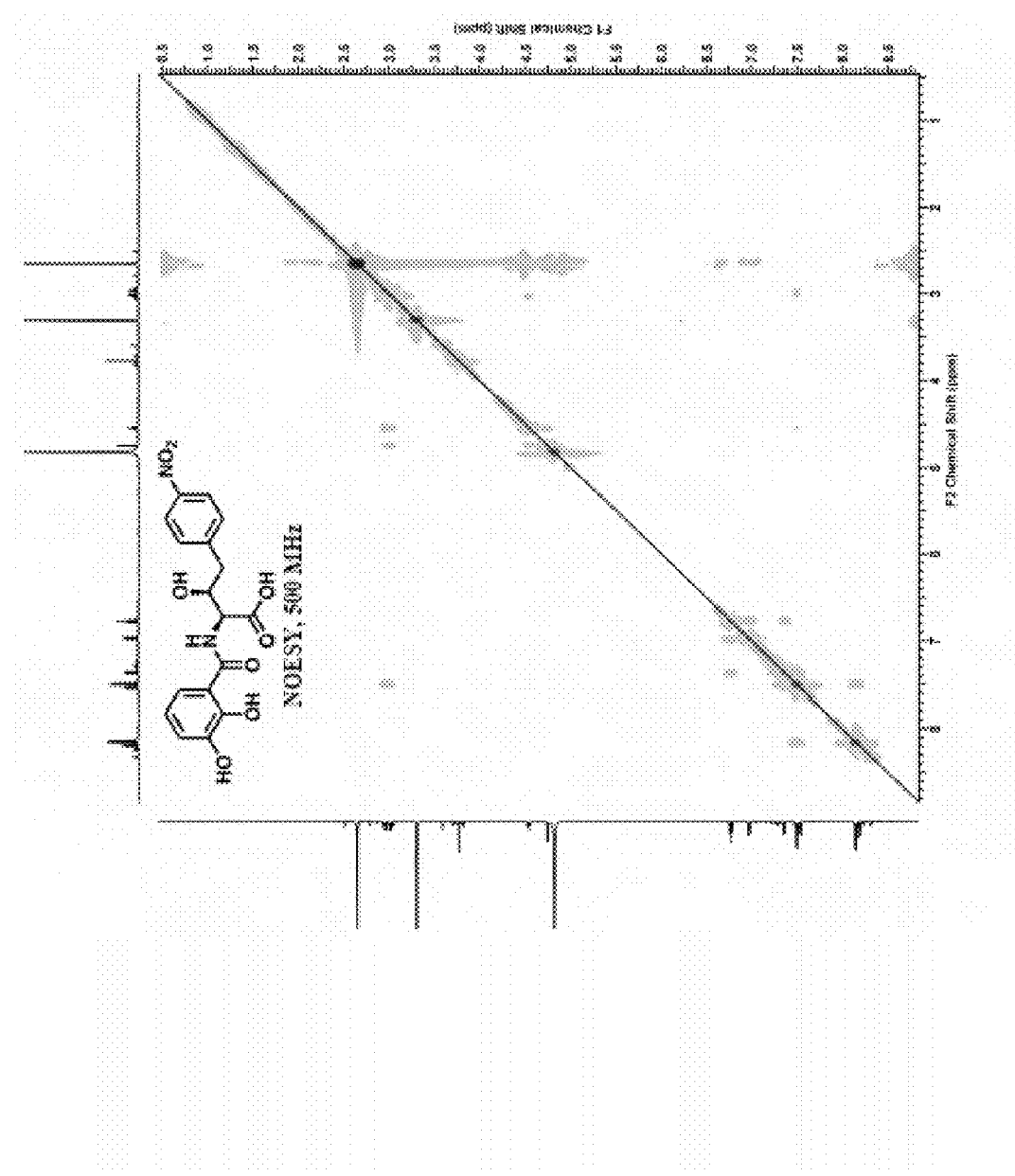
FIG. 31 is a $^1$H-$^{13}$C NOESY spectrum obtained from a sample containing the opened-ring obafluorin protein (RO-Obi).

Table 15 is a summary of the NMR data obtained from the RO-Obi fraction of the oil. NMR spectra obtained from the RO-Obi fraction of the oil are provided as FIG. 26 ($^1H$ NMR spectrum), FIG. 27 ($^{13}C$ NMR spectrum), FIG. 28 ($^1H$-$^{13}C$ HSQC spectrum), FIG. 29 ($^1H$-$^{13}C$ COSY), FIG. 30 ($^1H$-$^{13}C$ HMBC), and FIG. 31 ($^1H$-$^{13}C$ NOESY spectrum).

TABLE 15

Summary of NMR Data for Opened-Ring Obafluorin (RO-Obi)

| Atom | $^{13}C$ (ppm) | $^1H$ (ppm), multiplets in Hz | gCOSY $^1H$-$^1H$ 3 bond | HMBC $^1H$-$^{13}C$ 2-3 bond | NOESY $^1H$-$^1H$ Through space, 4 Å |
|---|---|---|---|---|---|
| 1 | 147.40 | | | 5, 6 | |
| 2 | 149.3 | | | 4, 6 | |
| 3 | 144.05 | | | 4, 5 | |
| 4 | 119.97 | 6.98 (d, J = 9.0 Hz, 1H) | 5 | 2, 5 | 5 |
| 5 | 120.12 | 6.78 (t, J = 8.1 Hz, 1H) | 4, 6 | 1, 4, 6 | 4, 6 |
| 6 | 120.18 | 7.37 (d, J = 9.6 Hz, 1H) | 5 | 1, 5, 7 | 5 |
| 7 | 170.32 | | | 6 | |
| 8 | | | | | |
| 9 | 57.70 | 4.75 (d, J = 2.4 Hz, 1H) | 11 | 7, 10, 11 | 11, 12 |
| 10 | 173.77 | | | 9 | |
| 11 | 73.27 | 4.54 (ddd, J = 2.1, 5.6, 8.0 Hz, 1H) | 9, 12 | | 9, 12 |
| 12 | 41.81 | a) 3.03 (t, J = 1.0 Hz, 1H) b) 2.96 (t, J = 1.0 Hz, 1H) | 11 | 9, 11, 13, 14 | 9, 11, 14 |
| 13 | 147.83 | | | 15 | |
| 14 | 131.81 | 7.50 (d, J = 8.4 Hz, 2H) | 15 | 12, 16 | 12, 15 |
| 15 | 124.54 | 8.15 (d, J = 8.4 Hz, 2H) | 14 | 13 | 14 |
| 16 | 148.29 | | | 14 | |

The results of these experiments resulted in the isolation and NMR characterization of purified RC-Obi and purified RO-Obi.

Example 14: Hydrolysis of RC-Obi and Obi-SNAC

To characterize the role of the TE domain of the ObiF enzyme in i-lactone formation, an N-acetylcysteamine (SNAC) thioester (Obi-SNAC) was prepared, and the following experiments were conducted to compare the rates of hydrolysis of RC-Obi and Obi-SNAC.

Figure 38A:
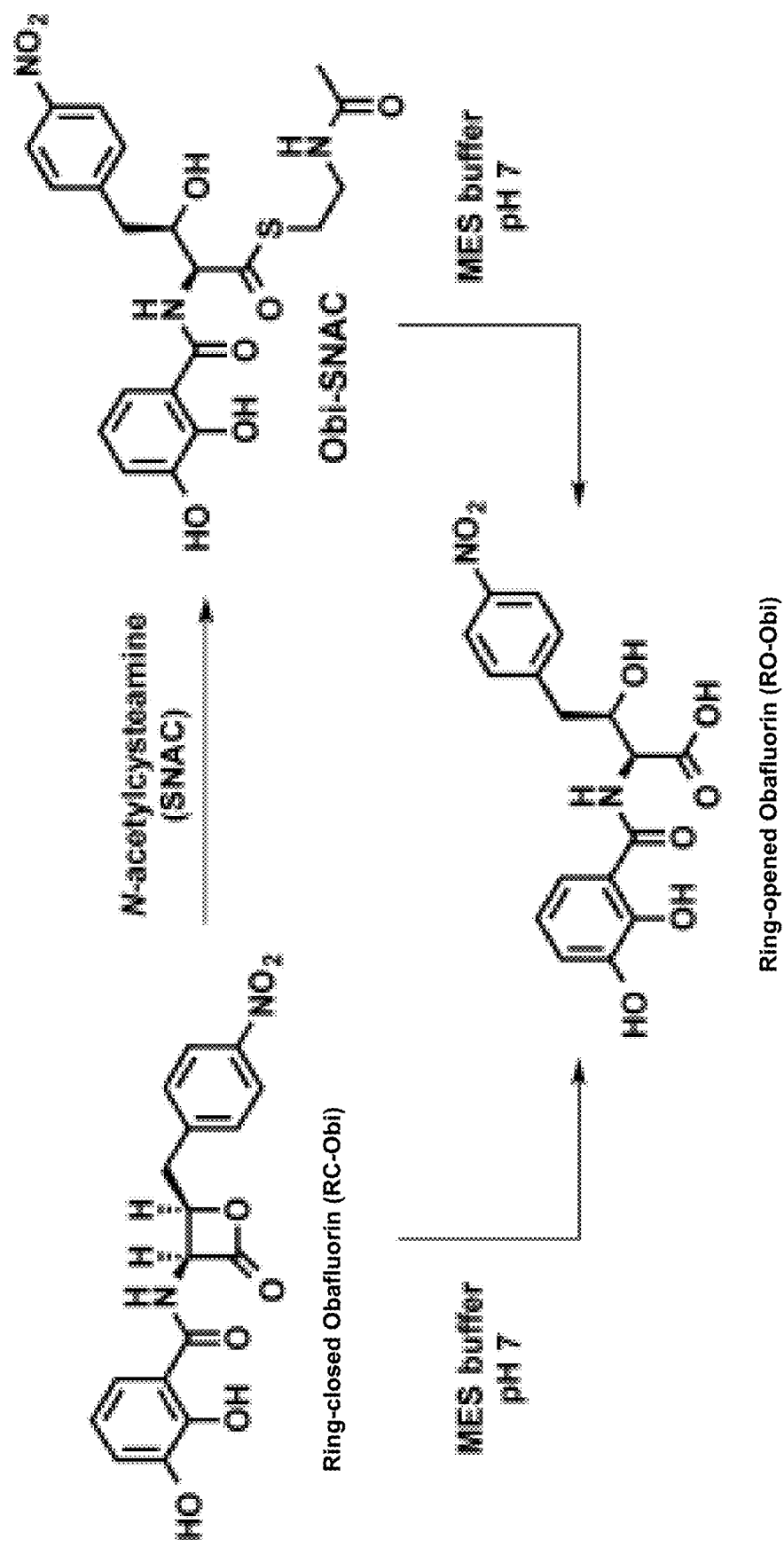
FIG. 38A is a schematic diagram showing a reaction scheme for the synthesis of Obi-SNAC and the hydrolysis of RC-Obi and Obi-SNAC to RO-Obi.

A purified Obi-SNAC solution was produced by treatment of a purified RC-Obi solution with neat N-acetylcysteamine (SNAC), as illustrated in the schematic diagram in FIG. 38A. 1 mg of purified RC-Obi β-lactone was dissolved in 5 mg N-acetylcysteamine (SNAC). The solution was left at room temperature overnight, and then diluted with 0.5 mL MeCN and purified by reverse phase preparatory HPLC (gradient of 5% B to 95% B over 20 min at flow rate of 10 mL/min). The product-containing fraction (retention time 21.2 min) was concentrated by rotary evaporation, dissolved in 0.5 mL DMSO, and transferred to a 1.5 mL Eppendorf tube.

Figure 46:
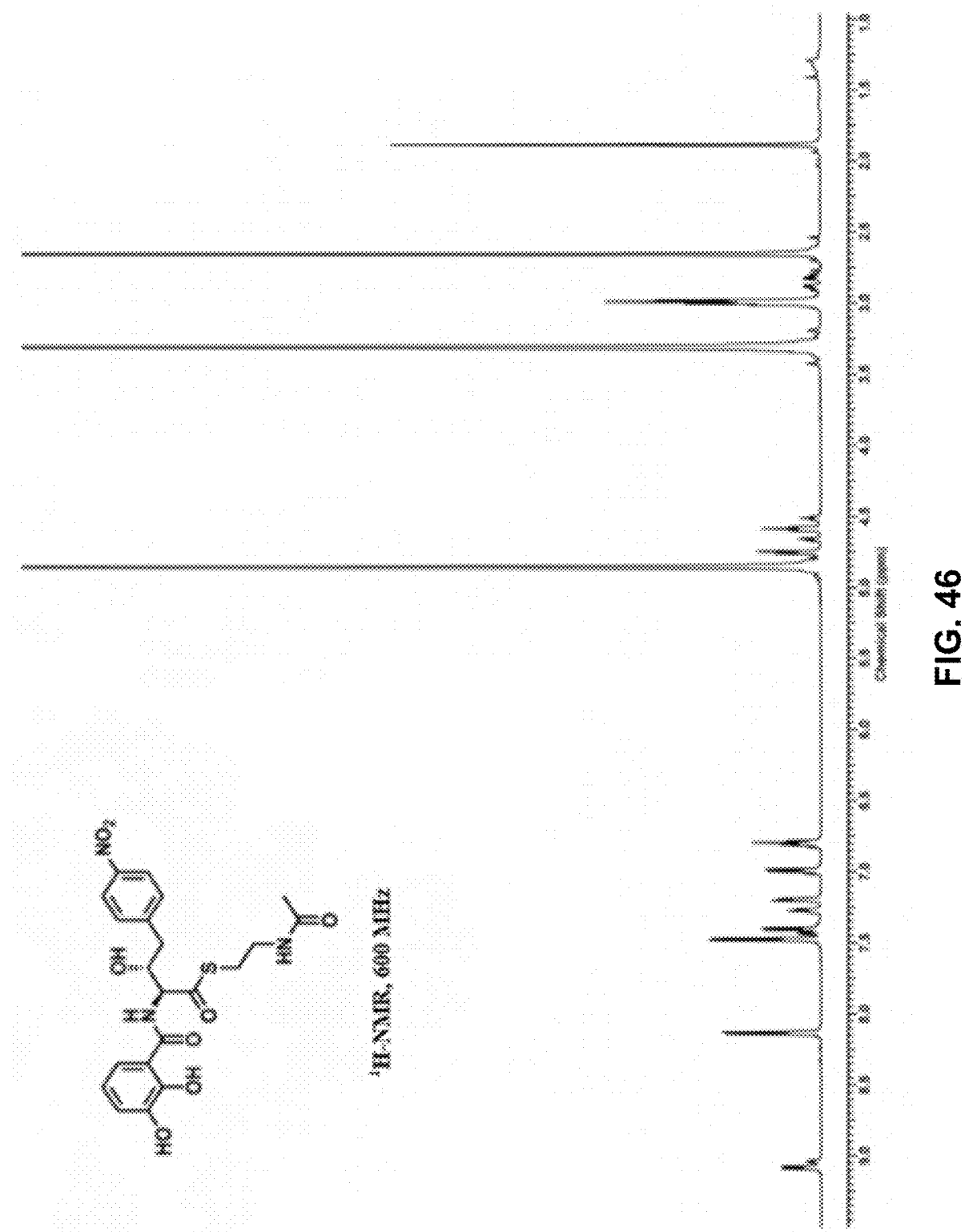
FIG. 46 is a $^1$H NMR spectrum obtained from a sample containing the obatfuorin SNAC thioester protein (Obi-SNAC).
Figure 47:
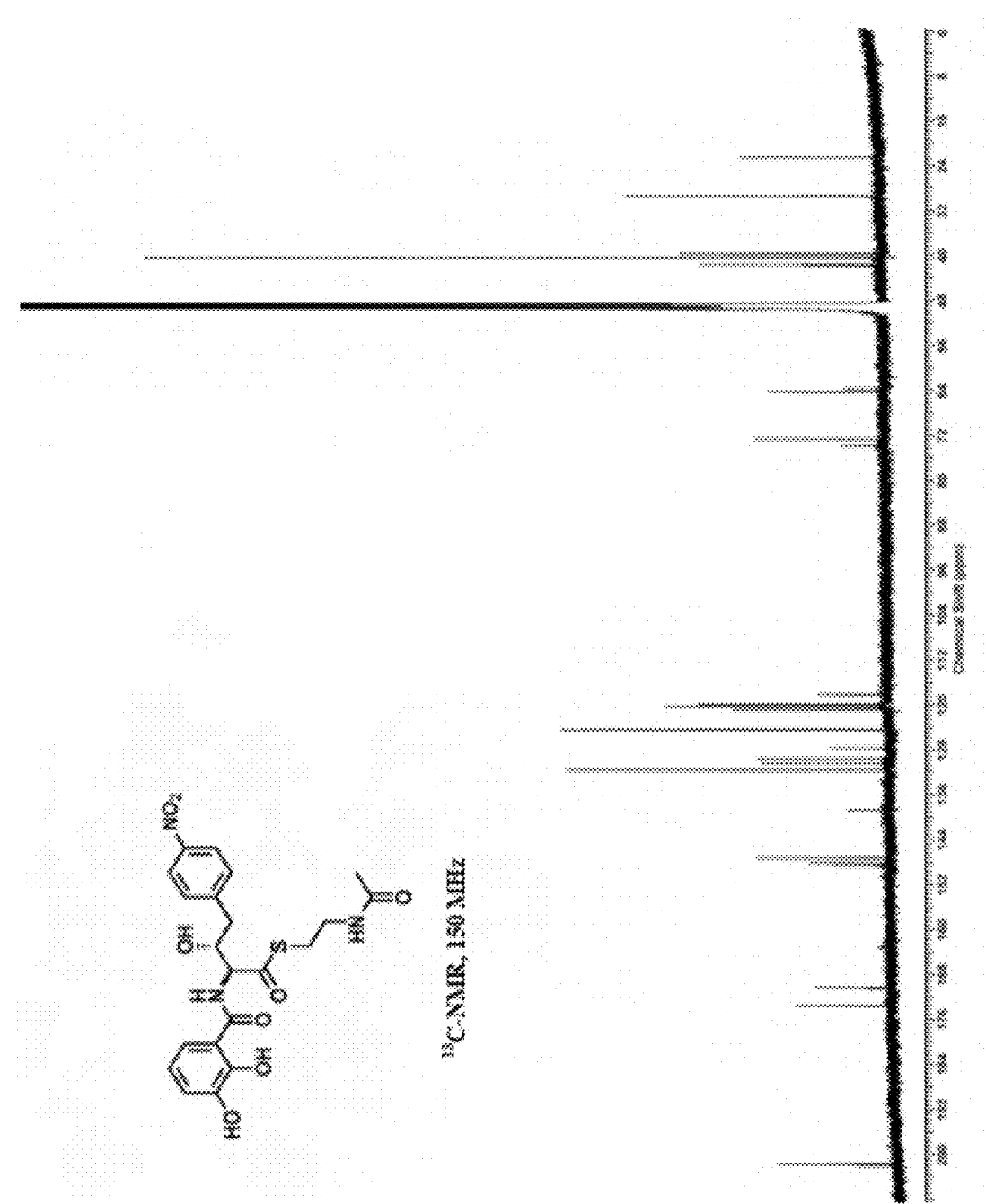
FIG. 47 is a $^{13}$C NMR spectrum obtained from a sample containing the obatfuorin SNAC thioester protein (Obi-SNAC).
Figure 48:
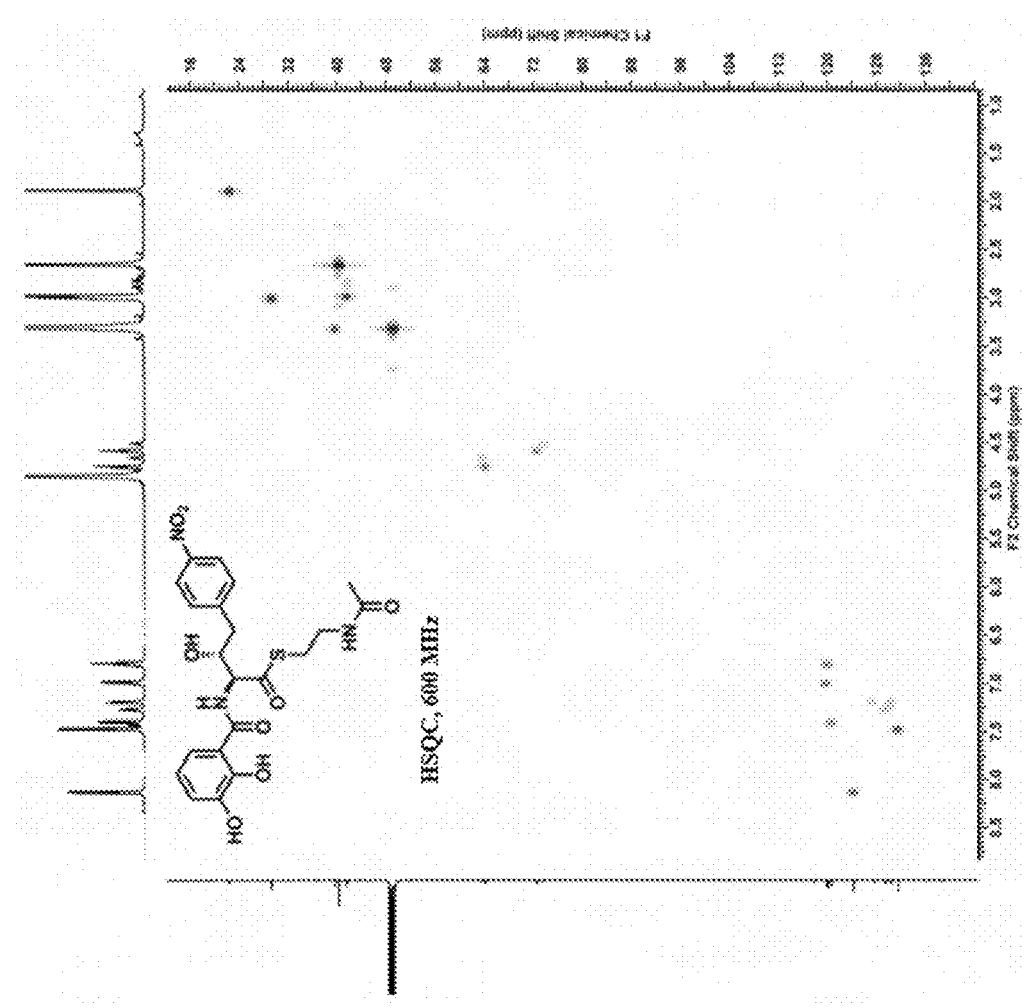
FIG. 48 is a $^1$H-$^{13}$C HSQC spectrum obtained from a sample containing the obafluorin SNAC thioester protein (Obi-SNAC).
Figure 49:
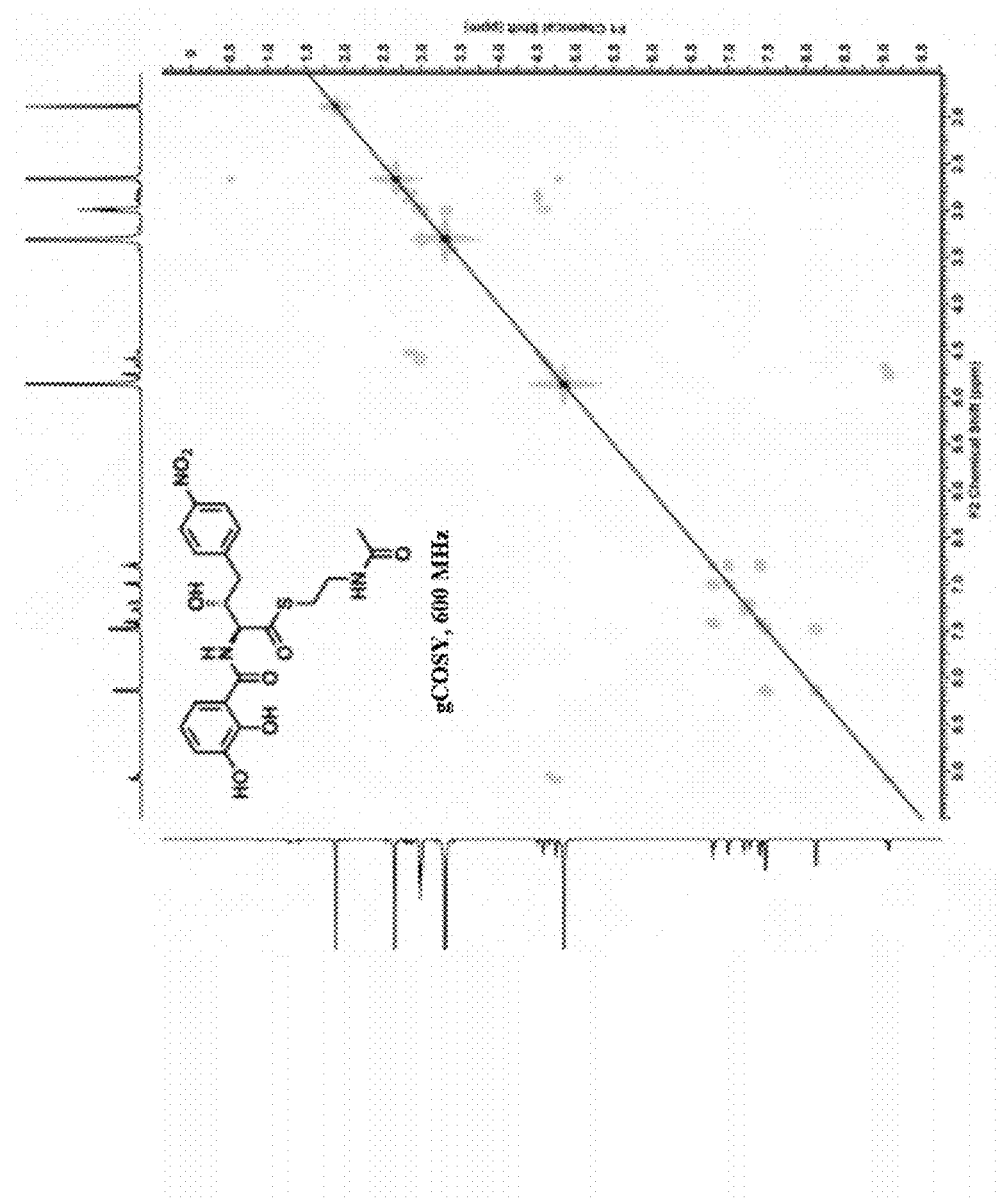
FIG. 49 is a $^1$H-$^{13}$C COSY spectrum obtained from a sample containing the obafluorin SNAC thioester protein (Obi-SNAC).
Figure 50:
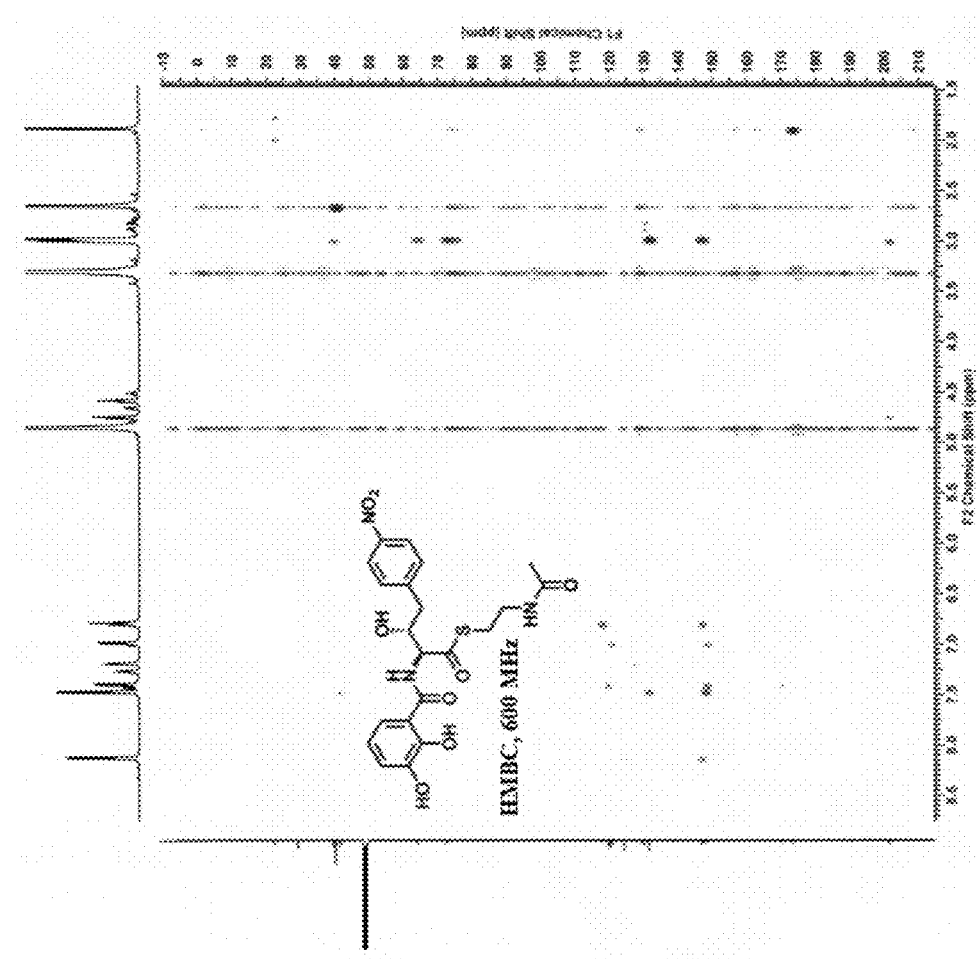
FIG. 50 is a $^1$H-$^{13}$C HMBC spectrum obtained from a sample containing the obafluorin SNAC thioester protein (Obi-SNAC).

The resulting purified Obi-SNAC solution was lyophilized overnight and dissolved in methanol-d4 for NMR analysis. Obi-SNAC forms a 2:1 mixture of rotamers in methanol-d4. The NMR data for the major rotamer are summarized in Table 16. The NMR spectra obtained from the Obi-SNAC solution are provided as FIG. 46 ($^1$H NMR spectrum), FIG. 47 ($^{13}$C NMR spectrum), FIG. 48 ($^1$H-$^{13}$C HSQC spectrum), FIG. 49 ($^1$H-$^{13}$C COSY), and FIG. 50 ($^1$H-$^{13}$C HMBC).

TABLE 16

Summary of NMR Data for N-acetylcysteamine (SNAC) thioester (Obi-SNAC)

| Atom[a] | $^{13}$C (ppm) | $^1$H (ppm), multiplets in Hz | gCOSY $^1$H-$^1$H (3 bond) | HMBC $^1$H-$^{13}$C (2-3 bond) |
|---|---|---|---|---|
| 1 | | | | |
| 2 | 148.58 | | | 4, 6 |
| 3 | 147.30 | | | 4, 5 |
| 4 | 119.91 | 6.99 (d, 7.9 Hz, 1H) | 5 | 6 |
| 5 | 120.19 | 6.8 (t, 7.9 Hz, 1H) | 4, 6 | 3 |
| 6 | 120.80 | 7.41 (d, 7.9 Hz, 1H) | 5 | 4, 7 |
| 7 | 170.32 | | | |
| 8 | | 9.08 (d, 8.7 Hz, 1H) | | |
| 9 | 64.24 | 4.75 (d, 8.7 Hz, 1H) | 8 | 8 |
| 10 | 201.68 | | | |
| 11 | 72.71 | 4.59 (t, 6.7 Hz, 1H) | 12 | 12 |
| 12 | 41.63 | 2.93-3.05 (m, 4H)[b] | 11 | 11 |
| 13 | 147.22 | | | |
| 14 | 131.70 | 7.48 (d, 7.4 Hz, 2H) | 15 | 15 |
| 15 | 124.41 | 8.13 (d, 8.13 Hz, 2H) | 14 | 14 |
| 16 | 148.16 | | | 18 |
| 17 | | | | |
| 18 | 29.43 | 2.93-3.05 (m, 4H)[b] | 18 | 17 |
| 19 | 39.77 | 3.21-3.39 (m, 2H)[c] | 17 | |
| 20 | | | | |
| 21 | 173.57 | | | |
| 22 | 22.49 | 1.89 (s, 3H) | | |

[a]Singlet at 2.65 ppm in the $^1$H-NMR and 40.5 ppm in the $^{13}$C-NMR is residual DMSO.
[b]multiplet consists of overlapping peaks from protons on C-12 and C-18, confirmed by HSQC and HMBC spectra.
[c]multiplet consists of protons on C18 overlapping with peaks from methanol, as confirmed by HSQC, HMBC, and COSY.

Solutions of purified RC-Obi (1 mM) and Obi-SNAC (1 mM) were prepared in MES buffer at pH ~7 to form two reaction mixtures. Aliquots (100 μL) of each reaction mixture were taken at various time points to be analyzed by HPLC (gradient of 5% B to 95% B over 20 min, 95% B to 100% B over 3 min, and 100% B to 5% B over 2 min at a flow rate of 1 mL/min) with detection by optical absorbance spectroscopy at 270 nm. HPLC peak identities were confirmed by LC-MS and retention times were normalized using an Fmoc-Ala internal standard. Experiments were performed in duplicate.

Figure 38C:
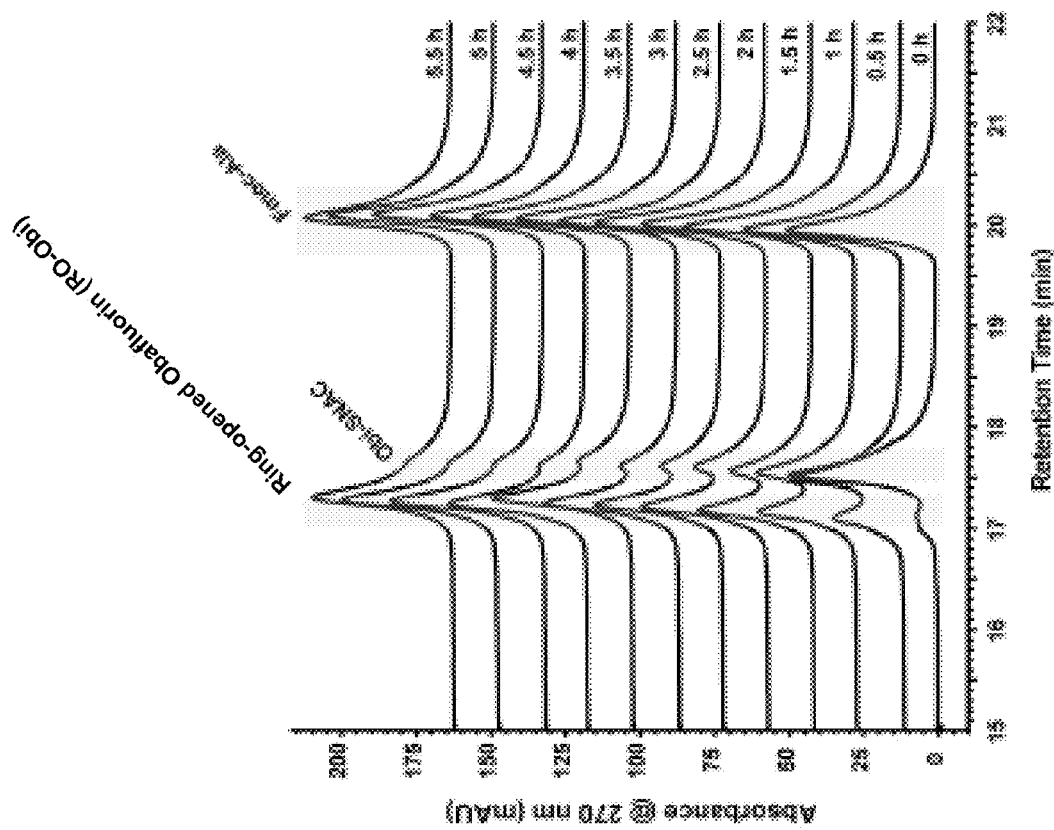
FIG. 38C is a graph showing a hydrolysis of Obi-SNAC as depicted in FIG. 38A above as monitored using HPLC with detection by optical absorbance spectroscopy at 270 nm using an Fmoc-L-Ala internal standard.
Figure 38B:
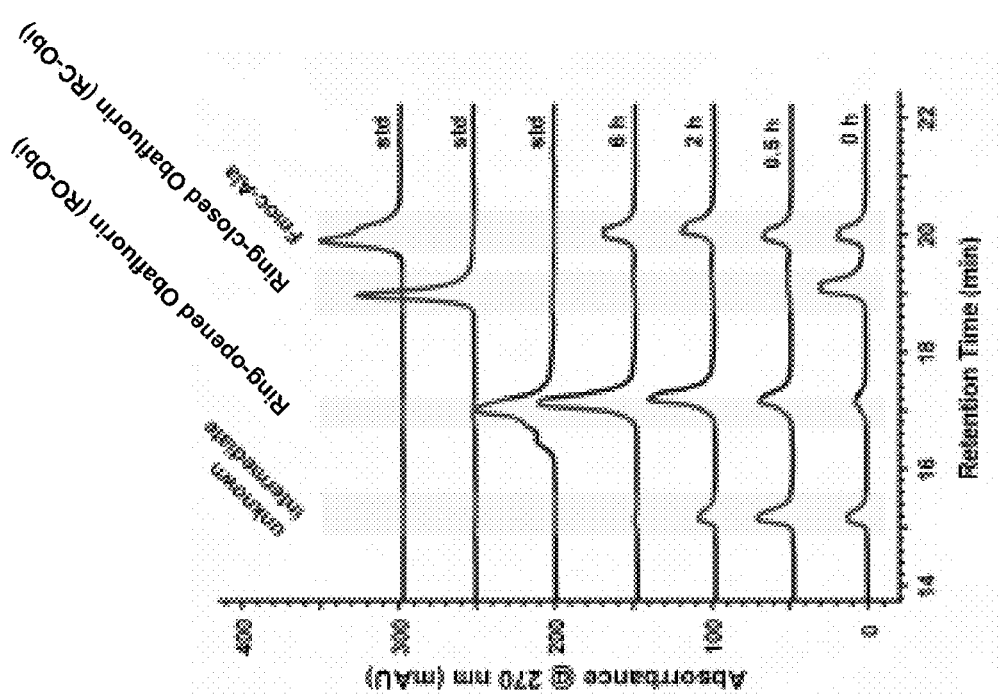
FIG. 38B is a graph showing a hydrolysis of RC-Obi as depicted in FIG. 38A above as monitored using HPLC with detection by optical absorbance spectroscopy at 270 nm using an Fmoc-L-Ala internal standard.

FIG. 38B is a graph summarizing the HPLC elution profiles for the RC-Obi hydrolysis reaction mixture at 0 h, 0.5 h, 2 h, and 6 h after initiation of the reaction, as well as reference HPLC elution profiles produced by standard solutions of RO-Obi, RC-Obi, and Fmoc-Ala. Rapid hydrolysis of RC-Obi in MES buffer at pH 7 was observed with a half-life of less than 30 min as well as the immediate formation of two products with retention times of 15.2 min and 17.2 min, respectively with optical absorbance spectra consistent with the presence of an aryl nitro group. Comparison of the elution profiles of the RC-Obi hydrolysis reaction mixture to an analytical standard solution of RO-Obi purified from P. fluorescens culture supernatant confirmed that the peak observed at 17.2 min was RO-Obi. The peak observed at 15.2 min was attributed to an uncharacterized intermediate that converted directly to Obi-COOH. A previous observation of RC-Obi hydrolysis using $^1$H-NMR in D$_2$O/CD$_3$CN (1:4) detected the formation of an oxazoline intermediate that hydrolyzes to give O-(2,3-dihydroxybenzoyl)-β-OH-p-NO$_2$-homoPhe. The unknown intermediate was observed to have converted entirely to Obi-COOH by 6 h after initiation of the hydrolysis reaction.

FIG. 38C is a graph summarizing the HPLC elution profiles for the RO-Obi hydrolysis reaction mixture at 0 h, 0.5 h, 1 h, 1.5 h, 2 h, 2.5 h, 3 h, 3.5 h, 4 h, 4.5 h, 5 h, and 5.5 h after initiation of the reaction, as well as reference HPLC elution profiles produced by standard solutions of RO-Obi, Obi-SNAC, and Fmoc-Ala. As illustrated in FIG. 38C, Obi-SNAC hydrolyzed directly to RO-Obi in the MES buffer at pH 7 with a half-life of about 3.2 hrs. The rate of hydrolysis of Obi-SNAC was comparable to that of the ObiF-C1141A mutant (see FIG. 2D, FIG. 2E), which supports the role of the ObiF TE domain as a catalyst for β-lactone ring formation.

Figure 68:
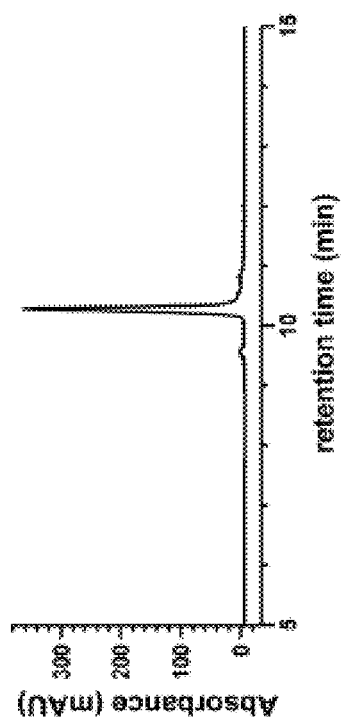

FIGS. 68, 69, 70, 71, 72, 73, 74, and 75 show LC-MS chromatograms analysis of Obi, Obi-COOH, and Obi-SNAC. FIG. 68 is a graph showing a LC-MS chromatogram (absorbance at 263 nm (y-axis) versus retention time (x-axis)) of an ethyl acetate extraction of the culture supernatant from Obi-producing P. fluorescens ATCC 39502. Both RC-Obi and RO-Obi are detected in P. fluorescens culture supernatant.

Figure 69:
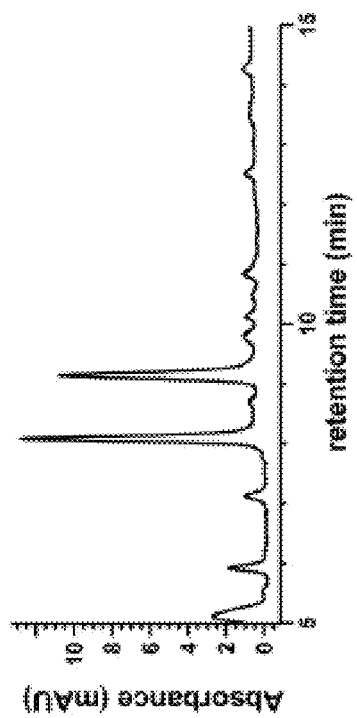

FIG. 69 is a graph showing a LC-MS chromatogram (extracted ion counts (y-axis) versus retention time (x-axis)) of an ethyl acetate extraction of the culture supernatant from Obi-producing P. fluorescens ATCC 39502. Both RC-Obi and RO-Obi are detected in P. fluorescens culture supernatant.

Figure 70:
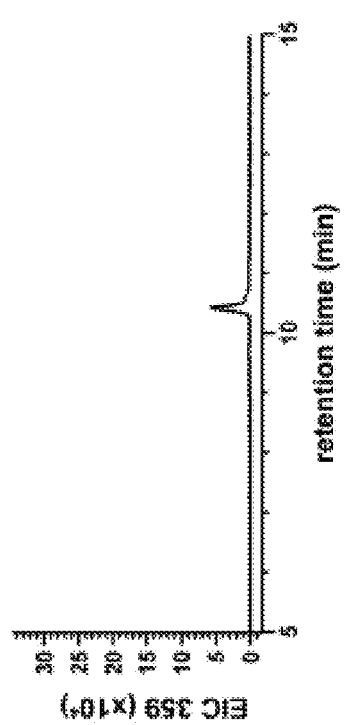

FIG. 70 is a graph showing a LC-MS chromatogram (absorbance at 263 nm (y-axis) versus retention time (x-axis)) of RC-Obi purified via RP-C18 prep-HPLC from P. fluorescens culture supernatant.

FIG. 71 is a graph showing a LC-MS chromatogram (extracted ion counts (y-axis) versus retention time (x-axis)) of RC-Obi purified via RP-C18 prep-HPLC from P. fluorescens culture supernatant.

FIG. 72 is a graph showing a LC-MS chromatogram (absorbance at 263 nm (y-axis) versus retention time (x-axis)) of RO-Obi purified via RP-C18 prep-HPLC from *P. fluorescens* culture supernatant.

FIG. 73 is a graph showing a LC-MS chromatogram (extracted ion counts (y-axis) versus retention time (x-axis)) of RO-Obi purified via RP-C18 prep-HPLC from *P. fluorescens* culture supernatant.

FIG. 74 is a graph showing a LC-MS chromatogram (absorbance at 263 nm (y-axis) versus retention time (x-axis)) of Obi-SNAC purified via RP-C18 prep-HPLC from *P. fluorescens* culture supernatant.

FIG. 75 is a graph showing a LC-MS chromatogram (extracted ion counts (y-axis) versus retention time (x-axis)) of Obi-SNAC purified via RP-C18 prep-HPLC from *P. fluorescens* culture supernatant.

The results of these experiments indicate that enzyme catalysis by the TE domain of the ObiF enzyme precedes the transformation of an Obi thioester to the corresponding cyclic β-lactone RC-Obi.

Example 15: Antibiotic Susceptibility Testing

To assess the antibiotic efficacy of RC-Obi and RO-Obi, the following experiments were conducted.

Bacterial strains (*E. coli* 29522 and *E. coli* X580) were grown from frozen glycerol stocks in LB media overnight at 37° C. with shaking. These starter cultures were used to inoculate fresh LB broth or M9 minimal media broth at an $OD_{600}$ of 0.3. Each well of a 96-well plate was filled with 100 μL of sterile media (LB or M9). A sterile solution of RC-Obi or RO-Obi in LB or M9 media was added to the first well of each row and was serially diluted two-fold down the entire row creating a compound concentration gradient of 0.3-0.0025 mM.

Each well of the plate was then filled with 100 μL of the $OD_{600}$ 0.3 bacterial cell suspensions to give a final volume of 200 μL per well. The plates were incubated at 37° C. and the $OD_{600}$ of each well was measured every 30 minutes over 24 hours. The plate was shaken briefly prior to each measurement to ensure an even cell suspension. All growth curves were generated in triplicate.

Figure 4A:
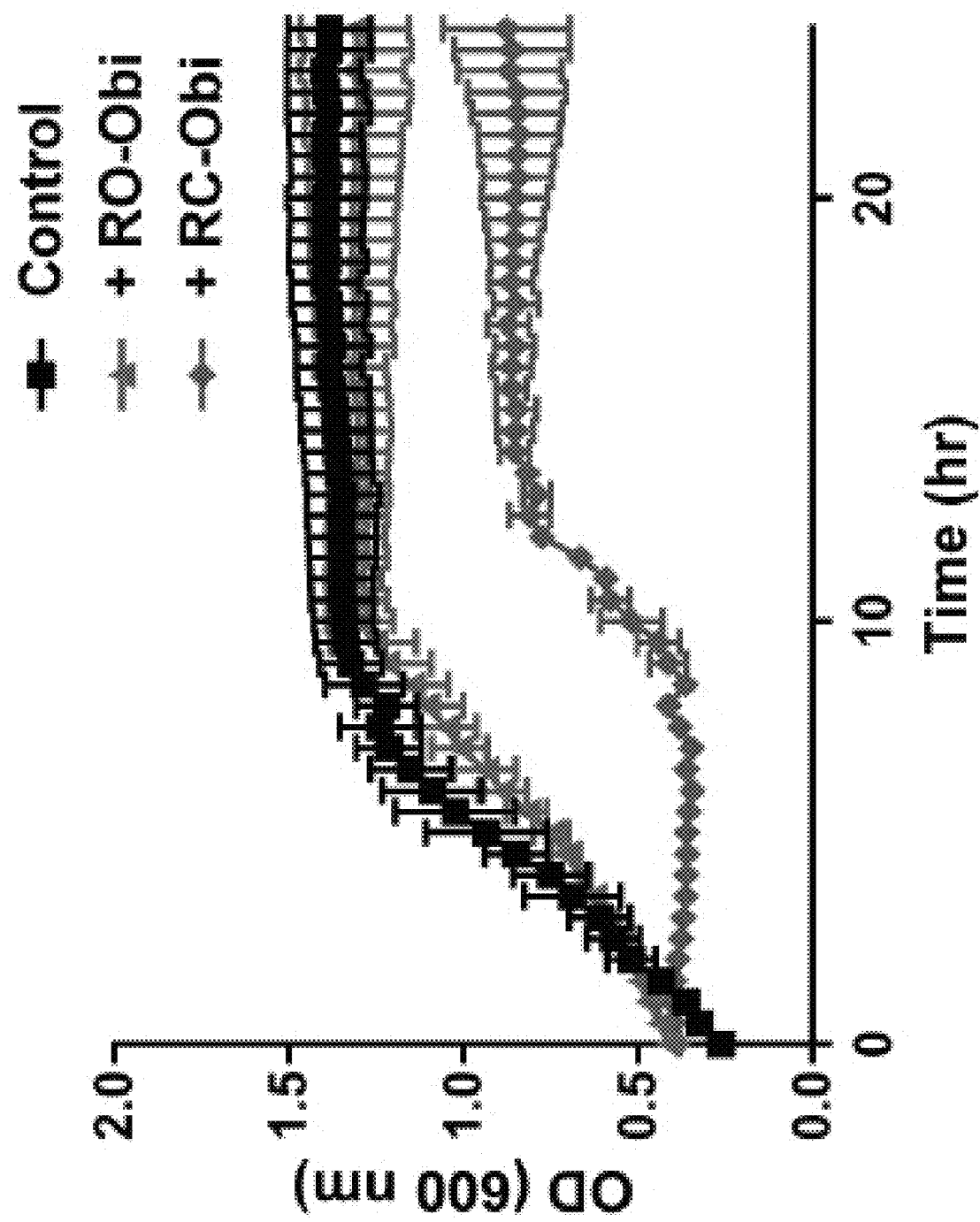
FIG. 4A is a graph showing *E. coli* ATCC 25922 growth curves generated by monitoring OD$_{600}$ in M9 minimal media in the presence of 150 μM RC-Obi, 150 μM RO-Obi, or buffer control.

FIG. 4A is a graph showing *E. coli* ATCC 25922 growth curves generated by monitoring $OD_{600}$ in M9 minimal media in the presence of 150 μM RC-Obi, 150 μM RO-Obi or buffer control. The β-lactone moiety of RC-Obi inhibited the growth of *E. coli* and induced a cell clumping phenotype.

Figure 16A:
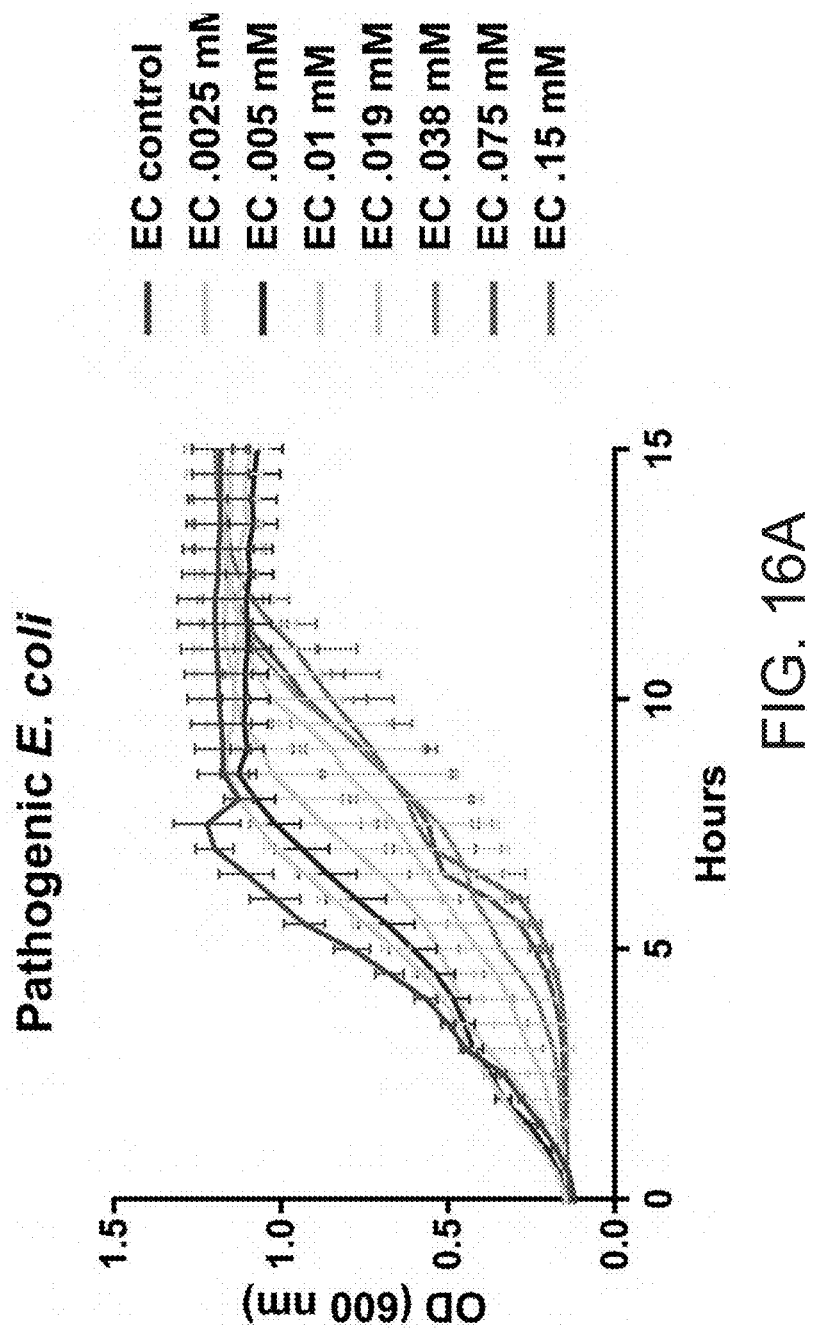
FIG. 16A is a graph showing *E. coli* ATCC 25922 growth curves generated by monitoring $OD_{600}$ in the presence of various concentrations of RC-Obi, or buffer control.

FIG. 16A is a graph showing *E. coli* ATCC 25922 growth curves generated by monitoring $OD_{600}$ in the presence of various concentrations of RC-Obi, or buffer control. The 1-lactone moiety of RC-Obi inhibited the growth of *E. coli* in a dose-dependent manner.

Figure 16B:
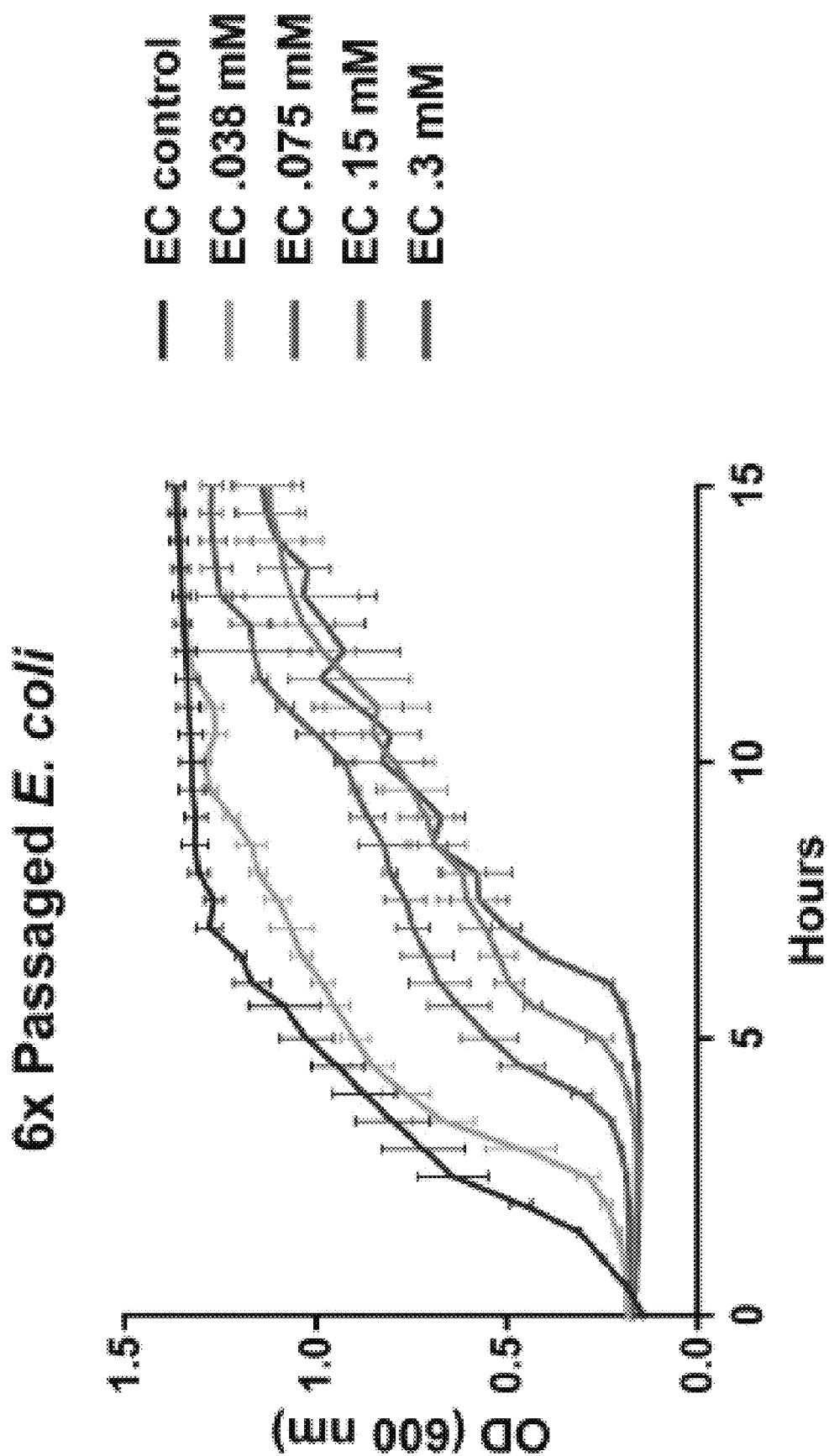
FIG. 16B is a graph showing 6× passaged *E. coli* ATCC 25922 growth curves generated by monitoring $OD_{600}$ in the presence of various concentrations of RC-Obi, or buffer control.
Figure 16C:
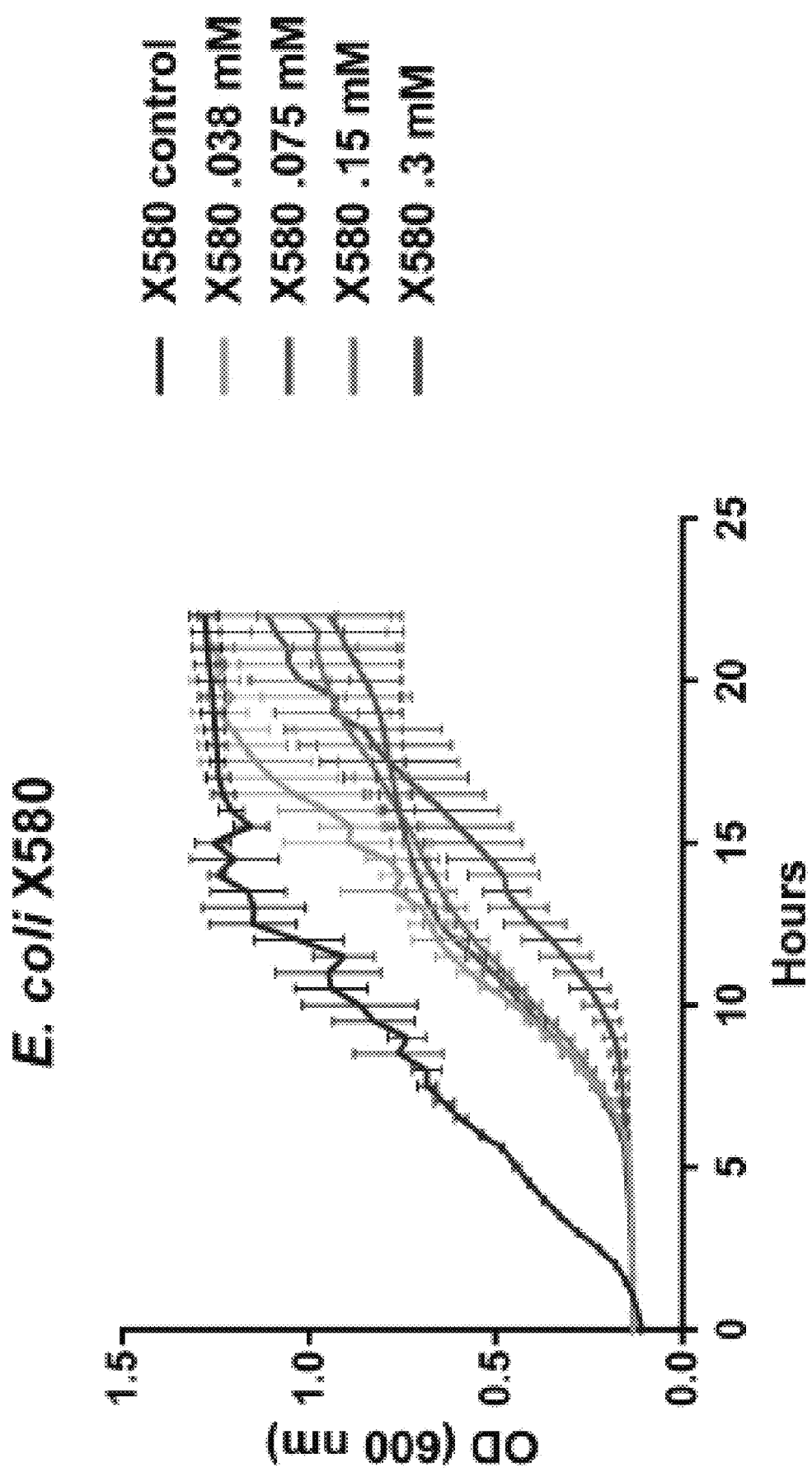
FIG. 16C is a graph showing *E. coli* X580 growth curves generated by monitoring $OD_{600}$ in the presence of various concentrations of RC-Obi, or buffer control.

*E. coli* ATCC 25922 was passaged in LB broth through 6 overnight cycles in the presence of 0.25 mM RC-Obi β-lactone with fresh doses of antibiotic added every 18 hours for 6 days straight. The 6× passaged *E. coli* was then treated with varying concentrations of RC-Obi β-lactone in LB broth and was still susceptible to the antibiotic (see FIG. 16B). Non-pathogenic *E. coli* X580 (a β-lactam hypersensitive strain from Eli Lilly & Co.) were similarly tested and showed enhanced sensitivity and slower growth recovery towards RC-Obi A-lactone compared to *E. coli* ATCC 29522 (see FIG. 16C).

The *E. coli* cells were also subjected to fluorescence microscopy after treatment with RC-Obi or RO-Obi. *E. coli* ATCC 29522 cells were grown in LB media for 8 hours at 37° C. then plated on agar media and incubated overnight at 37° C. A single colony was transferred into test tube with fresh LB media and allowed to grow to 0.3 $OD_{600}$ at 37° C. Cells were diluted by a factor of 10, allowed to grow to $OD_{600}$ 0.3 again. Aliquots of the cell suspension (2 mL each) were treated with RC-Obi (0.1 mM), RO-Obi (0.5 mM), ampicillin (50 μg/mL), or buffer control and incubated for 2 hours at 37° C. Culture aliquots of 250 μL were then used for staining and fluorescence microscopy. Cell membranes and DNA were labeled with the fixable dyes FM 4-64fx and DAPI, respectively, according to the manufacturer's instructions. Cells were fixed with 2.6% paraformaldehyde+ 0.008% glutaraldehyde as previously described. Fixed cells were imaged on 1% agarose pads with an Olympus BX51 microscope equipped with a CCD OrcaERG camera (Hamamatsu Photonics, Bridgewater, N.J.), an Olympus Plan N 100X/1.25 Oil Ph3 objective, and an X-Cite 120 LED light source (Lumen Dynamics). Nikon elements were used for image capture using the DAPI and rhodamine filter sets from Chroma. Images were processed using NIS—Elements Basic Research Microscope Imaging Software (Nikon Corp.).

Figure 4B:
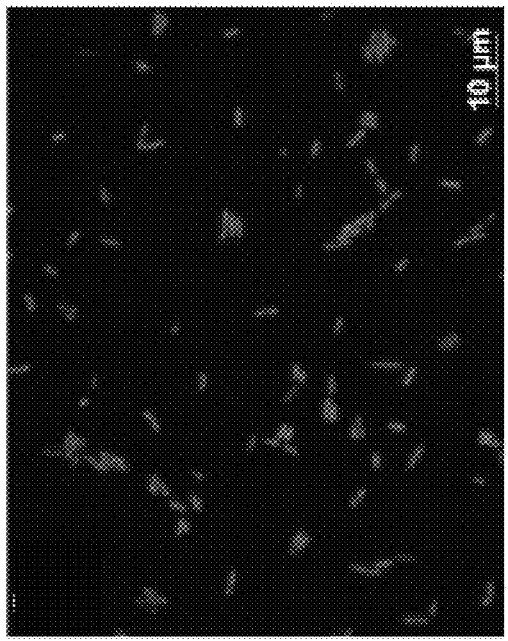
FIG. 4B is a fluorescence microscope images of *E. coli* ATCC 25922 fixed and stained with DAPI and FM 4-64$_{fx}$ after treatment with buffer control (rhodamine filter).
Figure 4C:
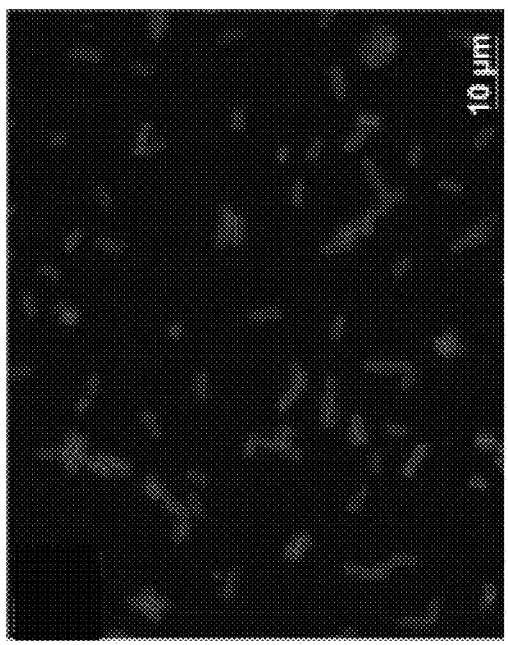
FIG. 4C is a fluorescence microscope images of *E. coli* ATCC 25922 fixed and stained with DAPI and FM 4-64$_{fx}$ after treatment with buffer control (DAPI filter).
Figure 4D:
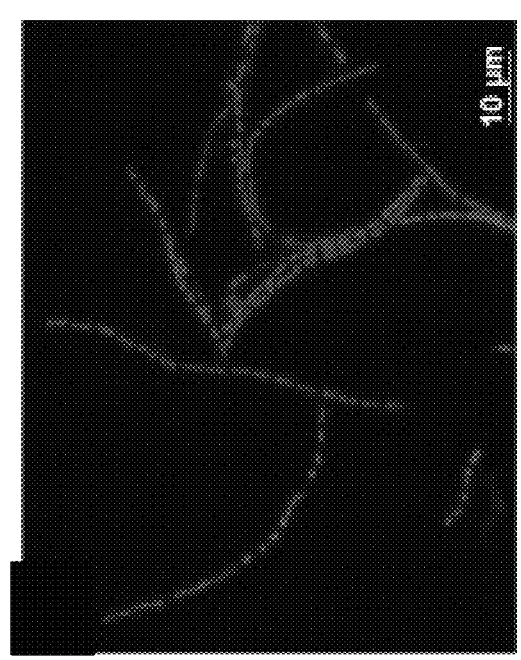
FIG. 4D is a fluorescence microscope image of *E. coli* ATCC 25922 fixed and stained with DAPI and FM 4-64$_{fx}$ after treatment with ampicillin (rhodamine filter).
Figure 4E:
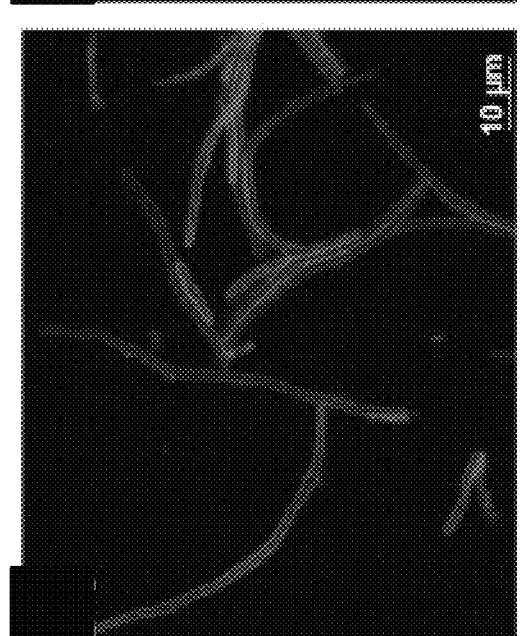
FIG. 4E is a fluorescence microscope image of *E. coli* ATCC 25922 fixed and stained with DAPI and FM 4-64$_{fx}$ after treatment with ampicillin (DAPI filter).
Figure 4G:
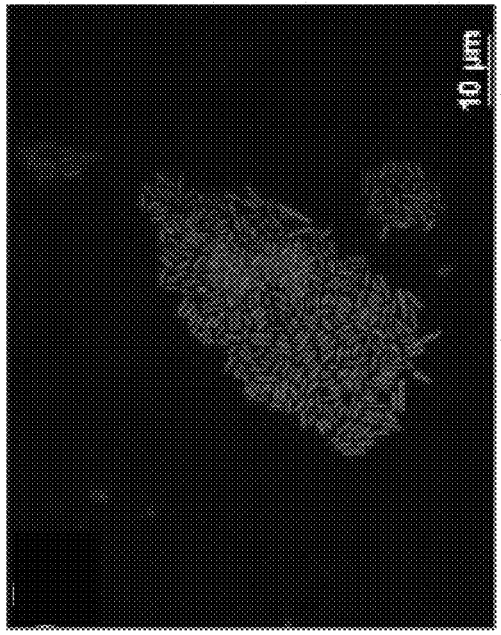
FIG. 4G is a fluorescence microscope images of *E. coli* ATCC 25922 fixed and stained with DAPI and FM 4-64$_{fx}$ after treatment with RC-Obi (DAPI filter).
Figure 4I:
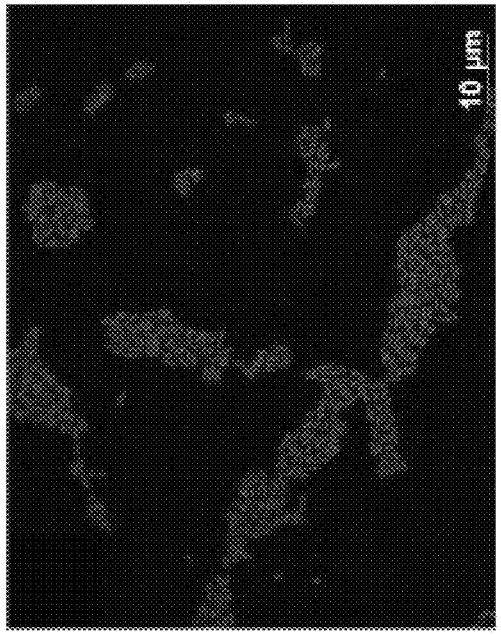
FIG. 4I is a fluorescence microscope images of *E. coli* ATCC 25922 fixed and stained with DAPI and FM 4-64$_{fx}$ after treatment with Obi-COOH (DAPI filter).
Figure 4F:
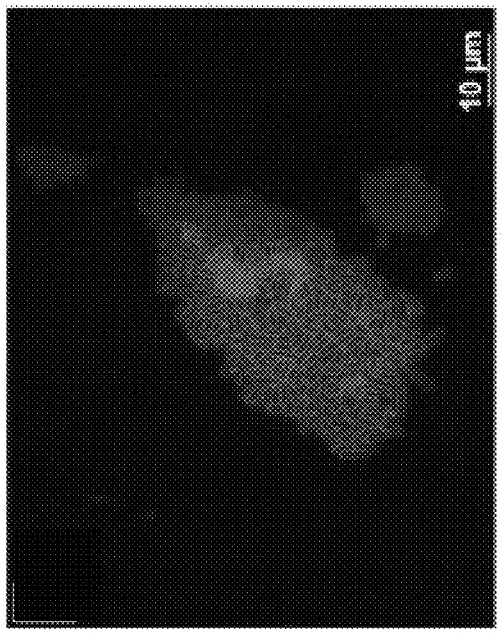
FIG. 4F is a fluorescence microscope image of *E. coli* ATCC 25922 fixed and stained with DAPI and FM 4-64$_{fx}$ after treatment with closed-ring obafluorin RC-Obi (rhodamine filter).
Figure 4H:
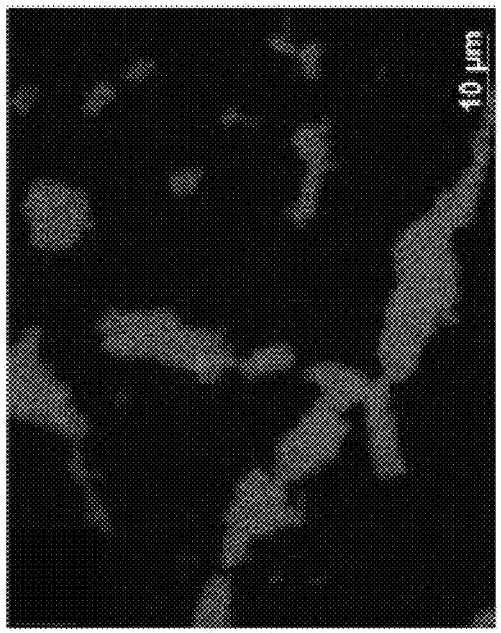
FIG. 4H is a fluorescence microscope images of *E. coli* ATCC 25922 fixed and stained with DAPI and FM 4-64$_{fx}$ after treatment with RO-Obi (rhodamine filter).
Figure 5B:
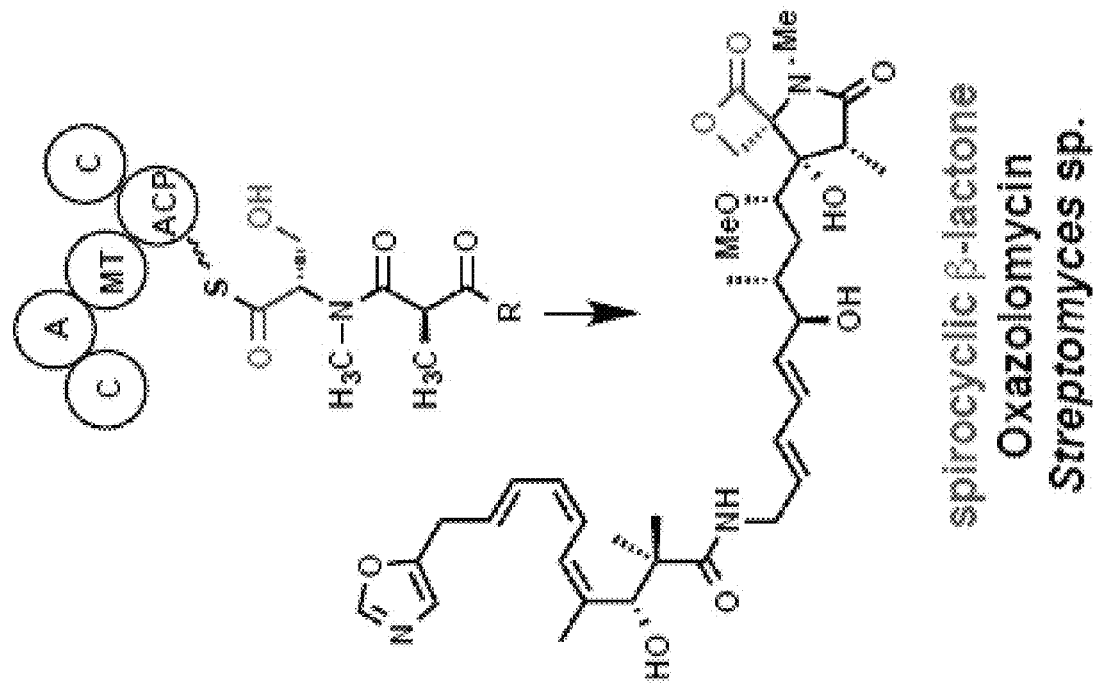
FIG. 5B is a schematic illustration showing the biosynthesis of a spirocyclic β-lactone (Oxazolomycin) by a *Streptomyces* spp. β-lactone biosynthetic cluster that lacks a terminal TE-domain.
Figure 5A:
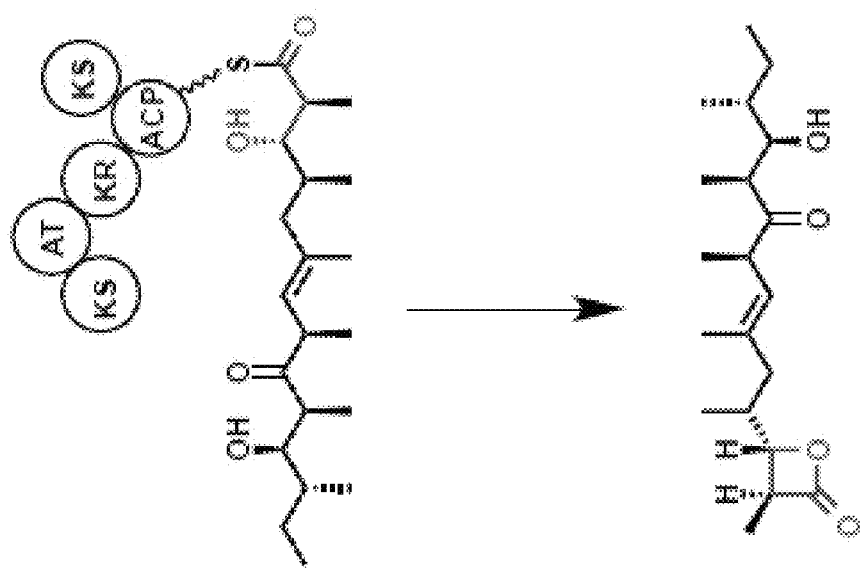
FIG. 5A is a schematic illustration showing the biosynthesis of a transmonocyclic β-lactone (Ebelactone A) by a *Streptomyces aburaviensis* β-lactone biosynthetic cluster that lacks a terminal TE-domain.
Figures 6A, 6B:
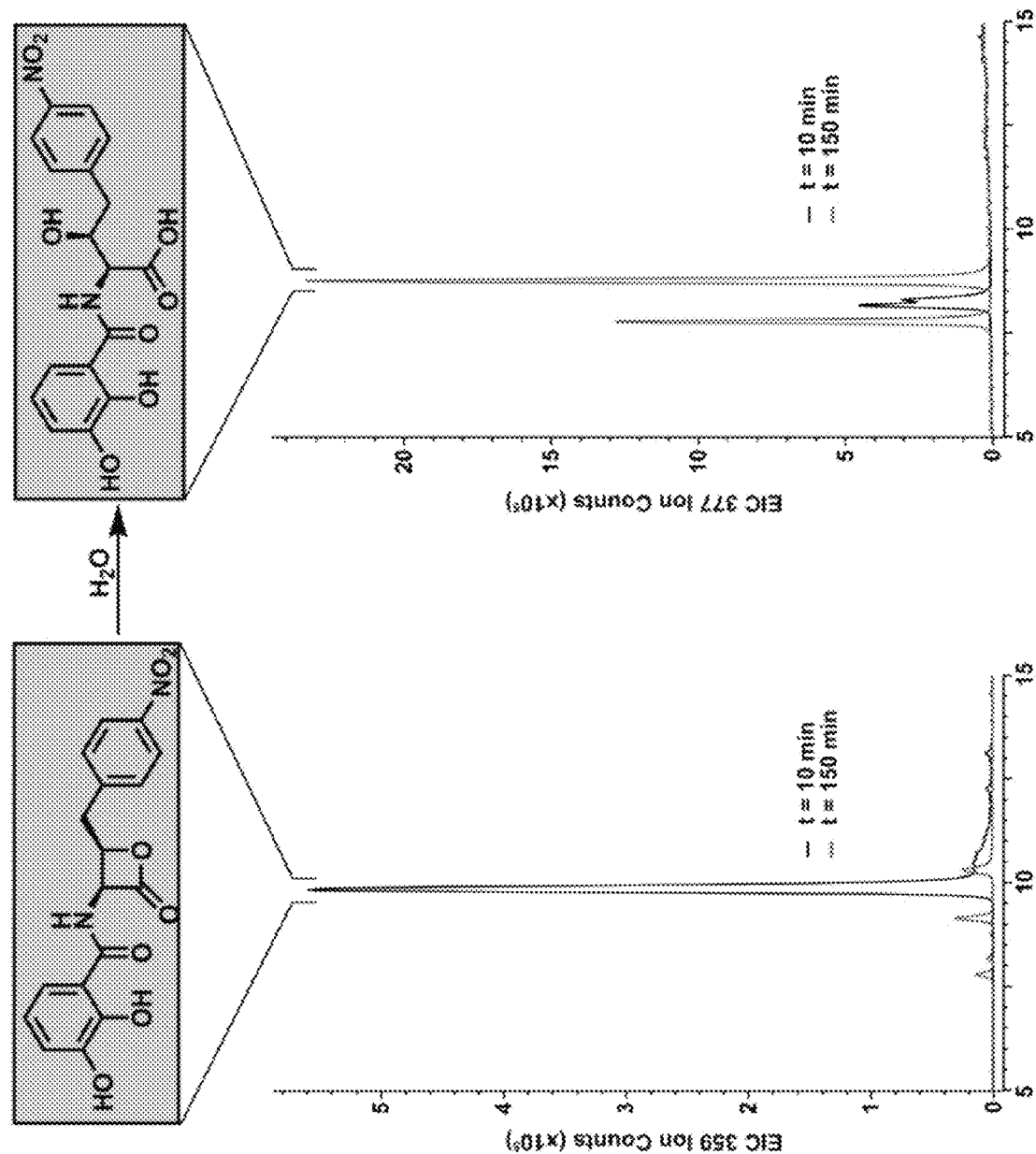
FIG. 6A is a graph showing an EIC chromatogram for RC-Obi, [M+H]$^+$=359, showing that the β-lactone form of obafluorin (i.e. RC-Obi) is present about 10 minutes after initiation of the reaction.
FIG. 6B is a graph showing an EIC chromatogram for RO-Obi, [M+H]$^+$=377, showing that the β-lactone of the RC-Obi rapidly hydrolyzes to the corresponding β-OH-carboxylate (i.e. RO-Obi) in LB broth at pH ~7 with a $t_{1/2}$<2 hours. The hydrolyzed p-OH-carboxylate form (i.e. RO-Obi) predominates after 150 min.

FIG. 4B is a fluorescence microscope images of *E. coli* ATCC 25922 fixed and stained with DAPI and FM 4-64$_{fx}$ after treatment with buffer control (rhodamine filter). FIG. 4C is a fluorescence microscope images of *E. coli* ATCC 25922 fixed and stained with DAPI and FM 4-64$_{fx}$, after treatment with buffer control (DAPI filter). FIG. 4D is a fluorescence microscope image of *E. coli* ATCC 25922 fixed and stained with DAPI and FM 4-64$_{fx}$, after treatment with ampicillin (rhodamine filter). FIG. 4E is a fluorescence microscope image of *E. coli* ATCC 25922 fixed and stained with DAPI and FM 4-64$_{fx}$ after treatment with ampicillin (DAPI filter). FIG. 4F is a fluorescence microscope image of *E. coli* ATCC 25922 fixed and stained with DAPI and FM 4-64$_{fx}$ after treatment with closed-ring obafluorin RC-Obi (rhodamine filter). FIG. 4G is a fluorescence microscope images of *E. coli* ATCC 25922 fixed and stained with DAPI and FM 4-64$_{fx}$ after treatment with RC-Obi (DAPI filter). FIG. 4H is a fluorescence microscope images of *E. coli* ATCC 25922 fixed and stained with DAPI and FM 4-64$_{fx}$, after treatment with RO-Obi (rhodamine filter). FIG. 4I is a fluorescence microscope images of *E. coli* ATCC 25922 fixed and stained with DAPI and FM 4-64$^{fx}$ after treatment with RO-Obi (DAPI filter). Treatment of *E. coli* with RO-Obi carboxylate induced moderate cell clumping and had minimal effect on *E. coli* growth compared to buffer control. Treatment with RC-Obi induced severe cell clumping and halted *E. coli* growth, which recovered to normal levels after ~10 hours.

The results of this experiment demonstrated the antibiotic efficacy of RC-Obi against *E. coli*.

Example 16: ObiHDF Optimization and Substrate Screen Testing

To assess the compatibility of various substrates and optimization of experimental conditions for the enzymatic synthesis of β-lactone rings described herein, the following experiments were conducted.

Various substrate compositions (see FIG. 80B) were used in the reaction scheme illustrated in FIG. 80A, and the concentrations of intermediate and products were used to screen each candidate substrate for compatibiility with the reaction illustrated in FIG. 80A.

Substrate screen compositions used in the enzymatic synthesis of β-lactone ring products were first tested to determine an optimization of intermediate ObiH production of beta-hydroxy-alpha-amino acid according to the reaction scheme illustrated in FIG. 81A. A list of substrate screen compositions is provided in FIG. 80B, wherein the substrate screen compositions are denoted by the stage of the reaction (i.e. 1, 2, 3, or 4, as shown in FIGS. 80A and 83A) and a letter unique to each substrate (e.g. 2k refers to the '$k^{th}$' substrate manifested in the 2nd stage of the enzymatic reaction).

To a 1.5 mL Eppendorf tube 25 mM sodium phosphate buffer, 2.5 mM L-threonine, 1 mM aldehyde, 10 µM PLP, and 10 µM ObiH were added, with the enzyme being added last to initiate the reaction. Total reaction volume was 1 mL in water. The reaction was allowed to progress at room temperature. After 1 hour, the reaction was quenched with the addition of 1 M HCl to bring to pH 2. L-phenylalanine was added as an internal standard at a final concentration of 100 µM. The reactions were run in triplicate and analyzed by LC-MS. For all screens, the LC-MS method used a reverse phase C18 column where solvent A was water buffered with 0.1% formic acid and solvent B was acetonitrile buffered with 0.1% formic acid. A gradient of 0% B to 5% B was formed over 5 min followed by a gradient of 5% B to 95% B over 10 minutes. The maximum ion counts for the ObiH products were used to calculate product concentration relative to an internal phenylalanine standard. Experiments were performed in triplicate as independent trails. The measured concentrations of products of the process illustrated in FIG. 81A for the various substrate screen compositions is provided in FIG. 80B are summarized in the bar graph shown in FIG. 81B.

As shown in FIG. 81B, substrate composition 2b was detected at the highest concentration of all substrate compositions tested, indicating the 1b-4b substrate screen (see FIG. 80A) produced the highest concentration of ObiH products. The 1b-4b substrate screen was utilized in further optimizing the product yield of the ObiH intermediate product (see FIG. 82A) using the following procedure.

To a 1.5 mL Eppendorf tube 25 mM sodium phosphate buffer, variable L-threonine (1-50 mM), variable phenylacetaldehyde (PAA; 2-10 mM), 10 µM PLP, and 10 µM ObiH were added, with the enzyme being added last to initiate the reaction. Total reaction volume was 1 mL in water containing 0%-50% DMSO or water containing 0%-50% MeOH. The reaction was allowed to progress at room temperature or 4° C. After 1 hour, the reaction was quenched with the addition of 1 M HCl to bring to pH 2. L-phenylalanine was added as an internal standard at a final concentration of 100 µM and the reactions were analyzed by LC-MS. The LC-MS method used a reverse phase C18 column where solvent A was water buffered with 0.1% formic acid and solvent B was acetonitrile buffered with 0.1% formic acid. A gradient of 0% B to 5% B was formed over 5 min followed by a gradient of 5% B to 95% B over 10 minutes. The maximum ion counts for the ObiH products were used to calculate product concentration relative to an internal phenylalanine standard. Experiments with variable L-threonine and PAA were performed in triplicate as independent trails. Experiments with variable DMSO and MeOH solvents were performed as single trials. The results of the optimization processes are illustrated in FIGS. 82B and 82C.

Substrate screens for the ObiH,F,D reaction (FIGS. 81A, 83A) were also analyzed using the following procedure.

ObiF and ObiD were pantetheinylated by a solution containing 180 µM CoASH, 5 mM DTT, 400 nM Sfp, 10 mM MgCl$_2$, 25 µM apo enzyme, and 25 mM sodium phosphate buffer. The pantetheinylation reaction was allowed to proceed at room temperature for 2 hours. After this reaction time, the solution was added to a 1.5 mL Eppendorf tube and contained 25 mM sodium phosphate buffer, 15 mM L-threonine, 10 µM PLP, 1 mM aldehyde, 1 mM 2,3-DHB, 5 mM DTT, 5 mM ATP, 10 µM ObiH, 2.5 µM holo-ObiF, and 2.5 µM holo-ObiD (holo-ObiF and -ObiD were used directly from the pantetheinylation reaction. The total reaction volume was 1 mL. The aldehydes were dissolved in a stock solution of 5% DMSO in water, making the final reaction 1% DMSO and 99% water by volume. The reaction was allowed to proceed at room temperature for 24 hours, at the end of which the reaction was quenched with 1 M HCl to a pH of 2 and analyzed by LC-MS. The LC-MS method used a reverse phase C18 column where solvent A was water buffered with 0.1% formic acid and solvent B was acetonitrile buffered with 0.1% formic acid. A gradient of 0% B to 5% B was formed over 5 min followed by a gradient of 5% B to 95% B over 10 minutes. The presence of ObiHDF products was confirmed by extracting the molecular ions from the total ion count from LC-MS analysis. Experiments were performed in triplicate as independent trails.

The compounds marked in blue in FIG. 83B are substrate compositions which provided products and all intermediates in significant quantities throughout the reaction shown in FIG. 83A (i.e. products and intermediates resulting from the substrate were present throughout stages 1, 2, 3, and 4).

Example 16: Synthesis of an Alkyne-Tagged Chemical Probe

To assess the application of the methods disclosed herein to the synthesis of alkyne-tagged chemical probes, the following experiments were conducted.

FIG. 84 is a diagram of the reaction scheme used to produce alkyne-tagged ObiHDF products in these experiments.

To a 1.5 mL Eppendorf tube 25 mM sodium phosphate buffer, 15 mM L-threonine, 1 mM aldehyde (5), 10 µM PLP, and 5 µM ObiH were added, with the enzyme being added last to initiate the reaction. Total reaction volume was 1 mL in 93% water/7% DMSO and the final pH was 7.5. The reaction was allowed to progress at room temperature for 3 hours. The reaction was quenched with the addition of 1 M HCl and analyzed by LC-MS. The LC-MS method used a reverse phase C18 column where solvent A was water buffered with 0.1% formic acid and solvent B was acetonitrile buffered with 0.1% formic acid. A gradient of 0% B to 5% B was formed over 5 min followed by a gradient of 5% B to 95% B over 10 minutes. The ObiH product 6 was detected in the LC-MS, as illustrated in the optical absorbance spectrum of FIG. 91. The presence of ObiH product 6 was confirmed by extracting the molecular ions from the total ion count from LC-MS analysis illustrated in FIG. 92 to obtain an extracted ion count at m/z=220 (FIG. 93).

The ObiH product (6) was purified by prep-HPLC giving 5.4 mg that was characterized by multi-dimensional NMR, the results of which are shown graphed in FIGS. 85, 86, 87, 88, 89, and 90. The results of the multi-dimensional NMR characterization of the ObiH product (6) are also shown summarized in Table 17 below.

TABLE 17

Summary of NMR Data for ObiH Product 6

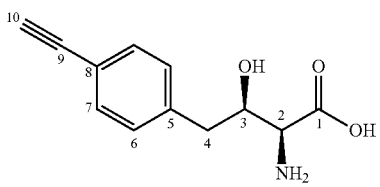

| Atom | $^{13}C$ (ppm) | $^1H$ (ppm), multiplets in Hz | gCOSY $^1H$-$^1H$ 3 bond | HSQC $^1H$-$^{13}C$ 1 bond | HMBC $^1H$-$^{13}C$ 2-3 bond |
|---|---|---|---|---|---|
| 1 | 171.32 | | | | |
| 2 | 59.32 | 3.74 (d, J = 3.8 Hz, 1H) | 3 | 2 | 4 |
| 3 | 71.49 | 4.32 (dt, J = 8.6, 4.2 Hz, 1H) | 2, 4 | 3 | 2 |
| 4 | 41.71 | 2.99-2.82 (m, 2H). | 3 | 4 | 7.42 |
| 5 | 122.12 | | | | 7.42, 10 |
| 6 | 130.77 | 7.42 (d, J = 8.1 Hz, 2H) | 7 | 6 | 6, 7, 10 |
| 7 | 133.25 | 7.28 (d, J = 8.1 Hz, 2H) | 6 | 7 | 6, 7, 4 |
| 8 | 139.25 | | | | 7.28, 10 |
| 9 | 84.29 | | | | |
| 10 | 78.63 | 3.44 (s, 1H) | | | |

ObiF and ObiD were pantetheinylated by a solution containing 180 µM CoASH, 5 mM DTT, 400 nM Sfp, 10 mM MgCl$_2$, 25 µM apo enzyme, and 25 mM sodium phosphate buffer. The pantetheinylation reaction was allowed to proceed at room temperature for 2 hours. After this reaction time, a second reaction mixture containing 5 µM holo-ObiF, 5 µM holo-ObiD, 5 mM ATP, 5 mM DTT, 500 µM 2,3-DHB, 500 µM β-OH-p-alkynyl-homoPhe (6), and 25 mM PBS at pH 7.5. The reaction was left at room temperature for 24 hours, then quenched with HCl to a pH of 2 and analyzed by LC-MS. The LC-MS method used a reverse phase C18 column where solvent A was water buffered with 0.1% formic acid and solvent B was acetonitrile buffered with 0.1% formic acid. A gradient of 0% B to 5% B was formed over 5 min followed by a gradient of 5% B to 95% B over 10 minutes.

The beta-lactone product 7 produced a relatively weak signal in the LC-MS, as illustrated in the optical absorbance spectrum of FIG. 97. The presence of ObiHDF products 7 and 8 was confirmed by extracting the molecular ions from the total ion count spectrum from LC-MS analysis illustrated in FIG. 95 to obtain extracted ion counts at m/z=356 (FIG. 96) and at m/z=338 (FIG. 97). The beta-lactone product 7 did not ionize very well, hence the weak signal in the LC-MS, as illustrated in the optical absorbance spectrum of FIG. 97. There are multiple peaks in the m/z=338 extracted ion chromatogram (FIG. 97) because compound 8 fragmented to give the same mass as compound 7 and there was a third degradation product that was an oxazoline with the same mass as compound 7.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of producing a peptide beta-lactone, the method comprising contacting a beta-hydroxy-alpha-amino acid, a benzoic acid derivative, an aryl carrier protein, and ATP with a non-ribosomal protein synthetase, wherein:
   - the beta-hydroxy-alpha-amino acid is selected from the group consisting of beta-OH-p-$NO_2$-homoPhe and beta-OH-homoPhe;
   - the aryl carrier protein comprises the amino acid sequence of SEQ ID NO:1;
   - the non-ribosomal protein synthetase comprises the amino acid sequence of any one of SEQ ID NOS:2, 25, and 26; and
   - the benzoic acid derivative is 2,3-dihydroxoybenzoic acid.

2. The method of claim 1, wherein the peptide beta-lactone is selected from the group consisting of an obafluorin and an obafluorin analog, the obafluorin analog comprising a compound with the structure:

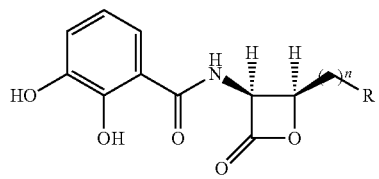

wherein n=0, 1, or 2; and
R=

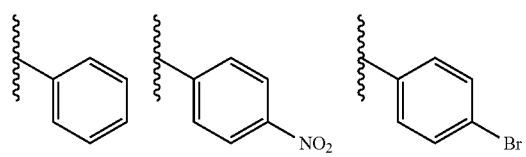

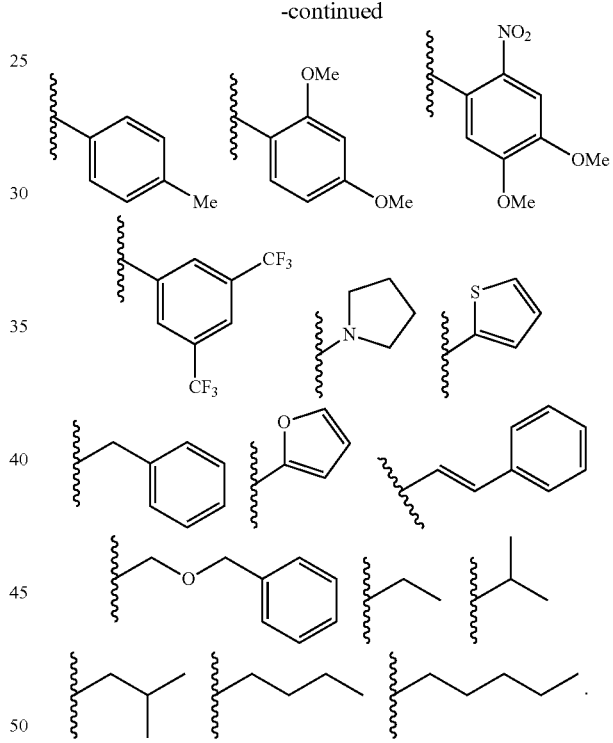

3. The method of claim 1, further comprising forming the beta-hydroxy-alpha-amino acid by contacting an aliphatic or aryl aldehyde or derivative thereof, an amino acid, and a pyridoxyl phosphate (PLP) cofactor with a serine hydroxymethyltransferase/threonine aldoloase, wherein:
   - the aliphatic or aryl aldehyde or derivative thereof is selected from the group consisting of aliphatic aldehydes, aromatic benzaldehydes, aromatic phenylacetaldehydes, and aromatic cinnamaldehydes;
   - the amino acid is selected from the group consisting of threonine, serine, glycine, and any isomer thereof; and
   - the serine hydroxymethyltransferase/threonine aldoloase comprises the amino acid sequence of SEQ ID NO:3.

4. The method of claim 3, further comprising forming the aliphatic or aryl aldehyde or derivative thereof by contacting an aliphatic or aryl pyruvate or derivative thereof and thiamine pyrophosphate (TPP) with a thiamine dependent pyruvate decarboxylase, wherein: the phenyl pyruvate or derivative thereof is selected from the group consisting of: p-nitrophenylpyruvate, p-hydroxyphenylpyruvate, and phenylpyruvate; and the thiamine dependent pyruvate decarboxylase comprises the amino acid sequence of SEQ ID NO:4.

5. The method of claim 4, further comprising forming the aliphatic or aryl pyruvate derivative consisting of p-nitrophenylpyruvate by contacting p-aminophenylpyruvate, oxygen, and Fe(II) with a p-aminobenzoate N-oxygenase, wherein the p-aminobenzoate N-oxygenase comprises the amino acid sequence of SEQ ID NO:5.

6. The method of claim 1, further comprising hydrolyzing the peptide beta-lactone to form a beta-hydroxy-acid, the beta-hydroxy-acid comprising a compound with any one of the structures given by:

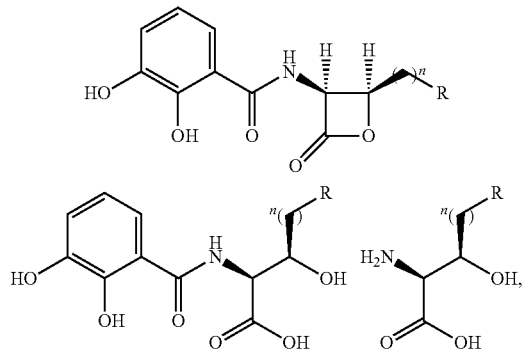

wherein n=0, 1, 2; and
R=

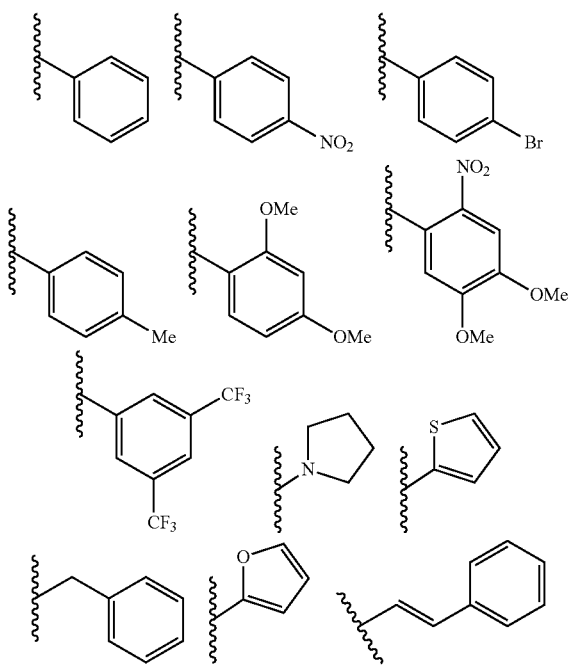

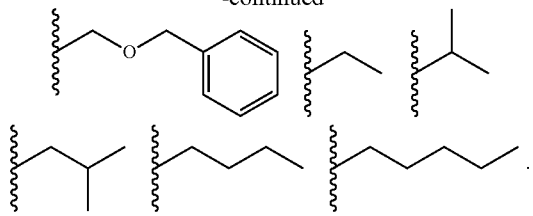

7. A method of producing a peptide beta-lactone, the method comprising:

forming a reaction mixture comprising:
a beta-hydroxy-alpha-amino acid selected from the group consisting of beta-OH-p-$NO_2$-homoPhe and beta-OH-homoPhe;

a benzoic acid derivative consisting of 2,3-dihydroxybenzoic acid;

ATP;

an aryl carrier protein comprising the amino acid sequence of SEQ ID NO:1; and a non-ribosomal protein synthetase comprising the amino acid sequence of any one of SEQ ID NOS:2, 25, and 26, the non-ribosomal protein synthetase further comprising a condensation domain (C), a first adenylation domain ($A_1$), a peptidyl carrier domain (PCP), a thioesterase domain (TE), and a second adenylation domain ($A_2$);

contacting the beta-hydroxy-alpha-amino acid with the non-ribosomal protein synthetase at the peptidyl carrier domain (PCP) with ATP activation by the first adenylation domain ($A_1$) to form a PCP-beta-hydroxy-alpha-amino acid thioester comprising an alpha-amino moiety;

ATP-activating the benzoic acid derivative at the second adenylation domain ($A_2$) and contacting the ATP-activated benzoic acid derivative with the aryl carrier protein to form a benzoic acid derivative-aryl carrier protein thioester comprising a carbonyl moiety;

contacting the benzoic acid derivative-aryl carrier protein thioester with the condensation domain (C) to catalyze an amide bond between the alpha-amino moiety and the carbonyl moiety to form a PCP-peptide beta-lactone precursor thioester;

contacting the PCP-peptide beta-lactone precursor thioester with the thioesterase domain (TE) to form a transthioesterified peptide beta-lactone precursor; and releasing the transthioesterified peptide beta-lactone precursor as a peptide beta-lactone from the non-ribosomal protein synthetase.

8. The method of claim 7, wherein the method further comprises contacting the aryl carrier protein with a phosphopantetheinyl transferase (Sfp) enzyme.

9. The method of claim 7, wherein the method further comprises contacting the non-ribosomal protein synthetase with a phosphopantetheinyl transferase (Sfp) enzyme.

10. The method of claim 7, wherein the peptide beta-lactone is selected from the group consisting of an obafluorin and an obafluorin analog, wherein the obafluorin analog comprises a compound with the structure:

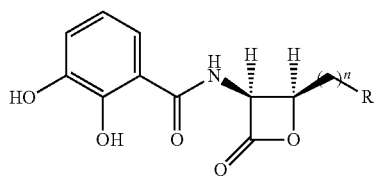

wherein n=0, 1, or 2; and
R=

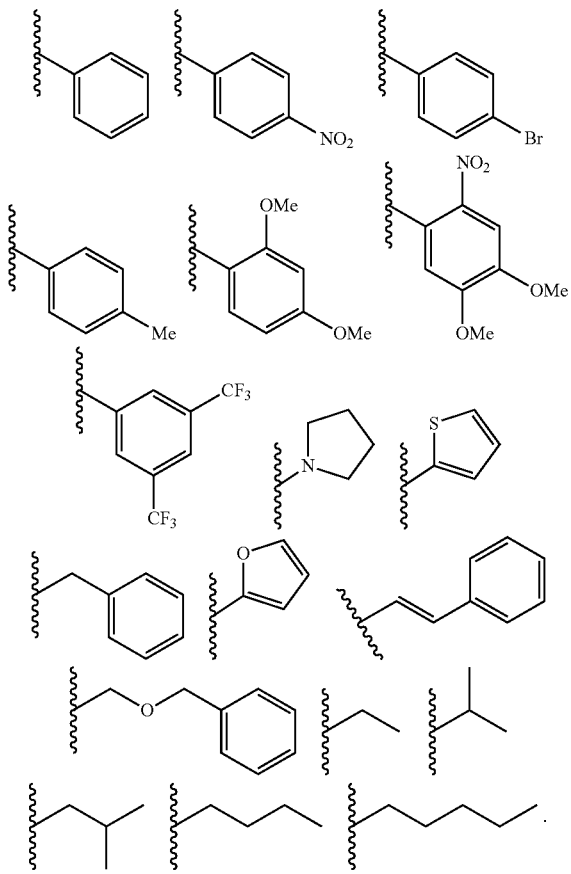

11. The method of claim 7, further comprising forming the beta-hydroxy-alpha-amino acid in the reaction mixture by contacting an aliphatic or aryl aldehyde or derivative thereof, an amino acid, and a pyridoxyl phosphate (PLP) cofactor with a serine hydroxymethyltransferase/threonine aldoloase, wherein:

the aliphatic or aryl aldehyde or derivative thereof is selected from the group consisting of aliphatic aldehydes, aromatic benzaldehydes, aromatic phenylacetaldehydes, and aromatic cinnamaldehydes the amino acid is selected from the group consisting of threonine, serine, glycine, and any isomer thereof;

the serine hydroxymethyltransferase/threonine aldoloase comprises the amino acid sequence of SEQ ID NO:3; and the reaction mixture further comprises the aliphatic or aryl aldehyde or derivative thereof, the amino acid and the serine hydroxymethyltransferase/threonine aldoloase and the pyridoxyl phosphate (PLP) cofactor.

12. The method of claim 11, further comprising forming the aliphatic or aryl aldehyde in the reaction mixture by contacting an aliphatic or aryl pyruvate and thiamine pyrophosphate (TPP) with a thiamine dependent pyruvate decarboxylase, wherein:

the phenyl pyruvate or derivative thereof is selected from the group consisting of: p-nitrophenylpyruvate, p-hydroxyphenylpyruvate, and phenylpyruvate;

the thiamine dependent pyruvate decarboxylase comprises the amino acid sequence of SEQ ID NO:4; and the reaction mixture further comprises the aliphatic or aryl pyruvate, the thiamine pyrophosphate (TPP), and the thiamine dependent pyruvate decarboxylase.

13. The method of claim 12, further comprising forming the aliphatic or aryl pyruvate derivative consisting of a p-nitrophenylpyruvate derivative in the reaction mixture by contacting a p-aminophenylpyruvate derivative, oxygen, and Fe(II) with a p-aminobenzoate N-oxygenase, wherein:

the p-aminobenzoate N-oxygenase comprises the amino acid sequence of SEQ ID NO:5; and the reaction mixture further comprises the p-nitrophenylpyruvate derivative, p-aminophenylpyruvate derivative, the oxygen, the Fe(II), and the p-aminobenzoate N-oxygenase.

14. The method of claim 13, further comprising hydrolyzing the peptide beta-lactone to form a beta-hydroxy acid, the beta-hydroxy acid comprising a compound with any one of the structures given by:

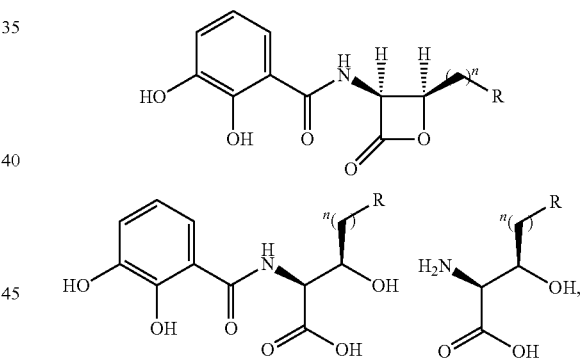

wherein n=0, 1, 2; and
R=

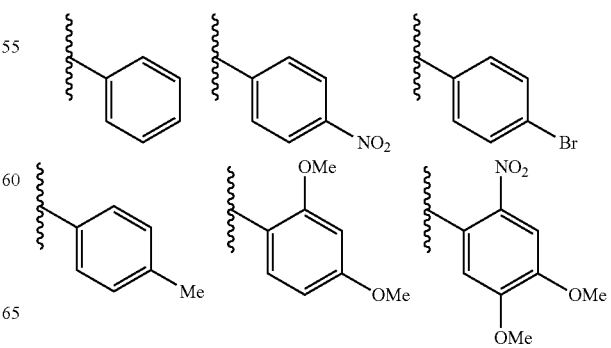

-continued
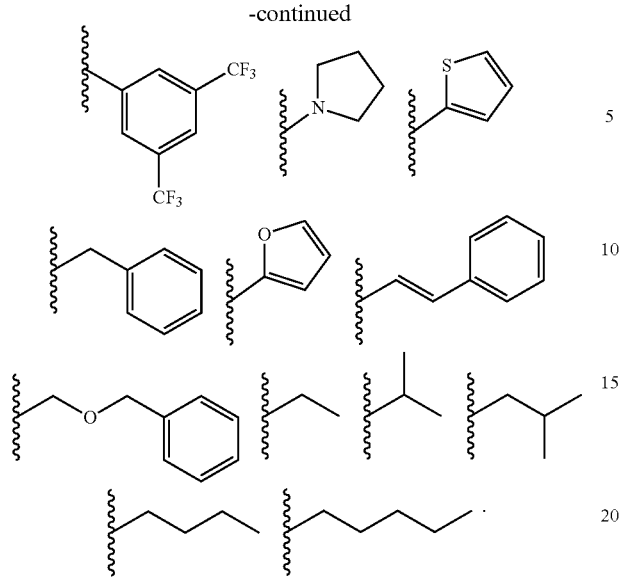
* * * * *

SEQUENCE LISTING

```
<160> NUMBER OF SEQ ID NOS: 28

<210> SEQ ID NO 1
<211> LENGTH: 88
<212> TYPE: PRT
<213> ORGANISM: Pseudomonas fluorescens

<400> SEQUENCE: 1

Met Thr Gln Gly Lys Leu Ile Tyr Asp Lys Ala Asp Phe Tyr Ala Glu
1               5                   10                  15

Ile Ala Ala Ile Leu Arg Ile Pro Thr Glu Glu Leu Ala Glu Leu Glu
            20                  25                  30

Ser Pro Gln Glu Ala Gly Val Asp Ser Val Arg Leu Leu Thr Leu Ser
        35                  40                  45

Glu Lys Trp Arg Lys Arg Gly Ile Asp Val Ser Phe Met Glu Leu Ala
    50                  55                  60
```

```
Glu Arg Pro Gly Phe Thr Ala Trp Trp Glu Leu Leu Ser Ala Arg Met
 65                  70                  75                  80

Pro Val Thr Glu Cys Glu Gln Pro
                 85
```

<210> SEQ ID NO 2
<211> LENGTH: 1910
<212> TYPE: PRT
<213> ORGANISM: Pseudomonas fluorescens

<400> SEQUENCE: 2

```
Met Ser Ala Ser Phe Thr Thr Ala Leu Thr Ser Ala Gln Gln Ser Ile
  1               5                  10                  15

Trp Met Gly His Gln Phe Asp Pro Gln Ser Pro Ala Tyr Asn Val Ala
                 20                  25                  30

Ser Tyr Ile Glu Met Ser Gly Asp Ile Asp Pro Gln Arg Leu Gln His
                 35                  40                  45

Ala Leu Gln Arg Ala Val Asp Asp Ile Glu Ala Leu Arg Ala Arg Phe
         50                  55                  60

His Glu Asp Glu Thr Gln Gly Gly Ala Leu Thr Gln Thr Ile Leu Ala
 65                  70                  75                  80

Gln Val Ala Val Glu Leu Asn Val Phe Ala Val Asp Ala Glu Gln Ala
                 85                  90                  95

Arg Ser Trp Met Glu Ser Asp Leu Ala Arg Pro Thr Asp Leu Thr Ser
                100                 105                 110

Gly Pro Ile Phe Ser Ser Ala Leu Leu Gln Val Ala Pro Asn Val Asn
                115                 120                 125

Tyr Trp Tyr Phe Lys Thr His His Ile Val Met Asp Gly Val Ala Leu
            130                 135                 140

Ser Met Leu Phe Lys Arg Val Ala Asp Leu Tyr Gly Gln Ala Pro Asp
145                 150                 155                 160

Leu Cys Ser Pro Ser Pro Phe Gly Ser Val Arg Gln Val Leu Glu Asn
                165                 170                 175

Glu Gln Ala Trp Arg Ala Ser Pro Ala Phe Ala Gln Asp Arg Glu Phe
                180                 185                 190

Trp Gln Gln His Cys Gln Asp Met Ala Glu Val Ala Ser Leu Asn Ser
            195                 200                 205

Asp Val Ala Gln Pro Ser Tyr Gln Ala Ile Gln His Arg Arg Val Leu
        210                 215                 220

Asp Glu Ser Ile Met Ala Ser Leu Arg Glu Arg Ala Glu Ala Met Asp
225                 230                 235                 240

Ser Gln Trp Val Asn Val Leu Ala Ala Phe Gly Ala Phe Val Gly
                245                 250                 255

Arg Ser Thr Gly Tyr Arg Gln Val Thr Val Gly Val Pro Met Met Asn
                260                 265                 270

Arg Phe Ala Thr Gly Ala Ile Asn Val Pro Cys Thr Leu Ala Asn Val
            275                 280                 285

Leu Pro Leu Arg Leu Asp Ile Lys Pro Gly Gln Ser Val Glu Gln Leu
        290                 295                 300

Val Ala Ser Val Gln Ala Gln Leu Asp Arg Met Arg Pro His Gln Arg
305                 310                 315                 320

Tyr Arg Ala Glu Asp Ile Arg Arg Asp Cys Asn Leu Leu Gly Asp Asn
                325                 330                 335

Arg Arg Leu Thr Gly Pro Gln Ile Asn Ile Asp Phe Phe Ser Ala Lys
```

-continued

```
                340             345             350
Leu Ser Phe Asp Gly Val Pro Gly Glu Val Asn Val Leu Ser Ala Gly
            355                 360                 365
Pro Ala Asp Asp Leu Ser Leu Leu Ile Gln Thr Pro Ala Asp Asp Lys
            370                 375                 380
Thr Leu Asn Ile Ile Ala Met Ala Asn Pro Ala Leu Tyr Ser Arg Ala
385                 390                 395                 400
Ala Leu Glu Arg His Val Gln Arg Phe Ile Asp Phe Val Glu Arg Phe
                405                 410                 415
Ala Ala Ala Ser Asp Thr Pro Leu Gly Gln Leu Asp Ala Tyr Asp Ala
                420                 425                 430
Thr Asp Pro Gly Tyr Ala Gln Gly Asn Ala Cys Phe Ser Pro Val Asn
            435                 440                 445
Gln Ala His Thr Leu Ala Gln Thr Leu Val Glu Arg Phe Glu Arg Ala
            450                 455                 460
Val His Ala Thr Pro Asp Ala Ile Ala Leu Thr Phe Asn Gly Glu His
465                 470                 475                 480
Leu Thr Tyr Gln Ala Leu Asn Gln Arg Ala Asn Arg Leu Ala His Leu
                485                 490                 495
Ile Gln Asp Gln Thr Gly Gln Thr Ser Pro Gln Pro Val Ala Leu Leu
            500                 505                 510
Leu Ala Arg Ser Val Gln Thr Phe Val Cys Ile Leu Gly Val Leu Lys
            515                 520                 525
Ala Gly Ala His Tyr Val Pro Leu Asp Pro Asp Ala Pro Ala Glu Arg
            530                 535                 540
Ile Thr Thr Ile Leu Glu Asp Thr Cys Pro Thr Leu Val Ile Cys Asp
545                 550                 555                 560
Gln Ser Ser Gln Ala Leu Val Ser Gly Ser Asp Val Lys Val Met Val
                565                 570                 575
Ile Asp Thr Pro Ser Cys Met Asp Ala Val Gln Gln Gln Ser Ile Asp
            580                 585                 590
Asn Leu Gln Ser Gly Pro Arg Ala Asn Asp Leu Ala Tyr Ile Ile Tyr
            595                 600                 605
Thr Ser Gly Ser Thr Gly Lys Pro Lys Gly Val Cys Ile Thr His His
            610                 615                 620
Asn Val Val Arg Leu Phe Glu Asn Thr His His Trp Phe Asp Tyr Arg
625                 630                 635                 640
Ser Ser Asp Val Trp Thr Ala Cys His Gly Tyr Ile Phe Asp Ala Ser
                645                 650                 655
Val Trp Glu Met Trp Gly Ala Phe Ala His Gly Gly Arg Leu Val Leu
                660                 665                 670
Val Pro Val Asp Thr Thr Arg Asp Pro Glu Lys Leu Leu Glu Leu Val
            675                 680                 685
Val Gln Glu Gln Val Thr Val Phe Gly Gln Ile Pro Ser Ala Phe Tyr
            690                 695                 700
Arg Phe Met Glu Ala Gln Ala Asp Gln Pro Ala Leu Ala Ala Arg Leu
705                 710                 715                 720
Asn Leu Arg Tyr Gln Cys Phe Gly Gly Glu Ala Leu Asp Leu Ser Arg
                725                 730                 735
Leu Lys Pro Trp Phe Glu His Tyr Gly His Ser Arg Thr Arg Leu Leu
            740                 745                 750
Asn Leu Tyr Gly Ile Thr Glu Thr Thr Ile Asn Ala Thr Tyr Gln Phe
            755                 760                 765
```

-continued

Val Thr Leu Glu Gln Val Gln Thr Asn Gln Gly Ser Leu Ile Gly Thr
    770                 775                 780

Val Tyr Asp Asp Leu Asp Ile Lys Val Leu Asp Ala Leu Arg Pro
785                 790                 795                 800

Val Pro Val Gly Gly Tyr Gly Glu Met Tyr Val Arg Gly Ala Gly Leu
                805                 810                 815

Ala Arg Gly Tyr Leu Asn Arg Gln Asp Leu Asp Ala Thr Arg Phe Val
            820                 825                 830

Ala Asp Pro Phe Gly Ala Pro Gly Glu Arg Met Tyr Arg Ser Gly Asp
        835                 840                 845

Val Ala Ala Leu Gln Glu Gly Gly Val Leu Glu Tyr Ile Gly Arg Ala
    850                 855                 860

Asp Gln Gln Val Lys Val Arg Gly Tyr Arg Ile Glu Leu Gly Glu Ile
865                 870                 875                 880

Glu Thr Gln Leu Arg Gly His Pro Leu Leu Ser Asp Ala Ile Ala Leu
                885                 890                 895

Val Val Thr Asp Ala Ser Gly Asp Pro Lys Leu Val Ala His Val Val
            900                 905                 910

Pro Lys Ala Thr Cys Arg Cys Glu Asp Ile Asp Thr Ala Gln Val Arg
        915                 920                 925

Asp Tyr Leu Arg Glu Arg Leu Pro Ser Tyr Met Val Pro Gly Ala Ile
    930                 935                 940

Gly Val Gln Glu Arg Leu Pro Val Thr Leu Ser Gly Lys Val Asp Arg
945                 950                 955                 960

Lys Ala Leu Pro Thr Ile Ala Leu Ser Gly Ala Arg Gln Val Glu Ala
                965                 970                 975

Pro Arg Asp Glu Leu Asp Glu Arg Val Leu Ala Ala Trp Ser Glu Gln
            980                 985                 990

Leu Glu Ile Asp Thr Leu Gly Ile Asp Asp Asn Phe Phe Asp Ile Gly
        995                 1000                1005

Gly Asp Ser Ile Lys Ala Ile Arg Ile Cys Arg Asp Leu Gly Leu
    1010                1015                1020

Pro Val Thr Glu Leu Phe Asp His Pro Thr Pro Arg Ala Asn Ala
    1025                1030                1035

Asp Tyr Leu Arg Asp His Gln Asp Asn Asp Ala Gln Gly Ala Val
    1040                1045                1050

Asn Trp Leu His Ala Phe Asp Lys Ser Ala Lys Lys Glu Arg Leu
    1055                1060                1065

Asn Leu Val Cys Val Pro Phe Ala Gly Gly Asn Ala Phe Ala Tyr
    1070                1075                1080

Arg Asn Leu Val Asn Gln Leu Ser Ser Val Phe Asn Cys Val Ser
    1085                1090                1095

Val Asn Leu Pro Gly His Asp Ile Met Arg Pro Asp Glu Gly Met
    1100                1105                1110

Gln Ala Leu Glu Val Val Ala Asp Ala Ala Thr Gln Glu Ile Leu
    1115                1120                1125

Ala Thr Leu Ser Gly Pro Ile Ile Val Tyr Gly His Cys Ala Gly
    1130                1135                1140

Asn Ala Thr Ala Ile Glu Ile Ala Arg Arg Leu Glu Gln Ala Gly
    1145                1150                1155

Ala Asp Leu Lys Ala Leu Val Ile Gly Gly Met Leu Leu Asp Gln
    1160                1165                1170

-continued

| | | | | | | | | | | | |
|---|---|---|---|---|---|---|---|---|---|---|---|
| Asp | Pro | Val | Asp | Val | Gln | Ala | Arg | Val | Ala | Asp | Gln | Ser | Gly | Glu |
| 1175 | | | | 1180 | | | | | 1185 | | |

Asp Pro Val Asp Val Gln Ala Arg Val Ala Asp Gln Ser Gly Glu
1175                1180                1185

Asn Ile Ile Asp Phe Leu Gln Gln Ile Gly Gly Phe Lys Glu Val
1190                1195                1200

Leu Asp Asp Ala Ser Met Ala Ser Ile Ala Arg Met Thr Lys His
1205                1210                1215

Asp Ala Thr Gln Thr Ala Arg Phe Phe Ala Glu Glu Ala Leu Asn
1220                1225                1230

Arg Gln Thr Leu Gln Ala Pro Ile His Val Ile Val Gly Asp Met
1235                1240                1245

Asp Pro Leu Thr Pro Asp Tyr Glu Glu Arg Tyr Lys Asp Trp Gln
1250                1255                1260

Met Tyr Ser Ser Asp Val Thr Leu Ser Val Ile Glu Gly Gly Gly
1265                1270                1275

His Tyr Phe Val Thr Asp Leu Ala Glu Pro Leu Ala Gln Val Leu
1280                1285                1290

Leu Ala Asn Tyr Lys His Leu Asn Pro Val Val Pro Val Arg Ala
1295                1300                1305

Pro Arg Ala Leu Arg Ala Phe His Asn Pro Phe Asp Asp Val Glu
1310                1315                1320

Gly Arg Phe Ser Leu Leu Ala Asn Asp Ala Arg Gln Leu Ser Leu
1325                1330                1335

Trp Pro Glu Phe Ala Pro Thr Pro Ala Gly Trp Thr Ala Leu Phe
1340                1345                1350

Gly Pro Ala Ser His Ser Glu Cys Leu Ala Arg Thr Gln Ala Tyr
1355                1360                1365

Asp His Glu Ala Leu Ile Ser Pro Pro Ala Pro Thr Glu Gly Leu
1370                1375                1380

Asp Ala Pro Tyr Trp Pro Glu Ala Phe Glu Ser Arg Tyr Arg Ala
1385                1390                1395

Ser Gly Trp Trp Thr Gly Glu Thr Leu Gly Ala Ile Leu Thr Arg
1400                1405                1410

His Ala Leu Leu Ala Pro Gln Arg Val Ala Val Thr Asp Gly Asp
1415                1420                1425

Arg Asn Leu Ser Tyr Ser Gln Leu Asp Ser Asn Ala Asp Arg Ile
1430                1435                1440

Ala Asp Gly Phe Ala Thr Leu Gly Val Lys Ala Gly Asp Arg Val
1445                1450                1455

Val Val Gln Leu Pro Asn Ser Met Glu Phe Ile Glu Thr Ile Phe
1460                1465                1470

Gly Leu Phe Arg Leu Gly Ala Ile Pro Val Phe Ala Leu Pro Ser
1475                1480                1485

Asp Arg Leu Asn Glu Ile Thr His Ile Phe Glu Ile Ser Gly Ala
1490                1495                1500

Ile Ala Tyr Val Ile Lys Asp Gln Ala Leu Gly Phe Asp Tyr Arg
1505                1510                1515

Arg Ile Ala Thr Glu Leu Thr Gln Gln Ile Ala Ser Ile Lys Gln
1520                1525                1530

Val Ile Val Val Gly Asp Ala Glu Gly Phe Val Pro Phe Ala Asn
1535                1540                1545

Leu Tyr Gly Arg Thr Ala Ala Trp Pro Gln Arg Ser Ser Arg Glu
1550                1555                1560

Pro Ala Leu Ile Thr Leu Ser Gly Gly Ser Thr Ala Leu Pro Lys

```
                   1565               1570               1575

Leu Ile Leu Arg Arg His Asp Asp Tyr Leu Tyr Ser Phe Lys Ala
    1580               1585               1590

Ser Ala Arg Ile Cys Gln Leu Asp Ser Asp Ser Val Tyr Leu Cys
    1595               1600               1605

Val Leu Pro Ala Gly His Asn Phe Thr Leu Ser Ser Pro Gly Phe
    1610               1615               1620

Leu Gly Val Leu Tyr Ala Gly Gly Arg Val Val Met Thr Ser Asp
    1625               1630               1635

Pro Ser Gly Ser Gly Ala Phe Ala Leu Ile Glu Arg Glu Arg Val
    1640               1645               1650

Thr Leu Thr Ser Val Val Pro Ser Leu Ala Gln Ala Trp Leu His
    1655               1660               1665

Ser Ser Arg Asp His Asp Leu Ser Ser Leu Gln Leu Leu Gln Val
    1670               1675               1680

Gly Gly Ala Arg Leu Ser Asp Asp Val Ala Glu Arg Leu Ala Thr
    1685               1690               1695

Ser Phe Asp Cys Gln Leu Gln Gln Val Tyr Gly Met Ser Glu Gly
    1700               1705               1710

Leu Val Cys Tyr Thr Ala Val Gly Asp Thr Glu Glu His Val Leu
    1715               1720               1725

His Thr Gln Gly Arg Pro Ile Ser Ser Gly Asp Glu Ile Leu Ile
    1730               1735               1740

Val Asp Glu Asn Asp Glu Pro Val Ala Asn Gly Val Ala Gly Gln
    1745               1750               1755

Leu Leu Val Arg Gly Pro Tyr Thr Ile Arg Gly Tyr Leu Asn Ala
    1760               1765               1770

Pro Glu His Asn Ala Arg Ala Phe Thr Pro Asp Gly Phe Tyr Arg
    1775               1780               1785

Thr Gly Asp Val Val Val Phe Arg Asp Asp Gly Tyr Leu Val Val
    1790               1795               1800

Thr Gly Arg Ile Lys Asp Gln Val Asn Arg Gly Gly Glu Lys Ile
    1805               1810               1815

Ala Ala Glu Glu Ile Glu Gly Tyr Leu Leu Ala His Pro Gly Val
    1820               1825               1830

Leu Glu Ala Gly Ile Ile Gly Leu Pro Asp Glu Tyr Leu Gly Glu
    1835               1840               1845

Val Ser Cys Ala Val Val Val Leu Ala Pro Gly Ala Gln Leu Thr
    1850               1855               1860

Ala Ser Ala Leu Lys Ser Phe Val Arg Gln Gln Gly Ile Ala Ala
    1865               1870               1875

Phe Lys Val Pro Asp Gln Val His Leu Val Pro Ser Leu Pro Lys
    1880               1885               1890

Thr Thr Leu Gly Lys Ile Asp Lys Lys Leu Leu Arg Val Gln Leu
    1895               1900               1905

Gly Gln
    1910

<210> SEQ ID NO 3
<211> LENGTH: 440
<212> TYPE: PRT
<213> ORGANISM: Pseudomonas fluorescens

<400> SEQUENCE: 3
```

```
Met Ser Asn Val Lys Gln Gln Thr Ala Gln Ile Val Asp Trp Leu Ser
1               5                   10                  15

Ser Thr Leu Gly Lys Asp His Gln Tyr Arg Glu Asp Ser Leu Ser Leu
            20                  25                  30

Thr Ala Asn Glu Asn Tyr Pro Ser Ala Leu Val Arg Leu Thr Ser Gly
        35                  40                  45

Ser Thr Ala Gly Ala Phe Tyr His Cys Ser Phe Pro Phe Glu Val Pro
50                      55                  60

Ala Gly Glu Trp His Phe Pro Glu Pro Gly His Met Asn Ala Ile Ala
65                  70                  75                  80

Asp Gln Val Arg Asp Leu Gly Lys Thr Leu Ile Gly Ala Gln Ala Phe
                85                  90                  95

Asp Trp Arg Pro Asn Gly Gly Ser Thr Ala Glu Gln Ala Leu Met Leu
            100                 105                 110

Ala Ala Cys Lys Pro Gly Glu Gly Phe Val His Phe Ala His Arg Asp
        115                 120                 125

Gly Gly His Phe Ala Leu Glu Ser Leu Ala Gln Lys Met Gly Ile Glu
    130                 135                 140

Ile Phe His Leu Pro Val Asn Pro Thr Ser Leu Leu Ile Asp Val Ala
145                 150                 155                 160

Lys Leu Asp Glu Met Val Arg Arg Asn Pro His Ile Arg Ile Val Ile
                165                 170                 175

Leu Asp Gln Ser Phe Lys Leu Arg Trp Gln Pro Leu Ala Glu Ile Arg
            180                 185                 190

Ser Val Leu Pro Asp Ser Cys Thr Leu Thr Tyr Asp Met Ser His Asp
        195                 200                 205

Gly Gly Leu Ile Met Gly Gly Val Phe Asp Ser Pro Leu Ser Cys Gly
    210                 215                 220

Ala Asp Ile Val His Gly Asn Thr His Lys Thr Ile Pro Gly Pro Gln
225                 230                 235                 240

Lys Gly Tyr Ile Gly Phe Lys Ser Ala Gln His Pro Leu Leu Val Asp
                245                 250                 255

Thr Ser Leu Trp Val Cys Pro His Leu Gln Ser Asn Cys His Ala Glu
            260                 265                 270

Gln Leu Pro Pro Met Trp Val Ala Phe Lys Glu Met Glu Leu Phe Gly
        275                 280                 285

Arg Asp Tyr Ala Ala Gln Ile Val Ser Asn Ala Lys Thr Leu Ala Arg
    290                 295                 300

His Leu His Glu Leu Gly Leu Asp Val Thr Gly Glu Ser Phe Gly Phe
305                 310                 315                 320

Thr Gln Thr His Gln Val His Phe Ala Val Gly Asp Leu Gln Lys Ala
                325                 330                 335

Leu Asp Leu Cys Val Asn Ser Leu His Ala Gly Gly Ile Arg Ser Thr
            340                 345                 350

Asn Ile Glu Ile Pro Gly Lys Pro Gly Val His Gly Ile Arg Leu Gly
        355                 360                 365

Val Gln Ala Met Thr Arg Arg Gly Met Lys Glu Lys Asp Phe Glu Val
    370                 375                 380

Val Ala Arg Phe Ile Ala Asp Leu Tyr Phe Lys Lys Thr Glu Pro Ala
385                 390                 395                 400

Lys Val Ala Gln Gln Ile Lys Glu Phe Leu Gln Ala Phe Pro Leu Ala
                405                 410                 415

Pro Leu Ala Tyr Ser Phe Asp Asn Tyr Leu Asp Glu Glu Leu Leu Ala
```

Ala Val Tyr Gln Gly Ala Gln Arg
            435                 440

<210> SEQ ID NO 4
<211> LENGTH: 567
<212> TYPE: PRT
<213> ORGANISM: Pseudomonas fluorescens

<400> SEQUENCE: 4

Met Thr Asn Leu Pro Ser Thr His Ile Asn Leu Thr Ser Glu Glu Val
1               5                   10                  15

Ser Leu Gly Asp Leu Val Gly Arg Val Leu Val Glu Ser Gly Ile Asp
                20                  25                  30

Asp Leu Phe Cys Ile Pro Gly Asp Phe Thr Met Gln Leu Ser Arg Glu
            35                  40                  45

Leu Leu Thr Thr Pro Gly Leu Ala Leu Arg Thr Met Ser His Glu Tyr
        50                  55                  60

Gly Thr Thr Leu Ala Ala Leu Gly Tyr Ala Val Gly Lys Gly Val Pro
65                  70                  75                  80

Gly Ala Val Cys Phe Thr Tyr Gly Val Gly Val Leu Asn Ala Thr Asn
                85                  90                  95

Ala Ile Ala Gln Ala Tyr Val Glu Arg Val Pro Leu Leu Val Phe Ser
            100                 105                 110

Gly Ser Pro Gly Thr Arg Glu Arg Gln Ala Pro Leu Phe Leu His His
        115                 120                 125

Thr Ile Val Asp His Gln Thr Gln Tyr Arg Ile Met Lys Glu Ile Thr
130                 135                 140

Val His Gln Val Cys Val Thr Asp Pro His Gln Val Leu Glu Gln Leu
145                 150                 155                 160

Arg Glu Ala Val Ala Leu Ala Val Leu His Ser Arg Pro Val Tyr Ile
                165                 170                 175

Glu Ile Pro Arg Asp Leu Phe Gln Ala Arg Val Arg Tyr Ser Pro Ala
            180                 185                 190

Arg Arg Val Pro Leu Glu Pro Ser Thr Arg Tyr Ser Gln Ala Ala Arg
        195                 200                 205

Gln Ala Ala Glu Leu Ala Tyr Ala Leu Val Arg Lys Ala Arg Asp Pro
210                 215                 220

Val Phe Val Pro Gly Leu Asp Leu Lys Arg Arg Gly Leu Thr Asp Leu
225                 230                 235                 240

Ala Met Arg Val Cys Glu Arg Leu Ala Met Pro Trp Val Ala Thr Pro
                245                 250                 255

Met Ser Arg Gly Gly Ile Pro Val Ser His Pro Asn Tyr Arg Gly Ile
            260                 265                 270

Tyr Ala Gly Pro Ala Ser Pro Ser Arg Val Thr Arg Glu Leu Leu Ala
        275                 280                 285

Lys Cys Asp Val Leu Met Leu Ile Gly Glu Pro Asn Ser Asp Val Asn
290                 295                 300

Met Gly Ile Ala Ser His Ile Ala Lys Gly Arg Leu Ile His Ala Asp
305                 310                 315                 320

Asp Gly Lys Ile Ser Val Gly Arg Gln His Phe Asn Ala Ser Thr Ala
                325                 330                 335

Glu Phe Leu Ile Ala Phe Ser Asp Val Ile His Asn Ala Lys Thr Pro
            340                 345                 350

```
Leu Ala Pro Leu Thr Glu Thr Gln Lys Asp Phe Ile Val Pro Thr Pro
            355                 360                 365

Ala Ser Leu Tyr Pro Ser Glu Glu Ser Pro Leu Thr Pro Phe Asp Ile
    370                 375                 380

Ile Asn Glu Leu Asn Arg His Phe Val Thr Gln Pro Asp Thr Gln Leu
385                 390                 395                 400

Val Val Asp Cys Gly Asp Val Phe Phe Met Ser Leu Gly Met Phe Pro
                405                 410                 415

Ala Asp Val Leu Thr Ser Pro Leu Tyr Met Ser Met Gly Ile Ala Val
            420                 425                 430

Pro Gly Ala Met Gly Tyr Gln Leu Gly Thr Gly Lys Arg Pro Ile Val
        435                 440                 445

Leu Val Gly Asp Gly Ala Phe His Met Thr Gly Asn Glu Leu Met Arg
    450                 455                 460

Ala Ala Lys Phe Gly Leu Ser Pro Ile Val Ile Val Leu Asn Asn Gln
465                 470                 475                 480

Arg Trp Ala Ser Leu Ser Ser Asp Ala Ala Asp Ile Ala Leu Thr Glu
                485                 490                 495

Gln Met Pro Met Ser Phe Ser Ala Ala Gly Gln Phe Leu Gln Val Gln
            500                 505                 510

Ala Phe Thr Ala Thr Thr Gly Arg Glu Leu Arg Gln His Leu Glu Glu
        515                 520                 525

Ala Leu Asn Met Asp Arg Pro Val Leu Ile Asp Ala Gln Val Asp Pro
    530                 535                 540

Ser Lys Arg Ser Tyr Leu Cys Glu Arg Phe Phe Asp Ala Val Lys Gly
545                 550                 555                 560

Gln Gln His Leu Pro Lys Ala
                565

<210> SEQ ID NO 5
<211> LENGTH: 316
<212> TYPE: PRT
<213> ORGANISM: Pseudomonas fluorescens

<400> SEQUENCE: 5

Met Pro Glu Ser Gln Leu Leu Asn Lys Ile Thr Asp Thr Trp Tyr Ala
1               5                   10                  15

Lys Ala Thr Val Arg Ser Thr Pro Arg Ile Leu Val Pro Asp Tyr Ser
            20                  25                  30

Ser Glu Gln Leu Ile Tyr Pro Val Ala Arg Cys Ser Ile Cys Glu His
        35                  40                  45

Pro Leu Val Leu Glu Leu Gly Pro Gln Val Arg Ser Tyr Ile Leu Thr
    50                  55                  60

Gln Ala Ala Tyr Gln Phe Leu Tyr Gly Val Gly Leu Leu Glu Thr Lys
65                  70                  75                  80

Phe Val Ile Gln Cys Cys Leu Asp Met Leu His Asn Asn Ile Lys Asp
                85                  90                  95

Ile Ser Asp Ala Ala Lys Leu Gln Ala Leu Thr Val Ile Val Asp Glu
            100                 105                 110

Gly Tyr His Ala His Val Ala Leu Asp Tyr Ile Ile Gln Met Lys Lys
        115                 120                 125

Lys Ser Ala Ile Glu Pro Leu Glu Val Pro Gln Thr Asn Arg Lys Leu
    130                 135                 140

Asp Ala Thr Ala Arg Ala Tyr Ala Ser Leu Pro Glu Ser Met Arg Met
145                 150                 155                 160
```

```
Asp Phe Gln Leu Leu Ala Val Thr Leu Ala Glu Asn Val Leu Thr Asp
            165                 170                 175

Glu Val Ala Asn Leu Gly Arg Glu Arg Glu Leu Ala Gln Ser Phe Thr
            180                 185                 190

Thr Leu Met Met Asp His Val Arg Asp Glu Gly Arg His Ser Arg Phe
            195                 200                 205

Phe Ala Asp Leu Met Lys Glu Arg Trp Pro Gln Leu Pro Arg Ala Thr
            210                 215                 220

Gln Glu His Phe Gly Leu Met Leu Pro Ala Tyr Leu Asp Asp Phe Leu
225                 230                 235                 240

Gly Ala Asp Leu Ser Arg Gly Phe Glu Arg Lys Ile Leu Ala His Cys
                245                 250                 255

Gly Leu Thr Glu Ala Gln Ala Glu Gln Val Ile His Glu Ser Asp Pro
            260                 265                 270

His Phe Ser Thr Asp Gln Ala Arg Met Lys Lys Ser Ile Leu Gln Arg
            275                 280                 285

Ile Tyr Arg Leu Leu Asn Gln Ile Gly Val Leu Glu Leu Asp Ser Val
            290                 295                 300

Lys Asp Ala Phe Ser Asp Arg Asn Tyr Val Thr Thr
305                 310                 315

<210> SEQ ID NO 6
<211> LENGTH: 1910
<212> TYPE: PRT
<213> ORGANISM: Artificial Sequence
<220> FEATURE:
<223> OTHER INFORMATION: ObiF with C1141A substitution

<400> SEQUENCE: 6

Met Ser Ala Ser Phe Thr Thr Ala Leu Thr Ser Ala Gln Gln Ser Ile
1               5                   10                  15

Trp Met Gly His Gln Phe Asp Pro Gln Ser Pro Ala Tyr Asn Val Ala
            20                  25                  30

Ser Tyr Ile Glu Met Ser Gly Asp Ile Asp Pro Gln Arg Leu Gln His
            35                  40                  45

Ala Leu Gln Arg Ala Val Asp Asp Ile Glu Ala Leu Arg Ala Arg Phe
        50                  55                  60

His Glu Asp Glu Thr Gln Gly Gly Ala Leu Thr Gln Thr Ile Leu Ala
65                  70                  75                  80

Gln Val Ala Val Glu Leu Asn Val Phe Ala Val Asp Ala Glu Gln Ala
                85                  90                  95

Arg Ser Trp Met Glu Ser Asp Leu Ala Arg Pro Thr Asp Leu Thr Ser
            100                 105                 110

Gly Pro Ile Phe Ser Ser Ala Leu Leu Gln Val Ala Pro Asn Val Asn
            115                 120                 125

Tyr Trp Tyr Phe Lys Thr His His Ile Val Met Asp Gly Val Ala Leu
        130                 135                 140

Ser Met Leu Phe Lys Arg Val Ala Asp Leu Tyr Gly Gln Ala Pro Asp
145                 150                 155                 160

Leu Cys Ser Pro Ser Pro Phe Gly Ser Val Arg Gln Val Leu Glu Asn
                165                 170                 175

Glu Gln Ala Trp Arg Ala Ser Pro Ala Phe Ala Gln Asp Arg Glu Phe
            180                 185                 190

Trp Gln Gln His Cys Gln Asp Met Ala Glu Val Ala Ser Leu Asn Ser
            195                 200                 205
```

-continued

Asp Val Ala Gln Pro Ser Tyr Gln Ala Ile Gln His Arg Arg Val Leu
210                 215                 220

Asp Glu Ser Ile Met Ala Ser Leu Arg Glu Arg Ala Glu Ala Met Asp
225                 230                 235                 240

Ser Gln Trp Val Asn Val Leu Leu Ala Ala Phe Gly Ala Phe Val Gly
            245                 250                 255

Arg Ser Thr Gly Tyr Arg Gln Val Thr Val Gly Val Pro Met Met Asn
            260                 265                 270

Arg Phe Ala Thr Gly Ala Ile Asn Val Pro Cys Thr Leu Ala Asn Val
    275                 280                 285

Leu Pro Leu Arg Leu Asp Ile Lys Pro Gly Gln Ser Val Glu Gln Leu
290                 295                 300

Val Ala Ser Val Gln Ala Gln Leu Asp Arg Met Arg Pro His Gln Arg
305                 310                 315                 320

Tyr Arg Ala Glu Asp Ile Arg Arg Asp Cys Asn Leu Leu Gly Asp Asn
                325                 330                 335

Arg Arg Leu Thr Gly Pro Gln Ile Asn Ile Asp Phe Phe Ser Ala Lys
            340                 345                 350

Leu Ser Phe Asp Gly Val Pro Gly Glu Val Asn Val Leu Ser Ala Gly
    355                 360                 365

Pro Ala Asp Asp Leu Ser Leu Leu Ile Gln Thr Pro Ala Asp Asp Lys
370                 375                 380

Thr Leu Asn Ile Ile Ala Met Ala Asn Pro Ala Leu Tyr Ser Arg Ala
385                 390                 395                 400

Ala Leu Glu Arg His Val Gln Arg Phe Ile Asp Phe Val Glu Arg Phe
                405                 410                 415

Ala Ala Ala Ser Asp Thr Pro Leu Gly Gln Leu Asp Ala Tyr Asp Ala
            420                 425                 430

Thr Asp Pro Gly Tyr Ala Gln Gly Asn Ala Cys Phe Ser Pro Val Asn
    435                 440                 445

Gln Ala His Thr Leu Ala Gln Thr Leu Val Glu Arg Phe Glu Arg Ala
450                 455                 460

Val His Ala Thr Pro Asp Ala Ile Ala Leu Thr Phe Asn Gly Glu His
465                 470                 475                 480

Leu Thr Tyr Gln Ala Leu Asn Gln Arg Ala Asn Arg Leu Ala His Leu
                485                 490                 495

Ile Gln Asp Gln Thr Gly Gln Thr Ser Pro Gln Pro Val Ala Leu Leu
            500                 505                 510

Leu Ala Arg Ser Val Gln Thr Phe Val Cys Ile Leu Gly Val Leu Lys
    515                 520                 525

Ala Gly Ala His Tyr Val Pro Leu Asp Pro Asp Ala Pro Ala Glu Arg
530                 535                 540

Ile Thr Thr Ile Leu Glu Asp Thr Cys Pro Thr Leu Val Ile Cys Asp
545                 550                 555                 560

Gln Ser Ser Gln Ala Leu Val Ser Gly Ser Asp Val Lys Val Met Val
                565                 570                 575

Ile Asp Thr Pro Ser Cys Met Asp Ala Val Gln Gln Ser Ile Asp
            580                 585                 590

Asn Leu Gln Ser Gly Pro Arg Ala Asn Asp Leu Ala Tyr Ile Ile Tyr
    595                 600                 605

Thr Ser Gly Ser Thr Gly Lys Pro Lys Gly Val Cys Ile Thr His His
610                 615                 620

-continued

```
Asn Val Val Arg Leu Phe Glu Asn Thr His His Trp Phe Asp Tyr Arg
625                 630                 635                 640

Ser Ser Asp Val Trp Thr Ala Cys His Gly Tyr Ile Phe Asp Ala Ser
            645                 650                 655

Val Trp Glu Met Trp Gly Ala Phe Ala His Gly Gly Arg Leu Val Leu
                660                 665                 670

Val Pro Val Asp Thr Thr Arg Asp Pro Glu Lys Leu Leu Glu Leu Val
        675                 680                 685

Val Gln Glu Gln Val Thr Val Phe Gly Gln Ile Pro Ser Ala Phe Tyr
690                 695                 700

Arg Phe Met Glu Ala Gln Ala Asp Gln Pro Ala Leu Ala Ala Arg Leu
705                 710                 715                 720

Asn Leu Arg Tyr Gln Cys Phe Gly Glu Ala Leu Asp Leu Ser Arg
                725                 730                 735

Leu Lys Pro Trp Phe Glu His Tyr Gly His Ser Arg Thr Arg Leu Leu
                740                 745                 750

Asn Leu Tyr Gly Ile Thr Glu Thr Thr Ile Asn Ala Thr Tyr Gln Phe
            755                 760                 765

Val Thr Leu Glu Gln Val Gln Thr Asn Gln Gly Ser Leu Ile Gly Thr
770                 775                 780

Val Tyr Asp Asp Leu Asp Ile Lys Val Leu Asp Ala Leu Arg Pro
785                 790                 795                 800

Val Pro Val Gly Gly Tyr Gly Glu Met Tyr Val Arg Gly Ala Gly Leu
                805                 810                 815

Ala Arg Gly Tyr Leu Asn Arg Gln Asp Leu Asp Ala Thr Arg Phe Val
                820                 825                 830

Ala Asp Pro Phe Gly Ala Pro Gly Glu Arg Met Tyr Arg Ser Gly Asp
                835                 840                 845

Val Ala Ala Leu Gln Glu Gly Gly Val Leu Glu Tyr Ile Gly Arg Ala
850                 855                 860

Asp Gln Gln Val Lys Val Arg Gly Tyr Arg Ile Glu Leu Gly Glu Ile
865                 870                 875                 880

Glu Thr Gln Leu Arg Gly His Pro Leu Leu Ser Asp Ala Ile Ala Leu
                885                 890                 895

Val Val Thr Asp Ala Ser Gly Asp Pro Lys Leu Val Ala His Val Val
                900                 905                 910

Pro Lys Ala Thr Cys Arg Cys Glu Asp Ile Asp Thr Ala Gln Val Arg
            915                 920                 925

Asp Tyr Leu Arg Glu Arg Leu Pro Ser Tyr Met Val Pro Gly Ala Ile
930                 935                 940

Gly Val Gln Glu Arg Leu Pro Val Thr Leu Ser Gly Lys Val Asp Arg
945                 950                 955                 960

Lys Ala Leu Pro Thr Ile Ala Leu Ser Gly Ala Arg Gln Val Glu Ala
                965                 970                 975

Pro Arg Asp Glu Leu Asp Glu Arg Val Leu Ala Ala Trp Ser Glu Gln
                980                 985                 990

Leu Glu Ile Asp Thr Leu Gly Ile Asp Asp Asn Phe Phe Asp Ile Gly
            995                 1000                1005

Gly Asp Ser Ile Lys Ala Ile Arg Ile Cys Arg Asp Leu Gly Leu
        1010                1015                1020

Pro Val Thr Glu Leu Phe Asp His Pro Thr Pro Arg Ala Asn Ala
    1025                1030                1035

Asp Tyr Leu Arg Asp His Gln Asp Asn Asp Ala Gln Gly Ala Val
```

-continued

```
            1040                1045                1050
Asn Trp Leu His Ala Phe Asp Lys Ser Ala Lys Lys Glu Arg Leu
            1055                1060                1065
Asn Leu Val Cys Val Pro Phe Ala Gly Gly Asn Ala Phe Ala Tyr
            1070                1075                1080
Arg Asn Leu Val Asn Gln Leu Ser Ser Val Phe Asn Cys Val Ser
            1085                1090                1095
Val Asn Leu Pro Gly His Asp Ile Met Arg Pro Asp Glu Gly Met
            1100                1105                1110
Gln Ala Leu Glu Val Val Ala Asp Ala Ala Thr Gln Glu Ile Leu
            1115                1120                1125
Ala Thr Leu Ser Gly Pro Ile Ile Val Tyr Gly His Ala Ala Gly
            1130                1135                1140
Asn Ala Thr Ala Ile Glu Ile Ala Arg Arg Leu Glu Gln Ala Gly
            1145                1150                1155
Ala Asp Leu Lys Ala Leu Val Ile Gly Gly Met Leu Leu Asp Gln
            1160                1165                1170
Asp Pro Val Asp Val Gln Ala Arg Val Ala Asp Gln Ser Gly Glu
            1175                1180                1185
Asn Ile Ile Asp Phe Leu Gln Gln Ile Gly Gly Phe Lys Glu Val
            1190                1195                1200
Leu Asp Asp Ala Ser Met Ala Ser Ile Ala Arg Met Thr Lys His
            1205                1210                1215
Asp Ala Thr Gln Thr Ala Arg Phe Phe Ala Glu Glu Ala Leu Asn
            1220                1225                1230
Arg Gln Thr Leu Gln Ala Pro Ile His Val Ile Val Gly Asp Met
            1235                1240                1245
Asp Pro Leu Thr Pro Asp Tyr Glu Glu Arg Tyr Lys Asp Trp Gln
            1250                1255                1260
Met Tyr Ser Ser Asp Val Thr Leu Ser Val Ile Glu Gly Gly Gly
            1265                1270                1275
His Tyr Phe Val Thr Asp Leu Ala Glu Pro Leu Ala Gln Val Leu
            1280                1285                1290
Leu Ala Asn Tyr Lys His Leu Asn Pro Val Val Pro Val Arg Ala
            1295                1300                1305
Pro Arg Ala Leu Arg Ala Phe His Asn Pro Phe Asp Asp Val Glu
            1310                1315                1320
Gly Arg Phe Ser Leu Leu Ala Asn Asp Ala Arg Gln Leu Ser Leu
            1325                1330                1335
Trp Pro Glu Phe Ala Pro Thr Pro Ala Gly Trp Thr Ala Leu Phe
            1340                1345                1350
Gly Pro Ala Ser His Ser Glu Cys Leu Ala Arg Thr Gln Ala Tyr
            1355                1360                1365
Asp His Glu Ala Leu Ile Ser Pro Pro Ala Pro Thr Glu Gly Leu
            1370                1375                1380
Asp Ala Pro Tyr Trp Pro Glu Ala Phe Glu Ser Arg Tyr Arg Ala
            1385                1390                1395
Ser Gly Trp Trp Thr Gly Glu Thr Leu Gly Ala Ile Leu Thr Arg
            1400                1405                1410
His Ala Leu Leu Ala Pro Gln Arg Val Ala Val Thr Asp Gly Asp
            1415                1420                1425
Arg Asn Leu Ser Tyr Ser Gln Leu Asp Ser Asn Ala Asp Arg Ile
            1430                1435                1440
```

```
Ala  Asp  Gly  Phe  Ala  Thr  Leu  Gly  Val  Lys  Ala  Gly  Asp  Arg  Val
     1445                1450                1455

Val  Val  Gln  Leu  Pro  Asn  Ser  Met  Glu  Phe  Ile  Glu  Thr  Ile  Phe
     1460                1465                1470

Gly  Leu  Phe  Arg  Leu  Gly  Ala  Ile  Pro  Val  Phe  Ala  Leu  Pro  Ser
     1475                1480                1485

Asp  Arg  Leu  Asn  Glu  Ile  Thr  His  Ile  Phe  Glu  Ile  Ser  Gly  Ala
     1490                1495                1500

Ile  Ala  Tyr  Val  Ile  Lys  Asp  Gln  Ala  Leu  Gly  Phe  Asp  Tyr  Arg
     1505                1510                1515

Arg  Ile  Ala  Thr  Glu  Leu  Thr  Gln  Gln  Ile  Ala  Ser  Ile  Lys  Gln
     1520                1525                1530

Val  Ile  Val  Val  Gly  Asp  Ala  Glu  Gly  Phe  Val  Pro  Phe  Ala  Asn
     1535                1540                1545

Leu  Tyr  Gly  Arg  Thr  Ala  Ala  Trp  Pro  Gln  Arg  Ser  Ser  Arg  Glu
     1550                1555                1560

Pro  Ala  Leu  Ile  Thr  Leu  Ser  Gly  Gly  Ser  Thr  Ala  Leu  Pro  Lys
     1565                1570                1575

Leu  Ile  Leu  Arg  Arg  His  Asp  Asp  Tyr  Leu  Tyr  Ser  Phe  Lys  Ala
     1580                1585                1590

Ser  Ala  Arg  Ile  Cys  Gln  Leu  Asp  Ser  Asp  Ser  Val  Tyr  Leu  Cys
     1595                1600                1605

Val  Leu  Pro  Ala  Gly  His  Asn  Phe  Thr  Leu  Ser  Ser  Pro  Gly  Phe
     1610                1615                1620

Leu  Gly  Val  Leu  Tyr  Ala  Gly  Gly  Arg  Val  Val  Met  Thr  Ser  Asp
     1625                1630                1635

Pro  Ser  Gly  Ser  Gly  Ala  Phe  Ala  Leu  Ile  Glu  Arg  Glu  Arg  Val
     1640                1645                1650

Thr  Leu  Thr  Ser  Val  Val  Pro  Ser  Leu  Ala  Gln  Ala  Trp  Leu  His
     1655                1660                1665

Ser  Ser  Arg  Asp  His  Asp  Leu  Ser  Ser  Leu  Gln  Leu  Leu  Gln  Val
     1670                1675                1680

Gly  Gly  Ala  Arg  Leu  Ser  Asp  Asp  Val  Ala  Glu  Arg  Leu  Ala  Thr
     1685                1690                1695

Ser  Phe  Asp  Cys  Gln  Leu  Gln  Gln  Val  Tyr  Gly  Met  Ser  Glu  Gly
     1700                1705                1710

Leu  Val  Cys  Tyr  Thr  Ala  Val  Gly  Asp  Thr  Glu  Glu  His  Val  Leu
     1715                1720                1725

His  Thr  Gln  Gly  Arg  Pro  Ile  Ser  Ser  Gly  Asp  Glu  Ile  Leu  Ile
     1730                1735                1740

Val  Asp  Glu  Asn  Asp  Glu  Pro  Val  Ala  Asn  Gly  Val  Ala  Gly  Gln
     1745                1750                1755

Leu  Leu  Val  Arg  Gly  Pro  Tyr  Thr  Ile  Arg  Gly  Tyr  Leu  Asn  Ala
     1760                1765                1770

Pro  Glu  His  Asn  Ala  Arg  Ala  Phe  Thr  Pro  Asp  Gly  Phe  Tyr  Arg
     1775                1780                1785

Thr  Gly  Asp  Val  Val  Phe  Arg  Asp  Asp  Gly  Tyr  Leu  Val  Val
     1790                1795                1800

Thr  Gly  Arg  Ile  Lys  Asp  Gln  Val  Asn  Arg  Gly  Gly  Glu  Lys  Ile
     1805                1810                1815

Ala  Ala  Glu  Glu  Ile  Glu  Gly  Tyr  Leu  Leu  Ala  His  Pro  Gly  Val
     1820                1825                1830
```

-continued

```
Leu Glu Ala Gly Ile Ile Gly Leu Pro Asp Glu Tyr Leu Gly Glu
    1835                1840                1845

Val Ser Cys Ala Val Val Leu Ala Pro Gly Ala Gln Leu Thr
    1850                1855                1860

Ala Ser Ala Leu Lys Ser Phe Val Arg Gln Gln Gly Ile Ala Ala
    1865                1870                1875

Phe Lys Val Pro Asp Gln Val His Leu Val Pro Ser Leu Pro Lys
    1880                1885                1890

Thr Thr Leu Gly Lys Ile Asp Lys Lys Leu Leu Arg Val Gln Leu
    1895                1900                1905

Gly Gln
    1910

<210> SEQ ID NO 7
<211> LENGTH: 1910
<212> TYPE: PRT
<213> ORGANISM: Artificial Sequence
<220> FEATURE:
<223> OTHER INFORMATION: ObiF with C1141S substitution

<400> SEQUENCE: 7

Met Ser Ala Ser Phe Thr Thr Ala Leu Thr Ser Ala Gln Gln Ser Ile
1               5                   10                  15

Trp Met Gly His Gln Phe Asp Pro Gln Ser Pro Ala Tyr Asn Val Ala
            20                  25                  30

Ser Tyr Ile Glu Met Ser Gly Asp Ile Asp Pro Gln Arg Leu Gln His
        35                  40                  45

Ala Leu Gln Arg Ala Val Asp Asp Ile Glu Ala Leu Arg Ala Arg Phe
    50                  55                  60

His Glu Asp Glu Thr Gln Gly Gly Ala Leu Thr Gln Thr Ile Leu Ala
65                  70                  75                  80

Gln Val Ala Val Glu Leu Asn Val Phe Ala Val Asp Ala Glu Gln Ala
                85                  90                  95

Arg Ser Trp Met Glu Ser Asp Leu Ala Arg Pro Thr Asp Leu Thr Ser
            100                 105                 110

Gly Pro Ile Phe Ser Ser Ala Leu Leu Gln Val Ala Pro Asn Val Asn
        115                 120                 125

Tyr Trp Tyr Phe Lys Thr His His Ile Val Met Asp Gly Val Ala Leu
    130                 135                 140

Ser Met Leu Phe Lys Arg Val Ala Asp Leu Tyr Gly Gln Ala Pro Asp
145                 150                 155                 160

Leu Cys Ser Pro Ser Pro Phe Gly Ser Val Arg Gln Val Leu Glu Asn
                165                 170                 175

Glu Gln Ala Trp Arg Ala Ser Pro Ala Phe Ala Gln Asp Arg Glu Phe
            180                 185                 190

Trp Gln Gln His Cys Gln Asp Met Ala Glu Val Ala Ser Leu Asn Ser
        195                 200                 205

Asp Val Ala Gln Pro Ser Tyr Gln Ala Ile Gln His Arg Arg Val Leu
    210                 215                 220

Asp Glu Ser Ile Met Ala Ser Leu Arg Glu Arg Ala Glu Ala Met Asp
225                 230                 235                 240

Ser Gln Trp Val Asn Val Leu Leu Ala Ala Phe Gly Ala Phe Val Gly
                245                 250                 255

Arg Ser Thr Gly Tyr Arg Gln Val Thr Val Gly Val Pro Met Met Asn
            260                 265                 270
```

```
Arg Phe Ala Thr Gly Ala Ile Asn Val Pro Cys Thr Leu Ala Asn Val
            275                 280                 285

Leu Pro Leu Arg Leu Asp Ile Lys Pro Gly Gln Ser Val Glu Gln Leu
290                 295                 300

Val Ala Ser Val Gln Ala Gln Leu Asp Arg Met Arg Pro His Gln Arg
305                 310                 315                 320

Tyr Arg Ala Glu Asp Ile Arg Arg Asp Cys Asn Leu Leu Gly Asp Asn
                325                 330                 335

Arg Arg Leu Thr Gly Pro Gln Ile Asn Ile Asp Phe Phe Ser Ala Lys
            340                 345                 350

Leu Ser Phe Asp Gly Val Pro Gly Glu Val Asn Val Leu Ser Ala Gly
        355                 360                 365

Pro Ala Asp Asp Leu Ser Leu Leu Ile Gln Thr Pro Ala Asp Asp Lys
    370                 375                 380

Thr Leu Asn Ile Ile Ala Met Ala Asn Pro Ala Leu Tyr Ser Arg Ala
385                 390                 395                 400

Ala Leu Glu Arg His Val Gln Arg Phe Ile Asp Phe Val Glu Arg Phe
                405                 410                 415

Ala Ala Ala Ser Asp Thr Pro Leu Gly Gln Leu Asp Ala Tyr Asp Ala
            420                 425                 430

Thr Asp Pro Gly Tyr Ala Gln Gly Asn Ala Cys Phe Ser Pro Val Asn
        435                 440                 445

Gln Ala His Thr Leu Ala Gln Thr Leu Val Glu Arg Phe Glu Arg Ala
    450                 455                 460

Val His Ala Thr Pro Asp Ala Ile Ala Leu Thr Phe Asn Gly Glu His
465                 470                 475                 480

Leu Thr Tyr Gln Ala Leu Asn Gln Arg Ala Asn Arg Leu Ala His Leu
                485                 490                 495

Ile Gln Asp Gln Thr Gly Gln Thr Ser Pro Gln Pro Val Ala Leu Leu
            500                 505                 510

Leu Ala Arg Ser Val Gln Thr Phe Val Cys Ile Leu Gly Val Leu Lys
        515                 520                 525

Ala Gly Ala His Tyr Val Pro Leu Asp Pro Asp Ala Pro Ala Glu Arg
    530                 535                 540

Ile Thr Thr Ile Leu Glu Asp Thr Cys Pro Thr Leu Val Ile Cys Asp
545                 550                 555                 560

Gln Ser Ser Gln Ala Leu Val Ser Gly Ser Asp Val Lys Val Met Val
                565                 570                 575

Ile Asp Thr Pro Ser Cys Met Asp Ala Val Gln Gln Ser Ile Asp
            580                 585                 590

Asn Leu Gln Ser Gly Pro Arg Ala Asn Asp Leu Ala Tyr Ile Ile Tyr
        595                 600                 605

Thr Ser Gly Ser Thr Gly Lys Pro Lys Gly Val Cys Ile Thr His His
    610                 615                 620

Asn Val Val Arg Leu Phe Glu Asn Thr His His Trp Phe Asp Tyr Arg
625                 630                 635                 640

Ser Ser Asp Val Trp Thr Ala Cys His Gly Tyr Ile Phe Asp Ala Ser
                645                 650                 655

Val Trp Glu Met Trp Gly Ala Phe Ala His Gly Gly Arg Leu Val Leu
            660                 665                 670

Val Pro Val Asp Thr Thr Arg Asp Pro Glu Lys Leu Leu Glu Leu Val
        675                 680                 685

Val Gln Glu Gln Val Thr Val Phe Gly Gln Ile Pro Ser Ala Phe Tyr
```

```
              690             695             700

Arg Phe Met Glu Ala Gln Ala Asp Gln Pro Ala Leu Ala Ala Arg Leu
705                     710                 715                 720

Asn Leu Arg Tyr Gln Cys Phe Gly Gly Glu Ala Leu Asp Leu Ser Arg
                    725                 730                 735

Leu Lys Pro Trp Phe Glu His Tyr Gly His Ser Arg Thr Arg Leu Leu
                740                 745                 750

Asn Leu Tyr Gly Ile Thr Glu Thr Thr Ile Asn Ala Thr Tyr Gln Phe
                755                 760                 765

Val Thr Leu Glu Gln Val Gln Thr Asn Gln Gly Ser Leu Ile Gly Thr
            770                 775                 780

Val Tyr Asp Asp Leu Asp Ile Lys Val Leu Asp Asp Ala Leu Arg Pro
785                 790                 795                 800

Val Pro Val Gly Gly Tyr Gly Glu Met Tyr Val Arg Gly Ala Gly Leu
                    805                 810                 815

Ala Arg Gly Tyr Leu Asn Arg Gln Asp Leu Asp Ala Thr Arg Phe Val
                820                 825                 830

Ala Asp Pro Phe Gly Ala Pro Gly Glu Arg Met Tyr Arg Ser Gly Asp
                835                 840                 845

Val Ala Ala Leu Gln Glu Gly Gly Val Leu Glu Tyr Ile Gly Arg Ala
850                 855                 860

Asp Gln Gln Val Lys Val Arg Gly Tyr Arg Ile Glu Leu Gly Glu Ile
865                 870                 875                 880

Glu Thr Gln Leu Arg Gly His Pro Leu Leu Ser Asp Ala Ile Ala Leu
                    885                 890                 895

Val Val Thr Asp Ala Ser Gly Asp Pro Lys Leu Val Ala His Val Val
                900                 905                 910

Pro Lys Ala Thr Cys Arg Cys Glu Asp Ile Asp Thr Ala Gln Val Arg
                915                 920                 925

Asp Tyr Leu Arg Glu Arg Leu Pro Ser Tyr Met Val Pro Gly Ala Ile
                930                 935                 940

Gly Val Gln Glu Arg Leu Pro Val Thr Leu Ser Gly Lys Val Asp Arg
945                 950                 955                 960

Lys Ala Leu Pro Thr Ile Ala Leu Ser Gly Ala Arg Gln Val Glu Ala
                    965                 970                 975

Pro Arg Asp Glu Leu Asp Glu Arg Val Leu Ala Ala Trp Ser Glu Gln
                980                 985                 990

Leu Glu Ile Asp Thr Leu Gly Ile Asp Asp Asn Phe Phe Asp Ile Gly
                    995                1000                1005

Gly Asp Ser Ile Lys Ala Ile Arg Ile Cys Arg Asp Leu Gly Leu
                1010                1015                1020

Pro Val Thr Glu Leu Phe Asp His Pro Thr Pro Arg Ala Asn Ala
                1025                1030                1035

Asp Tyr Leu Arg Asp His Gln Asp Asn Asp Ala Gln Gly Ala Val
                1040                1045                1050

Asn Trp Leu His Ala Phe Asp Lys Ser Ala Lys Lys Glu Arg Leu
                1055                1060                1065

Asn Leu Val Cys Val Pro Phe Ala Gly Gly Asn Ala Phe Ala Tyr
                1070                1075                1080

Arg Asn Leu Val Asn Gln Leu Ser Ser Val Phe Asn Cys Val Ser
                1085                1090                1095

Val Asn Leu Pro Gly His Asp Ile Met Arg Pro Asp Glu Gly Met
                1100                1105                1110
```

```
Gln Ala Leu Glu Val Val Ala Asp Ala Ala Thr Gln Glu Ile Leu
1115                1120                1125

Ala Thr Leu Ser Gly Pro Ile Ile Val Tyr Gly His Ser Ala Gly
1130                1135                1140

Asn Ala Thr Ala Ile Glu Ile Ala Arg Arg Leu Glu Gln Ala Gly
1145                1150                1155

Ala Asp Leu Lys Ala Leu Val Ile Gly Gly Met Leu Leu Asp Gln
1160                1165                1170

Asp Pro Val Asp Val Gln Ala Arg Val Ala Asp Gln Ser Gly Glu
1175                1180                1185

Asn Ile Ile Asp Phe Leu Gln Gln Ile Gly Gly Phe Lys Glu Val
1190                1195                1200

Leu Asp Asp Ala Ser Met Ala Ser Ile Ala Arg Met Thr Lys His
1205                1210                1215

Asp Ala Thr Gln Thr Ala Arg Phe Phe Ala Glu Glu Ala Leu Asn
1220                1225                1230

Arg Gln Thr Leu Gln Ala Pro Ile His Val Ile Val Gly Asp Met
1235                1240                1245

Asp Pro Leu Thr Pro Asp Tyr Glu Glu Arg Tyr Lys Asp Trp Gln
1250                1255                1260

Met Tyr Ser Ser Asp Val Thr Leu Ser Val Ile Glu Gly Gly Gly
1265                1270                1275

His Tyr Phe Val Thr Asp Leu Ala Glu Pro Leu Ala Gln Val Leu
1280                1285                1290

Leu Ala Asn Tyr Lys His Leu Asn Pro Val Val Pro Val Arg Ala
1295                1300                1305

Pro Arg Ala Leu Arg Ala Phe His Asn Pro Phe Asp Asp Val Glu
1310                1315                1320

Gly Arg Phe Ser Leu Leu Ala Asn Asp Ala Arg Gln Leu Ser Leu
1325                1330                1335

Trp Pro Glu Phe Ala Pro Thr Pro Ala Gly Trp Thr Ala Leu Phe
1340                1345                1350

Gly Pro Ala Ser His Ser Glu Cys Leu Ala Arg Thr Gln Ala Tyr
1355                1360                1365

Asp His Glu Ala Leu Ile Ser Pro Pro Ala Pro Thr Glu Gly Leu
1370                1375                1380

Asp Ala Pro Tyr Trp Pro Glu Ala Phe Glu Ser Arg Tyr Arg Ala
1385                1390                1395

Ser Gly Trp Trp Thr Gly Glu Thr Leu Gly Ala Ile Leu Thr Arg
1400                1405                1410

His Ala Leu Leu Ala Pro Gln Arg Val Ala Val Thr Asp Gly Asp
1415                1420                1425

Arg Asn Leu Ser Tyr Ser Gln Leu Asp Ser Asn Ala Asp Arg Ile
1430                1435                1440

Ala Asp Gly Phe Ala Thr Leu Gly Val Lys Ala Gly Asp Arg Val
1445                1450                1455

Val Val Gln Leu Pro Asn Ser Met Glu Phe Ile Glu Thr Ile Phe
1460                1465                1470

Gly Leu Phe Arg Leu Gly Ala Ile Pro Val Phe Ala Leu Pro Ser
1475                1480                1485

Asp Arg Leu Asn Glu Ile Thr His Ile Phe Glu Ile Ser Gly Ala
1490                1495                1500
```

```
Ile Ala Tyr Val Ile Lys Asp Gln Ala Leu Gly Phe Asp Tyr Arg
1505                1510                1515

Arg Ile Ala Thr Glu Leu Thr Gln Gln Ile Ala Ser Ile Lys Gln
1520                1525                1530

Val Ile Val Val Gly Asp Ala Glu Gly Phe Val Pro Phe Ala Asn
1535                1540                1545

Leu Tyr Gly Arg Thr Ala Ala Trp Pro Gln Arg Ser Ser Arg Glu
1550                1555                1560

Pro Ala Leu Ile Thr Leu Ser Gly Gly Ser Thr Ala Leu Pro Lys
1565                1570                1575

Leu Ile Leu Arg Arg His Asp Asp Tyr Leu Tyr Ser Phe Lys Ala
1580                1585                1590

Ser Ala Arg Ile Cys Gln Leu Asp Ser Asp Ser Val Tyr Leu Cys
1595                1600                1605

Val Leu Pro Ala Gly His Asn Phe Thr Leu Ser Ser Pro Gly Phe
1610                1615                1620

Leu Gly Val Leu Tyr Ala Gly Gly Arg Val Val Met Thr Ser Asp
1625                1630                1635

Pro Ser Gly Ser Gly Ala Phe Ala Leu Ile Glu Arg Glu Arg Val
1640                1645                1650

Thr Leu Thr Ser Val Val Pro Ser Leu Ala Gln Ala Trp Leu His
1655                1660                1665

Ser Ser Arg Asp His Asp Leu Ser Ser Leu Gln Leu Leu Gln Val
1670                1675                1680

Gly Gly Ala Arg Leu Ser Asp Asp Val Ala Glu Arg Leu Ala Thr
1685                1690                1695

Ser Phe Asp Cys Gln Leu Gln Gln Val Tyr Gly Met Ser Glu Gly
1700                1705                1710

Leu Val Cys Tyr Thr Ala Val Gly Asp Thr Glu Glu His Val Leu
1715                1720                1725

His Thr Gln Gly Arg Pro Ile Ser Ser Gly Asp Glu Ile Leu Ile
1730                1735                1740

Val Asp Glu Asn Asp Glu Pro Val Ala Asn Gly Val Ala Gly Gln
1745                1750                1755

Leu Leu Val Arg Gly Pro Tyr Thr Ile Arg Gly Tyr Leu Asn Ala
1760                1765                1770

Pro Glu His Asn Ala Arg Ala Phe Thr Pro Asp Gly Phe Tyr Arg
1775                1780                1785

Thr Gly Asp Val Val Val Phe Arg Asp Asp Gly Tyr Leu Val Val
1790                1795                1800

Thr Gly Arg Ile Lys Asp Gln Val Asn Arg Gly Gly Glu Lys Ile
1805                1810                1815

Ala Ala Glu Glu Ile Glu Gly Tyr Leu Leu Ala His Pro Gly Val
1820                1825                1830

Leu Glu Ala Gly Ile Ile Gly Leu Pro Asp Glu Tyr Leu Gly Glu
1835                1840                1845

Val Ser Cys Ala Val Val Val Leu Ala Pro Gly Ala Gln Leu Thr
1850                1855                1860

Ala Ser Ala Leu Lys Ser Phe Val Arg Gln Gln Gly Ile Ala Ala
1865                1870                1875

Phe Lys Val Pro Asp Gln Val His Leu Val Pro Ser Leu Pro Lys
1880                1885                1890

Thr Thr Leu Gly Lys Ile Asp Lys Lys Leu Leu Arg Val Gln Leu
```

Gly Gln
    1910

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
gaactgggga aggccatatg acccag                                        26

<210> SEQ ID NO 9
<211> LENGTH: 28
<212> TYPE: DNA
<213> ORGANISM: Artificial Sequence
<220> FEATURE:
<223> OTHER INFORMATION: Primer

<400> SEQUENCE: 9
tcgaaaagct tcatggctgc tcgcactc                                      28

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
gttaaactca tatgtcagcc tcattcac                                      28

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
ccagttaagc tttgggttta ttgg                                          24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
gtctacgggc acagcgccgg taac                                          24

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
gtctacgggc acgcagccgg taac                                          24

<210> SEQ ID NO 14

```
<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gataatcggc ccgctcaacg                                              20

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ggtgtatcag ctagcccaac gatg                                         24

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
ggtaaatgaa agcttggtca tgccttg                                      27

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
gcagagaaac catatgagca atgtc                                        25

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
gggaagcttg accatcgttg                                              20

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
catgtaatgc ccatatgcct gaatc                                        25

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
```

```
cgtatatcga agcttaacgc tcaag                                        25
```

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21

```
gcgctggcca tatgaacgc                                               19
```

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22

```
gtccatgcaa gcttccgtca aag                                          23
```

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23

```
gcgccccata tgccccac                                                18
```

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24

```
gtcaaaagct ttcattcggt cagg                                         24
```

<210> SEQ ID NO 25
<211> LENGTH: 229
<212> TYPE: PRT
<213> ORGANISM: Burkholderia diffusa

<400> SEQUENCE: 25

His Met Val Cys Val Pro Phe Ala Gly Gly Ser Ala Leu Ser Tyr Arg
1               5                   10                  15

Glu Leu Ala Arg Ala Leu Pro Asp Gly Phe Ala Cys Ser Ala Leu Gln
            20                  25                  30

Leu Pro Gly His Asp Pro Ala Ala Pro Asp Glu Ala Phe Val Asp Leu
        35                  40                  45

Asp Thr Thr Ile Asp Arg Ala Val Asp Arg Leu Leu Ala Glu Ala Ala
    50                  55                  60

Ala Pro Ile Val Val Tyr Gly His Cys Ala Gly Asn Ala Leu Ala Val
65                  70                  75                  80

Ala Leu Val Arg Arg Leu Ala Gly Ala Gly Ala Asn Val Ile Gly Leu
                85                  90                  95

Ala Ile Gly Gly Met Leu Leu Asp Glu Asp Ala Asp Ala Val Leu Asp
            100                 105                 110

```
Glu Val Gly Ala Arg Ser Gly Glu Asn Ile Val Asp Phe Leu Arg Gln
            115                 120                 125

Ile Gly Gly Phe Lys Asp Val Leu Asp Ala Gly Thr Leu Ala Ala Ile
130                 135                 140

Ala Arg Met Thr Lys His Asp Ala Met Gln Ala Ala Thr Phe Phe Ala
145                 150                 155                 160

Ala Glu Thr Arg Ala Pro Ala Arg Leu Asp Val Pro Leu His Val Val
            165                 170                 175

Ile Gly Gly Gln Asp Pro Leu Thr Pro Asp Tyr Ala Arg Arg Tyr Leu
            180                 185                 190

Asp Trp Arg Arg Tyr Ser Asp Ala Val Glu Leu Asp Val Ile Pro Asp
            195                 200                 205

Gly Gly His Tyr Phe Val Thr Glu His Ala Asp Thr Leu Ala Gly Leu
            210                 215                 220

Leu Ala Arg Trp Leu
225
```

<210> SEQ ID NO 26
<211> LENGTH: 227
<212> TYPE: PRT
<213> ORGANISM: Chitiniphilus shinanonensis

<400> SEQUENCE: 26

```
Val Thr Leu Val Cys Val Pro Phe Ala Gly Gly Asn Ala Phe Ala Phe
1               5                   10                  15

Arg Gly Leu Val Asp Gly Leu Ser Pro Arg Phe Ala Cys Val Ala Val
            20                  25                  30

Asn Leu Pro Gly His Asp Val Leu Arg Pro Asp Glu Ala Leu Glu Ser
            35                  40                  45

Ile Asp Thr Val Ala Thr Arg Ala Val Ala Glu Ile Val Glu Leu Ala
50                  55                  60

Gly Gly Pro Ile Val Val Tyr Gly His Cys Ala Gly Asn Ala Ile Ala
65                  70                  75                  80

Leu Ala Ile Ala Arg Lys Leu Glu Gln Ala Gly Ala Pro Leu Ala Ala
            85                  90                  95

Leu Val Ile Gly Gly Met Leu Pro Asp Ala Asp Pro Gln Ala Val Ala
            100                 105                 110

Ala Glu Val Asp Thr Gln Arg Gly Glu Asp Ile Ile Ala Phe Leu Arg
            115                 120                 125

Ser Ile Gly Gly Phe Lys Glu Thr Leu Asp Ala Ala Ser Leu Ala Ala
            130                 135                 140

Ile Ala Arg Val Thr Lys His Asp Ala Gly Glu Thr Ala Ala Phe Phe
145                 150                 155                 160

Ala Arg Asp Ala Ala Ala Arg Val Arg Leu Lys Ala Pro Ile His Val
            165                 170                 175

Val Ile Gly Asp Glu Asp Pro Leu Thr Pro Asp Tyr Ala Thr Arg Tyr
            180                 185                 190

Leu Asp Trp Arg Val Gln Ala Asp Asp Val Thr Leu Ser Val Ile Ala
            195                 200                 205

Gly Gly Gly His Tyr Phe Val Thr Asp Gln Pro Gln Ala Leu Ala Arg
            210                 215                 220

Val Leu Glu
225
```

```
<210> SEQ ID NO 27
<211> LENGTH: 270
<212> TYPE: PRT
<213> ORGANISM: Acinetobacter baumannii

<400> SEQUENCE: 27
```

| | | | | | | | | | | | | | | |
|---|---|---|---|---|---|---|---|---|---|---|---|---|---|---|
|Lys|Pro|Ser|Ile|Val|Ile|Glu|Leu|Arg|Arg|Gly|Thr|Tyr|Glu|Gln|Pro|
|1| | | |5| | | | |10| | | | |15| |

Leu Trp Leu Phe His Pro Ile Gly Gly Ser Thr Phe Cys Tyr Met Glu
            20                  25                  30

Leu Ser Arg His Leu Asn Pro Asn Arg Thr Leu Arg Ala Ile Gln Ser
        35                  40                  45

Pro Gly Leu Ile Glu Ala Asp Ala Ala Glu Val Ala Ile Glu Glu Val
    50                  55                  60

Ala Thr Leu Tyr Ile Ala Glu Met Gln Lys Met Gln Pro Gln Gly Pro
65                  70                  75                  80

Tyr Phe Leu Gly Gly Trp Cys Phe Gly Gly Ala Ile Ala Tyr Glu Ile
                85                  90                  95

Ser Arg Gln Leu Arg Gln Met Gly Gln Gln Val Thr Gly Ile Val Met
            100                 105                 110

Ile Asp Thr Arg Ala Pro Ile Pro Glu Asn Val Pro Glu Asp Ala Asp
        115                 120                 125

Asp Ala Met Leu Leu Ser Trp Phe Ala Arg Asp Leu Ala Ala Pro Tyr
130                 135                 140

Gly Lys Lys Leu Thr Ile Pro Ala Gln Tyr Leu Arg Glu Leu Ser Pro
145                 150                 155                 160

Asp Gln Met Phe Asp His Val Leu Lys Glu Ala Lys Ala Ile Asn Val
                165                 170                 175

Leu Pro Leu Asp Ala Asp Pro Ser Asp Phe Arg Leu Tyr Phe Asp Thr
            180                 185                 190

Tyr Leu Ala Asn Gly Ile Ala Leu Gln Thr Tyr Phe Pro Glu Pro Glu
        195                 200                 205

Asp Phe Pro Ile Leu Leu Val Lys Ala Lys Asp Glu Gln Glu Asp Phe
    210                 215                 220

Gly Glu Ser Leu Gly Trp Asp Gln Leu Val Lys Asp Thr Leu Thr Gln
225                 230                 235                 240

Val Asp Leu Pro Gly Asp His Ser Ser Ile Met Tyr Ala Glu Asn Val
                245                 250                 255

Val Ala Val Ala Gln Thr Ile Asp Gln Met Tyr Pro Ile Pro
            260                 265                 270

```
<210> SEQ ID NO 28
<211> LENGTH: 192
<212> TYPE: PRT
<213> ORGANISM: Escherichia coli

<400> SEQUENCE: 28
```

Arg Pro Asn Gly Pro Met Gln Thr Ala Ala Asn Leu Asp Glu Val Cys
1               5                   10                  15

Glu Ala His Leu Ala Thr Leu Leu Glu Gln Gln Pro His Gly Pro Tyr
            20                  25                  30

Tyr Leu Leu Gly Tyr Ser Leu Gly Gly Thr Leu Ala Gln Gly Ile Ala
        35                  40                  45

Ala Arg Leu Arg Ala Arg Gly Glu Gln Val Ala Phe Leu Gly Leu Leu
    50                  55                  60

Asp Thr Trp Pro Pro Glu Thr Gln Asn Trp Gln Glu Lys Glu Ala Asn

```
65                  70                  75                  80

Gly Leu Asp Pro Glu Val Leu Ala Glu Ile Asn Arg Glu Arg Glu Ala
            85                  90                  95

Phe Leu Ala Ala Gln Gln Gly Ser Thr Ser Thr Glu Leu Phe Thr Thr
                100                 105                 110

Ile Glu Gly Asn Tyr Ala Asp Ala Val Arg Leu Leu Thr Thr Ala His
            115                 120                 125

Ser Val Pro Phe Asp Gly Lys Ala Thr Leu Phe Val Ala Glu Arg Thr
            130                 135                 140

Leu Gln Glu Gly Met Ser Pro Glu Arg Ala Trp Ser Pro Trp Ala Glu
145                 150                 155                 160

Leu Asp Ile Tyr Arg Gln Asp Cys Ala His Val Asp Ile Ile Ser Pro
                165                 170                 175

Gly Thr Phe Glu Lys Ile Gly Pro Ile Ile Arg Ala Thr Leu Asn Arg
                180                 185                 190
```